US011236084B2

(12) United States Patent
Hynd et al.

(10) Patent No.: US 11,236,084 B2
(45) Date of Patent: Feb. 1, 2022

(54) SUBSTITUTED AZAINDOLINE DERIVATIVES AS NIK INHIBITORS

(71) Applicant: Janssen Pharmaceutica NV, Beerse (BE)

(72) Inventors: George Hynd, Epping (GB); Calum Macleod, Buntingford (GB); Samuel Edward Mann, London (GB); Janusz Jozef Kulagowski, Sawbridgeworth (GB); Ian Stansfield, Fourqueux (FR); Olivier Alexis Georges Querolle, Vigor (FR); Virginie Sophie Poncelet, Le Manoir sur Seine (FR); Gerhard Max Gross, Fuldabruck (DE); Edgar Jacoby, Vosselaar (BE); Lieven Meerpoel, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 41 days.

(21) Appl. No.: 16/622,016

(22) PCT Filed: Jul. 4, 2018

(86) PCT No.: PCT/EP2018/068048
§ 371 (c)(1),
(2) Date: Dec. 12, 2019

(87) PCT Pub. No.: WO2019/008011
PCT Pub. Date: Jan. 10, 2019

(65) Prior Publication Data
US 2021/0188840 A1    Jun. 24, 2021

(30) Foreign Application Priority Data

Jul. 6, 2017  (EP) ..................... 17180010

(51) Int. Cl.
*C07D 471/04*     (2006.01)
*C07D 519/00*     (2006.01)

(52) U.S. Cl.
CPC ......... *C07D 471/04* (2013.01); *C07D 519/00* (2013.01)

(58) Field of Classification Search
None
See application file for complete search history.

(56) References Cited

FOREIGN PATENT DOCUMENTS

| EP | 3 112 364 B1 | 1/2017 |
| WO | WO 2002/079197 A1 | 10/2002 |
| WO | WO 2003/030909 A1 | 4/2003 |
| WO | WO 2010/042337 A1 | 4/2010 |
| WO | WO 2014/056871 A1 | 4/2014 |
| WO | WO2017114510 | * 6/2017 |

OTHER PUBLICATIONS

Cheng et al., Pharmacological inhibition of NF-k-inducing kinase (NIK) with small molecules for the treatment of human disease. RSC Medicinal Chemistry, 2021, 12, 552-565.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Allen, I.C., et al., "NLPR12 Suppresses Colon Inflammation and Tumorigenesis Through the Negative Regulation of Noncanonical NF-κB Signaling", Immunity, (2012), vol. 36, pp. 742-754.
Annunziata, C.M., et al., "Frequent Engagement of the Classical and Alternative NF-κb Pathways By Diverse Genetic Abnormalities in Multiple Myeloma", Cancer Cell, (2007), vol. 12, pp. 115-130.
Aya, K., et al., "NF-κb-Iducing Kinase Controls Lymphocyte and Osteoclast Activities in Inflammatory Arthritis", J. Clin. Invest., (2005), vol. 115, No. 7, pp. 1848-1854.
Bhattacharyya, S., et al., "Tumor Necrosis Factor α-Induced Inflammation is Increased but Apoptosis is Inhibited By Common Food Additive Carrageenan", J. Biol. Chem., (2011), vol. 285, No. 50, pp. 39511-39522.
Bitar, M.S., et al., "Inflammation and Apoptosis in Aortic Tissues of Aged Type II Diabeies: Amelioration With α-Lipoic Acid Through Phosphatidylinositol 3-Kinase/AκT-Dependent Mechanism", Life Sciences, (2010), vol. 86, pp. 844-853.
Choudhary, S., et al., "NF-κB-Inducing Kinase (NIK) Mediates Skeletal Muscle Insulin Resistance: Blockade By Adiponectin", Endocrinology, (2011), vol. 152, No. 10, pp. 3622-3627.
Chung, S., et al., "NF-κB Inducing Kinase, NIK Mediates Cigarette Smoke/TNFα-Induced Histone Acetylation and Inflammation Through Differential Activation of IKKS", PLoS One, (2011), vol. 6, No. 8, pp. e23488.

(Continued)

*Primary Examiner* — Po-Chih Chen

(57) ABSTRACT

The present invention relates to pharmaceutical agents useful for therapy and/or prophylaxis in a mammal, and in particular to inhibitors of NF-κB-inducing kinase (NIK—also known as MAP3K14) useful for treating diseases such as cancer, inflammatory disorders, metabolic disorders and autoimmune disorders. The invention is also directed to pharmaceutical compositions comprising such compounds, and to the use of such compounds or pharmaceutical compositions for the prevention or treatment of diseases such as cancer, inflammatory disorders, metabolic disorders including obesity and diabetes, and autoimmune disorders.

15 Claims, No Drawings

(56) References Cited

OTHER PUBLICATIONS

Demchenko, Y.N. et al., "Classical and/or Alternative NF-κB Pathway Activation in Multiple Myeloma", Blood, (2010), vol. 115, No. 17, pp. 3541-3552.
Keats, J.J., et al., "Promiscuous Mutations Activate the Noncanonical NF-κB Pathway in Multiple Myeloma", Cancer Cell, (2007), vol. 12, pp. 131-144.
Nishina, T., et al., "NIK is Involved in Constitutive Activation of the Alternative NF-κB Pathway and Proliferation of Pancreatic Cancer Cells", Biochem. Bioph. Res. Co., (2009), vol. 388, pp. 96-101.
Pham, L.V., et al., "Constitutive BR3 Receptor Signaling in Diffuse, Large B-Cell Lymphomas Stabilizes Nuclear Factor-κB-Inducing Kinase While Activating Both Canonical and Alternative Nuclear Factor-κB Pathways", Blood, (2011), vol. 117, No. 1, pp. 200-210.
Ranuncolo, S.M., et al., "Hodgkin Lymphoma Requires Stabilized NIK and Constitutive Relb Expression for Survival", Blood, (2012), vol. 120, No. 18, pp. 3756-3763.
Rosebeck, S., et al., "Cleavage of NIK By the API2-MALT1 Fusion Onoprotein Leads To Noncanonical NF-κB Activation", Science, (2011), vol. 331, pp. 468-472.
Saitoh, Y., et al., "Overexpressed NF-κB-Inducing Kinase Contributes to the Tumorigenesis of Adult T-Cell Leukemia and Hodgkin Reed-Sternberg Cells", Blood, (2008), vol. 111, No. 10, pp. 5118-5129.
Shuto, T., et al., "Activation of NF-B By Nontypeable Hemophilus Influenzae is Mediated By Toll-Like Receptor 2-TAK1-Dependent NIK-IKKα/B-IκBαand MKK3/6-p38 Map Kinase Signaling Pathways in Epithelial Cells", PNAS, (2001), vol. 98, No. 15, pp. 8774-8779.
Thu, Y.M., et al., "NF-κb Inducing Kinase (NIK) Modulates Melanoma Tumorigenesis By Regulating Expression of Pro-Survival Factors Through the β-Catenin Pathway", Oncogene, (2012), vol. 31, No. 20, pp. 2580-2592.

Thu and Richmond, "NF-κB Inducing Kinase: A Key Regulator in the Immune System and in Cancer", Cytokine & Growth Factor Reviews, (2010), vol. 21, pp. 213-226.
Wixted, W.E., et al., "A Model To Identify Novel Targets Involved in Oxidative Stress-Induced Apoptosis in Human Lung Epithelial Cells By RNA Interference", Toxicology in Vitro, (2010), vol. 24, pp. 310-318.
Yamamoto, M., et al., "Epigenetic Alteration of The NF-κB-Inducing Kinase (NIK) Gene is Involved in Enhanced NIK Expression in Basal-Like Breast Cancer", Cancer Science, (2010), vol. 101, No. 11, pp. 2391-2397.
Yang, C., et al., "NIK Stabilization in Osteoclasts Results in Osteoporosis and Enhanced Inflammatory Osteolysis", PLoS One, (2010), vol. 5, No. 11, pp. e15383.
Zhao, Y., et al., "NF-κB-Inducing Kinase Increases Renal Tubule Epithelial Inflammation Associated With Diabetes", Experimental Diabetes Research, (2011), vol. 2011, pp. 1-9.
Greene, T.W., et al., "Greene's Protective Groups in Organic Synthesis", $4^{th}$ ed., (2007), Wiley-Interscience, Hoboken, New Jersey.
International Search Report dated Aug. 17, 2018 for PCT/EP2018/068048.
Gennaro, A.R., Remington's $18^{th}$ ed., Mack Publishing Company, (1990) see especially Part 8: Pharmaceutical preparations and their Manufacture, pp. 1435-1712.
Bushell, K.R., et al., "Genetic inactivation of TRAF3 in canine and human B-cell lymphoma", Blood, (2015), vol. 125, No. 6, pp. 999-1005.
Rahal, R., et al., "Pharmacological and genomic profiling identifies NF-κB-targeted treatment strategies for mantle cell lymphoma", Nature Medicine, (2014), vol. 20, No. 1, pp. 87-92.

\* cited by examiner

SUBSTITUTED AZAINDOLINE DERIVATIVES AS NIK INHIBITORS

CROSS REFERENCE TO RELATED APPLICATIONS

This application is a national stage of PCT Application No. PCT/EP2018/068048, filed Jul. 4, 2018, which claims priority for EPO Patent Application No. 17180010.5, filed Jul. 6, 2017.

FIELD OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer (in particular B-cell malignancies including leukemias, lymphomas and myeloma), inflammatory disorders, metabolic disorders including obesity and diabetes, and autoimmune disorders. The invention is also directed to pharmaceutical compositions comprising such compounds, and to the use of such compounds or pharmaceutical compositions for the prevention or treatment of diseases such as cancer, inflammatory disorders, metabolic disorders including obesity and diabetes, and autoimmune disorders.

BACKGROUND OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer and inflammatory disorders. Nuclear factor-kappa B (NF-κB) is a transcription factor regulating the expression of various genes involved in the immune response, cell proliferation, adhesion, apoptosis, and carcinogenesis. NF-κB dependent transcriptional activation is a tightly controlled signaling pathway, through sequential events including phosphorylation and protein degradation. NIK is a serine/threonine kinase which regulates NF-κB pathway activation. There are two NF-κB signaling pathways, the canonical and the non-canonical. NIK is indispensable for the non-canonical signaling pathway where it phosphorylates IKKα, leading to the partial proteolysis of p100; liberating p52 which then heterodimerizes with RelB, translocates to the nucleus and mediates gene expression. The non-canonical pathway is activated by only a handful of ligands such as CD40 ligands, B-cell activating factor (BAFF), lymphotoxin β receptor ligands and TNF-related weak inducer of apoptosis (TWEAK) and NIK has been shown to be required for activation of the pathway by these ligands. Because of its key role, NIK expression is tightly regulated. Under normal non-stimulated conditions NIK protein levels are very low, this is due to its interaction with a range of TNF receptor associated factors (TRAF2 and TRAF3), which are ubiquitin ligases and result in degradation of NIK. It is believed that when the non-canonical pathway is stimulated by ligands, the activated receptors now compete for TRAFs, dissociating the TRAF-NIK complexes and thereby increasing the levels of NIK. (Thu and Richmond, *Cytokine Growth F. R.* 2010, 21, 213-226) Research has shown that blocking the NF-κB signaling pathway in cancer cells can cause cells to stop proliferating, to die and to become more sensitive to the action of other anti-cancer therapies. A role for NIK has been shown in the pathogenesis of both hematological malignancies and solid tumours.

The NF-κB pathway is dysregulated in multiple myeloma due to a range of diverse genetic abnormalities that lead to the engagement of the canonical and non-canonical pathways (Annuziata et al. *Cancer Cell* 2007, 12, 115-130; Keats et al. *Cancer Cell* 2007, 12, 131-144; Demchenko et al. *Blood* 2010, 115, 3541-3552). Myeloma patient samples frequently have increased levels of NIK activity. This can be due to chromosomal amplification, translocations (that result in NIK proteins that have lost TRAF binding domains), mutations (in the TRAF binding domain of NIK) or TRAF loss of function mutations. Researchers have shown that myeloma cell lines can be dependent on NIK for proliferation; in these cell lines if NIK activity is reduced by either shRNA or compound inhibition, this leads to a failure in NF-κB signaling and the induction of cell death (Annuziata 2007).

In a similar manner, mutations in TRAF and increased levels of NIK have also been seen in samples from Hodgkin lymphoma (HL) patients. Once again proliferation of cell lines derived from HL patients is susceptible to inhibition of NIK function by both shRNA and compounds (Ranuncolo et al. *Blood* First Edition Paper, 2012, DOI 10.1182/blood-2012-01-405951).

NIK levels are also enhanced in adult T cell leukemia (ATL) cells and targeting NIK with shRNA reduced ATL growth in vivo (Saitoh et al. *Blood* 2008, 111, 5118-5129). It has been demonstrated that the API2-MALT1 fusion oncoprotein created by the recurrent translocation t(11;18)(q21;q21) in mucosa-associated lymphoid tissue (MALT) lymphoma induces proteolytic cleavage of NF-κB-inducing kinase (NIK) at arginine 325. NIK cleavage generates a C-terminal NIK fragment that retains kinase activity and is resistant to proteasomal degradation (due to loss of TRAF binding region). The presence of this truncated NIK leads to constitutive non-canonical NF-κB signaling, enhanced B cell adhesion, and apoptosis resistance. Thus NIK inhibitors could represent a new treatment approach for refractory t(11;18)-positive MALT lymphoma (Rosebeck et al. *Science* 2011, 331, 468-472).

NIK aberrantly accumulates in diffuse large B-cell lymphoma (DLBCL) cells due to constitutive activation of B-cell activation factor (BAFF) through interaction with autochthonous B-lymphocyte stimulator (BLyS) ligand. NIK accumulation in human DLBCL cell lines and patient tumor samples suggested that constitutive NIK kinase activation is likely to be a key signaling mechanism involved in abnormal lymphoma tumor cell proliferation. Growth assays showed that using shRNA to inhibit NIK kinase protein expression in GCB- and ABC-like DLBCL cells decreased lymphoma cell growth in vitro, implicating NIK-induced NF-κB pathway activation as having a significant role in DLBCL proliferation (Pham et al. *Blood* 2011, 117, 200-210). More recently, also loss-of-function mutations in TRAF3 have been characterized in human and canine DLBCL (Bushell et al., *Blood* 2015, 125, 999-1005).

Recently, similar mutations in the non-cannonical NFkB signaling pathway (TRAF2, TRAF3, NIK, BIRC3) were found in ibrutinib-refractory mantle cell lymphoma cell lines (Rahal et al., *Nat Med* 2014, 1, 87-92).

As mentioned a role of NIK in tumour cell proliferation is not restricted to hematological cells, there are reports that NIK protein levels are stabilised in some pancreatic cancer cell lines and as seen in blood cells proliferation of these pancreatic cancer lines are susceptible to NIK siRNA treatment (Nishina et al. *Biochem. Bioph. Res. Co.* 2009, 388, 96-101). Constitutive activation of NF-κB, is preferentially involved in the proliferation of basal-like subtype breast cancer cell lines, including elevated NIK protein levels in specific lines (Yamamoto et al. *Cancer Sci.* 2010, 101, 2391-2397). In melanoma tumours, tissue microarray analysis of NIK expression revealed that there was a statistically significant elevation in NIK expression when compared with benign tissue. Moreover, shRNA techniques were used to knock-don NIK, the resultant NIK-depleted melanoma cell lines exhibited decreased proliferation, increased apoptosis, delayed cell cycle progression and reduced tumor growth in a mouse xenograft model (Thu et al. *Oncogene* 2012, 31(20), 2580-92). A wealth of evidence showed that NF-κB is often constitutively activated in non-small cell lung cancer tissue specimens and cell lines. Depletion of NIK by RNAi induced apoptosis and affected efficiency of anchorage-independent NSCLC cell growth.

In addition research has shown that NF-κB controls the expression of many genes involved in inflammation and that NF-κB signalling is found to be chronically active in many inflammatory diseases, such as rheumatoid arthritis, inflammatory bowel disease, sepsis and others. Thus pharmaceutical agents capable of inhibiting NIK and thereby reducing NF-κB signaling pathway can have a therapeutic benefit for the treatment of diseases and disorders for which over-activation of NF-κB signaling is observed.

Dysregulated NF-κB activity is associated with colonic inflammation and cancer, and it has been shown that Nlrp12 deficient mice were highly susceptible to colitis and colitis-associated colon cancer. In this context work showed that NLRP12 functions as a negative regulator of the NF-κB pathway through its interaction and regulation of NIK and TRAF3, and as a checkpoint of critical pathways associated with inflammation and inflammation-associated tumorigenesis (Allen et al. *Immunity* 2012, 36, 742-754).

Tumor necrosis factor (TNF)-α, is secreted in response to inflammatory stimuli in diseases such as rheumatoid arthritis and inflammatory bowel disease. In a series of experiments in colonic epithelial cells and mouse embryonic fibroblasts, TNF-α mediates both apoptosis and inflammation, stimulating an inflammatory cascade through the non-canonical pathway of NF-κB activation, leading to increased nuclear RelB and p52. TNF-α induced the ubiquitination of TRAFs, which interacts with NIK, leading to increased levels of phospho-NIK (Bhattacharyya et al. *J Biol. Chem.* 2011, 285, 39511-39522).

Inflammatory responses are a key component of chronic obstructive pulmonary disease (COPD) as such it has been shown that NIK plays a key role in exacerbating the disease following infection with the Gram-negative bacterium non-typeable *Hemophilus influenza* (Shuto et al. *PNAS* 2001, 98, 8774-8779). Likewise cigarette smoke (CS) contains numerous reactive oxygen/nitrogen species, reactive aldehydes, and quinones, which are considered to be some of the most important causes of the pathogenesis of chronic inflammatory lung diseases, such as COPD and lung cancer. Increased levels of NIK and p-IKKα have been observed in peripheral lungs of smokers and patients with COPD. In addition it has been shown that endogenous NIK is recruited to promoter sites of pro-inflammatory genes to induce post-translational modification of histones, thereby modifying gene expression profiles, in response to CS or TNFα (Chung et al. *PLoS ONE* 2011, 6(8): e23488. doi:10.1371/journal.pone.0023488). A shRNA screen was used in an in vitro model of oxidative stress induced cell death (as a model of COPD) to interrogate a human druggable genome siRNA library in order to identify genes that modulate the cellular response to stress. NIK was one of the genes identified in this screen as a potential new therapeutic target to modulate epithelial apoptosis in chronic lung diseases (Wixted et al. *Toxicol. In Vitro* 2010, 24, 310-318).

Diabetic individuals can be troubled by a range of additional manifestations associated with inflammation. One such complication is cardiovascular disease and it has been shown that there are elevated levels of p-NIK, p-IKK-α/β and p-IκB-α in diabetic aortic tissues (Bitar et al. *Life Sci.* 2010, 86, 844-853). In a similar manner, NIK has been shown to regulate proinflammatory responses of renal proximal tubular epithelial cells via mechanisms involving TRAF3. This suggests a role for NF-κB noncanonical pathway activation in modulating diabetes-induced inflammation in renal tubular epithelium (Zhao et al. *Exp. Diabetes Res.* 2011, 1-9). The same group has shown that NIK plays a critical role in noncanonical NF-κB pathway activation, induced skeletal muscle insulin resistance in vitro. suggesting that NIK could be an important therapeutic target for the treatment of insulin resistance associated with inflammation in obesity and type 2 diabetes (Choudhary et al. *Endocrinology* 2011, 152, 3622-3627).

NF-κB is an important component of both autoimmunity and bone destruction in rheumatoid arthritis (RA). Mice lacking functional NIK have no peripheral lymph nodes, defective B and T cells, and impaired receptor activator of NF-κB ligand-stimulated osteoclastogenesis. Aya et al. (*J. Clin. Invest.* 2005, 115, 1848-1854) investigated the role of NIK in murine models of inflammatory arthritis using Nik−/− mice. The serum transfer arthritis model was initiated by preformed antibodies and required only intact neutrophil and complement systems in recipients. While Nik−/− mice had inflammation equivalent to that of Nik+/+ controls, they showed significantly less periarticular osteoclastogenesis and less bone erosion. In contrast, Nik−/− mice were completely resistant to antigen-induced arthritis (AIA), which requires intact antigen presentation and lymphocyte function but not lymph nodes. Additionally, transfer of Nik+/+ splenocytes or T cells to Rag2−/− mice conferred susceptibility to AIA, while transfer of Nik−/− cells did not. Nik−/− mice were also resistant to a genetic, spontaneous form of arthritis, generated in mice expressing both the KRN T cell receptor and H-2g7. The same group used transgenic mice with OC-lineage expression of NIK lacking its TRAF3 binding domain (NT3), to demonstrate that constitutive activation of NIK drives enhanced osteoclastogenesis and bone resorption, both in basal conditions and in response to inflammatory stimuli (Yang et al. *PLoS ONE* 2010, 5(11): e15383. doi:10.1371/journal.pone.0015383). Thus this group concluded that NIK is important in the immune and bone-destructive components of inflammatory arthritis and represents a possible therapeutic target for these diseases.

It has also been hypothesized that manipulating levels of NIK in T cells may have therapeutic value. Decreasing NIK activity in T cells might significantly ameliorate autoimmune responses and alloresponses, like GVHD (Graft Versus Host Disease) and transplant rejection, without crippling the immune system as severely as do inhibitors of canonical NF-κB activation.

WO2003030909 describes the preparation of 2- and 4-aminopyrimidines N-substituted by a bicyclic ring for use as kinase inhibitors in the treatment of cancer.

WO2002079197 describes 4-aryl-substituted 2-pyrimidinamines and 2-pyridinamines, useful as inhibitors of c-Jun N-terminal kinases (JNK) and other protein kinases.

DESCRIPTION OF THE INVENTION

The present invention concerns novel compounds of Formula (I):

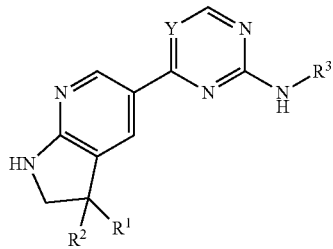

tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$ or N;
$R^4$ represents hydrogen or halo;
$R^5$ represents halo, cyano, $Het^{3a}$, $-NR^{6a}R^{6b}$, or $-OR^7$;
$R^{6a}$ represents hydrogen or $C_{1-4}$alkyl;
$R^{6b}$ represents hydrogen; $C_{1-4}$alkyl; $C_{3-6}$cycloalkyl; $-C(=O)-C_{1-4}$alkyl; $-C(=O)-Het^4$; $-S(=O)_2-C_{1-4}$alkyl; $-C(=O)-C_{1-6}$alkyl substituted with one substituent selected from the group consisting of $-OH$ and $-NR^{16a}R^{16b}$; or $C_{1-4}$alkyl substituted with one substituent selected from the group consisting of $-OH$ and $-S(=O)_2-C_{1-4}$alkyl;
$R^7$ represents hydrogen, $C_{1-4}$alkyl, $-C_{1-4}$alkyl-$NR^{8a}R^{8b}$, $-C(=O)-R^9$, $-S(=O)_2-OH$, $-P(=O)_2-OH$, $-(C=O)-CH(NH_2)-C_{1-4}$alkyl-$Ar^1$, or $-C_{1-4}$alkyl-$Het^{3b}$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-4}$alkyl, or $C_{1-6}$alkyl substituted with one substituent selected from the group consisting of $-NH_2$, $-COOH$, and $Het^6$;
$R^{16a}$ and $R^{16b}$ each independently represents hydrogen, $C_{1-4}$alkyl or $C_{3-6}$cycloalkyl;
$R^3$ represents phenyl optionally substituted with one, two or three substituents each independently selected from the group consisting of halo; cyano; $C_{1-6}$alkyl; $-O-C_{1-4}$alkyl; $-C(=O)-R^{10}$; $-S(=O)_2-C_{1-4}$alkyl; $-S(=O)(=N-R^{20a})-C_{1-4}$alkyl; $-O-C_{1-4}$alkyl substituted with one, two or three halo atoms; $-O-C_{1-4}$alkyl-$R^{12}$; $C_{3-6}$cycloalkyl; $-O-C_{3-6}$cycloalkyl; $Het^{1a}$; $-O-Het^{1b}$; $R^{18}$; $R^{21}$; $-P(=O)-(C_{1-4}$alkyl$)_2$; $-NH-C(=O)-C_{1-4}$alkyl; $-NH-C(=O)-Het^{1g}$; $-NR^{17a}R^{17b}$; $C_{1-6}$alkyl substituted with one, two or three halo atoms; $C_{1-4}$alkyl substituted with one, two or three $-OH$ substituents; $C_{1-4}$alkyl substituted with one $R^{13}$; $C_{1-4}$alkyl substituted with one $R^{18}$; $C_{2-6}$alkenyl; $C_{2-6}$alkenyl substituted with one $R^{13}$; $C_{2-6}$alkynyl; and $C_{2-6}$alkynyl substituted with one $R^{13}$;
$R^{10}$ represents $-OH$, $-O-C_{1-4}$alkyl, $-NR^{11a}R^{11b}$ or $Het^2$;
$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;
$Het^{1a}$, $Het^{1c}$ and $Het^{1d}$ each independently represents a 4- to 7-membered monocyclic saturated heterocyclyl containing one or two heteroatoms each independently selected from O, S, $S(=O)_p$ and N; or a 6- to 11-membered bicyclic saturated heterocyclyl, including fused, spiro and bridged cycles, containing one, two or three heteroatoms each independently selected from O, S, $S(=O)_p$ and N;
wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of $-OH$ and $-O-C_{1-4}$alkyl; and
wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of $-OH$, halo, $C_{1-4}$alkyl, cyano, $-C(=O)-C_{1-4}$alkyl, $-O-C_{1-4}$alkyl, $-NH_2$, $-NH(C_{1-4}$alkyl), and $-N(C_{1-4}$alkyl$)_2$;
$Het^{1b}$, $Het^{1e}$, $Het^{1g}$, $Het^4$, $Het^7$ and $Het^8$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$, $Het^4$, $Het^7$ and $Het^8$ containing one or two heteroatoms each independently selected from O, S, $S(=O)_p$ and N;
wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of $-OH$ and $-O-C_{1-4}$alkyl; and
wherein said 4- to 7-membered monocyclic saturated heterocyclyl may optionally be substituted on one, two or three ring C-atoms with one or two substituents each independently selected from the group consisting of $-OH$, halo, $C_{1-4}$alkyl, cyano, $-C(=O)-C_{1-4}$alkyl, $-O-C_{1-4}$alkyl, $-NH_2$, $-NH(C_{1-4}$alkyl), and $-N(C_{1-4}$alkyl$)_2$;
$Het^2$ represents a heterocyclyl of formula (b-1):

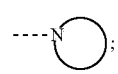

(b-1) represents a N-linked 4- to 7-membered monocyclic saturated heterocyclyl optionally containing one additional heteroatom selected from O, S, $S(=O)_p$ and N, or a N-linked 6- to 11-membered bicyclic saturated heterocyclyl, including fused, spiro and bridged cycles, optionally containing one or two additional heteroatoms each independently selected from O, S, $S(=O)_p$ and N;
wherein in case (b-1) contains one or two additional N-atoms, said one or two N-atoms may optionally be substituted with a substituent each independently selected from the group consisting of $C_{1-4}$alkyl, $C_{3-6}$cycloalkyl and $Het^7$; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; Het$^{1e}$; $C_{1-4}$alkyl; —$C_{1-4}$alkyl-Het$^5$; —$C_{1-4}$alkyl-Het$^8$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, or —C(=O)—Het$^{1f}$;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

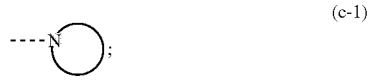

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-6}$alkyl; $C_{3-6}$cycloalkyl; —C(=O)—$C_{1-4}$alkyl; $C_{1-4}$alkyl substituted with one substituent selected from the group consisting of halo, —OH and —O—$C_{1-4}$alkyl; —C(=O)—$C_{1-4}$alkyl substituted with one substituent selected from the group consisting of halo, —OH and —O—$C_{1-4}$alkyl; or —S(=O)$_2$—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention also relates to a pharmaceutical composition comprising a therapeutically effective amount of a compound of Formula (I), a pharmaceutically acceptable addition salt, or a solvate thereof, and a pharmaceutically acceptable carrier or excipient.

Additionally, the invention relates to a compound of Formula (I), a pharmaceutically acceptable addition salt, or a solvate thereof, for use as a medicament, and to a compound of Formula (I), a pharmaceutically acceptable addition salt, or a solvate thereof, for use in the treatment or in the prevention of cancer, inflammatory disorders, autoimmune disorders, and metabolic disorders such as diabetes and obesity.

In a particular embodiment, the invention relates to a compound of Formula (I), a pharmaceutically acceptable addition salt, or a solvate thereof, for use in the treatment or in the prevention of a haematological malignancy or solid tumour.

In a specific embodiment said haematological malignancy is selected from the group consisting of multiple myeloma, Hodgkin lymphoma, T-cell leukaemia, mucosa-associated lymphoid tissue lymphoma, diffuse large B-cell lymphoma and mantle cell lymphoma. In another specific embodiment of the present invention, the solid tumour is selected from the group consisting of pancreatic cancer, breast cancer, melanoma and non-small cell lung cancer.

The invention also relates to the use of a compound of Formula (I), a pharmaceutically acceptable addition salt, or a solvate thereof, in combination with an additional pharmaceutical agent for use in the treatment or prevention of cancer, inflammatory disorders, autoimmune disorders, and metabolic disorders such as diabetes and obesity. Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable addition salt, or a solvate thereof.

The invention also relates to a product comprising a compound of Formula (I), a pharmaceutically acceptable addition salt, or a solvate thereof, and an additional pharmaceutical agent, as a combined preparation for simultaneous, separate or sequential use in the treatment or prevention of cancer, inflammatory disorders, autoimmune disorders, and metabolic disorders such as diabetes and obesity.

Additionally, the invention relates to a method of treating or preventing a cell proliferative disease in a warm-blooded animal which comprises administering to the said animal an effective amount of a compound of Formula (I), a pharmaceutically acceptable addition salt, or a solvate thereof, as defined herein, or a pharmaceutical composition or combination as defined herein.

Some of the compounds of the present invention may undergo metabolism to a more active form in vivo (prodrugs).

DETAILED DESCRIPTION OF THE INVENTION

The term 'halo' or 'halogen' as used herein represents fluoro, chloro, bromo and iodo.

The prefix '$C_{x-y}$' (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, and so on.

The term '$C_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term '$C_{1-6}$alkyl' as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like.

The term "$C_{2-6}$alkenyl" as used herein as a group or part of a group represents a straight or branched chain hydrocarbon group containing from 2 to 6 carbon atoms and containing a carbon carbon double bond such as, but not limited to, ethenyl, propenyl, butenyl, pentenyl, 1-propen-2-yl, hexenyl and the like.

The term "$C_{2-6}$alkynyl" as used herein as a group or part of a group represents a straight or branched chain hydrocarbon group having from 2 to 6 carbon atoms and containing a carbon carbon triple bond.

The term '$C_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

In general, whenever the term "substituted" is used in the present invention, it is meant, unless otherwise is indicated or is clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

The skilled person will understand that the term "optionally substituted" means that the atom or radical indicated in the expression using "optionally substituted" may or may not be substituted (this means substituted or unsubstituted respectively).

When two or more substituents are present on a moiety they may, where possible and unless otherwise is indicated or is clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom (e.g. a hydrogen on a nitrogen atom may be replaced by a substituent), for example in saturated heterocyclyl groups or 5-membered aromatic rings as used in the definition of $R^{18}$.

C(O) or C(=O) represents a carbonyl moiety.
S(=O)$_2$ or SO$_2$ represents a sulfonyl moiety.
The skilled person will understand that —S(=O)(=N—$R^{20a}$)—$C_{1-4}$alkyl corresponds with

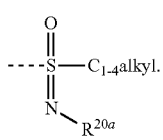

Within the context of this invention 'saturated' means 'fully saturated', if not otherwise specified.

Het$^{1a}$, Het$^{1c}$ and Het$^{1d}$, may be attached to the remainder of the molecule of Formula (I) through any available ring carbon or nitrogen atom as appropriate, if not otherwise specified.

The 5-membered aromatic ring containing one, two or three N-atoms as referred to in the definition of $R^{18}$, may be attached to the remainder of the molecule of Formula (I) through any available ring carbon or nitrogen atom as, if not otherwise specified.

It will be clear that in case a saturated cyclic moiety is substituted on two ring carbon atoms with one substituent, in total two carbon-linked substituents are present on the saturated cyclic moiety (one substituent on each carbon atom).

It will be clear that in case a saturated cyclic moiety is substituted on two ring carbon atoms with two substituents, in total four carbon-linked substituents are present on the saturated cyclic moiety (two substituents on each carbon atom).

It will be clear that in case a saturated cyclic moiety is substituted on three ring carbon atoms with two substituents, in total six carbon-linked substituents are present on the saturated cyclic moiety (two substituents on each carbon atom).

It will be clear that in case a saturated cyclic moiety is substituted on two ring N-atoms with a substituent, in total two N-linked substituents are present on the saturated cyclic moiety (a substituent on each N-atom).

It will be clear that a saturated cyclic moiety may, where possible, have substituents on both carbon and N-atoms, unless otherwise is indicated or is clear from the context.

Within the context of this invention, bicyclic saturated heterocyclyl groups include fused, spiro and bridged saturated heterocycles.

Fused bicyclic groups are two cycles that share two atoms and the bond between these atoms.

Spiro bicyclic groups are two cycles that are joined at a single atom.

Bridged bicyclic groups are two cycles that share more than two atoms.

Examples of N-linked 6- to 11-membered fused bicyclic saturated heterocyclyl groups, include, but are not limited to,

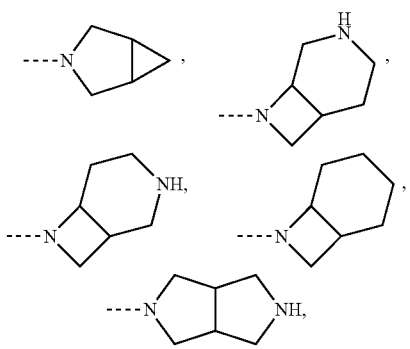

and the like.

Examples of N-linked 6- to 11-membered bridged bicyclic saturated heterocyclyl groups, include, but are not limited to

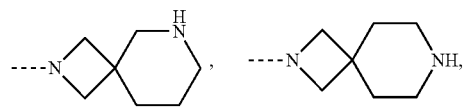

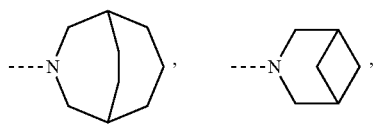

and the like.

Examples of N-linked 6- to 11-membered bridged bicyclic saturated heterocyclyl groups, include, but are not limited to

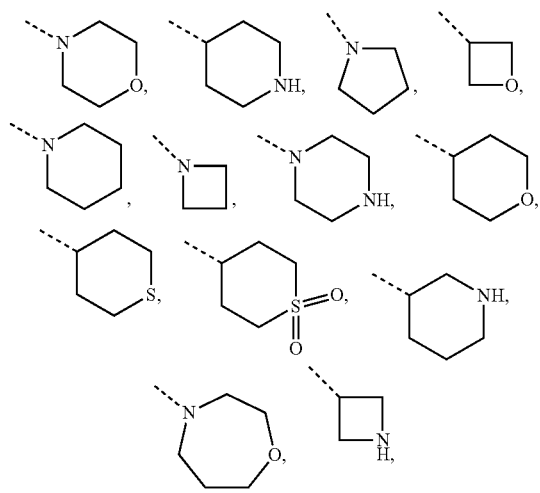

and the like.

The skilled person will realize that the definition of $Het^{1a}$, $Het^{1c}$ and $Het^{1d}$ also includes C-linked bicycles (attached to the remainder of the molecule of Formula (I) through any available ring carbon atom).

It should be understood that the exemplified bicyclic saturated heterocyclyl groups referred to above may optionally be substituted, where possible, on carbon and/or nitrogen atoms according to any of the embodiments.

Non-limiting examples of 4- to 7-membered monocyclic saturated heterocyclyl moieties containing one or two heteroatoms each independently selected from O, S, $S(=O)_p$ and N (as in the definition of $Het^{1a}$, $Het^{1c}$, and $Het^{1d}$) are shown below:

and the like.

Each of which may optionally be substituted, where possible, on carbon and/or nitrogen atoms according to any of the embodiments.

Non-limiting examples of 4- to 7-membered monocyclic saturated heterocyclyl moieties, attached to the remainder of the molecule of Formula (I) through any available ring carbon atom (C-linked), and containing one or two heteroatoms each independently selected from O, S, $S(=O)_p$ and N (as in the definition of $Het^{1b}$, $Het^{1e}$, $Het^{1g}$, $Het^4$, $Het^7$ and $Het^8$) are shown below:

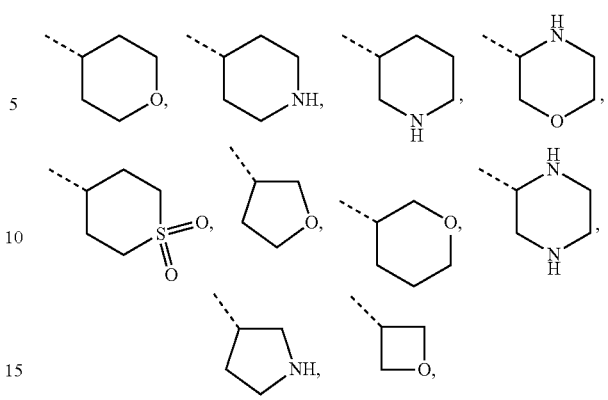

and the like.

Each of which may optionally be substituted, where possible, on carbon and/or nitrogen atoms according to any of the embodiments.

Non-limiting examples of N-linked 4- to 7-membered monocyclic saturated heterocyclyl moieties optionally containing one additional heteroatom selected from O, S, $S(=O)_p$ and N (as in the definition of (b-1) and (c-1)) are shown below:

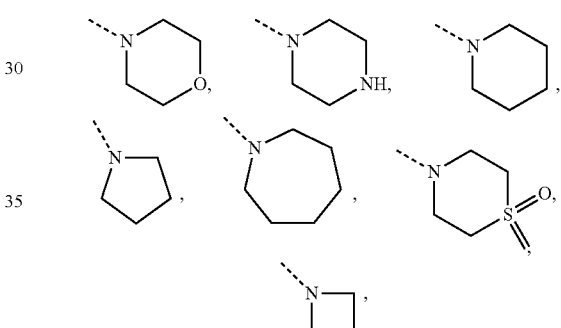

and the like.

Each of which may optionally be substituted, where possible, on carbon and/or nitrogen atoms according to any of the embodiments.

Non-limiting examples of 5-membered aromatic ring containing one, two or three N-atoms as referred to in the definition of $R^{18}$ are shown below:

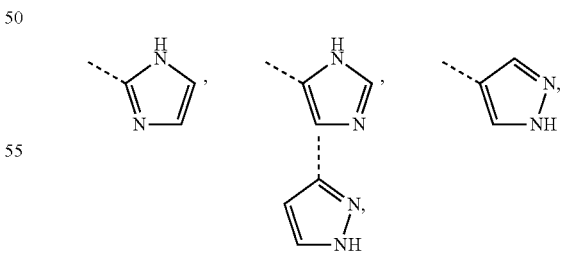

and the like.

Each of which may optionally be substituted, where possible, on carbon and/or nitrogen atoms according to any of the embodiments.

Whenever substituents are represented by chemical structure, "---" represents the bond of attachment to the remainder of the molecule of Formula (I).

Lines (such as "---") drawn into ring systems indicate that the bond may be attached to any of the suitable ring atoms.

When any variable occurs more than one time in any constituent, each definition is independent.

When any variable occurs more than one time in any formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable addition salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

Pharmaceutically-acceptable addition salts include acid addition salts and base addition salts. Such salts may be formed by conventional means, for example by reaction of a free acid or a free base form with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable addition salts as mentioned hereinabove or hereinafter are meant to comprise the therapeutically active non-toxic acid and base addition salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases.

Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention.

Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy.

The present invention relates in particular to compounds of Formula (I) as defined herein, tautomers and stereoisomeric forms thereof, wherein $R^1$ represents $C_{1-4}$alkyl;

$R^2$ represents $C_{1-4}$alkyl, or $C_{1-6}$-alkyl substituted with one $R^5$;

Y represents $CR^4$;

$R^4$ represents hydrogen or halo;

$R^5$ represents cyano or —$OR^7$;

$R^7$ represents hydrogen;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl substituted with one, two or three halo atoms; —O—$C_{1-4}$alkyl-$R^{12}$; $C_{3-6}$cycloalkyl; Het$^{1a}$; —O-Het$^{1b}$; $R^{18}$; —NH—C(=O)—$C_{1-4}$alkyl; —$NR^{17a}R^{17b}$; $C_{1-6}$alkyl substituted with one, two or three halo atoms; $C_{1-4}$alkyl substituted with one, two or three —OH substituents; $C_{1-4}$alkyl substituted with one $R^{13}$; and $C_{1-4}$alkyl substituted with one $R^{18}$;

$R^{10}$ represents —OH, —$NR^{11a}R^{11b}$ or Het$^2$;

$R^{18}$ represents a 5-membered aromatic ring containing one, two or three N-atoms; wherein said 5-membered aromatic ring may optionally be substituted with one $C_{1-4}$alkyl;

Het$^{1a}$, Het$^{1c}$ and Het$^{1d}$ each independently represents a 4- to 7-membered monocyclic saturated heterocyclyl containing one or two heteroatoms each independently selected from O and N; or a 6- to 11-membered bicyclic saturated heterocyclyl, including fused, spiro and bridged cycles, containing one, two or three heteroatoms each independently selected from O and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —O—$C_{1-4}$alkyl, and —N($C_{1-4}$alkyl)$_2$;

Het$^{1b}$ and Het$^{1e}$ each independently represents a 4- to 7-membered monocyclic saturated heterocyclyl, attached to the remainder of the molecule of Formula (I) through any available ring carbon atom, said Het$^{1b}$ and Het$^{1e}$ containing one or two heteroatoms each independently selected from O and N;

wherein said 4- to 7-membered monocyclic saturated heterocyclyl may optionally be substituted, where possible, on one or two ring N-atoms with $C_{1-4}$alkyl;

Het$^2$ represents a heterocyclyl of formula (b-1):

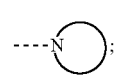

(b-1)

(b-1) represents a N-linked 4- to 7-membered monocyclic saturated heterocyclyl optionally containing one additional heteroatom selected from O, S(=O)$_p$ and N; wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of —OH, cyano, $C_{1-4}$alkyl, —O—$C_{1-4}$alkyl, and $C_{1-4}$alkyl-OH;

$R^{11b}$ represents $Het^{1e}$; $C_{1-4}$alkyl; $C_{1-4}$alkyl substituted with one, two or three substituents each independently selected from the group consisting of —OH and —O—$C_{1-4}$alkyl;

$R^{13}$ represents —O—$C_{1-4}$alkyl, —$NR^{19a}R^{19b}$, or $Het^{1d}$;

$R^{12}$ represents —O—$C_{1-4}$alkyl, —$NR^{14a}R^{14b}$, —C(=O)$NR^{14c}R^{14d}$, or $Het^{1c}$;

$R^{11a}$, $R^{14a}$, $R^{14c}$, $R^{17a}$ and $R^{19a}$ each independently represents hydrogen or $C_{1-4}$alkyl;

$R^{14b}$, $R^{14d}$, $R^{17b}$ and $R^{19b}$ each independently represents hydrogen; $C_{1-6}$alkyl; —C(=O)—$C_{1-4}$alkyl; $C_{1-6}$alkyl substituted with one —O—$C_{1-4}$alkyl; or —C(=O)—$C_{1-4}$alkyl substituted with one —O—$C_{1-4}$alkyl;

p represents 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-4}$alkyl substituted with one $R^5$;

Y represents $CR^4$;

$R^4$ represents hydrogen;

$R^5$ represents —$OR^7$;

$R^7$ represents hydrogen;

$R^3$ represents phenyl optionally substituted with one, two or three substituents each independently selected from the group consisting of halo; $C_{1-6}$alkyl; —O—$C_{1-4}$alkyl; —C(=O)—$R^{10}$; $Het^{1a}$; —O-$Het^{1b}$; and $C_{1-4}$alkyl substituted with one $R^{13}$;

$R^{10}$ represents —$NR^{11a}R^{11b}$ or $Het^2$;

$Het^{1a}$ represents a 4- to 7-membered monocyclic saturated heterocyclyl containing one or two heteroatoms each independently selected from O and N; or a 6- to 11-membered bicyclic saturated heterocyclyl, including fused, spiro and bridged cycles, containing one, two or three heteroatoms each independently selected from O and N; wherein said 4- to 7-membered monocyclic saturated heterocyclyl or said 6- to 11-membered bicyclic saturated heterocyclyl may optionally be substituted, where possible, on one, two or three ring N-atoms with $C_{1-4}$alkyl;

$Het^{1b}$ and $Het^{1e}$ each independently represents a 4- to 7-membered monocyclic saturated heterocyclyl, attached to the remainder of the molecule of Formula (I) through any available ring carbon atom, said $Het^{1b}$ and $Het^{1e}$ containing one or two heteroatoms each independently selected from O and N;

wherein said 4- to 7-membered monocyclic saturated heterocyclyl may optionally be substituted, where possible, on one or two ring N-atoms with $C_{1-4}$alkyl;

$Het^2$ represents a heterocyclyl of formula (b-1):

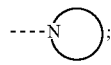

(b-1) represents a N-linked 4- to 7-membered monocyclic saturated heterocyclyl; wherein (b-1) may optionally be substituted on one, two or three ring C-atoms with one —O—$C_{1-4}$alkyl;

$R^{11b}$ represents $Het^{1e}$;

$R^{13}$ represents —$NR^{19a}R^{19b}$;

$R^{11a}$ and $R^{19a}$ each independently represents hydrogen;

$R^{19b}$ represents —C(=O)—$C_{1-4}$alkyl;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen or halo;

$R^5$ represents $Het^{3a}$, —$NR^{6a}R^{6b}$, or —$OR^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-6}$alkyl-$NR^{8a}R^{8b}$, —C(=O)—R, —S(=O)$_2$—OH, —P(=O)$_2$—OH, —(C=O)—CH($NH_2$)—$C_{1-4}$alkyl-$Ar^1$, or —$C_{1-4}$alkyl-$Het^{3b}$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-4}$alkyl, or $C_{1-4}$alkyl substituted with one substituent selected from the group consisting of —$NH_2$, —COOH, and $Het^6$;

$R^{16a}$ and $R^{16b}$ each independently represents hydrogen, $C_{1-4}$alkyl or $C_{3-6}$cycloalkyl;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;

$R^{10}$ represents —OH, —O—$C_{1-4}$alkyl, —$NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^{1b}$, Het$^{1e}$, and Het$^{1g}$ each independently represents a 4- to 7-membered monocyclic saturated heterocyclyl, attached to the remainder of the molecule of Formula (I) through any available ring carbon atom, said Het$^{1b}$, Het$^{1e}$, and Het$^{1g}$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-6}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH($C_{1-4}$alkyl), and —N($C_{1-4}$alkyl)$_2$;

Het$^2$ represents a heterocyclyl of formula (b-1):

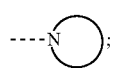

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

R$^{11b}$ represents hydrogen; Het$^{1e}$; $C_{1-4}$alkyl; —$C_{1-4}$alkyl-Het$^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

R$^{13}$ represents —$C_{1-4}$alkyl, —C(=O)NR$^{15a}$R$^{15b}$, —NR$^{19a}$R$^{19b}$, $C_{3-6}$cycloalkyl, Het$^{1d}$, or —C(=O)—Het$^{1f}$;

R$^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

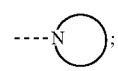

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

R$^{11a}$, R$^{14a}$, R$^{14c}$, R$^{15a}$, R$^{17a}$ and R$^{19a}$ each independently represents hydrogen or $C_{1-4}$alkyl;

R$^{14b}$, R$^{14d}$, R$^{17b}$ and R$^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

R$^{20a}$ and R$^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein R$^1$ represents $C_{1-4}$alkyl;

R$^2$ represents $C_{1-6}$alkyl, or $C_{1-6}$alkyl substituted with one R$^5$;

Y represents CR$^4$ or N;

R$^4$ represents hydrogen or halo;

R$^5$ represents halo, Het$^{3a}$, —NR$^{6a}$R$^{6b}$, or —OR$^7$;

R$^{6a}$ represents hydrogen or $C_{1-4}$alkyl;

R$^{6b}$ represents hydrogen; $C_{1-4}$alkyl; $C_{3-6}$cycloalkyl; —C(=O)—$C_{1-4}$alkyl; —C(=O)—Het$^4$; —S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;

R$^7$ represents hydrogen, $C_{1-4}$alkyl, —$C_{1-4}$alkyl-NR$^{8a}$R$^{8b}$, —C(=O)—R$^9$, —S(=O)$_2$—OH, —P(=O)$_2$—OH, —(C=O)—CH(NH$_2$)—$C_{1-4}$alkyl-Ar$^1$, or —$C_{1-4}$alkyl-Het$^{3b}$;

R$^{8a}$ represents hydrogen or $C_{1-4}$alkyl;

R$^{8b}$ represents hydrogen, $C_{1-4}$alkyl, or $C_{3-6}$cycloalkyl;

R$^9$ represents $C_{1-4}$alkyl, or $C_{1-4}$alkyl substituted with one substituent selected from the group consisting of —NH$_2$, —COOH, and Het$^6$;

R$^{16a}$ and R$^{16b}$ each independently represents hydrogen, $C_{1-4}$alkyl or $C_{3-6}$cycloalkyl;

R$^3$ represents phenyl optionally substituted with one, two or three substituents each independently selected from the group consisting of halo; cyano; $C_{1-6}$alkyl; —O—$C_{1-4}$alkyl;

—C(=O)—R$^{10}$; —S(=O)$_2$—C$_{1-4}$alkyl; —S(=O)(=N—R$^{20a}$)—C$_{1-4}$alkyl; —O—C$_{1-6}$alkyl substituted with one, two or three halo atoms: —O—C$_{1-4}$alkyl-R$^{12}$; C$_{3-6}$cycloalkyl; —O—C$_{3-6}$cycloalkyl; Het$^{1a}$; —O-Het$^{1b}$; R$^{18}$; R$^{21}$; —P(=O)—(C$_{1-4}$alkyl)$_2$; —NH—C(=O)—C$_{1-4}$alkyl; —NH—C(=O)—Het$^{1g}$; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; C$_{2-6}$alkenyl substituted with one R$^{13}$; C$_{2-6}$alkynyl; and C$_{2-6}$alkynyl substituted with one R$^{13}$;

R$^{10}$ represents —OH, —O—C$_{1-4}$alkyl, —NR$^{11a}$R$^{11b}$ or Het$^2$;

R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;

R$^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with C$_{1-4}$alkyl or C$_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one substituent each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^{1b}$, Het$^{1e}$, Het$^{1g}$, Het$^4$, Het$^7$ and Het$^8$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$, Het$^4$, Het$^7$ and Het$^8$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl may optionally be substituted on one, two or three ring C-atoms with one substituent each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^2$ represents a heterocyclyl of formula (b-1):

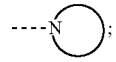

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with a substituent each independently selected from the group consisting of C$_{1-4}$alkyl, C$_{3-6}$cycloalkyl and Het$^7$; and wherein (b-1) may optionally be substituted on one, two or three ring C-atoms with one substituent each independently selected from the group consisting of halo, —OH, cyano, C$_{1-4}$alkyl, —O—C$_{1-4}$alkyl, —NH$_2$, —NH(C$_{1-4}$alkyl), —N(C$_{1-4}$alkyl)$_2$, and C$_{1-4}$alkyl-OH;

R$^{11b}$ represents hydrogen; Het$^{1e}$; C$_{1-4}$alkyl; —C$_{1-4}$alkyl-Het$^5$; —C$_{1-4}$alkyl-Het$^8$; C$_{1-4}$alkyl substituted with one, two or three substituents each independently selected from the group consisting of halo, —OH and —O—C$_{1-6}$alkyl; C$_{3-6}$cycloalkyl; or C$_{3-6}$cycloalkyl substituted with one, two or three substituents each independently selected from the group consisting of halo, —OH and —O—C$_{1-4}$alkyl;

R$^{13}$ represents —O—C$_{1-4}$alkyl, —C(=O)NR$^{15a}$R$^{15b}$, —NR$^{19a}$R$^{19b}$, C$_{3-6}$cycloalkyl, Het$^{1d}$, or —C(=O)—Het$^{1f}$;

R$^{12}$ represents —OH, —O—C$_{1-4}$alkyl, —NR$^{14a}$R$^{14b}$, —C(=O)NR$^{14c}$R$^{14d}$, —S(=O)$_2$—C$_{1-4}$alkyl, —S(=O)(=N—R$^{20b}$)—C$_{1-4}$alkyl, C$_{3-6}$cycloalkyl, Ar$^2$, or Het$^{1c}$;

Ar$^1$ represents phenyl optionally substituted with one hydroxy;

Ar$^2$ represents phenyl optionally substituted with one C$_{1-4}$alkyl;

Het$^{3a}$, Het$^{3b}$, Het$^5$, Het$^6$ and Het$^{1f}$ each independently represents a heterocyclyl of formula (c-1):

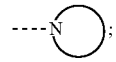

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with C$_{1-4}$alkyl or C$_{3-6}$cycloalkyl; and wherein (c-1) may optionally be substituted on one or two ring C-atoms atoms with one substituent each independently selected from the group consisting of halo, C$_{1-4}$alkyl, and C$_{3-6}$cycloalkyl;

R$^{11a}$, R$^{14a}$, R$^{14c}$, R$^{15a}$, R$^{17a}$ and R$^{19a}$ each independently represents hydrogen or C$_{1-4}$alkyl;

R$^{14b}$, R$^{14d}$, R$^{15b}$, R$^{17b}$ and R$^{19b}$ each independently represents hydrogen; C$_{1-4}$alkyl; C$_{3-6}$cycloalkyl; —C(=O)—C$_{1-4}$alkyl; C$_{1-4}$alkyl substituted with one substituent selected from the group consisting of halo, —OH and —O—C$_{1-4}$alkyl; —C(=O)—C$_{1-4}$alkyl substituted with one substituent selected from the group consisting of halo, —OH and —O—C$_{1-4}$alkyl; or —S(=O)$_2$—C$_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen or halo;

$R^5$ represents $Het^{3a}$, —$NR^{6a}R^{6b}$, or —$OR^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —C(=O)—$Het^4$; —S(=O)$_2$—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, —(C=O)—CH($NH_2$)—$C_{1-4}$alkyl-$Ar^1$, or —$C_{1-4}$-alkyl-$Het^{3b}$;

$R^{8a}$ represents hydrogen or $C_{1-6}$alkyl;

$R^{8b}$ represents hydrogen, $C_{1-4}$alkyl, or $C_{3-6}$cycloalkyl;

$R^9$ represents $C_{1-4}$alkyl, or $C_{1-4}$alkyl substituted with one substituent selected from the group consisting of —$NH_2$, —COOH, and $Het^6$;

$R^{16a}$ and $R^{16b}$ each independently represents hydrogen, $C_{1-4}$alkyl or $C_{3-6}$cycloalkyl;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-6}$alkyl-$R^{12}$; $C_{3-6}$cycloalkyl; —O—$C_{3-6}$cycloalkyl; $Het^{1a}$; —O-$Het^{1b}$; $R^{18}$; $R^{21}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{1-4}$alkyl substituted with one $R^{18}$; $C_{2-6}$alkenyl; and $C_{2-6}$alkenyl substituted with one $R^{13}$;

$R^{10}$ represents —OH, —O—$C_{1-6}$alkyl, —$NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

$Het^{1a}$, $Het^{1c}$ and $Het^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one substituent each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

$Het^{1b}$, $Het^{1e}$, $Het^{1g}$ and $Het^4$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$ and $Het^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one substituent each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

$Het^2$ represents a heterocyclyl of formula (b-1):

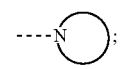

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one substituent each independently selected from the group consisting of halo, —OH, cyano, $C_{1-4}$alkyl, —O—$C_{1-6}$alkyl, —$NH_2$, —NH($C_{1-4}$alkyl), —N($C_{1-4}$alkyl)$_2$, and $C_{1-6}$alkyl-OH;

$R^{11b}$ represents hydrogen; $Het^{1e}$; $C_{1-4}$alkyl; $C_{1-4}$alkyl-$Het^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, or —C(=O)—$Het^{1f}$;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar$^2$, or Het$^{1c}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

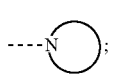 (c-1);

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one substituent each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents CR$^4$ or N;

$R^4$ represents hydrogen or halo;

$R^5$ represents halo, —NR$^{6a}$R$^{6b}$, or —OR$^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-4}$alkyl-NR$^{8a}$R$^{8b}$, —C(=O)—R$^9$, —S(=O)$_2$—OH, —P(=O)$_2$—OH, or —(C=O)—CH(NH$_2$)—$C_{1-4}$alkyl-Ar$^1$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-4}$alkyl, or $C_{1-4}$alkyl substituted with one substituent selected from the group consisting of —NH$_2$ and —COOH;

$R^{16a}$ and $R^{16b}$ each independently represents hydrogen, $C_{1-4}$alkyl or $C_{3-6}$cycloalkyl;

$R^3$ represents phenyl optionally substituted with one, two or three substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; —P(=O)—($C_{1-4}$alkyl)$_2$; —NH—C(=O)—$C_{1-4}$alkyl; —NR$^{17a}$R$^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{2-6}$alkenyl; $C_{2-6}$alkenyl substituted with one $R^{13}$; $C_{2-6}$alkynyl; and $C_{2-6}$alkynyl substituted with one $R^{13}$;

$R^{10}$ represents —OH, —O—$C_{1-4}$alkyl, or —NR$^{11a}$R$^{11b}$;

$R^{11b}$ represents hydrogen; $C_{1-4}$alkyl; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —$C_{1-4}$alkyl, —C(=O)NR$^{15a}$R$^{15b}$, —NR$^{19a}$R$^{19b}$, or $C_{3-6}$cycloalkyl;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, or Ar$^2$;

Ar$^1$ represents phenyl optionally substituted with one hydroxy;

Ar$^2$ represents phenyl optionally substituted with one $C_{1-4}$alkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of halo, —OH and —O—$C_{1-4}$alkyl; —C(=O)—$C_{1-4}$alkyl substituted with one substituent selected from the group consisting of halo, —OH and —O—$C_{1-4}$alkyl; or —S(=O)$_2$—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents CR$^4$;

$R^4$ represents hydrogen or halo:

$R^5$ represents —NR$^{6a}$R$^{6b}$, or —OR$^7$;

$R^{6a}$ represents hydrogen or $C_{1-6}$alkyl;

$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one substituent selected from the group consisting of —OH and —S(=O)$_2$—$C_{1-4}$alkyl;

$R^7$ represents hydrogen, $C_{1-4}$alkyl, —$C_{1-6}$alkyl-NR$^{8a}$R$^{8b}$, —C(=O)—R$^9$, —S(=O)$_2$—OH, —P(=O)$_2$—OH, or —(C=O)—CH(NH$_2$)—$C_{1-4}$alkyl-Ar$^1$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-4}$alkyl, or $C_{1-4}$alkyl substituted with one substituent selected from the group consisting of —$NH_2$ and —COOH;

$R^{16a}$ and $R^{16b}$ each independently represents hydrogen, $C_{1-4}$alkyl or $C_{3-6}$cycloalkyl;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; —P(=O)—($C_{1-4}$alkyl)$_2$; —NH—C(=O)—$C_{1-4}$alkyl; —$NR^{17a}R^{17b}$; $C_{1-4}$alkyl substituted with one, two or three halo atoms; $C_{1-6}$alkyl substituted with one, two or three —OH substituents; $C_{1-4}$alkyl substituted with one $R^{13}$; $C_{2-6}$alkenyl; and $C_{2-6}$alkenyl substituted with one $R^{13}$;

$R^{10}$ represents —OH, —O—$C_{1-4}$alkyl, or —$NR^{11a}R^{11b}$;

$R^{11b}$ represents hydrogen; $C_{1-4}$alkyl; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)$NR^{15a}R^{15b}$, —$NR^{19a}R^{19b}$, or $C_{3-6}$cycloalkyl;

$R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, —S(=O)(=N—$R^{20b}$)—$C_{1-4}$alkyl, $C_{3-6}$cycloalkyl, or $Ar^2$;

$Ar^1$ represents phenyl optionally substituted with one hydroxy;

$Ar^2$ represents phenyl optionally substituted with one $C_{1-4}$alkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20a}$ and $R^{20b}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$ or N;

$R^4$ represents hydrogen or halo;

$R^5$ represents halo, —$NR^{6a}R^{6b}$, or —$OR^7$;

$R^{6a}$ represents hydrogen;

$R^{6b}$ represents —C(=O)—$C_{1-4}$alkyl; or —S(=O)$_2$—$C_{1-4}$ alkyl;

$R^7$ represents hydrogen, —$C_{1-4}$alkyl-$NR^{8a}R^{8b}$, —C(=O)—$R^9$, —S(=O)$_2$—OH, or —(C=O)—CH(NH$_2$)$C_{1-4}$alkyl-$Ar^1$;

$R^{8a}$ represents hydrogen;

$R^{8b}$ represents $C_{3-6}$cycloalkyl;

$R^9$ represents $C_{1-4}$alkyl, or $C_{1-6}$alkyl substituted with one substituent selected from the group consisting of —$NH_2$, —COOH, and $Het^6$;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; —P(=O)—($C_{1-4}$alkyl)$_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-4}$alkyl substituted with one $R^{13}$; $C_{2-6}$alkenyl substituted with one $R^{13}$; and $C_{2-6}$alkynyl substituted with one $R^{13}$;

$R^{10}$ represents —OH, —O—$C_{1-4}$alkyl, —$NR^{11a}R^{11b}$ or $Het^2$;

$R^{18}$ represents a 5-membered aromatic ring containing one, two or three N-atoms: wherein said 5-membered aromatic ring may optionally be substituted with one substituent selected from the group consisting of $C_{1-4}$alkyl;

$Het^{1a}$, $Het^{1c}$ and $Het^{1d}$ each independently represents a 4- to 7-membered monocyclic saturated heterocyclyl containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, —O—$C_{1-4}$alkyl, and —N($C_{1-4}$alkyl)$_2$;

$Het^{1b}$, $Het^{1e}$, $Het^{1g}$, $Het^7$ and $Het^8$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$, $Het^7$ and $Het^8$ containing one or two heteroatoms each independently selected from O and N; wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and wherein said 4- to 7-membered monocyclic saturated heterocyclyl may optionally be substituted on one, two or three ring C-atoms with one or two substituents each independently selected from the group consisting of —OH, and halo;

$Het^2$ represents a heterocyclyl of formula (b-1):

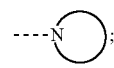

(b-1) represents a N-linked 4- to 7-membered monocyclic saturated heterocyclyl optionally containing one additional heteroatom selected from O and N, or a N-linked 6- to 11-membered bicyclic saturated heterocyclyl, including fused, spiro and bridged cycles, optionally containing one or two additional N-atoms;

wherein in case (b-1) contains one or two additional N-atoms, said one or two N-atoms may optionally be substituted with a substituent each independently selected from the group consisting of $C_{1-4}$alkyl, $C_{3-6}$cycloalkyl and $Het^7$; and wherein (b-1) may optionally be substituted on one, two or three ring C-atoms with one or two substituents each independently selected from the group consisting of —OH, cyano, $C_{1-4}$alkyl, and $C_{1-4}$alkyl-OH;

$R^{11b}$ represents $Het^{1e}$; $C_{1-4}$alkyl; —$C_{1-4}$alkyl-$Het^5$; —$C_{1-4}$ alkyl-$Het^8$, $C_{1-4}$alkyl substituted with one, two or three OH substituents; or $C_{3-6}$cycloalkyl substituted with one, two or three substituents each independently selected from the group consisting of halo and —OH;

$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, or —C(=O)—$Het^{1f}$;

$R^{12}$ represents —OH, —O—$C_{1-4}$alkyl, —$NR^{14}R^{14b}$, —C(=O)$NR^{14c}R^{14d}$, —S(=O)$_2$—$C_{1-4}$alkyl, $C_{3-6}$cycloalkyl, $Ar^2$, or $Het^{1c}$;

$Ar^1$ represents phenyl;

$Ar^2$ represents phenyl optionally substituted with one $C_{1-4}$alkyl;

$Het^5$, $Het^6$ and $Het^{1f}$ each independently represents a heterocyclyl of formula (c-1):

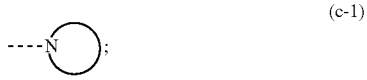

(c-1) represents a N-linked 4- to 7-membered monocyclic saturated heterocyclyl optionally containing one additional heteroatom selected from O and N;

wherein in case (c-1) contains one additional N-atom, said additional N-atom may optionally be substituted with $C_{1-6}$alkyl;

$R^{11a}$, $R^{14a}$, $R^{14c}$, $R^{15a}$, $R^{17a}$ and $R^{19a}$ each independently represents hydrogen or $C_{1-4}$alkyl;

$R^{14b}$, $R^{14d}$, $R^{15b}$, $R^{17b}$ and $R^{19b}$ each independently represents hydrogen; $C_{1-4}$alkyl; $C_{3-6}$cycloalkyl; —C(=O)—$C_{1-4}$alkyl; $C_{1-4}$alkyl substituted with one substituent selected from the group consisting of —OH and —O—$C_{1-4}$alkyl; or —S(=O)$_2$—$C_{1-4}$alkyl;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-4}$alkyl substituted with one $R^5$;

Y represents $CR^4$;

$R^4$ represents hydrogen or halo;

$R^5$ represents —$NR^{6a}R^{6b}$, or —$OR^7$;

$R^{6a}$ represents hydrogen;

$R^{6b}$ represents —C(=O)—$C_{1-4}$alkyl; or —S(=O)$_2$—$C_{1-4}$ alkyl;

$R^7$ represents hydrogen, —C(=O)—$R^9$, —S(=O)$_2$—OH, or —(C=O)—CH($NH_2$)—$C_{1-4}$alkyl-$Ar^1$;

$R^9$ represents $C_{1-4}$alkyl, or $C_{1-4}$alkyl substituted with one substituent selected from the group consisting of —$NH_2$, —COOH, and $Het^b$;

$R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^2$; $C_{3-6}$cycloalkyl; —O—$C_{3-6}$cycloalkyl; $Het^{1a}$; —O-$Het^{1b}$; $R^{18}$; —P(=O)—($C_{1-4}$alkyl)$_2$; —NH—C(=O)—$C_{1-4}$alkyl; —NH—C(=O)—$Het^{1g}$; $C_{1-4}$alkyl substituted with one, two or three halo atoms; $C_{1-4}$alkyl substituted with one, two or three —OH substituents; and $C_{1-4}$alkyl substituted with one $R^{13}$;

$R^{10}$ represents —OH, —O—$C_{1-4}$alkyl, —$NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl;

$Het^{1a}$, $Het^{1c}$ and $Het^{1d}$ each independently represents a 4- to 7-membered monocyclic saturated heterocyclyl containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, —O—C-alkyl, and —N($C_{1-4}$alkyl)$_2$;

$Het^{1b}$, $Het^{1e}$, and $Het^{1g}$ each independently represents a 4- to 7-membered monocyclic saturated heterocyclyl, attached to the remainder of the molecule of Formula (I) through any available ring carbon atom, said $Het^{1b}$, $Het^{1e}$ and $Het^{1g}$ containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and wherein said 4- to 7-membered monocyclic saturated heterocyclyl may optionally be substituted on one, two or three ring C-atoms with one or two —OH substituents;

$Het^2$ represents a heterocyclyl of formula (b-1):

(b-1) represents a N-linked 4- to 7-membered monocyclic saturated heterocyclyl optionally containing one additional N-atom, or a N-linked 6- to 11-membered bicyclic saturated heterocyclyl, including fused, spiro and bridged cycles, optionally containing one or two additional N-atoms;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of —OH, cyano, and $C_{1-4}$alkyl-OH;

$R^{13}$ represents $Het^{1e}$; $C_{1-4}$alkyl; —$C_{1-4}$alkyl-$Het^5$; $C_{1-4}$alkyl substituted with one, two or three OH substituents; or $C_{3-6}$cycloalkyl substituted with one, two or three substituents each independently selected from the group consisting of halo and —OH;

$R^{13}$ represents —O—$C_{1-4}$alkyl, —C(=O)$NR^{15a}R^{15b}$, —$NR^{19a}R^{19b}$, $C_{3-6}$cycloalkyl, $Het^{1d}$, or —C(=O)—$Het^{1f}$;

$R^{12}$ represents —OH, —O—$C_{1-4}$alkyl, —$NR^{14a}R^{14b}$, —C(=O)$NR^{14a}R^{14b}$, —S(=O)$_2$—$C_{1-4}$alkyl, $C_{3-6}$cycloalkyl, $Ar^2$, or $Het^{1c}$;

Ar¹ represents phenyl;

Ar² represents phenyl optionally substituted with one C₁₋₄alkyl;

Het⁵, Het⁶ and Het^(1f) each independently represents a heterocyclyl of formula (c-1):

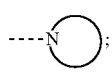

(c-1) represents a N-linked 4- to 7-membered monocyclic saturated heterocyclyl optionally containing one additional heteroatom selected from O and N;

wherein in case (c-1) contains one additional N-atom, said additional N-atom may optionally be substituted with C₁₋₄alkyl;

$R^{11a}$, $R^{14a}$, $R^{14c}$, $R^{15a}$, and $R^{19a}$ each independently represents hydrogen or C₁₋₄alkyl;

$R^{14b}$, $R^{14d}$, $R^{15b}$, and $R^{19b}$ each independently represents hydrogen; C₁₋₄alkyl; C₃₋₆cyclo-alkyl; or C₁₋₄alkyl substituted with one —O—C₁₋₄alkyl;

and the pharmaceutically acceptable addition salts, and the solvates thereof.

The present invention relates in particular to compounds of Formula (I) as defined herein, tautomers and stereoisomeric forms thereof, wherein R¹ represents C₁₋₄alkyl;

R² represents C₁₋₆alkyl, or C₁₋₆alkyl substituted with one R⁵;

Y represents CR⁴;

R⁴ represents hydrogen or halo;

R⁵ represents —OR⁷;

R⁷ represents hydrogen or —C(=O)—R⁹;

R⁹ represents C₁₋₄alkyl;

R³ represents phenyl optionally substituted with one, two or three substituents each independently selected from the group consisting of halo; cyano C₁₋₆alkyl; —O—C₁₋₄alkyl; —C(=O)—R¹⁰; —S(=O)₂—C₁₋₄alkyl; —O—C₁₋₄alkyl-R¹²; C₃₋₆cycloalkyl; —O—C₃₋₆cycloalkyl; Het^(1a); —O-Het^(1b); —P(=O)—(C₁₋₄alkyl)₂; —NH—C(=O)—C₁₋₄ alkyl; —NH—C(=O)-Het^(1g); C₁₋₄alkyl substituted with one, two or three halo atoms; C₁₋₄alkyl substituted with one, two or three —OH substituents; and C₁₋₄alkyl substituted with one R¹³;

R¹⁰ represents —O—C₁₋₄alkyl, —NR^(11a)R^(11b) or Het²;

Het^(1a), Het^(1c) and Het^(1d) each independently represents a 4- to 7-membered monocyclic saturated heterocyclyl containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of C₁₋₄alkyl, C₃₋₆cycloalkyl, and C₁₋₄alkyl substituted with one —O—C₁₋₄alkyl; and wherein said 4- to 7-membered monocyclic saturated heterocyclyl may optionally be substituted on one, two or three ring C-atoms with one or two substituents each independently selected from the group consisting of —OH, C₁₋₄alkyl, —O—C₁₋₆alkyl, and —N(C₁₋₄alkyl)₂;

Het^(1b), Het^(1e), and Het^(1g) each independently represents a 4- to 7-membered monocyclic saturated heterocyclyl, attached to the remainder of the molecule of Formula (I) through any available ring carbon atom, said Het^(1b), Het^(1e) and Het^(1g) containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of C₁₋₄alkyl and C₃₋₆cycloalkyl; and wherein said 4- to 7-membered monocyclic saturated heterocyclyl may optionally be substituted on one, two or three ring C-atoms with one or two —OH substituents;

Het² represents a heterocyclyl of formula (b-1):

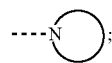

(b-1) represents a N-lined 4- to 7-membered monocyclic saturated heterocyclyl optionally containing one additional N-atom, or a N-linked 6- to 11-membered bicyclic saturated heterocyclyl, including fused, spiro and bridged cycles, optionally containing one or two additional N-atoms;

wherein in case (b-1) contains one or two additional N-atoms, said one or two N-atoms may optionally be substituted with C₁₋₄alkyl; and wherein (b-1) may optionally be substituted on one, two or three ring C-atoms with one or two substituents each independently selected from the group consisting of —OH, cyano, and C₁₋₄alkyl-OH;

$R^{11b}$ represents Het; C₁₋₄alkyl; C₁₋₄alkyl substituted with one, two or three OH substituents; or C₃₋₆cycloalkyl substituted with one, two or three substituents each independently selected from the group consisting of halo and —OH;

$R^{13}$ represents —O—C₁₋₄alkyl, —C(=O)NR^(15a)R^(15b), C₃₋₆cycloalkyl, Het^(1d), or —C(=O)—Het^(1f);

$R^{12}$ represents —OH, —O—C₁₋₆alkyl, —NR^(14a)R^(14b), —C(=O)NR^(14c)R^(14d), —S(=O)₂—C₁₋₄alkyl, C₃₋₆cycloalkyl, Ar², or Het^(1c);

Ar² represents phenyl optionally substituted with one C₁₋₄alkyl;

Het^(1f) represents a heterocyclyl of formula (c-1):

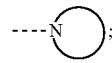

(c-1) represents a N-linked 4- to 7-membered monocyclic saturated heterocyclyl optionally containing one additional heteroatom selected from O and N;

wherein in case (c-1) contains one additional N-atom, said additional N-atom may optionally be substituted with C₁₋₄alkyl;

$R^{11a}$, $R^{14a}$, $R^{14c}$, and $R^{15a}$ each independently represents hydrogen or C₁₋₄alkyl;

$R^{14b}$, $R^{14d}$, and $R^{15b}$ each independently represents hydrogen; C₁₋₄alkyl; or C₃₋₆cycloalkyl;

and the pharmaceutically acceptable addition salts, and the solvates thereof.

The present invention relates in particular to compounds of Formula (I) as defined herein, tautomers and stereoisomeric forms thereof, wherein R¹ represents C₁₋₄alkyl;

R² represents C₁₋₆alkyl, or C₁₋₄alkyl substituted with one R⁵;

Y represents $CR^4$;
$R^4$ represents hydrogen;
$R^5$ represents $-OR^7$;
$R^7$ represents hydrogen or $-C(=O)-R^9$;
$R^9$ represents $C_{1-4}$alkyl; or $C_{1-4}$alkyl substituted with one $-NH_2$ substituent;
$R^3$ represents phenyl substituted with one, two or three substituents each independently selected from the group consisting of halo; cyano; $C_{1-6}$alkyl; $-O-C_{1-4}$alkyl; $-C(=O)-R^{10}$; $-S(=O)_2-C_{1-4}$alkyl; $-O-C_{1-4}$alkyl-$R^{12}$; $-O-C_{3-6}$cycloalkyl; $-O-Het^{1b}$; $-NH-C(=O)-Het^{1g}$; and $C_{1-4}$alkyl substituted with one $R^{13}$;
$R^{10}$ represents $-NR^{11a}R^{11b}$ or $Het^2$;
$Het^{1g}$ represents a 4- to 7-membered monocyclic saturated heterocyclyl, attached to the remainder of the molecule of Formula (I) through any available ring carbon atom, said $Het^{1g}$ containing one or two N-atoms;
wherein said 4- to 7-membered monocyclic saturated heterocyclyl may optionally be substituted, where possible, on one or two ring N-atoms with a $C_{1-4}$alkyl substituent;
$Het^{1b}$ represents a 4- to 7-membered monocyclic saturated heterocyclyl, attached to the remainder of the molecule of Formula (I) through any available ring carbon atom, said $Het^{1b}$ containing one or two N-atoms;
wherein said 4- to 7-membered monocyclic saturated heterocyclyl may optionally be substituted, where possible, on one or two ring N-atoms with a $C_{1-4}$alkyl substituent; and
wherein said 4- to 7-membered monocyclic saturated heterocyclyl may optionally be substituted on one ring C-atom with one halo substituent;
$Het^2$ represents a heterocyclyl of formula (b-1):

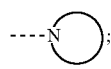
(b-1)

(b-1) represents a N-linked 4- to 7-membered monocyclic saturated heterocyclyl wherein (b-1) may optionally be substituted on one C-atom with one $-OH$ substituent;
$R^{11b}$ represents $C_{1-4}$alkyl;
$R^{13}$ represents $-O-C_{1-4}$alkyl.
$R^{12}$ represents $-O-C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-4}$alkyl substituted with one $R^5$;
Y represents $CR^4$;
$R^4$ represents hydrogen;
$R^5$ represents $-OR^7$;
$R^7$ represents hydrogen or $-C(=O)-R^9$;
$R^9$ represents $C_{1-4}$alkyl;
$R^3$ represents phenyl substituted with one, two or three substituents each independently selected from the group consisting of halo; cyano; $C_{1-6}$alkyl; $-O-C_{1-4}$alkyl; $-C(=O)-R^{10}$; $-S(=O)_2-C_{1-4}$alkyl; $-O-C_{1-4}$alkyl-$R^{12}$; $-NH-C(=O)-Het^{1g}$; and $C_{1-4}$alkyl substituted with one $R^{13}$;
$R^{10}$ represents $-NR^{11a}R^{11b}$ or $Het^2$;
$Het^{1g}$ represents a 4- to 7-membered monocyclic saturated heterocyclyl, attached to the remainder of the molecule of Formula (I) through any available ring carbon atom, said $Het^{1g}$ containing one or two N-atoms;
wherein said 4- to 7-membered monocyclic saturated heterocyclyl may optionally be substituted, where possible, on one or two ring N-atoms with a $C_{1-4}$alkyl substituent;
$Het^2$ represents a heterocyclyl of formula (b-1):

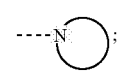
(b-1)

(b-1) represents a N-linked 4- to 7-membered monocyclic saturated heterocyclyl wherein (b-1) may optionally be substituted on one C-atom with one $-OH$ substituent;
$R^{11b}$ represents $C_{1-4}$alkyl;
$R^{13}$ represents $-O-C_{1-4}$alkyl;
$R^{12}$ represents $-O-C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl, or $C_{1-6}$alkyl substituted with one $R^5$;
Y represents $CR^4$;
$R^4$ represents hydrogen;
$R^5$ represents $-OR^7$;
$R^7$ represents hydrogen or $-C(=O)-R^9$;
$R^9$ represents $C_{1-4}$alkyl;
$R^3$ represents phenyl substituted with one, two or three substituents each independently selected from the group consisting of halo; cyano; $C_{1-4}$alkyl; $-O-C_{1-4}$alkyl; $-C(=O)-R^{10}$; $-S(=O)_2-C_{1-4}$alkyl; $-O-C_{1-4}$alkyl-$R^{12}$; $-O-C_{3-6}$cycloalkyl; and $C_{1-4}$alkyl substituted with one $R^{13}$;
$R^{10}$ represents $-NR^{11a}R^{11b}$;
$R^{11b}$ represents $C_{1-4}$alkyl;
$R^{13}$ represents $-O-C_{1-4}$alkyl.

$R^{12}$ represents —O—$C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents —$OR^7$;
$R^7$ represents hydrogen or —C(=O)—$R^9$;
$R^9$ represents $C_{1-6}$alkyl; or $C_{1-4}$alkyl substituted with one —$NH_2$ substituent;
$R^3$ represents phenyl substituted with one, two or three substituents each independently selected from the group consisting of halo; cyano; $C_{1-6}$alkyl; —O—$C_{1-4}$alkyl; —C(=O)—$R^{10}$; —O—$C_{3-6}$cycloalkyl; and —O-Het$^{1b}$;
$R^{10}$ represents —$NR^{11a}R^{11b}$;
Het$^{1b}$ represents a 4- to 7-membered monocyclic saturated heterocyclyl, attached to the remainder of the molecule of Formula (I) through any available ring carbon atom, said Het$^{1b}$ containing one or two N-atoms;
wherein said 4- to 7-membered monocyclic saturated heterocyclyl may optionally be substituted, where possible, on one or two ring N-atoms with a $C_{1-4}$alkyl substituent; and
wherein said 4- to 7-membered monocyclic saturated heterocyclyl may optionally be substituted on one ring C-atom with one halo substituent;
$R^{11b}$ represents $C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-4}$alkyl substituted with one $R^5$;
Y represents $CR^4$;
$R^4$ represents hydrogen;
$R^5$ represents —$OR^7$;
$R^7$ represents hydrogen;
$R^3$ represents phenyl substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; —O—$C_{3-6}$cycloalkyl; —O-Het$^{1b}$; —NH—C(=O)—Het$^{1g}$; and $C_{1-4}$alkyl substituted with one $R^{13}$;
$R^{10}$ represents —$NR^{11a}R^{11b}$;
Het$^{1b}$ represents a pyrrolidine attached to the remainder of the molecule of Formula (I) through any available ring carbon atom, wherein the N-atom is substituted with methyl and one ring C-atom is substituted with one halo substituent;
Het$^{1g}$ represents 4-piperidinyl wherein the N-atom is substituted with methyl;
$R^{11b}$ represents $C_{1-4}$alkyl;
$R^{13}$ represents —O—$C_{1-4}$alkyl;
$R^{12}$ represents —O—$C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-4}$alkyl substituted with one $R^5$;
Y represents $CR^4$;
$R^4$ represents hydrogen;
$R^5$ represents —$OR^7$;
$R^7$ represents hydrogen;
$R^3$ represents phenyl substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; —NH—C(=O)—Het$^{1g}$; and $C_{1-4}$alkyl substituted with one $R^{13}$;
in particular $R^3$ represents phenyl substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; and $C_{1-4}$alkyl substituted with one $R^{13}$;
$R^{10}$ represents —$NR^{11a}R^{11b}$;
Het$^{1g}$ represents 4-piperidinyl wherein the N-atom is substituted with methyl;
$R^{11b}$ represents $C_{1-4}$alkyl;
$R^{13}$ represents —O—$C_{1-4}$alkyl;
$R^{12}$ represents —O—$C_{1-4}$alkyl;
$R^{11a}$ represents hydrogen;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents —$OR^7$;
$R^7$ represents hydrogen or —C(=O)—$R^9$;
$R^9$ represents $C_{1-4}$alkyl; or $C_{1-4}$alkyl substituted with one substituent selected from the group consisting of —$NH_2$ and —COOH;
$R^3$ represents phenyl substituted with one, two or three substituents each independently selected from the group consisting of halo; cyano; and $C_{1-6}$alkyl;
and the pharmaceutically acceptable addition salts, and the solvates thereof.

The present invention relates in particular to compounds of Formula (I) as defined herein, tautomers and stereoisomeric forms thereof, wherein
$R^1$ represents $C_{1-4}$alkyl;
$R^2$ represents $C_{1-6}$alkyl substituted with one $R^5$;
Y represents $CR^4$;
$R^4$ represents hydrogen;
$R^5$ represents —$OR^7$;
$R^7$ represents hydrogen;
$R^3$ represents phenyl substituted with one, two or three substituents each independently selected from the group consisting of halo; cyano; and $C_{1-6}$alkyl;
and the pharmaceutically acceptable addition salts, and the solvates thereof.

The present invention relates in particular to compounds of Formula (I) as defined herein, tautomers and stereoisomeric forms thereof, wherein
$R^1$ represents methyl;
$R^2$ represents methyl substituted with one $R^5$;
Y represents $CR^4$;
$R^4$ represents hydrogen;
$R^5$ represents —$OR^7$;
$R^7$ represents hydrogen or —C(=O)—$R^9$;
$R^9$ represents $C_{1-4}$alkyl substituted with one —$NH_2$ substituent;

$R^3$ represents phenyl substituted with one, two or three substituents each independently selected from the group consisting of cyano; and $C_{1-6}$alkyl;

and the pharmaceutically acceptable addition salts, and the solvates thereof.

The present invention relates in particular to compounds of Formula (I) as defined herein, tautomers and stereoisomeric forms thereof, wherein $R^1$ represents methyl;
$R^2$ represents methyl substituted with one $R^5$;
Y represents $CR^4$;
$R^4$ represents hydrogen;
$R^5$ represents —$OR^7$;
$R^7$ represents hydrogen;
$R^3$ represents phenyl substituted with one, two or three substituents each independently selected from the group consisting of cyano; and $C_{1-6}$alkyl;

and the pharmaceutically acceptable addition salts, and the solvates thereof.

In an embodiment, the present invention relates to those compounds of Formula (I) and the pharmaceutically acceptable addition salts, and the solvates thereof, or any subgroup thereof as mentioned in any of the other embodiments, wherein $R^5$ represents —$NR^{6a}R^{6b}$, or —$OR^7$;
$R^{6b}$ represents hydrogen; $C_{1-4}$alkyl; $C_{3-6}$cycloalkyl; —C(=O)—$C_{1-4}$alkyl; —S(=O)$_2$—$C_{1-4}$alkyl; —C(=O)—$C_{1-4}$alkyl substituted with one substituent selected from the group consisting of —OH and —$NR^{16}R^{16b}$; or $C_{1-4}$alkyl substituted with one substituent selected from the group consisting of —OH and —S(=O)$_2$—$C_{1-4}$alkyl;
$R^7$ represents hydrogen, $C_{1-4}$alkyl, —$C_{1-4}$alkyl-$NR^{8a}R^{8b}$, —C(=O)—$R^9$, —S(=O)$_2$—OH, —P(=O)$_2$—OH, or —(C=O)—CH(NH$_2$)—$C_{1-4}$alkyl-$Ar^1$.

Another embodiment of the present invention relates to those compounds of Formula (I) and the pharmaceutically acceptable addition salts, and the solvates thereof, or any subgroup thereof as mentioned in any of the other embodiments wherein Y represents $CR^4$ or N, in particular wherein Y represents $CR^4$; and wherein one or more of the following restrictions apply:

(a) $R^5$ represents halo, —$NR^{6a}R^{6b}$, or —$OR^7$; in particular $R^5$ represents —$NR^{6a}R^{6b}$, or —$OR^7$;
(b) $R^{6a}$ represents hydrogen;
(c) $R^{6b}$ represents —C(=O)—$C_{1-4}$alkyl; or —S(=O)$_2$—$C_{1-4}$alkyl;
(d) $R^7$ represents hydrogen, —$C_{1-4}$alkyl-$NR^{8a}R^{8b}$, —C(=O)—$R^9$, —S(=O)$_2$—OH, or —(C=O)—CH(NH$_2$)—$C_{1-4}$alkyl-$Ar^1$; in particular $R^7$ represents hydrogen, —C(=O)—$R^9$, —S(=O)$_2$—OH, or —(C=O)—CH(NH$_2$)—$C_{1-4}$alkyl-$Ar^1$;
(e) $R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; —P(=O)—($C_{1-4}$alkyl)$_2$; —NH—C(=O)—$C_{1-4}$alkyl; —NH—C(=O)—Het$^{1g}$; —$NR^{17a}R^{17b}$; $C_{1-4}$alkyl substituted with one, two or three halo atoms: $C_{1-4}$alkyl substituted with one, two or three —OH substituents; $C_{1-4}$alkyl substituted with one $R^{13}$; $C_{2-6}$alkenyl substituted with one $R^{13}$; and $C_{2-6}$alkynyl substituted with one $R^{13}$;

in particular $R^3$ represents phenyl optionally substituted with one, two or three substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —O—$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; —P(=O)—($C_{1-4}$alkyl)$_2$; —NH—C(=O)—$C_{1-4}$alkyl; —NH—C(=O)—Het$^{1g}$; $C_{1-4}$alkyl substituted with one, two or three halo atoms; $C_{1-4}$alkyl substituted with one, two or three —OH substituents; and $C_{1-4}$alkyl substituted with one $R^{13}$;

(f) $R^{18}$ represents a 5-membered aromatic ring containing one, two or three N-atoms; wherein said 5-membered aromatic ring may optionally be substituted with one substituent selected from the group consisting of $C_{1-4}$alkyl;

(g) Het$^{1a}$, Het$^{1c}$ and Het$^{1d}$ each independently represents a 4- to 7-membered monocyclic saturated heterocyclyl containing one or two heteroatoms each independently selected from O and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-6}$alkyl, —O—$C_{1-4}$alkyl, and —N($C_{1-4}$alkyl)$_2$;

(h) Het$^{1b}$, Het$^{1e}$, Het$^{1g}$, Het$^7$ and Het$^8$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$, Het$^7$ and Het$^8$ containing one or two heteroatoms each independently selected from O and N; wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and wherein said 4- to 7-membered monocyclic saturated heterocyclyl may optionally be substituted on one, two or three ring C-atoms with one or two substituents each independently selected from the group consisting of —OH, and halo; in particular Het$^{1b}$, Het$^{1e}$, and Het$^{1g}$ each independently represents a 4- to 7-membered monocyclic saturated heterocyclyl, attached to the remainder of the molecule of Formula (I) through any available ring carbon atom, said Het$^{1b}$, Het$^{1e}$ and Het$^{1g}$ containing one or two heteroatoms each independently selected from O and N:

wherein said 4- to 7-membered monocyclic saturated heterocyclyl may optionally be substituted, where possible, on one or two ring N-atoms with a substituent each independently selected from the group consisting of $C_{1-4}$alkyl and $C_{3-6}$cycloalkyl; and wherein said 4- to 7-membered monocyclic saturated heterocyclyl may optionally be substituted on one, two or three ring C-atoms with one or two —OH substituents;

(i) Het$^2$ represents a heterocyclyl of formula (b-1):

(b-1) represents a N-linked 4- to 7-membered monocyclic saturated heterocyclyl optionally containing one additional heteroatom selected from O and N, or a N-linked 6- to 11-membered bicyclic saturated heterocyclyl, including fused, spiro and bridged cycles, optionally containing one or two additional N-atoms;

wherein in case (b-1) contains one or two additional N-atoms, said one or two N-atoms may optionally be substituted with a substituent each independently selected from the group consisting of $C_{1-4}$alkyl, $C_{3-6}$cycloalkyl and Het$^7$; and wherein (b-1) may optionally be substituted on one, two or three ring C-atoms with one or two substituents each independently selected from the group consisting of —OH, cyano, $C_{1-4}$alkyl, and $C_{1-4}$alkyl-OH;

in particular Het$^2$ represents a heterocyclyl of formula (b-1):

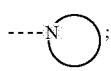

(b-1)

(b-1) represents a N-linked 4- to 7-membered monocyclic saturated heterocyclyl optionally containing one additional N-atom, or a N-linked 6- to 11-membered bicyclic saturated heterocyclyl, including fused, spiro and bridged cycles, optionally containing one or two additional N-atoms;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of —OH, cyano, and $C_{1-4}$alkyl-OH;

(j) R$^{11b}$ represents Het$^{1e}$; $C_{1-4}$alkyl; —$C_{1-4}$alkyl-Het$^5$; —$C_{1-4}$alkyl-Het$^8$, $C_{1-4}$alkyl substituted with one, two or three OH substituents; or $C_{3-6}$cycloalkyl substituted with one, two or three substituents each independently selected from the group consisting of halo and —OH; in particular R$^{11b}$ represents Het$^{1e}$; $C_{1-6}$alkyl; —$C_{1-4}$alkyl-Het$^5$; $C_{1-4}$alkyl substituted with one, two or three OH substituents; or $C_{3-6}$cycloalkyl substituted with one, two or three substituents each independently selected from the group consisting of halo and —OH;

(k) R represents —O—$C_{1-4}$alkyl, —$C(=O)NR^{15a}R^{15b}$, —NR$^{19a}$R$^{19b}$, $C_{3-6}$cycloalkyl, Het$^{1d}$, or —$C(=O)$—Het$^{1f}$;

(l) R$^{12}$ represents —OH, —O—$C_{1-4}$alkyl, —NR$^{14a}$R$^{14b}$, —$C(=O)NR^{14c}R^{14d}$, —$S(=O)_2$—$C_{1-4}$alkyl, $C_{3-6}$cycloalkyl, Ar$^2$, or Het$^{1c}$;

(m) Ar$^1$ represents phenyl;

(n) Het$^5$, Het$^6$ and Het$^{1f}$ each independently represents a heterocyclyl of formula (c-1):

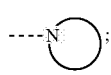

(c-1)

(c-1) represents a N-linked 4- to 7-membered monocyclic saturated heterocyclyl optionally containing one additional heteroatom selected from O and N;

wherein in case (c-1) contains one additional N-atom, said additional N-atom may optionally be substituted with $C_{1-4}$alkyl;

(o) R$^{14b}$, R$^{14d}$, R$^{15b}$, R$^{17b}$ and R$^{19b}$ each independently represents hydrogen; $C_{1-4}$alkyl; $C_{3-6}$cycloalkyl; —$C(=O)$—$C_{1-4}$alkyl; $C_{1-4}$alkyl substituted with one substituent selected from the group consisting of —OH and —O—$C_{1-4}$alkyl; or —$S(=O)_2$—$C_{1-4}$alkyl; in particular R$^{14b}$, R$^{14d}$, R$^{15b}$, and R$^{19b}$ each independently represents hydrogen; $C_{1-4}$alkyl; $C_{3-6}$cycloalkyl; or $C_{1-4}$alkyl substituted with one —O—$C_{1-6}$alkyl.

Another embodiment of the present invention relates to those compounds of Formula (I) and the pharmaceutically acceptable addition salts, and the solvates thereof, or any subgroup thereof as mentioned in any of the other embodiments wherein Y represents CR$^4$ or N, in particular wherein Y represents CR$^4$; and wherein one or more of the following restrictions apply:

(a) R$^4$ represents hydrogen;
(b) R$^5$ represents —OR$^7$;
(c) R$^7$ represents hydrogen or —$C(=O)$—R$^9$;
(d) R$^9$ represents $C_{1-4}$alkyl;
(e) R$^3$ represents phenyl substituted with one, two or three substituents each independently selected from the group consisting of halo; cyano; $C_{1-6}$alkyl; —O—$C_{1-4}$alkyl; —$C(=O)$—R$^{10}$; —$S(=O)_2$—$C_{1-4}$alkyl; —O—$C_{1-6}$alkyl-R$^{12}$; —NH—$C(=O)$-Het$^{1g}$; and $C_{1-4}$alkyl substituted with one R$^{13}$;
(f) R$^{10}$ represents —NR$^{11a}$R$^{11b}$ or Het$^2$;
(g) Het$^{1g}$ represents a 4- to 7-membered monocyclic saturated heterocyclyl, attached to the remainder of the molecule of Formula (I) through any available ring carbon atom, said Het$^{1g}$ containing one or two N-atoms;

wherein said 4- to 7-membered monocyclic saturated heterocyclyl may optionally be substituted, where possible, on one or two ring N-atoms with a $C_{1-4}$alkyl substituent;

(h) Het$^2$ represents a heterocyclyl of formula (b-1):

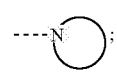

(b-1)

(b-1) represents a N-linked 4- to 7-membered monocyclic saturated heterocyclyl wherein (b-1) may optionally be substituted on one C-atom with one —OH substituent;

(i) R$^{11b}$ represents $C_{1-4}$alkyl;
(j) R$^{13}$ represents —O—$C_{1-4}$alkyl;
(k) R represents —O—$C_{1-4}$alkyl;
(l) R$^{11a}$ represents hydrogen.

In an embodiment, the present invention relates to a subgroup of Formula (I), hereby named compounds of Formula (I'), and the pharmaceutically acceptable addition salts, and the solvates thereof:

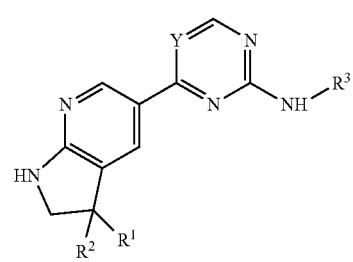

(I')

R stereochemistry wherein R¹ represents $C_{1-4}$alkyl;

R² represents $C_{1-6}$alkyl substituted with one R⁵;

in particular wherein R¹ represents $C_{1-4}$alkyl;

R² represents $C_{1-6}$-alkyl substituted with one R¹;

R⁵ represents —OR⁷;

more in particular wherein R¹ represents $C_{1-4}$alkyl;

R² represents $C_{1-6}$alkyl substituted with one R¹;

R⁵ represents —OR⁷;

R⁷ represents hydrogen;

and wherein all other variables are defined according to any of the other embodiments.

In an embodiment, the present invention relates to a subgroup of Formula (I), hereby named compounds of Formula (I″), and the pharmaceutically acceptable addition salts, and the solvates thereof:

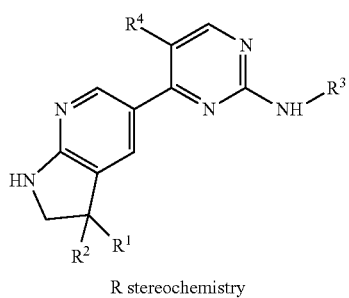

(I″)

R stereochemistry wherein all variables are defined according to any of the other embodiments.

In an embodiment, the present invention relates to a subgroup of Formula (I), hereby named compounds of Formula (I‴), and the pharmaceutically acceptable addition salts and the solvates thereof:

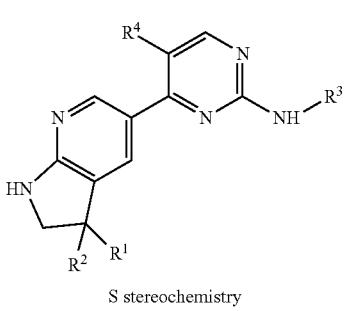

(I‴)

S stereochemistry wherein all variables are defined according to any of the other embodiments.

In an embodiment, the present invention relates to a subgroup of Formula (I), hereby named compounds of Formula (I″), and the pharmaceutically acceptable addition salts, and the solvates thereof:

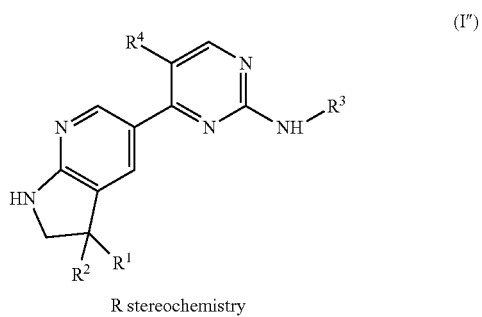

(I″)

R stereochemistry wherein R¹ represents $C_{1-4}$alkyl;

R² represents $C_{1-6}$alkyl substituted with one R⁵;

in particular wherein R¹ represents $C_{1-4}$alkyl;

R² represents $C_{1-6}$alkyl substituted with one R¹;

R⁵ represents —OR⁷;

more in particular wherein R represents $C_{1-4}$alkyl;

R² represents $C_{1-4}$alkyl substituted with one R⁵;

R⁵ represents —OR⁷;

R⁷ represents hydrogen;

and wherein all other variables are defined according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein R¹ represents methyl;

R² represents methyl or —CH₂—OH.

In an embodiment, the present invention relates to those compounds of Formula (I) and the pharmaceutically acceptable addition salts, and the solvates thereof, or any subgroup thereof as mentioned in any of the other embodiments, wherein Y represents CR⁴.

In an embodiment, the present invention relates to those compounds of Formula (I) and the pharmaceutically acceptable addition salts, and the solvates thereof, or any subgroup thereof as mentioned in any of the other embodiments, wherein R¹ represents methyl; R² represents —CH₂—OH.

In an embodiment, the present invention relates to those compounds of Formula (I) and the pharmaceutically acceptable addition salts, and the solvates thereof, or any subgroup thereof as mentioned in any of the other embodiments, wherein R³ represents phenyl which is substituted with one, two or three substituents according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein R³ represents phenyl optionally substituted with one, two or three substituents according to any of the other embodiments, provided however that the substituents are not selected from the group consisting of —S(=O)₂—$C_{1-4}$alkyl; —S(=O)(=N—R²⁰ᵃ)—$C_{1-4}$alkyl; and —P(=O)—($C_{1-4}$alkyl)₂.

In an embodiment, the present invention relates to those compounds of Formula (I) and the pharmaceutically acceptable addition salts, and the solvates thereof, or any subgroup thereof as mentioned in any of the other embodiments, wherein R⁴ is hydrogen or fluoro.

In an embodiment, the present invention relates to those compounds of Formula (I) and the pharmaceutically acceptable addition salts, and the solvates thereof, or any subgroup thereof as mentioned in any of the other embodiments, wherein $R^4$ is hydrogen.

In an embodiment, the present invention relates to those compounds of Formula (I) and the pharmaceutically acceptable addition salts, and the solvates thereof, or any subgroup thereof as mentioned in any of the other embodiments, wherein $R^7$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein $R^5$ represents —$OR^7$; and $R^7$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein $R^9$ represents $C_{1-4}$alkyl, or $C_{1-4}$alkyl substituted with one substituent selected from the group consisting of —$NH_2$, —COOH, and $Het^6$.

In an embodiment, the present invention relates to those compounds of Formula (I) and the pharmaceutically acceptable addition salts, and the solvates thereof, or any subgroup thereof as mentioned in any of the other embodiments, wherein $R^{18}$ is attached to the remainder of the molecule of Formula (I) via a carbon atom.

In an embodiment, the present invention relates to those compounds of Formula (I) and the pharmaceutically acceptable addition salts, and the solvates thereof, or any subgroup thereof as mentioned in any of the other embodiments, wherein $R^{18}$ represents

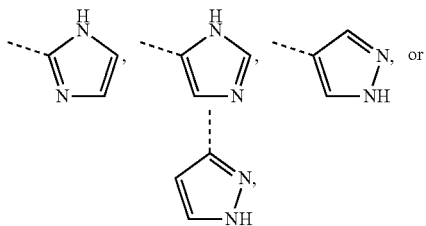

in particular

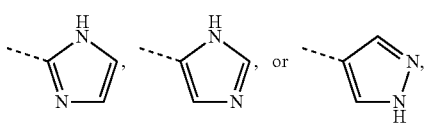

each substituted on the NH with $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents morpholinyl, piperidinyl, pyrrolidinyl, oxetanyl, azetidinyl, piperazinyl, tetrahydro-2H-pyranyl, or hexahydro-1,4-oxazepinyl, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents

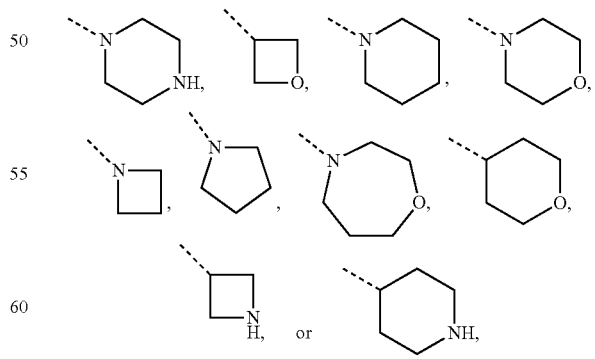

each optionally substituted on carbon and/or nitrogen atoms according to any of the other embodiments.

In an embodiment, the present invention relates to those compounds of Formula (I) and the pharmaceutically accept-

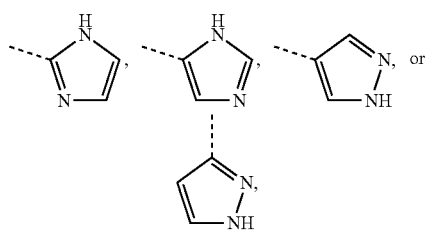

in particular

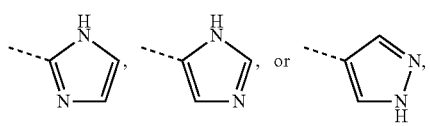

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $R^{18}$ represents able addition salts, and the solvates thereof, or any subgroup thereof as mentioned in any of the other embodiments, wherein Het$^{1a}$ represents

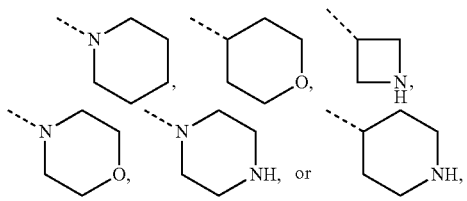

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1c}$ represents

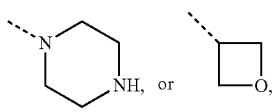

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1d}$ represents

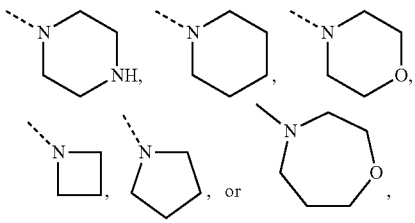

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$, Het$^{1c}$. Het$^{1g}$ and Het$^4$ each independently represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl, attached to the remainder of the molecule of Formula (I) through any available ring carbon atom, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$, Het$^{1e}$, Het$^{1g}$ and Het$^4$ each independently represents piperidinyl, tetrahydro-2H-pyranyl, or pyrrolidinyl, attached to the remainder of the molecule of Formula (I) through any available ring carbon atom, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$, Het$^{1e}$, Het$^{1g}$ and Het$^4$ each independently represents

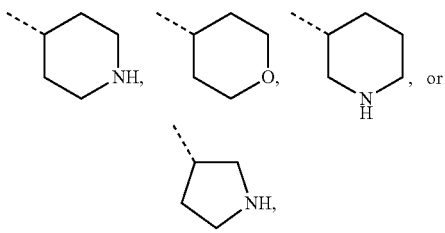

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1g}$ represents

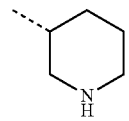

optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1e}$ represents

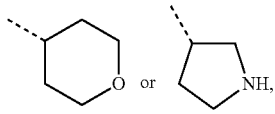

each optionally substituted on carbon an r nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1b}$ represents

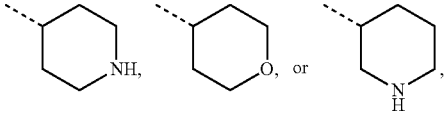

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het² represents

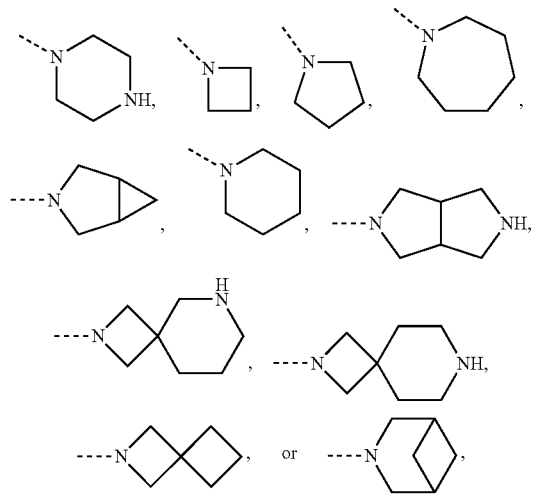

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{3a}$, Het$^{3b}$, Het$^5$, Het$^6$ and Het$^{1f}$ each independently represents

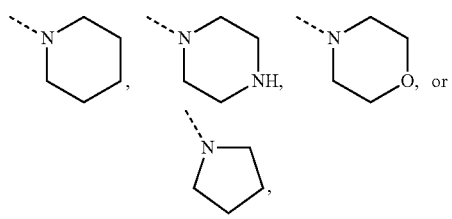

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het⁴ represents pyrrolidinyl, piperidinyl, tetrahydropyranyl, azetidinyl, or 1,1-dioxidethiopyranyl;

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het⁵ represents

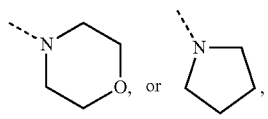

each optionally substituted according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het⁶ represents

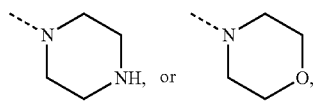

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1f}$ represents

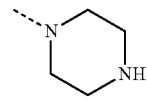

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het⁷ and Het⁸ each independently represent

optionally substituted on carbon atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(═O)—$C_{1-4}$alkyl, —O—$C_{1-4}$alkyl, —NH$_2$, —NH($C_{1-4}$alkyl), and —N($C_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein Het$^2$ represents a heterocyclyl of formula (b-1):

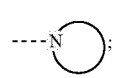

(b-1)

(b-1) represents a N-linked 4- to 7-membered monocyclic saturated heterocyclyl optionally containing one additional heteroatom selected from O, S, S(═O)$_p$ and N;

wherein in case (b-1) contains one additional N-atom, said N-atom may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH.

In an embodiment, the present invention relates to those compounds of Formula (I) and the pharmaceutically acceptable addition salts, and the solvates thereof, or any subgroup thereof as mentioned in any of the other embodiments, wherein Het$^{1a}$ represents a 4- to 7-membered monocyclic saturated heterocyclyl containing one or two heteroatoms each independently selected from O, S, S(═O)$_p$ and N; or a 6- to 11-membered bicyclic saturated heterocyclyl, including fused, spiro and bridged cycles, containing one, two or three heteroatoms each independently selected from O, S, S(═O)$_p$ and N;

wherein said 4- to 7-membered monocyclic saturated heterocyclyl or said 6- to 11-membered bicyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(═O)—$C_{1-4}$alkyl, —O—$C_{1-4}$alkyl, —NH$_2$, —NH($C_{1-4}$alkyl), and —N($C_{1-4}$alkyl)$_2$;

Het$^{1c}$ and Het$^{1d}$ each independently represents a 4- to 7-membered monocyclic saturated heterocyclyl containing one or two heteroatoms each independently selected from O, S, S(═O)$_p$ and N; or in case Het$^{1c}$ and Het$^{1d}$ are attached to the remainder of the molecule of Formula (I) through an N-atom, Het$^{1c}$ and Het$^{1d}$ may also represent a N-linked 6- to 11-membered bicyclic saturated heterocyclyl, including fused, spiro and bridged cycles, optionally containing one or two additional heteroatoms each independently selected from O, S, S(═O)$_p$ and N;

wherein said 4- to 7-membered monocyclic saturated heterocyclyl or said N-linked 6- to 11-membered bicyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl or said N-linked 6- to 11-membered bicyclic saturated heterocyclyl may optionally be substituted on one, two or three ring C-atoms with one or two substituents each independently selected from the group consisting of —OH, halo, $C_{1-4}$alkyl, cyano, —C(═O)—$C_{1-4}$alkyl, —O—$C_{1-4}$alkyl, —NH$_2$, —NH($C_{1-4}$alkyl), and —N($C_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein Y represents CR$^4$;

in particular wherein Y represents CR$^4$ and wherein R$^4$ represents hydrogen.

In an embodiment, the present invention relates to a subgroup of Formula (I), hereby named compounds of Formula (I-x), and the pharmaceutically acceptable addition salts, and the solvates thereof:

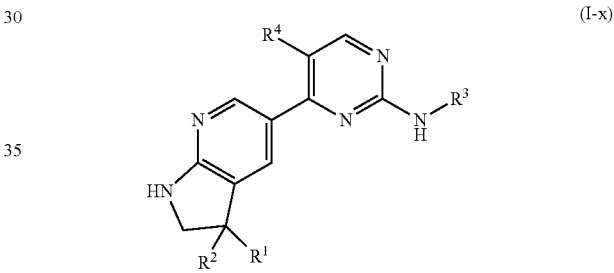

(I-x)

wherein all variables are defined according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Y represents N.

In an embodiment, the present invention relates to a subgroup of Formula (I), hereby named compounds of Formula (I-y), and the pharmaceutically acceptable addition salts, and the solvates thereof:

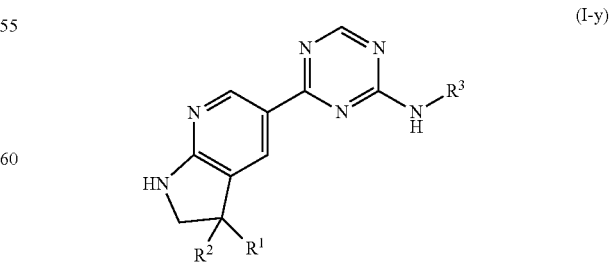

(I-y)

wherein all variables are defined according to any of the other embodiments.

In an embodiment, the present invention relates to a subgroup of Formula (I) as defined in the general reaction schemes.

In an embodiment the compound of Formula (I) is selected from the group consisting of compounds 2, 3S, 6S, 7S, 8, 9, 12, 14, 15 and 16, tautomers and stereoisomeric forms thereof, and the free bases, any pharmaceutically acceptable addition salts, and the solvates thereof.

In an embodiment the compound of Formula (I) is selected from the group consisting of compounds 2, 3S, 6S, 7S, 8, 9, 12, 14, 15 and 16.

In an embodiment the compound of Formula (I) is selected from the group consisting of any of the exemplified compounds, tautomers and stereoisomeric forms thereof, and the free bases, any pharmaceutically acceptable addition salts, and the solvates thereof.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realise that functionalization reactions illustrated in the Schemes below for compounds of Formula (I) wherein Y is $CR^4$, may also be carried out for compounds wherein Y is N. The skilled person will realise this applies, for example and without limitation, to steps 3 and 4 of scheme 2 and scheme 18.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. For example in Scheme 6, the NH moiety on the pyrimidinyl can be protected with a t-butoxycarbonyl protecting group. In general, conventional protecting groups can be used in accordance with standard practice. The protecting groups may be removed at a convenient subsequent stage using methods known from the art. This is illustrated in the specific examples.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of formula (I).

The skilled person will realize that intermediates and final compounds shown in the schemes below may be further functionalized according to methods well-known by the person skilled in the art.

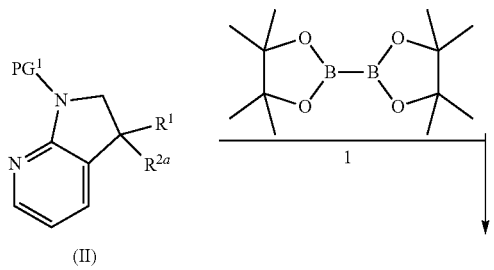

Scheme 1

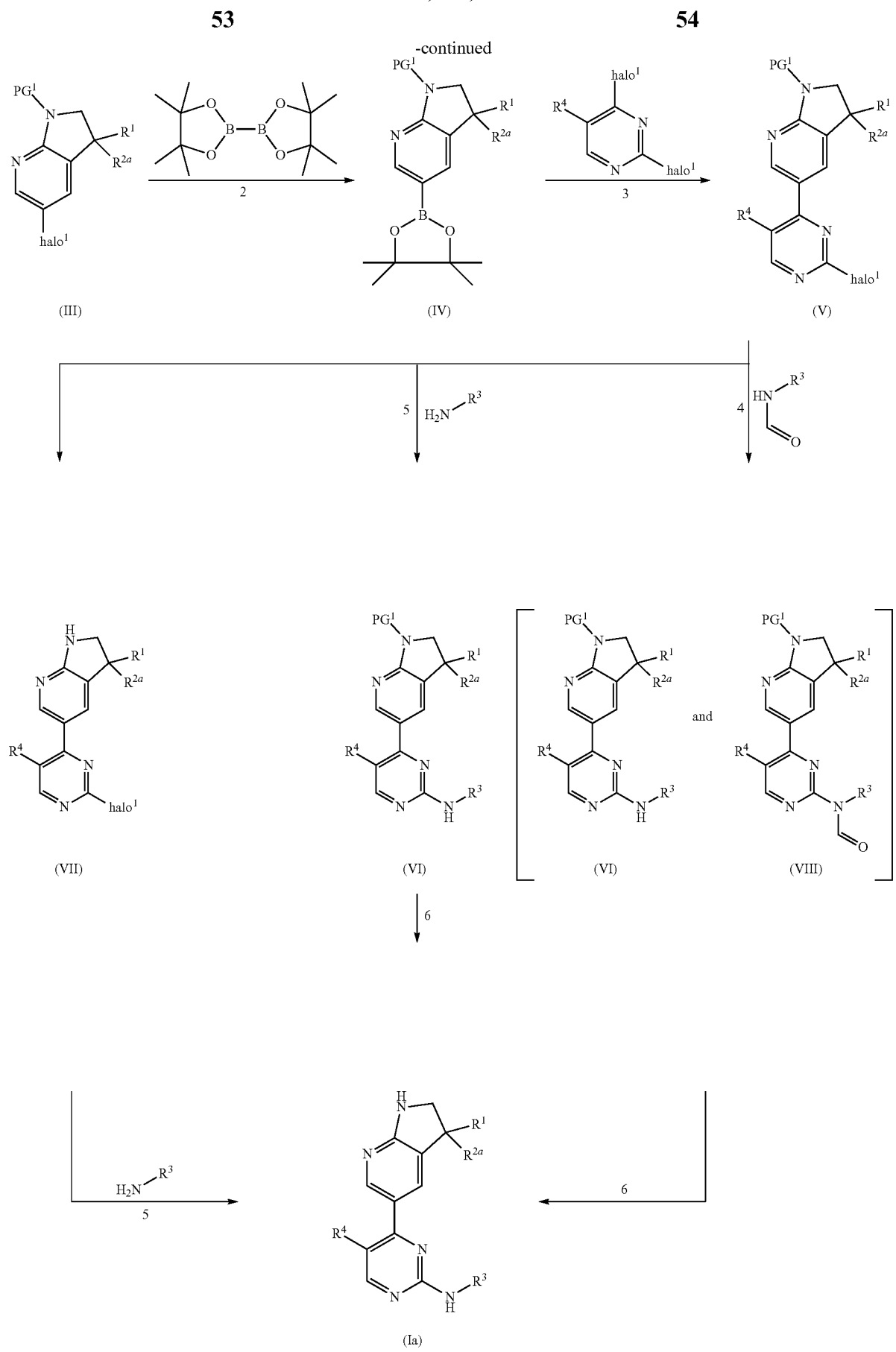

-continued

1: at a suitable temperature such as for example 80° C., in the presence of a suitable ligand such as for example 4,4'-di-tert-butyl-2,2'-dipyridyl, a suitable catalyst such as for example bis(1,5-cyclooctadiene)di-μ-methoxydiiridium (I) ([Ir(OCH₃)(C₈H₁₂)]₂), and a suitable solvent such as for example heptane;
2: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;
3: at a suitable temperature such as for example 85° C., in the presence of a suitable catalyst such as for example palladium tetrakis (Pd(PPh₃)₄), a suitable base such as for example sodium carbonate, and a suitable solvent such as for example 1,4-dioxane;
4: at a suitable temperature such as for example room temperature, in presence of a suitable base such as for example sodium hydride, and a suitable solvent such as for example dimethylformamide;
5: at a suitable temperature such as for example 100° C., in the presence of a suitable catalyst such as for example palladium acetate (Pd(OAc)₂), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;
or alternatively at a suitable temperature such as for example 95° C., in the presence of a suitable acid such as for example p-toluenesulfonic acid and a suitable solvent such as for example 1,4-dioxane;
6: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $R^{2\,0}$ being $C_{1-6}$alkyl, Y is $CR^4$, and wherein all the other variables are defined according to the scope of the present invention, hereby named compounds of Formula (Ia), can be prepared according to the following reaction Scheme 1. In Scheme 1 halo¹ is defined as Cl, Br or I; and $PG^1$ represents a suitable protecting group, such as for example tert-(butoxycarbonyl). All other variables in Scheme 1 are defined according to the scope of the present invention.

In Scheme 1, the following reaction conditions apply:

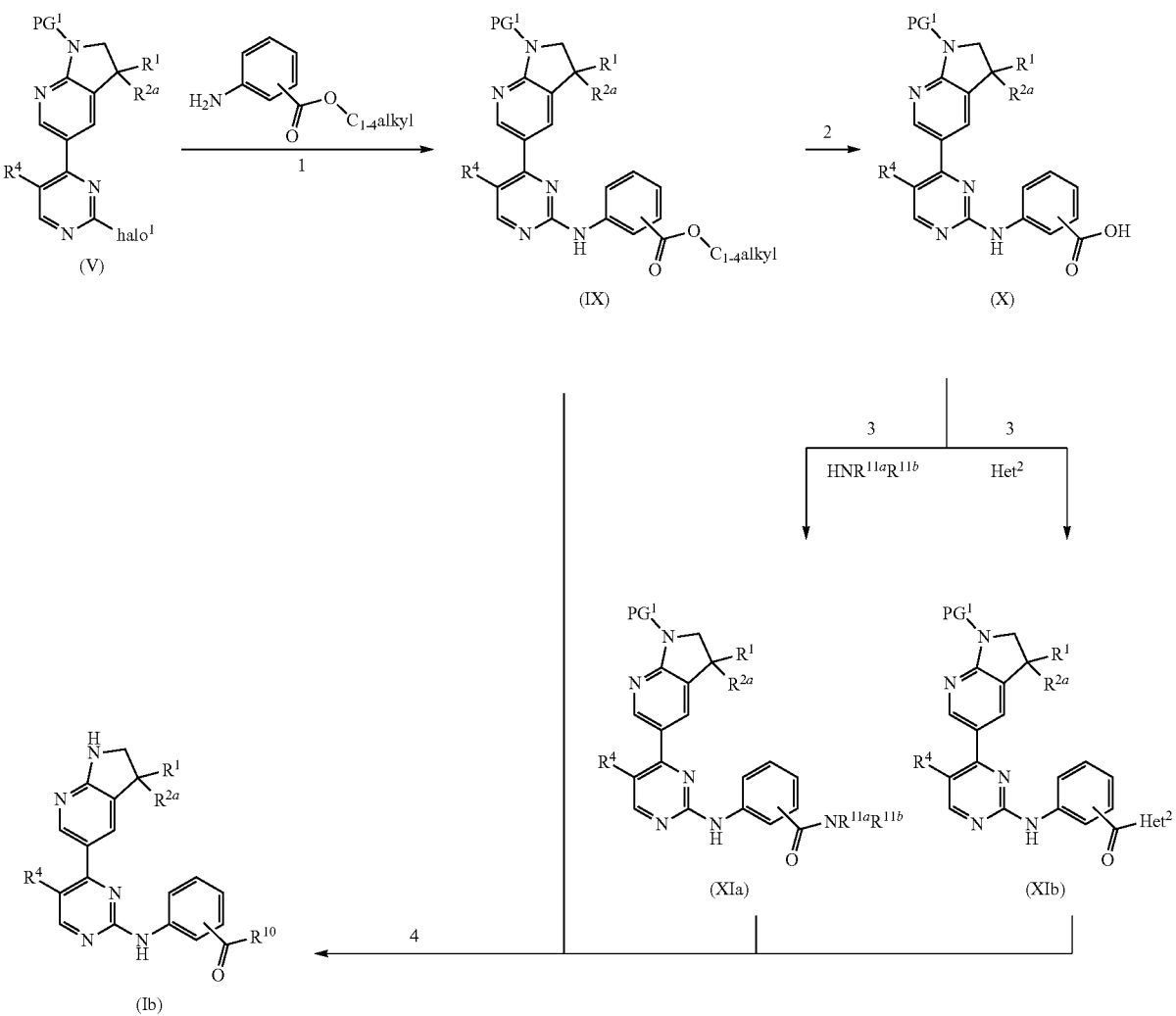

-continued

1: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;
2: at a suitable temperature such as for example 70° C., in the presence of a suitable base such as for example lithium hydroxide, and a suitable solvent such as for example a mixture of tetrahydrofuran and water;
3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide;
4: at a suitable temperature such as for example 0° C. or room temperature or reflux, in presence of a suitable acid as for example trifluoroacetic acid or aqueous hydrochloric acid with a suitable solvent such as for example dichloromethane, methanol, ethylacetate, or 1,4-dioxane, and a suitable time such as for example 3 hours.

In general, compounds of Formula (I) wherein $R^2$ is $R^{2a}$ being $C_{1-6}$alkyl, $R^3$ is phenyl substituted with —C(=O)—$R^{10}$ and optionally substituted with other substituents according to the scope of the present invention, Y is $CR^4$, and wherein all the other variables are as defined according to the scope of the present invention, hereby named compounds of Formula (Ib), can be prepared according to the following reaction Scheme 2. In Scheme 2 halo$^1$ is defined as Cl, Br or I; $PG^1$ represents a suitable protecting group, such as for example tert-(butoxycarbonyl). All other variables in Scheme 2 are defined according to the scope of the present invention.

In Scheme 2, the following reaction conditions apply:

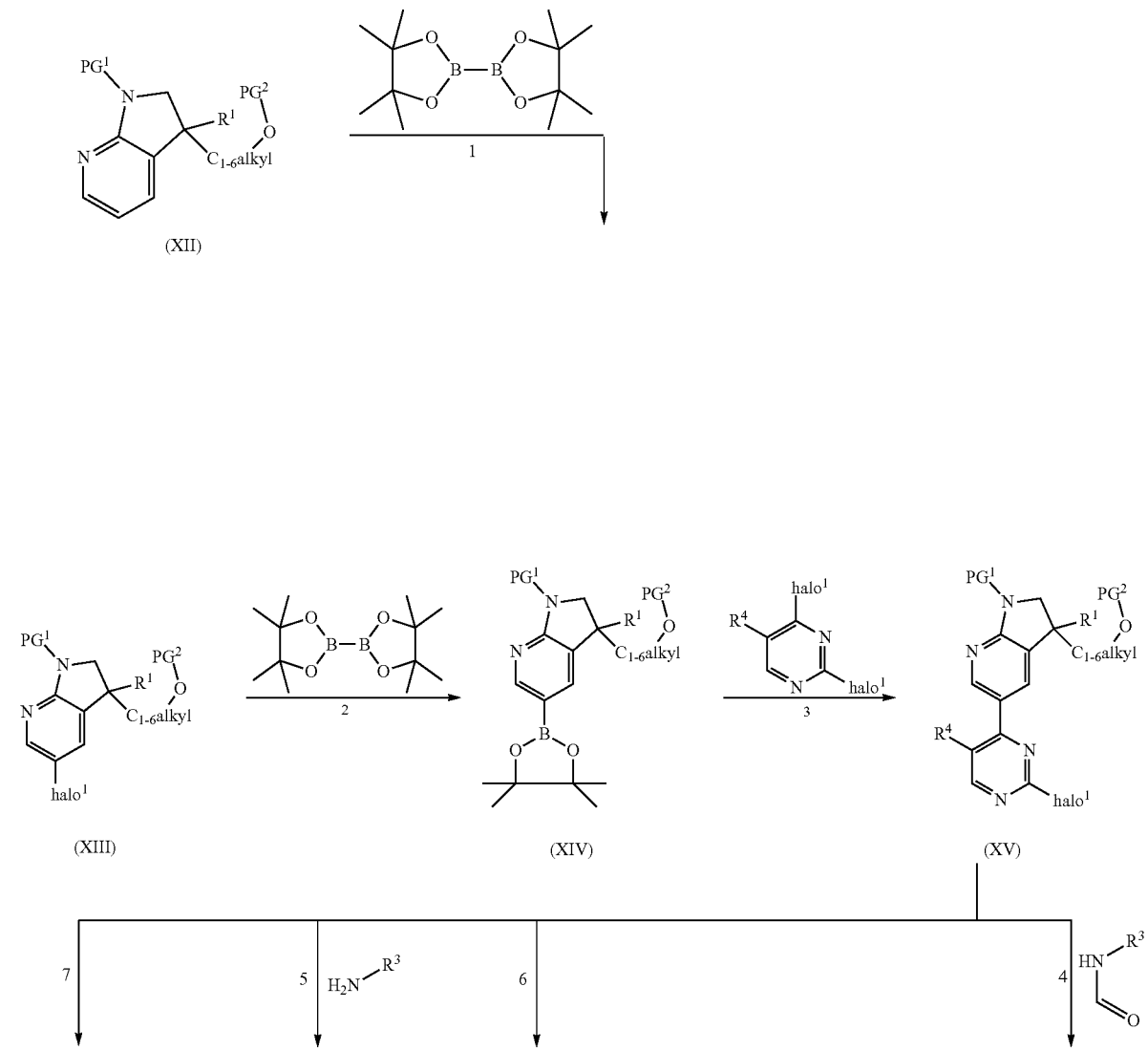

-continued

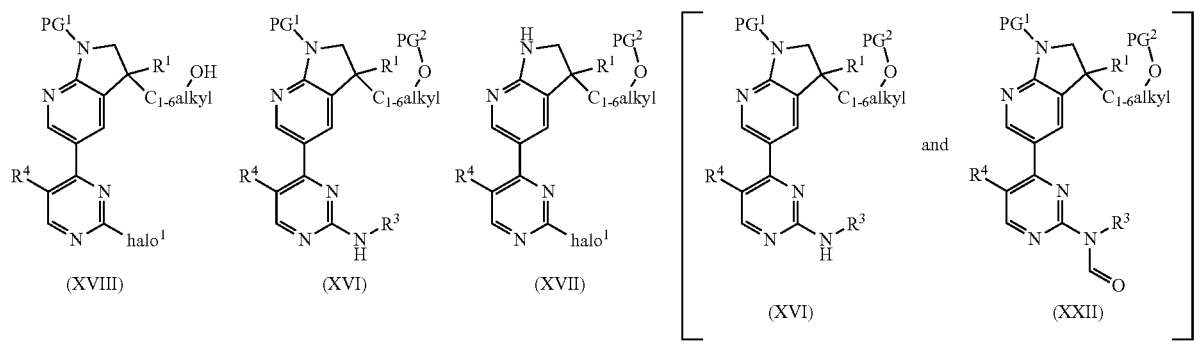

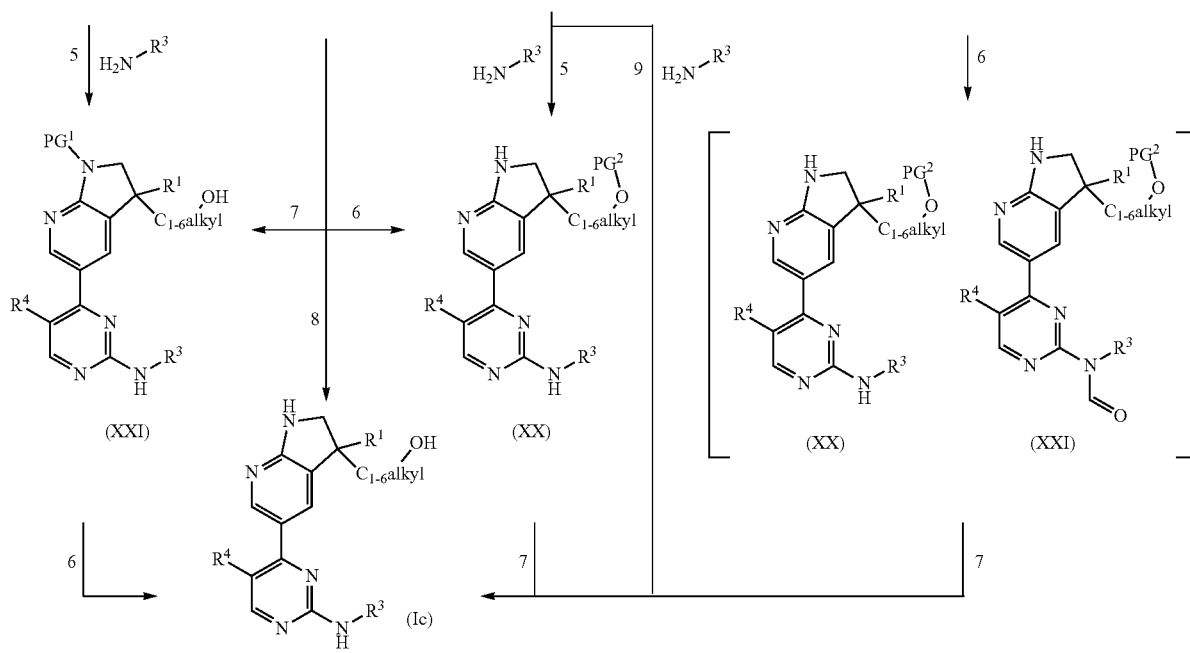

1: at a suitable temperature such as for example 80° C., in the presence of a suitable ligand such as for
example 4,4′-di-tert-butyl-2,2′-dipyridyl, a suitable catalyst such as for example bis(1,5-
cyclooctadiene)di-µ-methoxydiiridium (I) (Ir(OCH$_3$)(C$_8$H$_{12}$)]$_2$), and a suitable solvent such as for example heptane;
2: at a suitable temperature such as for example 85° C., in the presence of a suitable catalyst such as for example [1,1′-
bis(diphenylphosphino)ferrocene] dichloropalladium (II), optionally with dichloromethane complex,
a suitable base such as for example potassium acetate and a suitable solvent such as for example 1,4-dioxane;
3: at a suitable temperature such as for example 85° C., in the presence of a suitable catalyst such as
for example palladium tetrakis (Pd(PPh$_3$)$_4$), a suitable base such as for example sodium carbonate, and a
suitable solvent such as for example 1,4-dioxane;
4: at a suitable temperature such as for example room temperature, in presence of a suitable base such as for example
sodium hydride, and a suitable solvent such as for example dimethylformamide;
5: at a suitable temperature such as for example 100° C., in the presence of a suitable catalyst
such as for example palladium acetate (Pd(OAc)$_2$), a suitable ligand such as for example 2,2′-
bis(diphenylphosphino)-1,1′-binaphthyl (BINAP), a suitable base such as for example cesium carbonate,
and a suitable solvent such as for example 1,4-dioxane, optionally under microwave activation;
6: at a suitable temperature such as for example 0° C. or room temperature or reflux, in presence of a
suitable acid such as for example trifluoroacetic acid or aqueous hydrochloric acid with a suitable
solvent such as for example dichloromethane, methanol, ethyl acetate or 1,4-dioxane or alternatively in
the presence of silica in a suitable solvent such as for example toluene at a suitable temperature
such as for example 125° C., and a suitable time such as for example 3 hours;
7: at a suitable temperature such as for example room temperature, in presence of a suitable
desilylating agent such as for example tetra-n-butylammonium fluoride and a suitable solvent such as for example
2-methyltetrahydrofuran or tetrahydrofuran;
8: at a suitable temperature such as for example reflux, in presence of a suitable acid such as for
example aqueous hydrochloric acid with a suitable solvent such as for example dichloromethane, methanol,
ethyl acetate or 1,4-dioxane, and a suitable time such as for example 6 hours;
9: at a suitable temperature such as for example 95° C., in the presence of a suitable acid
such as for example p-toluenesulfonic acid and a suitable solvent such as for example 1,4-dioxane.

In general, compounds of Formula (I) wherein $R^2$ is $R^{2b}$ being $C_{1-6}$alkyl substituted with one OH, Y is $CR^4$, and wherein all the other variables are as defined according to the scope of the present invention, hereby named compounds of Formula (Ic), can be prepared according to the following reaction Scheme 3. In Scheme 3 halo[1] is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 3 are defined according to the scope of the present invention.

In Scheme 3, the following reaction conditions apply:

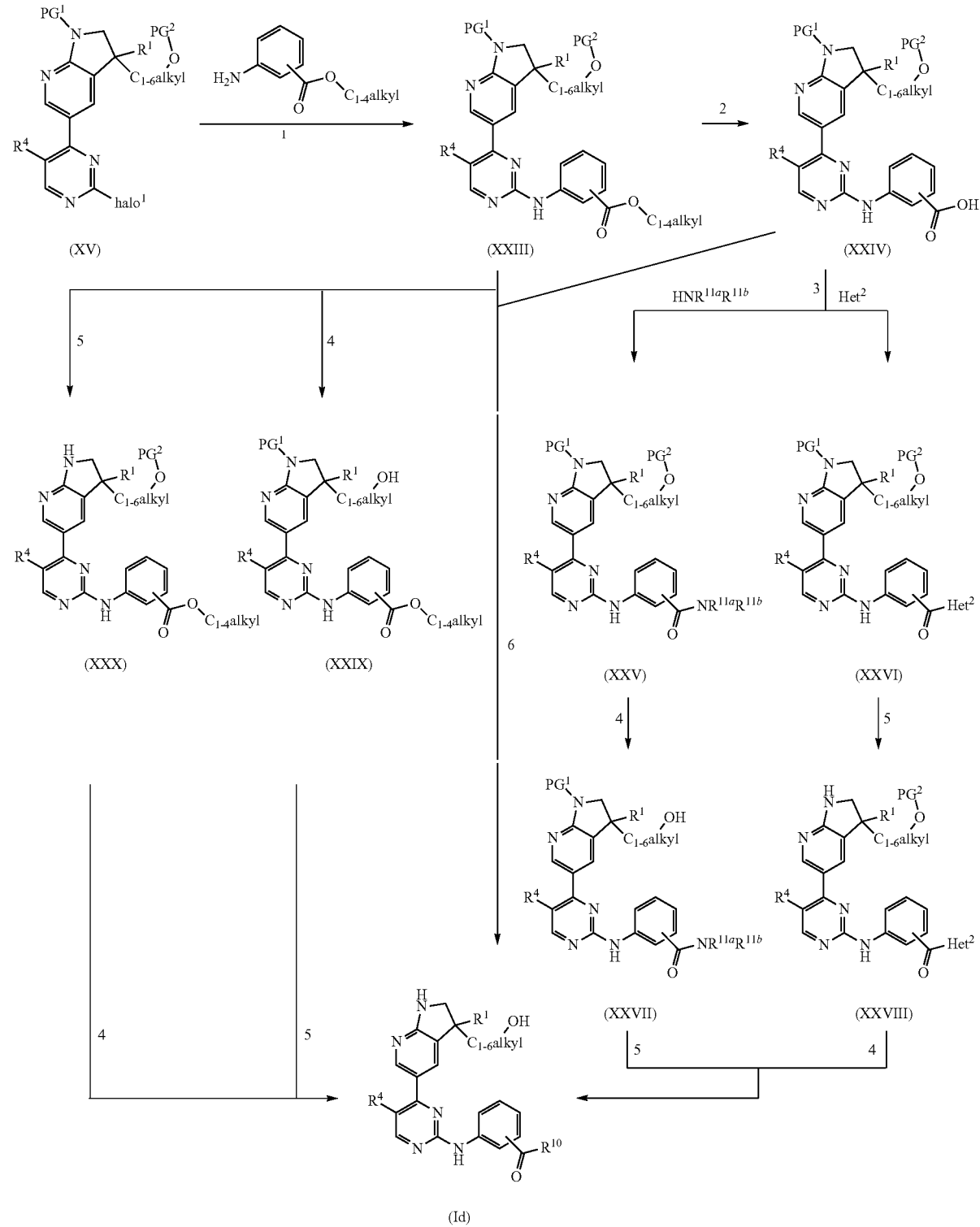

-continued

1: at a suitable temperature such as for example 100° C., in the presence of a suitable catalyst such as for example palladium acetate (Pd(OAc)$_2$),
a suitable ligand such as for example 2,2'-bis(diphenylphosphino)-1,1'-binaphthyl (BINAP), a suitable base such as for example cesium carbonate,
and a suitable solvent such as for example 1,4-dioxane, optionally under microwave activation;
2: at a suitable temperature such as for example 70° C., in presence of a suitable base such as for example lithium hydroxide, and a
suitable solvent such as for example a mixture of tetrahydrofuran and water;
3: at a suitable temperature such as for example room temperature, in presence of a suitable coupling reagent such as for example 1-[bis(dimethylamino)methylene]-1H-
1,2,3-triazolo[4,5-b]pyridinium 3-oxid hexafluorophosphate (HATU), a suitable base such as for example N,N-diisopropylethylamine,
and a suitable solvent such as for example dimethylformamide;
4: at a suitable temperature such as for example room temperature, in presence of a suitable desilyating agent such as for example tetra-n-butylammonium fluoride and a
suitable solvent such as for example 2-methyltetrahydrofuran or tetrahydrofuran;
5: at a suitable temperature such as for example 0° C. or room temperature or reflux, in presence of a suitable acid such as for example trifluoroacetic acid or
aqueous hydrochloric acid with a suitable solvent such as for example dichloromethane, methanol, ethyl acetate or 1,4-dioxane or alternatively in the presence
of silica in a suitable solvent such as for example toluene at a suitable temperature such as for example 125° C., and a suitable time such as for example 3 hours.
6: at a suitable temperature such as for example reflux, in presence of a suitable acid such as for example aqueous hydrochloric acid with a suitable solvent such as for example
dichloromethane, methanol, ethyl acetate or 1,4-dioxane, and a suitable time such as for example 6 hours.

In gene, compounds of Formula (I) wherein $R^2$ is $R^{2b}$ being $C_{1-6}$alkyl substituted with one OH, $R^3$ is phenyl substituted with —C(═O)—$R^{10}$ and optionally substituted with other substituents according to the scope of the present invention, Y is $CR^4$, and wherein all the other variables are as defined according to the scope of the present invention, hereby named compounds of Formula (Id), can be prepared according to the following reaction Scheme 4. In Scheme 4 halo$^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 4 are defined according to the scope of the present invention.

In Scheme 4, the following reaction conditions apply:

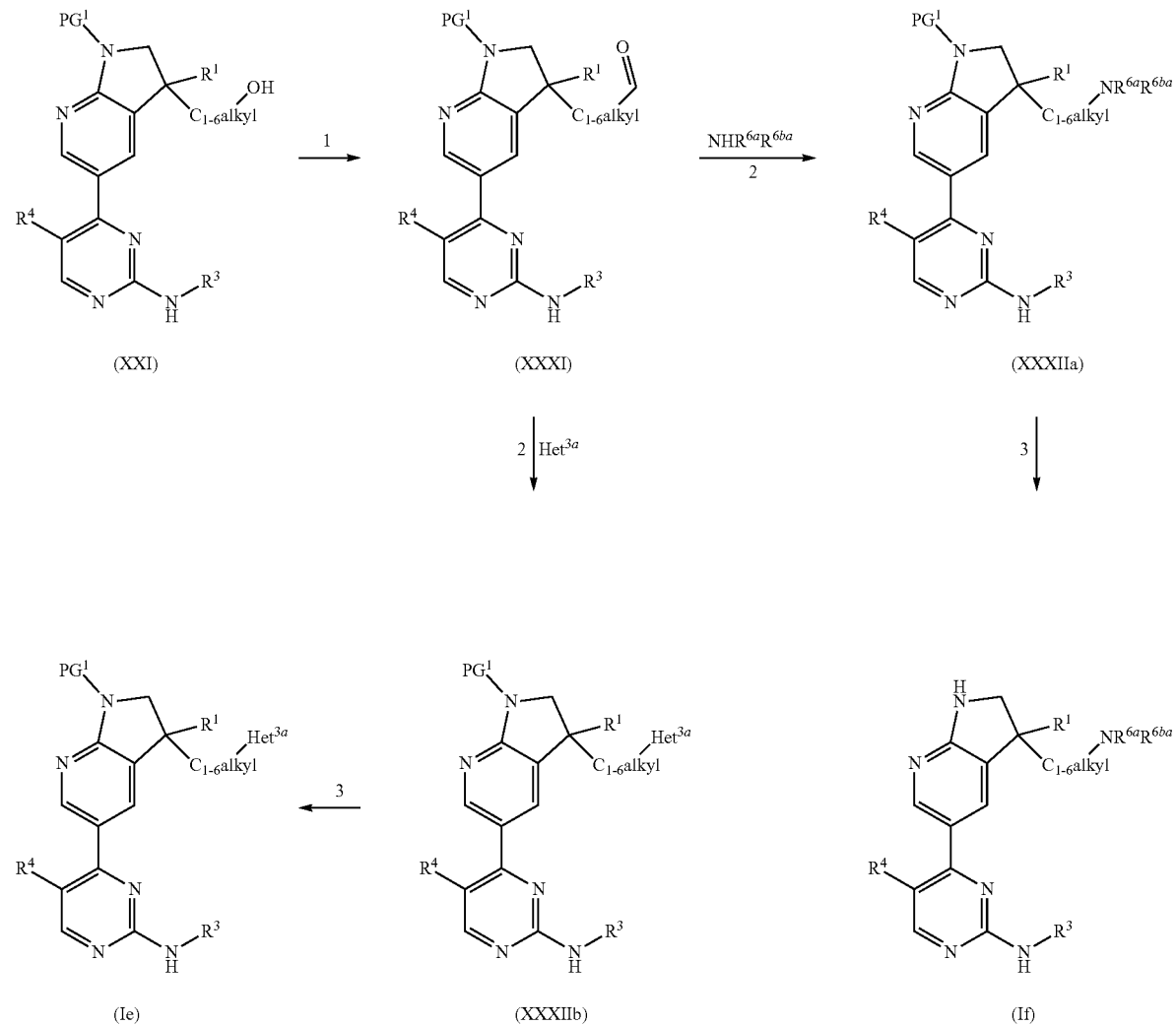

-continued

1: at a suitable temperature such as for example -78° C., in the presence of oxalyl chloride and dimethyl sulfoxide as reagents, a suitable base such as for example N,N-diisopropylethylamine, and a suitable solvent such as for example dichloromethane;
2: at a suitable temperature such as for example room temperature, in the presence of a suitable acid such as for example acetic acid, a suitable reducing agent such as for example sodium triacetoxyborohydride, and a suitable solvent such as for example dichloroethane;
3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $R^{2c}$ being $C_{1-6}$alkyl substituted with one $Het^{3a}$ or $-NR^{6a}R^{6b}$, wherein $R^{6b}$ is $R^{6ba}$ being H, $C_{1-4}$alkyl and $C_{3-6}$cycloalkyl, Y is $CR^4$, and wherein all the other variables are as defined according to the scope of the present invention, hereby named compounds of Formula (Ie) and Formula (If), can be prepared according to the following reaction Scheme 5. In Scheme 5 $PG^1$ represents a suitable protecting group, such as for example tert-(butoxycarbonyl). All other variables in Scheme 5 are defined according to the scope of the present invention.

In Scheme 5, the following reaction conditions apply:

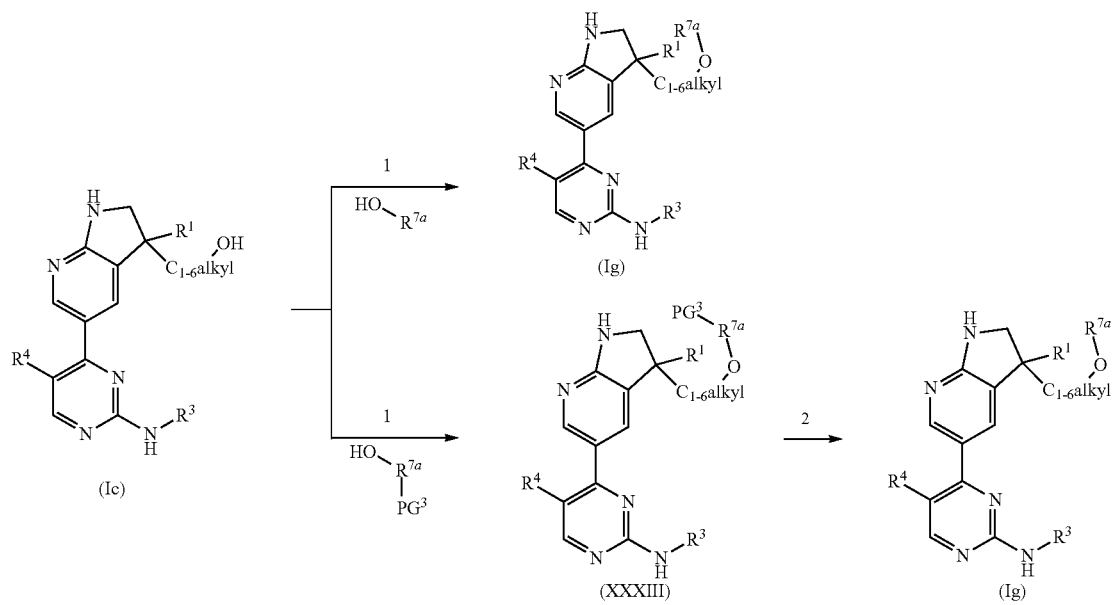

Scheme 6

1: at a suitable temperature such as for example room temperature, in the presence of a suitable coupling reagent such as for example 1-[bis(dimethylamino)methylene]-1H-1,2,3-triazolo[4,5-b]pyridinium 3-oxid hexafluorophosphate (HATU), in the presence of a suitable base as for example N,N-diisopropylethylamine, and a suitable solvent such as for example a mixture of tetrahydrofuran and dimethylformamide, and optionally followed by a deprotection step using a suitable acid such as for example hydrochloric acid in a suitable solvent such as for example 1,4-dioxane;
2: at a suitable temperature such as for example 0° C. or room temperature, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $C_{1-6}$alkyl substituted with one $OR^{7a}$, $R^{7a}$ being —C(=O)—$R^9$ or —(C=O)—CH(NH$_2$)—$C_{1-6}$alkyl-$Ar^1$), Y is $CR^4$, and wherein all the other variables are as defined according to the scope of the present invention, hereby named compounds of Formula (Ig), can be prepared according to the following reaction Scheme 6. In Scheme 6 $PG^3$ represents a suitable protecting group, such as for example a tert-(butoxycarbonyl), a tert-butyl or a benzyl. All other variables in Scheme 6 are defined according to the scope of the present invention.

In Scheme 6, the following reaction conditions apply:

Scheme 7

1: at a suitable temperature such as for example room temperature, in presence of a suitable desilylating agent such as for example tetra-n-butylammonium fluoride and a suitable solvent such as for example 2-methyltetrahydrofuran or tetrahydrofuran;

2: at a suitable temperature such as for example room temperature, in the presence of a suitable base such as for example sodium hydride, and a suitable solvent such as for example dimethylformamide;

3: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;

4: at a suitable temperature such as for example 80° C., in the presence of a suitable catalyst such as for example palladium tetrakis (Pd(PPh$_3$)$_4$), a suitable base such as for example sodium carbonate, and a suitable solvent such as for example 1,4-dioxane;

5: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BINAP), a suitable base such as for example cessium carbonate, and a suitable solvent such as for example 1,4-dioxane, optionally under microwave activation;

6: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $C_{1-6}$alkyl substituted with one $OR^{7b}$, $R^{7b}$ being $C_{1-4}$alkyl, Y is $CR^4$, and wherein all the other variables are as defined according to the scope of the present invention, hereby named compounds of Formula (Ih), can be prepared according to the following reaction Scheme 7. In Scheme 7 halo$^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl; W represents a leaving group, such as for example a methane sulfonate or toluene sulfonate or an halogen (Cl, Br or I). All other variables in Scheme 7 are defined according to the scope of the present invention.

In Scheme 7, the following reaction conditions apply:

Scheme 8

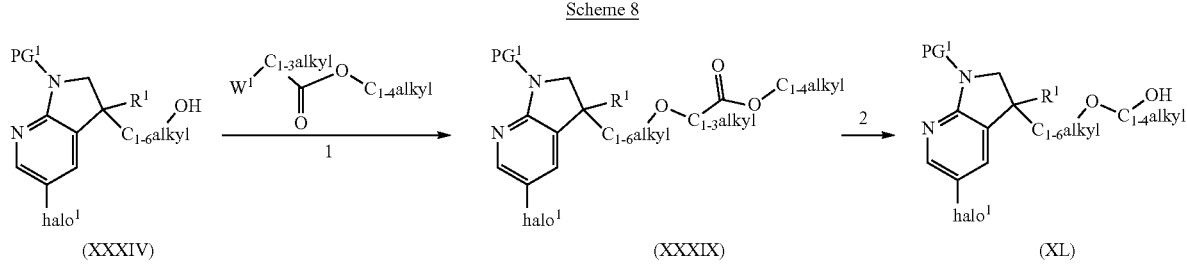

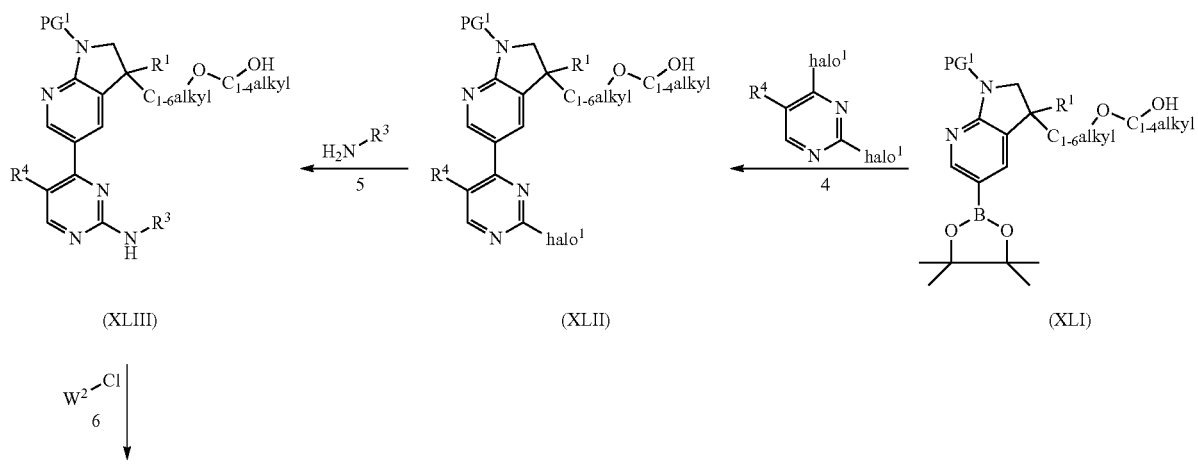

-continued

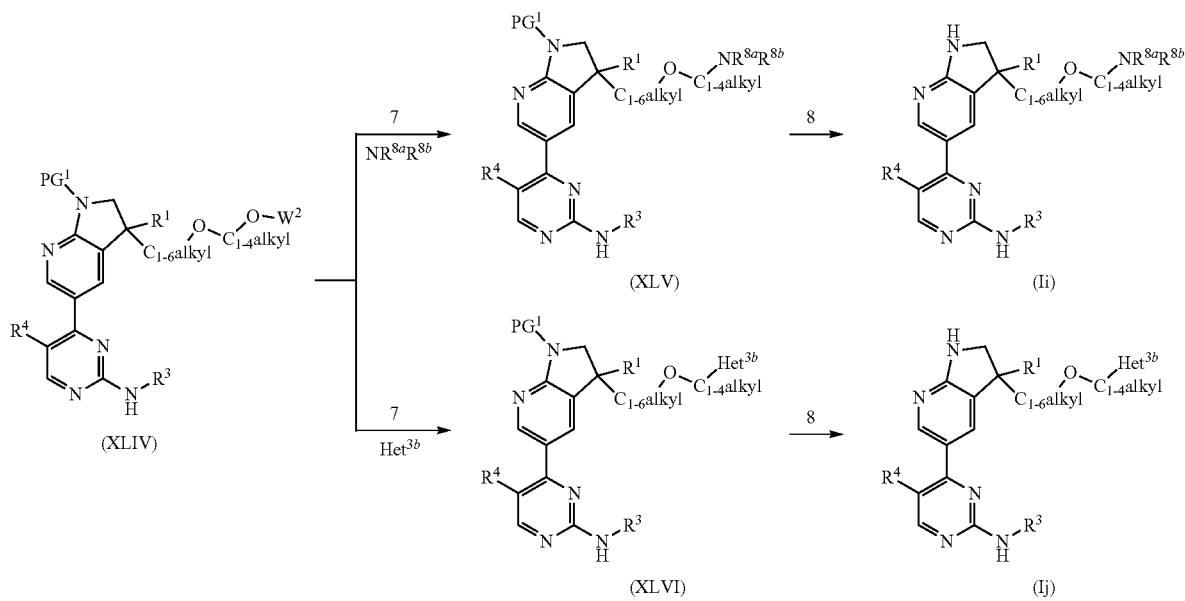

1: at a suitable temperature such as for example room temperature, in the presence of a suitable base as for example sodium hydride, and a suitable solvent such as for example dimethylformamide;
2: at a suitable temperature such as for example 55° C., in presence of reducing agent such as for example sodium borohydride and a suitable solvent such as for example a mixture of tetrahydrofuran and methanol;
3: at a suitable temperature such as for example 100° C., in the presence of a suitable catalyst such as for example [1,1′-bis(diphenylphosphino)ferrocene] dichloropalladium (II), optionally with dichloromethane complex, a suitable base such as for example potassium acetate and a suitable solvent such as for example 1,4-dioxane;
4: at a suitable temperature such as for example 85° C., in the presence of a suitable catalyst such as for example palladium tetrakis (Pd(PPh$_3$)$_4$), a suitable base such as for example sodium carbonate, and a suitable solvent such as for example 1,4-dioxane;
5: at a suitable temperature such as for example 120° C., in the presence of a suitable catalyst such as for example palladium acetate (Pd(OAc)$_2$), a suitable ligand such as for example 2,2′-bis(diphenylphosphino)-1,1′-binaphthyl (BINAP), a suitable base such as for example cesium carbonate, and a suitable solvent such as for example 1,4-dioxane, optionally under micorwave activation;
6: at a suitable temperature such as for example 5° C., in the presence of a suitable base such as for example triethylamine, and a suitable solvent such as for example dichloromethane;
7: at a suitable temperature such as for example 80° C., and a suitable solvent such as for example acetonitrile;
8: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $C_{1-6}$alkyl substituted with one $OR^{7c}$, $R^{7c}$ being $C_{1-6}$alkyl-$NR^{8a}R^{8b}$ or $C_{1-6}$alkyl-$Het^{3b}$, Y is $CR^4$, and wherein all the other variables are as defined according to the scope of the present invention, hereby named compounds of Formula (Ii) and Formula (Ij), can be prepared according to the following reaction Scheme 8. In Scheme 8 halo$^1$ is defined as Cl, Br or; $PG^1$ represents a suitable protecting group, such as for example tert-(butoxycarbonyl); $W^1$ represents a leaving group, such as for example a methane sulfonate or toluene sulfonate or an halogen (Cl, Br or I); $W^2$ represents a leaving group, such as for example a mesyl or a tosyl. All other variables in Scheme 8 are defined according to the scope of the present invention.

In Scheme 8, the following reaction conditions apply:

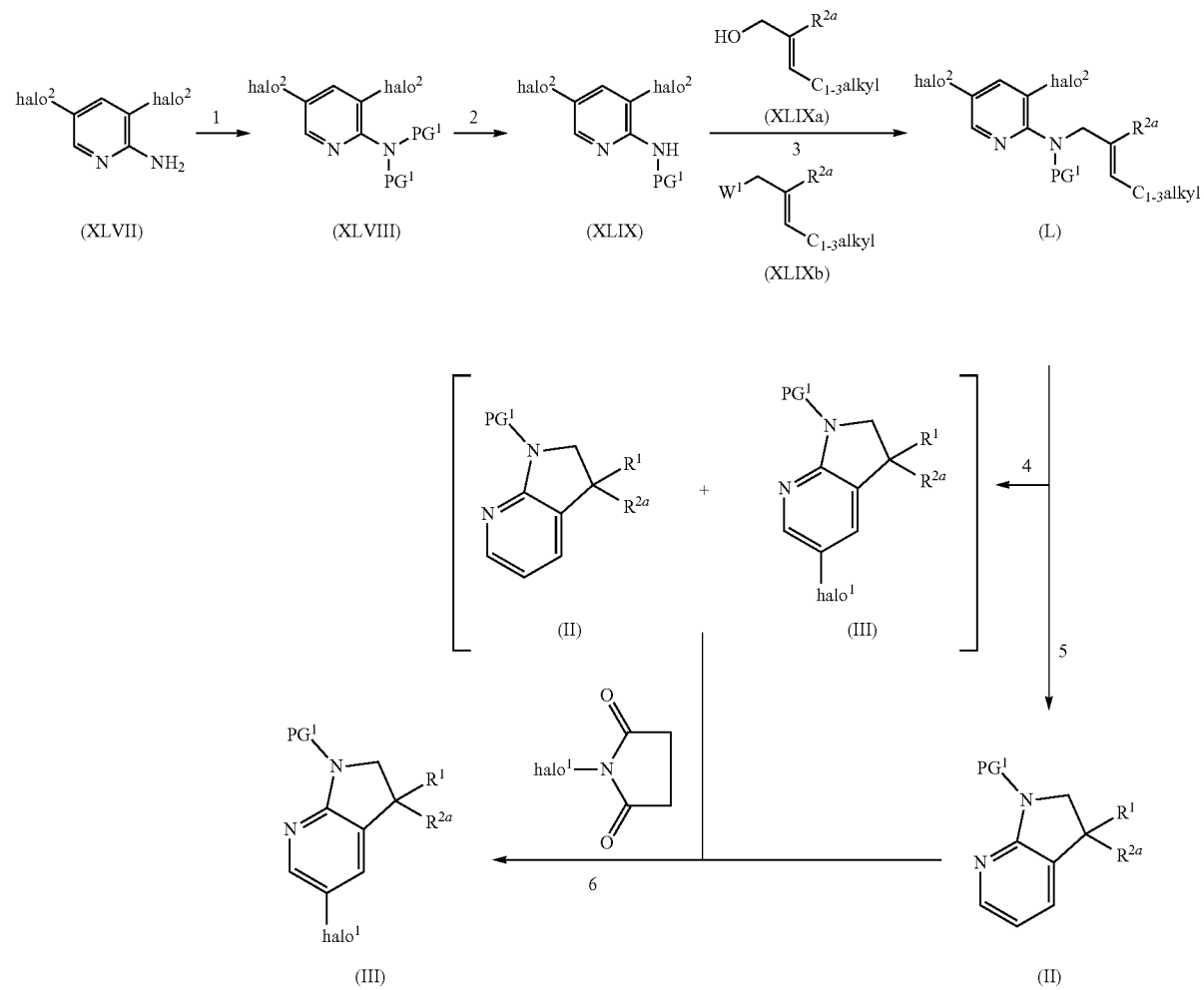

1: at a suitable temperature such as for example 45° C., in the presence of a suitable reagent such as for example di-tert-butyl dicarbonate, in the presence of a suitable catalyst such as for example 4-dimethylaminopyridine (DMAP), and a suitable solvent such as for example dichloromethane;
2: at a suitable temperature such as for example 65° C. and a suitable solvent such as for example methanol;
3: in case of (XLIXa), at a suitable temperature such as for example at room temperature, in the presence of tri-n-butylphosphine and 1,1′-(azodicarbonyl)piperidine and a suitable solvent such as for example 2-methyltetrahydrofuran;
In case of (XLIXb), at a suitable temperature such as for example 80° C., in the presence of a suitable base such as for example potassium carbonate, a suitable additive such as for example sodium iodide, in a suitable solvent such as for example acetonitrile;
4: at a suitable temperature such as for example 85° C., in the presence of sodium acetate, sodium formate and tetraethylammonium chloride, a suitable catalyst such as for example palladium acetate (Pd(OAc)$_2$), and a suitable solvent such as for example dimethylformamide;
5: at a suitable temperature such as for example 60° C., in the presence of sodium acetate, sodium formate dehydrate and tetraethylammonium chloride, a suitable catalyst such as for example [1,1′-bis(diphenylphosphino) ferrocene] palladium, (II) chloride optionally with dichloromethane complex, and a suitable solvent such as for example dimethyformamide;
6: at a suitable temperature such as for example 40° C., in the presence of N-halogeno-succinimide, and a suitable solvent such as for example acetonitrile. Alternatively, in the presence of a suitable reagent such as for example 1,3-dibromo-5,5-dimethylhydantoin, in a suitable solvent such as for example acetonitrile.

In general, intermediates of Formula (II) and (III) wherein $R^2$ is $R^{2a}$ being $C_{1-6}$alkyl, and wherein all the other variables are as defined according to the scope of the present invention, hereby named compounds of Formula (II) and (III), can be prepared according to the following reaction Scheme 9. In Scheme 9 halo$^1$ is defined as Cl, Br, I; halo$^2$ is defined as Cl, Br, I; PG$^1$ represents a suitable protecting group, such as for example tert-(butoxycarbonyl); W$^1$ represents a leaving group, such as for example a methane sulfonate or toluene sulfonate or an halogen (Cl, Br, or I). All other variables in Scheme 9 are defined according to the scope of the present invention.

In Scheme 9, the following reaction conditions apply:

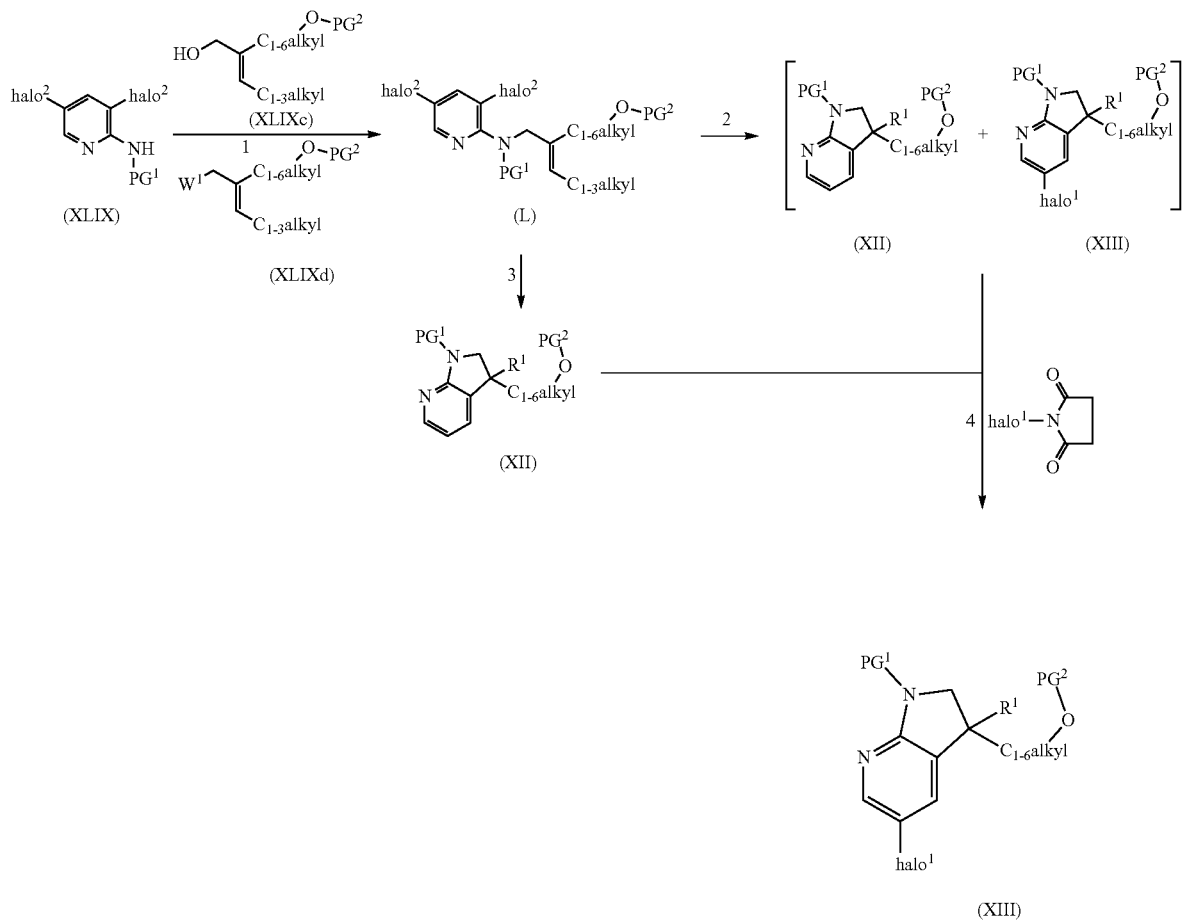

Scheme 10

1: in case of (XLIXc), at a suitable temperature such as for example at room temperature, in the presence of tri-n-butylphosphine and 1,1′-(azodicarbonyl)piperidine and a suitable solvent such as for example 2-methyltetrahydrofuran; In case of (XLIXd), at a suitable temperature such as for example 80° C., in the presence of a suitable base such as for example potassium carbonate, a suitable additive such as for example sodium iodide, in a suitable solvent such as for example acetonitrile;
2: at a suitable temperature such as for example 85° C., in the presence of sodium acetate, sodium formate and tetraethylammonium chloride, a suitable catalyst such as for example palladium acetate (Pd(OAc)$_2$), and a suitable solvent such as for example diemthylformamide;
3: at a suitable temperature such as for example 60° C., in the presence of sodium acetate, sodium formate dehydrate and tetraethylammonium chloride, a suitable catalyst such as for example [1,1′-bis(diphenylphosphino) ferrocene] palladium, (II) chloride optionally with dichloromethane complex, and a suitable solvent such as for example dimethylformamide;
4: at a suitable temperature such as for example 40° C., in the presence of N-halogenosuccinimide, and a suitable solvent such as for example acetonitrile. Alternatively, in the presence of a suitable reagent such as for example 1,3-dibromo-5,5-dimethyl-hydantoin, in a suitable solvent such as for example acetonitrile.

In general, intermediates of Formula (XII) and (XII) wherein $R^2$ is $R^{2b}$ being $C_{1-6}$alkyl substituted with one OH, and wherein all the other variables are as defined according to the scope of the present invention, hereby named compounds of Formula (XII) and (XIII), can be prepared according to the following reaction Scheme 10. In Scheme 10 halo[1] is defined as Cl, Br, I; halo[2] is defined as Cl, Br, I; $PG^1$ represents a suitable protecting group, such as for example tert-(butoxycarbonyl) and $PG^2$ represents a suitable protecting group, such as for example tert-butyl-dimethylsilyl. All other variables in Scheme 10 are defined according to the scope of the present invention.

In Scheme 10, the following reaction conditions apply:

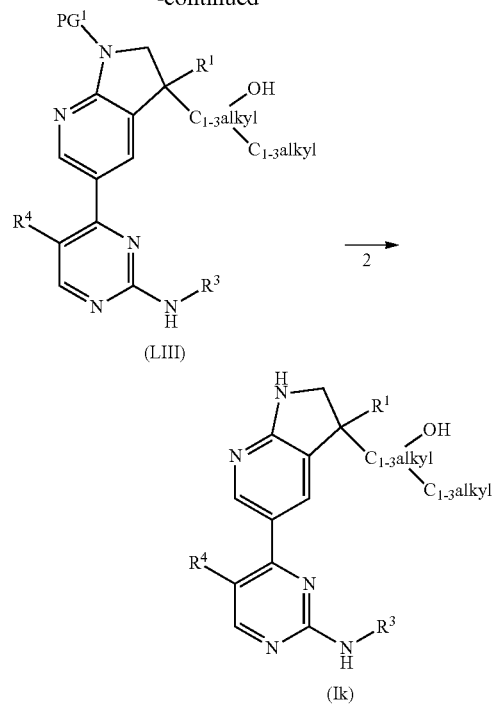

1: at a suitable temperature such as for example at room temperature, and a suitable solvent such as for example tetrahydrofuran;
2: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a ssuitable time such as for example 3 hours.

In general, compounds of Formula (I) wherein $R^2$ is as shown in the scheme 11, Y is $CR^4$, and wherein all the other variables are as defined according to the scope of the present invention, hereby named compounds of Formula (Ik) can be prepared according to the following reaction Scheme 11. In Scheme 11 $PG^1$ represents a suitable protecting group, such as for example tert-(butoxycarbonyl). All other variables in Scheme 11 are defined according to the scope of the present invention.

In Scheme 11, the following reaction conditions apply:

Scheme 11

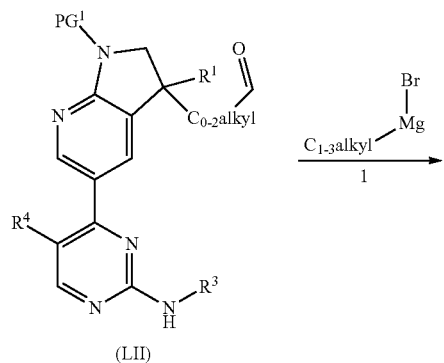

Scheme 12

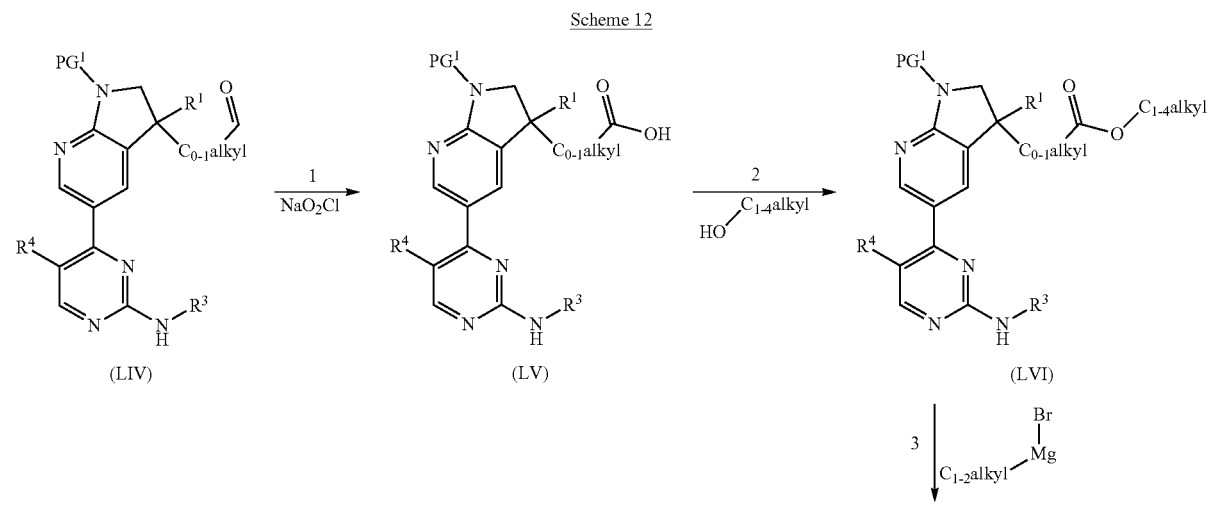

-continued

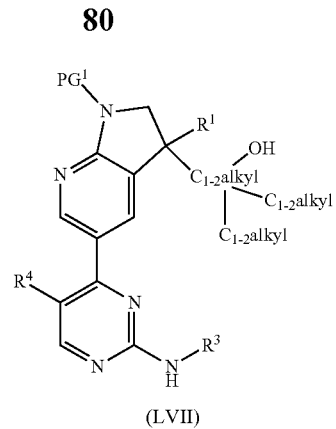

(LVII)

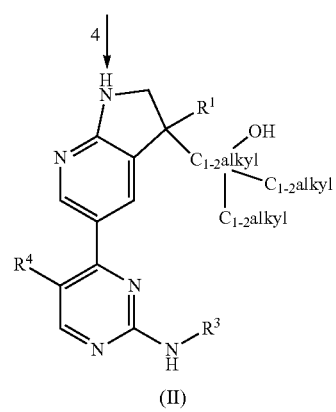

(II)

1: at a suitable temperature such as for example at room temperature, in the presence of tert-butyl alcohol, 2-methyl-2-butene, sodium dihydrogenophosphate and distilled water;
2: at a suitable temperature such as for exmaple at room temperature, in presence of 1-[bis(dimethylamino)methylene]-1H-1,2,3-triazolo[4,5-b]pyridinium 3-ocid hexafluorophosphate (HATU) and dimethyl aminopyridine (DMAP), a suitable base such as for example DIPEA and a suitable solvent such as for example dimethylformamide;
3: at a suitable temperature such as for example at room temperature, and a suitable solvent such as for example tetrahydrofuran;
4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate, or 1,4-dioxane or alternatively in the presence of silica in a suitable solvent such as for example toluene at a suitable temperature such as for example 125° C. and a suitable time such as form example 3 hours.

In general, compounds of Formula (I) wherein $R^2$ is as shown in the scheme 12, Y is $CR^4$, and wherein all the other variables are as defined according to the scope of the present invention, hereby named compounds of Formula (II) can be prepared according to the following reaction Scheme 12. In Scheme 12 $PG^1$ represents a suitable protecting group, such as for example tert-(butoxycarbonyl). All other variables in Scheme 12 are defined according to the scope of the present invention.

In Scheme 12, the following reaction conditions apply:

Scheme 13

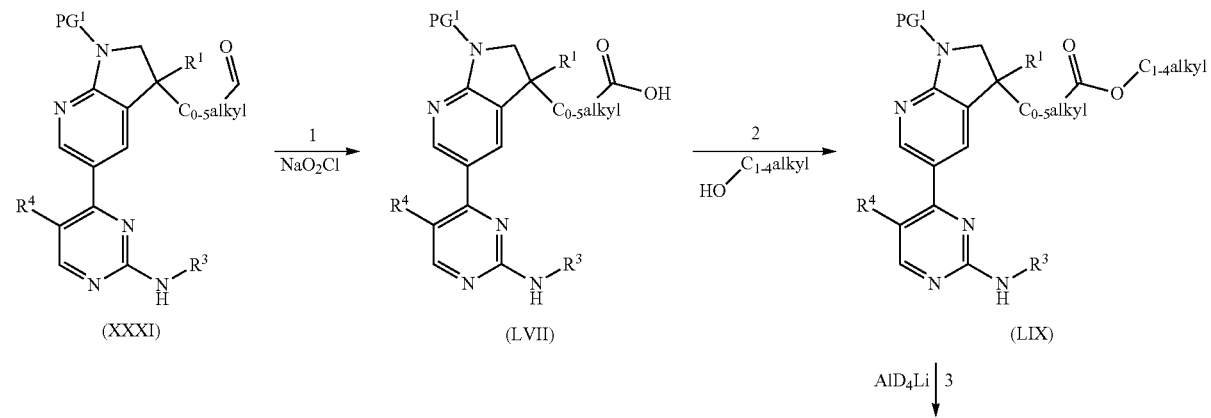

-continued

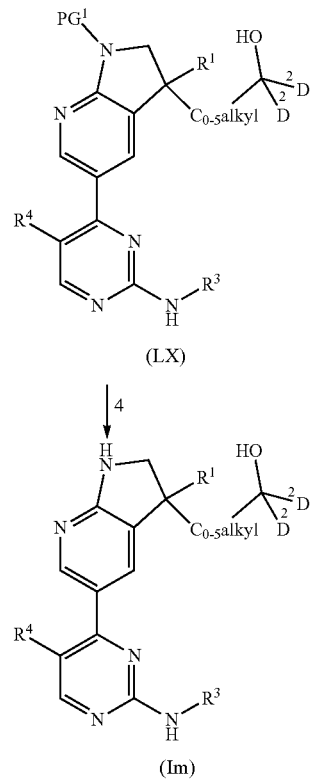

(LX)

↓ 4

(Im)

1: at a suitable temperature such as for example at room temperature, in the presence of tert-butyl alcohol, 2-methyl-2-butene, sodium dihydrogenophosphate and distilled water;
2: at a suitable temperature such as for exmaple at room temperature, in presence of 1-[bis(dimethylamino)methylene]-1H-1,2,3-triazolo[4,5-b]pyridinium 3-ocid hexafluorophosphate (HATU) and dimethyl aminopyridine (DMAP), a suitable base such as for example DIPEA and a suitable solvent such as for example dimethylformamide;
3: at a suitable temperature such as for example 0° C., and a suitable solvent such as for example tetrahydrofuran ("aLD$_4$Li" means lithium aluminium deuteride);
4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate, or 1,4-dioxane or alternatively in the presence of silica in a suitable solvent such as for example toluene at a suitable temperature such as for example 125° C. and a suitable time such as form example 3 hours.

In general, compounds of Formula (I) wherein R$^2$ is as shown in the scheme 13, Y is CR$^4$, and wherein all the other variables are as defined according to the scope of the present invention, hereby named compounds of Formula (Im) can be prepared according to the following reaction Scheme 13. In Scheme 13 PG$^1$ represents a suitable protecting group, such as for example tert-(butoxycarbonyl). All other variables in Scheme 13 are defined according to the scope of the present invention.

In Scheme 13, the following reaction conditions apply:

Scheme 14

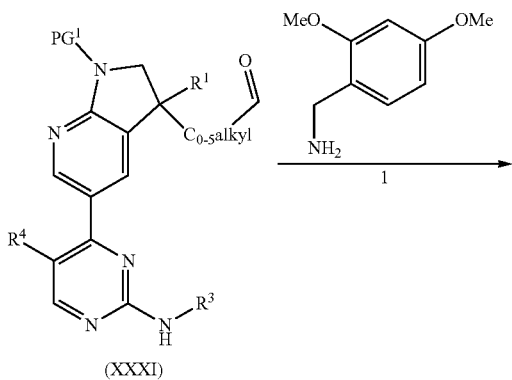

(XXXI)

-continued

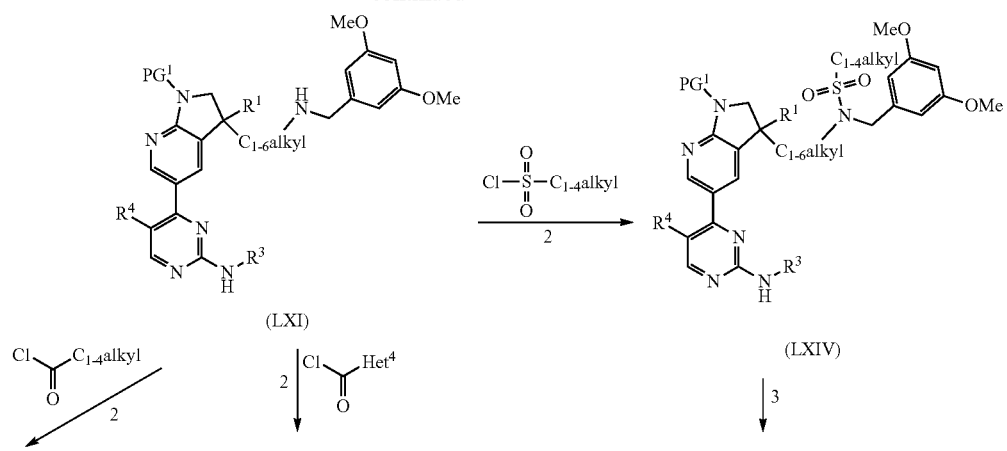

(LXI)

(LXIV)

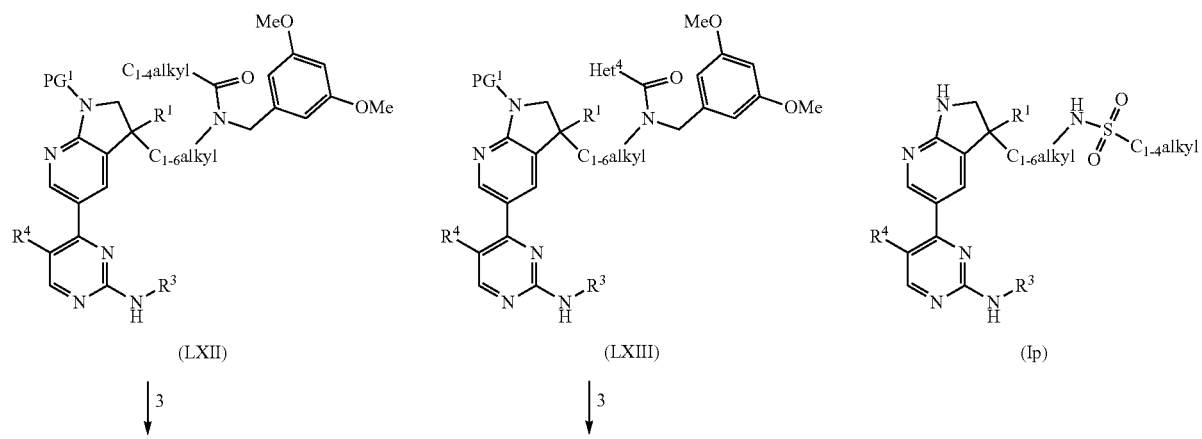

(LXII)

(LXIII)

(Ip)

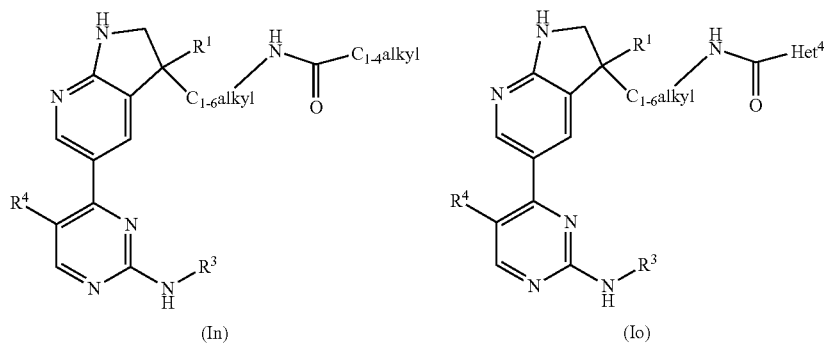

(In)

(Io)

1: at a suitable temperature such as for example at room temperature, in the presence of a suitable acid such as for example acetic acid, in the presence of a suitable reducing agent such as for example sodium triacetoxyborohydride, in a suitable solvent such as for example dichloroethane;
2: at a suitable temperature such as for example at room temperature, in the presence of a suitable base such as for example triethylamine, in a suitable solvent such as for example tetrahydrofuran;
3: at a suitable temperature such as for example at room temperature, in the presence of a suitable acid such as for example trifluoroacetic acid, in a suitable solvent such as for example dichloromethane.

In general, compounds of Formula (I) wherein $R^2$ is being $C_{1-6}$alkyl substituted with one Het$^1$ or —NR$^{6a}$R$^{6b}$, wherein R$^{6b}$ is being H, R$^6$ is being —C(=O)—C$_{1-4}$alkyl; —C(=O)—Het$^4$; —S(=O)$_2$—C$_{1-4}$alkyl, Y is CR$^4$, and wherein all the other variables are as defined according to the scope of the present invention, hereby named compounds of Formula (In), Formula (Io) and Formula (Ip), can be prepared according to the following reaction Scheme 14. In Scheme 14, PG$^1$ represents a suitable protecting group, such as for example tert-(butoxycarbonyl). All other variables in Scheme 14 are defined according to the scope of the present invention.

In Scheme 14, the following reaction conditions apply:

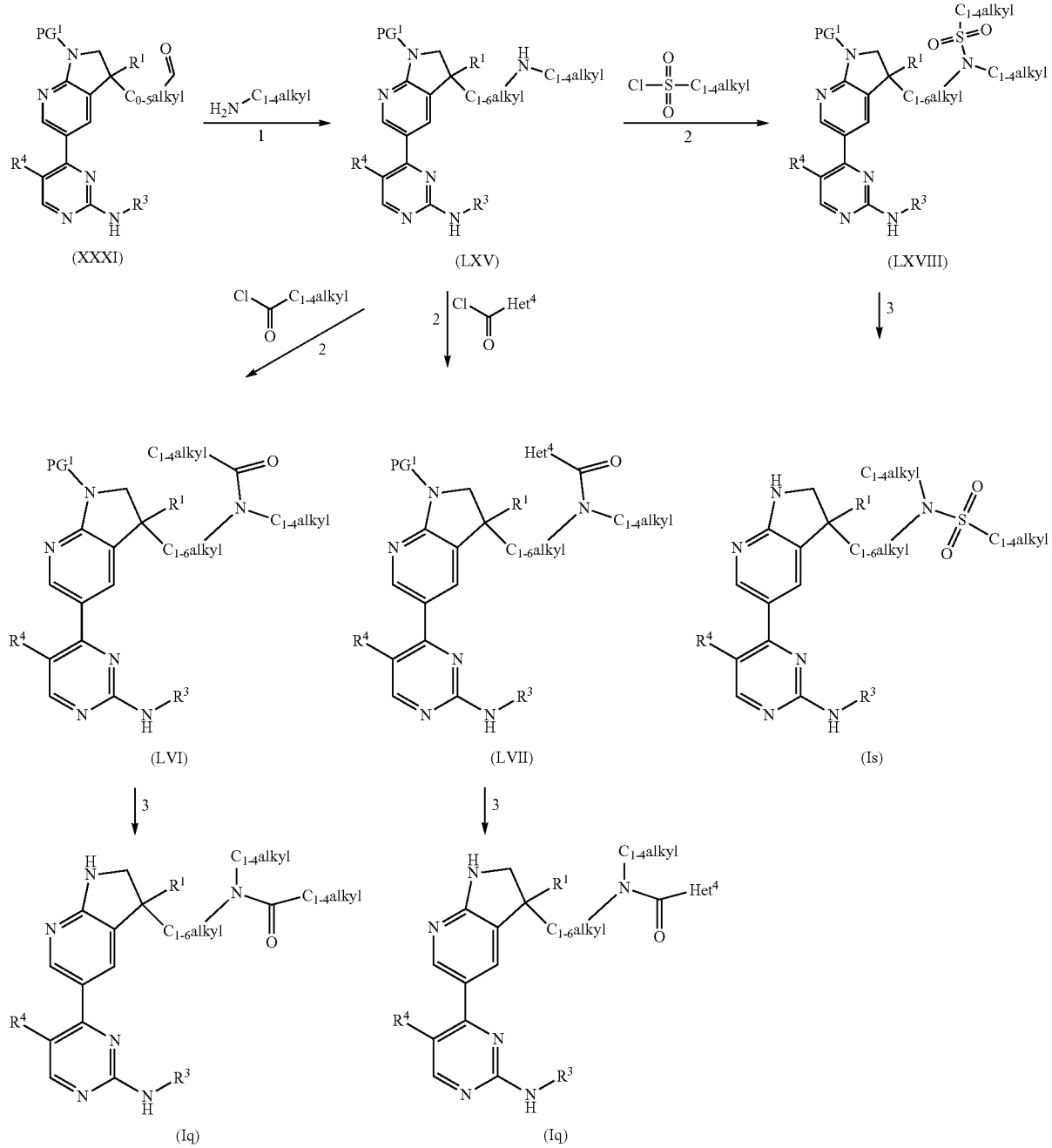

Scheme 15

1: at a suitable temperature such as for example at room temperature, in the presence of a suitable acid such as for example acetic acid, in the presence of a suitable reducing agent such as for example sodium triacetoxyborohydride, in a suitable solvent such as for example dichloroethane;
2: at a suitable temperature such as for example at room temperature, in the presence of a suitable base such as for example triethylamine, in a suitable solvent such as for example tetrahydrofuran;
3: at a suitable temperature such as for example at room temperature, in the presence of a suitable acid such as for example trifluoroacetic acid, in a suitable solvent such as for example dichloromethane.

In general, compounds of Formula (I) wherein $R^2$ is being $C_{1-6}$alkyl substituted with one $Het^{3a}$ or $-NR^{6a}R^{6b}$, wherein $R^{6a}$ is being $C_{1-4}$alkyl, $R^{6b}$ is being $-C(=O)-C_{1-4}$alkyl; $-C(=O)-Het^4$; $-S(=O)_2-C_{1-4}$alkyl, Y is $CR^4$, and wherein all the other variables are as defined according to the scope of the present invention, hereby named compounds of Formula (Iq), Formula (Ir) and Formula (Is), can be prepared according to the following reaction Scheme 15. In Scheme 15, $PG^1$ represents a suitable protecting group, such as for example tert-(butoxycarbonyl). All other variables in Scheme 15 are defined according to the scope of the present invention.

In Scheme 15, the following reaction conditions apply:

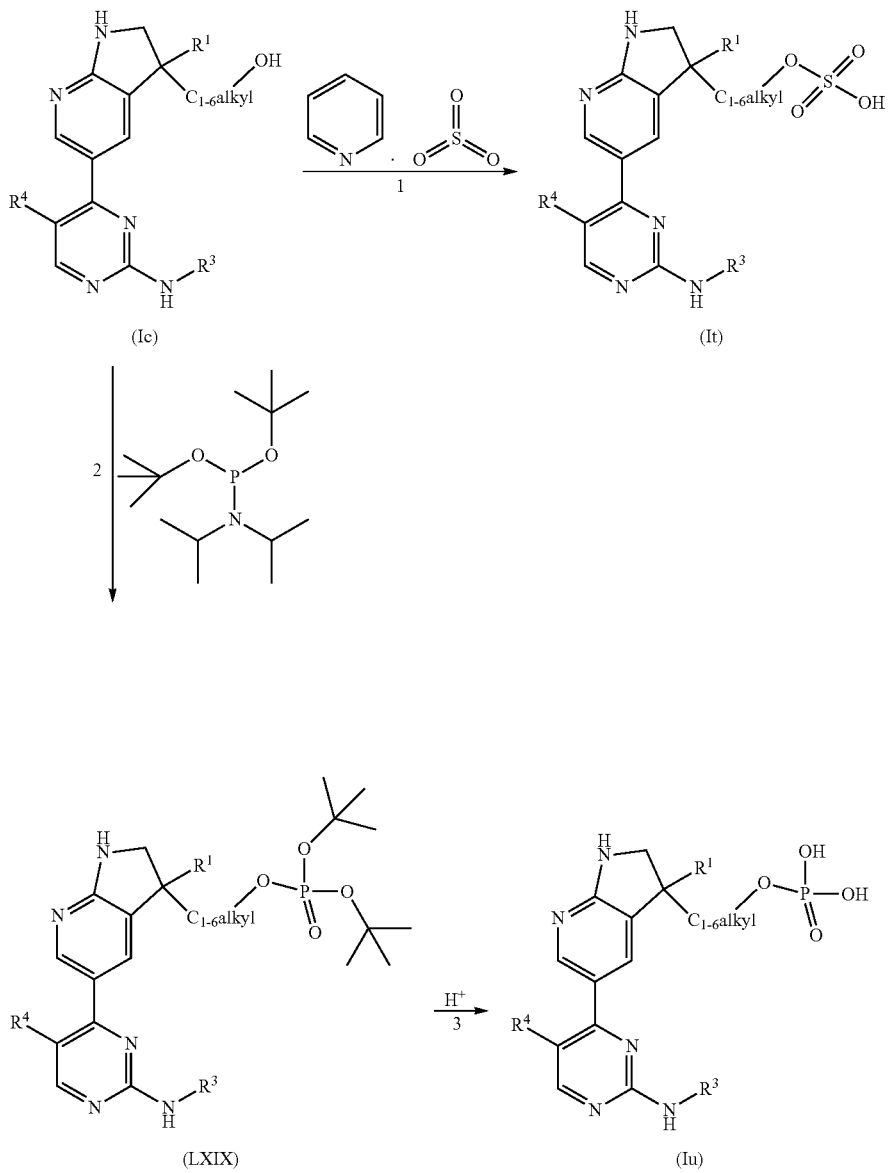

Scheme 16

1: at a suitable temperature such as for example at room temperature, in a suitable solvent such as for example tetrahydrofuran, in the presence of a suitable base such as for example sodium hydroxide;
2: in the presence of a suitable reagent such as for example tetrazole, in the presence of a suitable oxidixing agent such as for example meta-chloroperbenzoic acid, in a suitable solvent such as for example acetonitrile;
3: at a suitable temperature such as for example at room temperature, in the presence of a suitable acid such as for example hydrochloric acid, in a suitable solvent such as for example acetonitrile.

In general compounds of Formula (I) wherein $R^2$ is $C_{1-6}$alkyl substituted with one $OR^{7d}$, $R^{7d}$ being —S(=O)—OH or —P(=O)—(OH)$_2$, Y is $CR^4$, and wherein all the other variables areas defined according to the scope of the present invention, hereby named compounds of Formula (It) and Formula (Iu), can be prepared according to the following reaction Scheme 16. All other variables in Scheme 16 are defined according to the scope of the present invention.

In Scheme 16, the following reaction conditions apply:

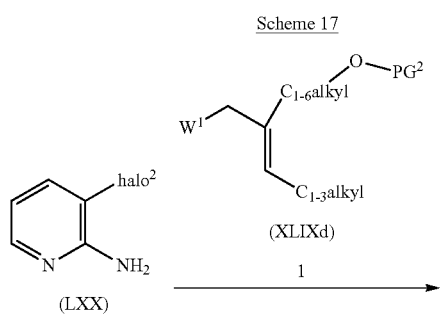

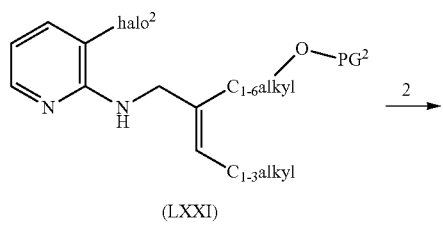

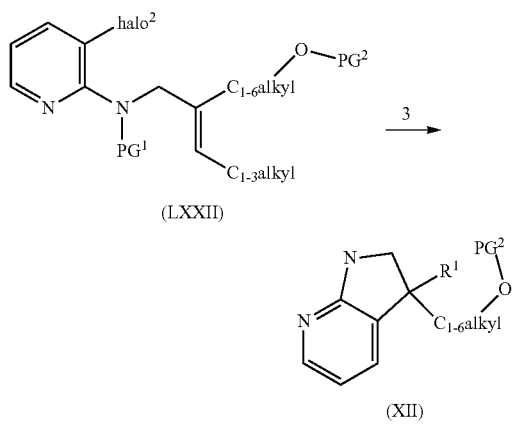

1: At a suitable temperature range between -5° C. and 5° C., in the presence of a suitable base such as for example sodium tert-butoxide in a suitable solvent such as for example tetrahydrofuran;
2: at a suitable temperature ranged between 65 and 70° C., in the presence of a suitable reagent such as for example di-tert-butyl dicarbonate, in the presence of a suitable catalyst such as for example 4-dimethylaminopyridine (DMAP), and a suitable solvent such as for example tetrahydrofuran;
3: at a suitable temperature ranged between 45 and 50° C., in the presence of sodium acetate, sodium formate dehydrate and tetraethylammonium chloride, a suitable catalyst such as for example palladium acetate or [1,1'-bis(diphenylphosphino)ferrocene]palladium, (II) chloride optionally with dichloromethane complex, and a suitable solvent such as for example dimethylformamide.

In general, intermediates of Formula (XII) wherein all the variables are as defined according to the scope of the present invention can be prepared according to the following reaction Scheme 17.

In Scheme 17, the following reaction conditions apply:

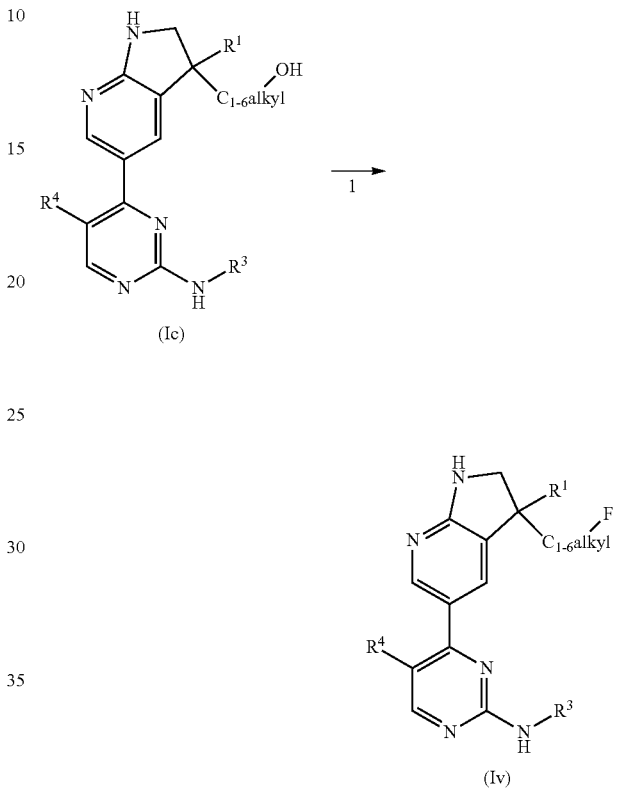

1: in the presence of a suitable fluorinating reagent such as for example diethylaminosulfur trifluoride, a suitable solvent such as for example dichloromethane, at a suitable temperature such as for example room temperature.

In general, compounds of Formula (I) wherein $R^2$ is $C_{1-6}$alkyl substituted with one $R^5$, $R^5$ being a fluorine, Y is $CR^4$, and wherein all the other variables are as defined according to the scope of the present invention, hereby named compounds of Formula (Iv), can be prepared according to the following reaction Scheme 18. All other variables in Scheme 18 are defined according to the scope of the present invention.

In Scheme 18, the following reaction conditions apply:

Scheme 19

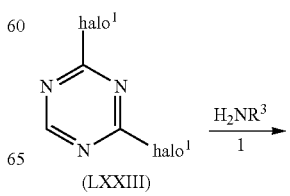

-continued

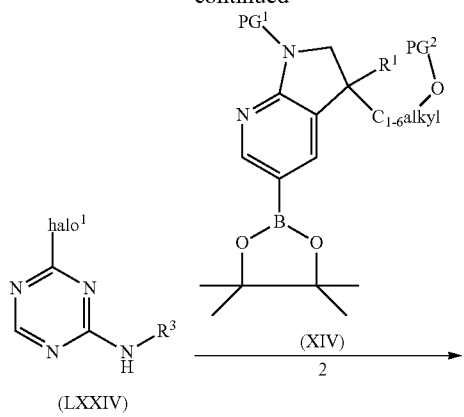

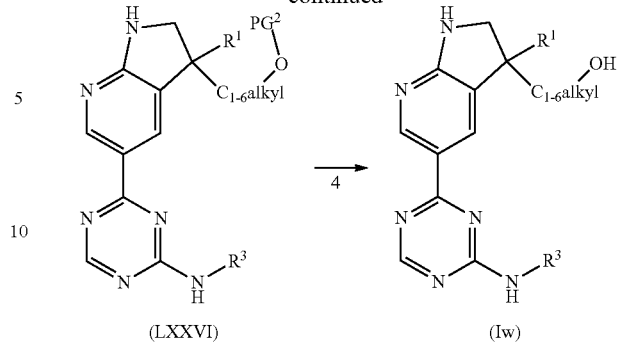

1: in the presence of a suitable base such as for example diisopropylethylamine, in a suitable solvent such as for example acetonitrile;
2: in the presence of a suitable catalyst such as for example [1,1'-bis(diphenylphosphino)ferrocene] dichloropalladium (II), optionally with dichloromethane complex, a suitable base such as an aqueous solution of hydrogenocarbonate at a suitable temperature such as 80° C.;
3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours;
4: at a suitable temperature such as for example room temperature, in presence of a suitable desilylating agent such as for example tetra-n-butylammonium fluoride and a suitable solvent such as for example 2-methyltetrahydrofuran or tetrahydrofuran.

In general, compounds of Formula (I) wherein $R^2$ is $R^{2b}$ being $C_{1-6}$alkyl substituted with one OH, Y is N, and wherein all the other variables are as defined according to the scope of the present invention, hereby named compounds of Formula (Iw), can be prepared according to the following reaction Scheme 19. In Scheme 19, $halo^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 19 are defined according to the scope of the present invention.

In Scheme 19, the following reaction conditions apply:

Scheme 20

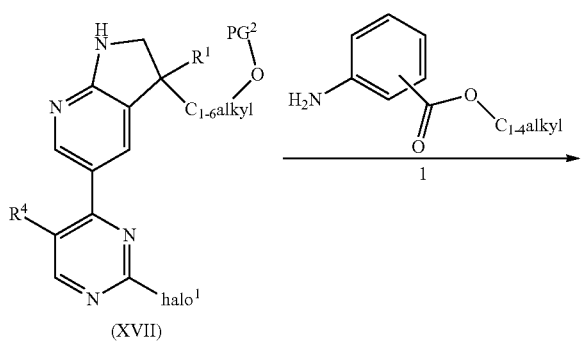

-continued

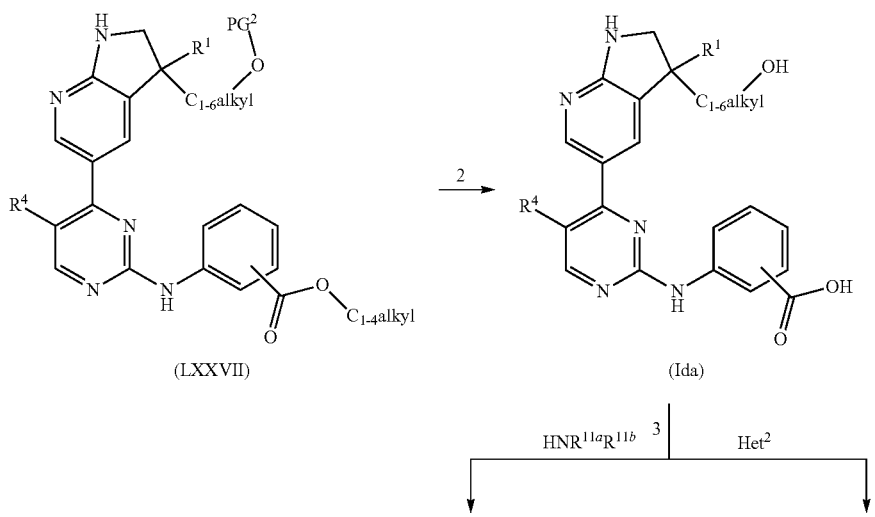

(LXXVII) → (Ida)

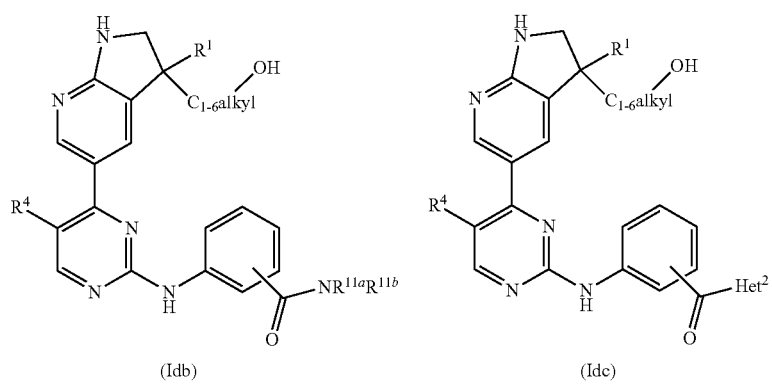

(Idb) (Idc)

1: at a suitable temperature such as for example 120° C., in the presence of a suitable catalyst such as for example palladium acetate (Pd(OAc)$_2$), a suitable ligand such as for example 2,2′-bis(diphenylphosphino)-1,1′-binaphthyl (BINAP), a suitable base such as for example cesium carbonate, and a suitable solvent such as for example 1,4-dioxane, optionally under microwave activation;

2: at a suitable temperature such as for example 60° C., in presence of a suitable base such as for example lithium hydroxide, and a suitable solvent such as for example a mixture of tetrahydrofuran and water;

3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethlamine, and a suitable solvent such as for example dimethylformamide or dichloromethane.

In general, compounds of Formula (I) wherein $R^2$ is $R^{2b}$ being $C_{1-6}$alkyl substituted with one OH, $R^3$ is phenyl substituted with —C(=O)—$R^{10}$ and optionally substituted with other substituents according to the scope of the present invention, Y is $CR^4$, and wherein all the other variables are as defined according to the scope of the present invention, hereby named compounds of Formula (Ida), (Idb) and (Idc) can be prepared according to the following reaction Scheme 20. In Scheme 20, halo$^1$ is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 20 are defined according to the scope of the present invention.

In Scheme 20, the following reaction conditions apply:

Scheme 21

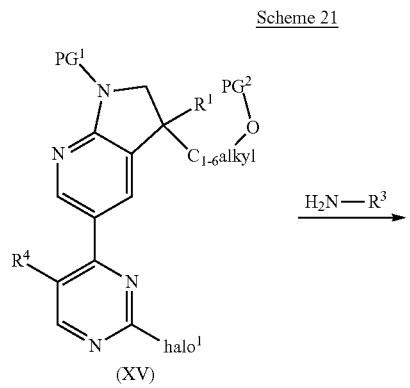

(XV)

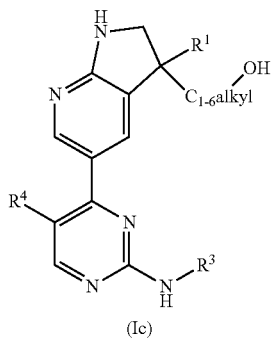

(Ic)

1: at a suitable temperature such as for example 90° C., in the presence of a suitable acid such as for example p-toluenesulfonic acid and a suitable solvent such as for example 1,4-dioxane.

In general, compounds of Formula (I) wherein $R^2$ is $R^{2b}$ being $C_{1-6}$alkyl substituted with one OH, Y is $CR^4$, and wherein all the other variables are as defined according to the scope of the present invention, hereby named compounds of Formula (Ic), can be prepared according to the following reaction Scheme 21. All other variables in Scheme 21 are defined according to the scope of the present invention or as above.

In scheme 21, the following conditions apply:

Scheme 22

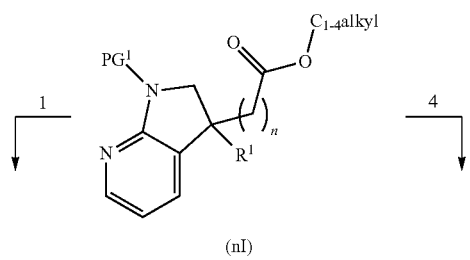

(nI)

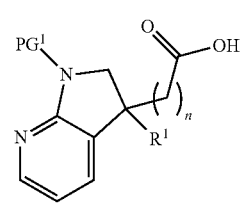

(nII)

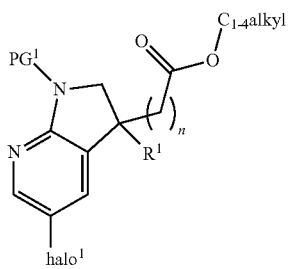

(nVIII)

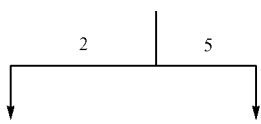

-continued

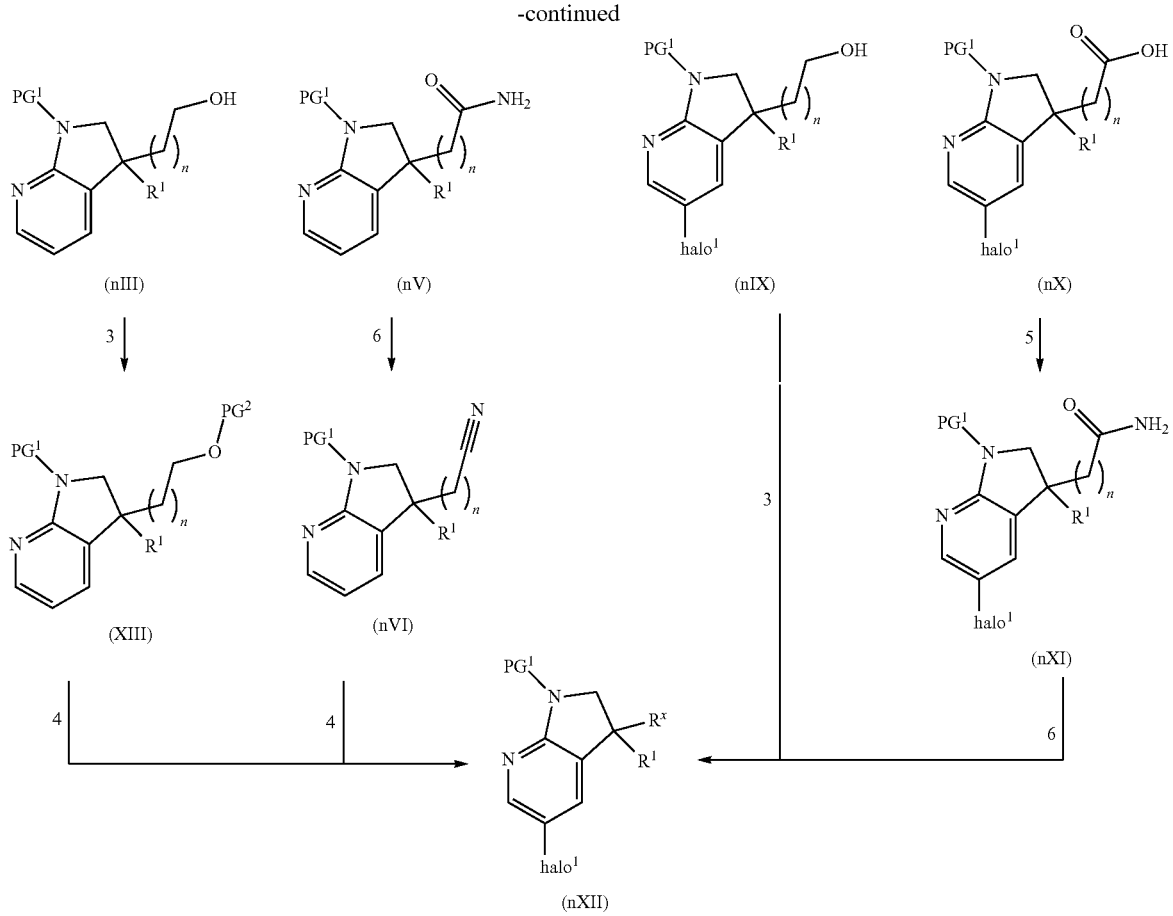

1: at a suitable temperature such as for example room temperature, in the presence of a suitable reagent such as for example lithium hydroxide, and a suitable solvent such as for example a 1/1 mixture of THF and water, and a suitable time such as for example 90 minutes or 4 hours;
2: at a suitable temperature such as for example 0° C., in the presence of a suitable reagent such as for example ethyl chloroformate, a suitable base such as for example TEA and a suitable solvent such as for example THF, followed by the the addition of a suitable reagant such as for example sodium borohydride and a suitable time such as for example 30 minutes;
3: at a suitable temperature such for example 0° C. to room temperature, in the presence of a suitable reagent such as for example tert-butyldimethylsilyl chloride, suitable bases such as for example triethylamine and DMAP, and a suitable solvent such as for example dichloromethane, and a suitable time such as for exmaple between 2 and 20 hours;
4: at a suitable temperature such as for example 40° C., in the presence of a suitable reagent such as for example NBS, and a suitable solvent such as for example acetonitrile, and a suitable time such as for example 16 hours;
5: at a suitable temperature such as for example room temperature, in the presence of suitable reagents such as for example HATU and a solution of ammonia in methanol, a suitable base such as for example DIPEA, a suitable solvent such as for example dichloromethane, and a suitable time such as for example 4 or 16 hours;
6: at a suitable temperature such as for example 0° C., in the presence of suitable reagents such as for example imidazole and POCl₃, a suitable solvent/base such as for example pyridine, a suitable co-solvent such as for example dichloromethane and a suitable time such as for example 1 hour;
7: at a suitable temperature such as for example room temperature up to 50° C., in the presence of a suitable reagent such as for example sodium borohydride and a suitable solvent such as for example a 3/1 mixture of THF and methanol, and a suitable time such as for example between 4 and 24 hours.

In general, intermediates of Formula (nXII) wherein $R^2$ is $R^x$ being the options illustrated in Scheme 22, can be prepared according to the following reaction Scheme 22. In Scheme 22 halo¹ is defined as Cl, Br or I; and PG¹ represents a suitable protecting group, such as for example tert-(butoxycarbonyl). The value of 'n' (indicating the number of CH₂ groups) is determined by the limits of the scope. All other variables in Scheme 1 are defined according to the scope of the present invention or as defined before.

The starting material (nI) in Scheme 22, can be prepared by standard synthetic processes commonly used by those skilled in the art. For example, it can be prepared by analogous methodology to that illustrated in Schemes 10 and 17. For the preparation of (nI), alkylation of the aniline prior to Heck cyclization was typically performed using a base such as for Example NaH, in a solvent such as typically DMF, at a temperature typically between 0° C. to room temperature.

A skilled person will realize that intermediates of Formula (nXII) as obtained according to Scheme 22, can be further reacted according to reaction protocols as described in other Schemes such as for example Scheme 1 or Scheme 3.

In Scheme 22, the following reaction conditions apply:

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

Pharmacology

It has been found that the compounds of the present invention inhibit NF-κB-inducing kinase (NIK—also known as MAP3K14). Some of the compounds of the present invention may undergo metabolism to a more active form in vivo (prodrugs). Therefore the compounds according to the invention and the pharmaceutical compositions comprising such compounds may be useful for treating or preventing diseases such as cancer, inflammatory disorders, metabolic disorders including obesity and diabetes, and autoimmune disorders. In particular, the compounds according to the present invention and the pharmaceutical compositions thereof may be useful in the treatment of a haematological malignancy or solid tumour. In a specific embodiment said haematological malignancy is selected from the group consisting of multiple myeloma, non-Hodgkin's lymphoma, Hodgkin lymphoma, T-cell leukaemia, mucosa-associated lymphoid tissue lymphoma, diffuse large B-cell lymphoma and mantle cell lymphoma, in a particular embodiment mantle cell lymphoma. In another specific embodiment of the present invention, the solid tumour is selected from the group consisting of pancreatic cancer, breast cancer, melanoma and non-small cell lung cancer.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma, mantle cell lymphoma), T-cell leukaemia/lymphoma, Hodgkin's lymphoma, non-Hodgkin's lymphoma, hairy cell lymphoma, or Burkett's lymphoma: a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma, teratocarcinoma, osteosarcoma; xeroderma pigmentosum; keratoctanthoma; thyroid follicular cancer; or Kaposi's sarcoma.

Particular examples of cancers which may be treated (or inhibited) include B-cell malignancies, such as multiple myeloma, hodgkins lymphoma, mantle cell lymphoma, diffuse large B-cell lymphoma or chronic lymphocytic leukemia, with mutations in the non-canonical NFkB signalling pathway (eg in NIK (MAP3K14), TRAF3, TRAF2, BIRC2 or BIRC3 genes).

Hence, the invention relates to compounds of Formula (I), the tautomers and the stereoisomeric forms thereof, and the pharmaceutically acceptable addition salts, and the solvates thereof, for use as a medicament.

The invention also relates to the use of a compound of Formula (I), a tautomer or a stereoisomeric form thereof, or a pharmaceutically acceptable addition salt, or a solvate thereof, or a pharmaceutical composition according to the invention, for the manufacture of a medicament.

The present invention also relates to a compound of Formula (I), a tautomer or a stereoisomeric form thereof, or a pharmaceutically acceptable addition salt, or a solvate thereof, or a pharmaceutical composition according to the invention, for use in the treatment, prevention, amelioration, control or reduction of the risk of disorders associated with NF-κB-inducing kinase dysfunction in a mammal, including a human, the treatment or prevention of which is affected or facilitated by inhibition of NF-κB-inducing kinase.

Also, the present invention relates to the use of a compound of Formula (I), a tautomer or a stereoisomeric form thereof, or a pharmaceutically acceptable addition salt, or a solvate thereof, or a pharmaceutical composition according to the invention, for the manufacture of a medicament for treating, preventing, ameliorating, controlling or reducing the risk of disorders associated with NF-κB-inducing kinase dysfunction in a mammal, including a human, the treatment or prevention of which is affected or facilitated by inhibition of NF-κB-inducing kinase.

The invention also relates to a compound of Formula (I), a tautomer or a stereoisomeric form thereof, or a pharmaceutically acceptable addition salt, or a solvate thereof, for use in the treatment or prevention of any one of the diseases mentioned hereinbefore.

The invention also relates to a compound of Formula (I), a tautomer or a stereoisomeric form thereof, or a pharmaceutically acceptable addition salt, or a solvate thereof, for use in treating or preventing any one of the diseases mentioned hereinbefore.

The invention also relates to the use of a compound of Formula (I), a tautomer or a stereoisomeric form thereof, or a pharmaceutically acceptable addition salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), a tautomer or a stereoisomeric form thereof, or a pharmaceutically acceptable addition salt, or a solvate thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof, or a pharmaceutically acceptable addition salt, or a solvate thereof, to warm-blooded animals, including humans.

Therefore, the invention also relates to a method for the treatment of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be from about 10 mg/kg body weight to 40 mg/kg body weight. A particular effective therapeutic daily amount might be 1 mg/kg body weight, 2 mg/kg body weight, 4 mg/kg body weight, or 8 mg/kg body weight. The amount of a compound according to the present invention, also referred to here as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), a tautomer or a stereoisomeric form thereof, or a pharmaceutically acceptable addition salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences ($18^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

Therefore, an embodiment of the present invention relates to a product containing as first active ingredient a compound according to the invention and as further active ingredient one or more medicinal agent, more particularly, with one or more anticancer agent or adjuvant, as a combined preparation for simultaneous, separate or sequential use in the treatment of patients suffering from cancer.

Accordingly, for the treatment of the conditions mentioned hereinbefore, the compounds of the invention may be advantageously employed in combination with one or more other medicinal agents (also referred to as therapeutic agents), more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclo-phosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil, anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticolden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacytidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, quisinostat, trichostatin A, vorinostat;

Inhibitors of the ubiquitin-proteasome pathway for example PS-341, Velcade (MLN-341) or bortezomib;

Yondelis;

Telomerase inhibitors for example telomestatin;

Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b;

MAPK inhibitors;

Retinoids for example alitretinoin, bexarotene, tretinoin;

Arsenic trioxide;

Asparaginase;

Steroids for example dromostanolone propionate, megestrol acetate, nandrolone (decanoate, phenpropionate), dexamethasone;

Gonadotropin releasing hormone agonists or antagonists for example abarelix, goserelin acetate, histrelin acetate, leuprolide acetate;

Thalidomide, lenalidomide;

Mercaptopurine, mitotane, pamidronate, pegademase, pegaspargase, rasburicase;

BH3 mimetics for example ABT-199;

MEK inhibitors for example PD98059, AZD6244, CI-1040;

colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;

a steroidal cytochrome P450 17alpha-hydroxylase-17,20-lyase inhibitor (CYP17), e.g. abiraterone, abiraterone acetate.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m2) of body surface area, for example 50 to 400 mg/m2, particularly for cisplatin in a dosage of about 75 mg/m2 and for carboplatin in about 300 mg/m2 per course of treatment.

The taxane compound is advantageously administered in a dosage of 50 to 400 mg per square meter (mg/m2) of body surface area, for example 75 to 250 mg/m2, particularly for paclitaxel in a dosage of about 175 to 250 mg/m2 and for docetaxel in about 75 to 150 mg/m2 per course of treatment.

The camptothecin compound is advantageously administered in a dosage of 0.1 to 400 mg per square meter (mg/m2) of body surface area, for example 1 to 300 mg/m2, particularly for irinotecan in a dosage of about 100 to 350 mg/m2 and for topotecan in about 1 to 2 mg/m2 per course of treatment.

The anti-tumour podophyllotoxin derivative is advantageously administered in a dosage of 30 to 300 mg per square meter (mg/m2) of body surface area, for example 50 to 250 mg/m2, particularly for etoposide in a dosage of about 35 to 100 mg/m2 and for teniposide in about 50 to 250 mg/m2 per course of treatment.

The anti-tumour vinca alkaloid is advantageously administered in a dosage of 2 to 30 mg per square meter (mg/m2) of body surface area, particularly for vinblastine in a dosage of about 3 to 12 mg/m2, for vincristine in a dosage of about 1 to 2 mg/m2, and for vinorelbine in dosage of about 10 to 30 mg/m2 per course of treatment.

The anti-tumour nucleoside derivative is advantageously administered in a dosage of 200 to 2500 mg per square meter (mg/m2) of body surface area, for example 700 to 1500 mg/m2, particularly for 5-FU in a dosage of 200 to 500 mg/m2, for gemcitabine in a dosage of about 800 to 1200 mg/m2 and for capecitabine in about 1000 to 2500 mg/m2 per course of treatment.

The alkylating agents such as nitrogen mustard or nitrosourea is advantageously administered in a dosage of 100 to 500 mg per square meter (mg/m2) of body surface area, for example 120 to 200 mg/m2, particularly for cyclophosphamide in a dosage of about 100 to 500 mg/m2, for chlorambucil in a dosage of about 0.1 to 0.2 mg/kg, for carmustine in a dosage of about 150 to 200 mg/m2, and for lomustine in a dosage of about 100 to 150 mg/m2 per course of treatment.

The anti-tumour anthracycline derivative is advantageously administered in a dosage of 10 to 75 mg per square meter (mg/m2) of body surface area, for example 15 to 60 mg/m2, particularly for doxorubicin in a dosage of about 40 to 75 mg/m2, for daunorubicin in a dosage of about 25 to 45 mg/m2, and for idarubicin in a dosage of about 10 to 15 mg/m2 per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m2) of body surface area, or as known in the art, if different. Trastuzumab is advantageously administered in a dosage of 1 to 5 mg per square meter (mg/m2) of body surface area, particularly 2 to 4 mg/m2 per course of treatment.

These dosages may be administered for example once, twice or more per course of treatment, which may be repeated for example every 7, 14, 21 or 28 days.

The following examples further illustrate the present invention.

EXAMPLES

Several methods for preparing the compounds of this invention are illustrated in the following examples. Unless otherwise noted, all starting materials were obtained from commercial suppliers and used without further purification.

Hereinafter, the terms: 'AIBN' means azobisisobutyronitrile, 'Ar' means Argon, 'BINAP' means 2,2'-bis(diphenylphosphino)-1,1'-binaphthyl, 'BOC' or 'Boc' means tert-butyloxcarbonyl. 'Boc$_2$O' means di-tert-butyl dicarbonate, 'Celite®' means diatomaceous earth, 'CV' means column volumes, 'DCE' means 1,2-dichloroethylene, 'DCM or CH$_2$Cl$_2$' means dichloromethane, 'DEA' means diethanolamine, 'DIPEA' means diisopropylethylamine, 'DMAP' means dimethylaminopyridine, 'DMF' means dimethylformamide, 'EDC' means 1-ethyl-3-(3-dimethylaminopropyl) carbodiimide hydrochloride, 'ee' means enantiomeric excess, 'equiv.' means equivalent(s), 'EtOAc' means ethyl acetate, 'EtOH' means ethanol, 'h' means hours(s), 'HATU' means 1-[Bis(dimethylamino)methylene]-1H-1,2,3-triazolo[4,5-b]pyridinium 3-oxid hexafluorophosphate, 'HPLC' means High-performance Liquid Chromatography, 'HOAt' means 2-chloro-1,3-dimethylimidazolidinium hexafluorophosphate, 'HOBt' means 1-hydroxybenzotriazole, 'iPrOH' means isopropyl alcohol, 'KHMDS' means potassium bis(trimethylsilyl)amide, 'KMnO$_4$' means potassium permanganate, 'KNO$_3$' means potassium nitrate, 'KOAc' means potassium acetate, 'LC/MS' means Liquid Chromatography/Mass Spectrometry, 'mCPBA' means meta-chloroperbenzoic acid, 'MDAP' means Mass Directed Auto-purification system, 'Me-THF' means 2-methyl-tetrahydrofuran, 'MeOH' means methanol, 'min' means minute(s), 'M.P.' or 'm.p.' means melting point, 'MsCl' means methanesulfonyl chloride, 'NaOAc' means sodium acetate, 'NBS' means N-bromosuccinimide, 'NCS' means N-chlorosuccinimide, 'NMR' means Nuclear Magnetic Resonance, 'OR' means optical rotation, 'Pd/C 10%' means palladium on carbon loading 10%, 'Pd(dppf)Cl$_2$' means [1,1'-Bis(diphenylphosphino)ferrocene]dichloropalladium(II), 'Pd(dppf)Cl$_2$.CH$_2$Cl$_2$' means [1,1'-Bis(diphenylphosphino)ferrocene]dichloropalladium(II), dichloromethane, 'Pd(OAc)$_2$' means palladium (II) acetate, 'Pd(PPh$_3$)$_4$' means tetrakis(triphenylphosphine)palladium(0), 'PtO$_2$' means platinum oxide, 'Quant.' means quantitative, 'rt or room temp.' means room temperature, 'R$_t$' means retention time, 'SFC' means supercritical fluid chromatography, 'TBAF' means tetrabutylammonium fluoride, 'TBDMS' or 'SMDBT' means tert-butyldimethylsilyl, 'TEA' means triethylamine, 'TEAC' means tetraethylammonium chloride, 'TFA' means trifluoroacetic acid, 'THF' means tetrahydrofuran, 'TLC' means thin layer chromatography, 'Xantphos' means 4,5-Bis(diphenylphosphino)-9,9-dimethylxanthene, 'PPh$_3$' means triphenylphosphine, 'CS$_2$CO$_3$' means cesium carbonate, 'Na$_2$SO$_4$' means sodium sulfate, 'MgSO$_4$' means magnesium sulfate, 'H$_2$SO$_4$' means sulfuric acid, 'H$_2$' means hydrogen, 'atm' means atmosphere, 'NH$_4$Cl' means ammonium chloride, 'MDAP' means Mass Directed Autopurification System, 'TBDMSCl' means chloro tert-butyldimethylsilane, 'ACN or CH$_3$CN' means acetonitrile, 'block temp.' means block temperature, 'NaHCO$_3$' means sodium hydrogenocarbonate, 'K$_2$CO$_3$' means potassium carbonate, 'SCX column' means strong cation exchange column, 'IMS' means Industrial Methylated Spirit, 'Si-PPC' means prepacked silica cartridge (or column).

When a stereocenter is indicated with 'RS' this means that a racemic mixture was obtained.

Intermediates containing a double bond with substituents which may be in the E or the Z configuration are show in one particular configuration in the experimental part below. However, unless explicitly indicated by (E) or (Z), it is unknown if these intermediates were obtained in the E or Z configuration or as a mixture of both configurations. For example intermediates 175, 176, 177, 185, 186, 187, and 188 might be in the E or Z configuration or might be mixtures thereof.

It is well known to one skilled in the art that protecting groups such as TBDMS can routinely be removed with TBAF in a variety of solvents such as for example THF. Similarly, conditions for removal of BOC protecting groups are well known to one skilled in the art, commonly including for example TFA in a solvent such as for example DCM, or HCl in a solvent such as for example dioxane.

The skilled person will realize that in some cases where an organic layer was obtained at the end of an experimental protocol, it was necessary to dry the organic layer with a typical drying agent such as for example MgSO$_4$, or by azeotropic distillation, and to evaporate the solvent before using the product as a starting material in the next reaction step.

A. Preparation of the Intermediates

Example A1

Preparation of Intermediate 1:

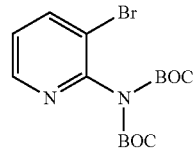 [SMILES: CC(C)(C)OC(=O)N(C(=O)OC(C)(C)C)c1ncccc1Br]

To a solution of 2-amino-3-bromopyridine (9.00 g, 52.02 mmol) in DCM (200 mL) were added Boc$_2$O (34.06 g, 156.06 mmol) and DMAP (636.00 mg, 5.20 mmol) and the reaction mixture was stirred at 38° C. for 18 h under nitrogen. The completion of the reaction was determined by TLC (30% EtOAc, 70% cyclohexane). The reaction mixture was washed with sat. NaHCO$_3$ and brine, dried over Na$_2$SO$_4$ and concentrated in vacuo. The residue was sonicated with diethyl ether and the solid formed was collected by filtration, washed with diethyl ether and dried in vacuo to give a first batch of 8.83 g of intermediate 1. The filtrate was concentrated in vacuo and the residue was purified by flash chromatography (50 g silica column, from 0% EtOAc, 100% cyclohexane to 30% EtOAc, 70% cyclohexane). The pure fractions were concentrated in vacuo to afford an additional batch of 5.99 g of intermediate 1 (76% total yield, white solid).

Preparation of Intermediate 2:

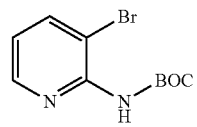 [SMILES: CC(C)(C)OC(=O)Nc1ncccc1Br]

To a solution of intermediate 1 (14.82 g, 39.65 mmol) in MeOH (280 mL) was added K$_2$CO$_3$ (16.44 g, 118.96 mmol) and the reaction mixture was stirred at 60° C. for 2 h. The reaction mixture was left stirring for a further 1 h at 60° C. The reaction mixture was filtered and the filtrate was concentrated in vacuo. The residue was diluted with ethyl acetate, washed with water and brine, dried over Na$_2$SO$_4$ and concentrated in vacuo. The crude residue was purified by flash chromatography (100 g silica column, from 0% EtOAc, 100% cyclohexane to 30% EtOAc, 70% cyclohexane). The relevant fractions were joined and concentrated in vacuo to give 8 g of intermediate 2 (74% yield, white solid) which was used directly in the next step without further purification.

Alternative Preparation of Intermediate 2:

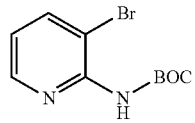

A solution of 2-amino-3-bromopyridine (100 g, 578 mmol) in DCM (700 mL) was treated with TEA (170 mL, 1219.7 mmol) and DMAP (3.50 g, 5.73 mmol) and a solution of Boc$_2$O (265 g, 1214.22 mmol) in DCM (100 mL) was added over 30 min. The solution was stirred at room temp for 2 h. The completion of the reaction was determined by TLC (EtOAc 30%, cyclohexane 70%). The mixture was evaporated under vacuum and the residue was dissolved in MeOH (1000 mL), treated with K$_2$CO$_3$ (200 g, 1447.12 mmol) and heated to 65° C. for 5 h. The reaction mixture was filtered and the filtrate was evaporated under vacuum. The residue was partitioned between ethyl dichloromethane and water and the organic layer was washed with water, 1M citric acid solution, brine, dried over Na$_2$SO$_4$ and filtered. The filtrate was stirred with flash silica gel, filtered and evaporated under vacuum. The residue was triturated with petroleum ether 40-60° C. to give 99.7 g of intermediate 2 (63% yield, pinkish solid).

Example A2

Preparation of Intermediate 3:

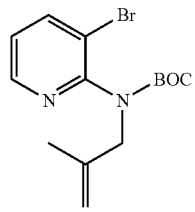 [SMILES: C=C(C)CN(C(=O)OC(C)(C)C)c1ncccc1Br]

To a cooled (ice/salt) solution of intermediate 2 (5.00 g, 18.31 mmol), 2-methyl-2-propen-1-ol (3.08 mL, 36.61 mmol) and tri-n-butylphosphine (9.14 mL, 36.61 mmol) in THF (100 mL) was added dropwise a solution of 1,1'-(azodicarbonyl)dipiperidine (10.17 g, 40.30 mmol) in THF (100 mL). The reaction mixture was stirred at rt for 72 h. The reaction mixture was concentrated in vacuo. The residue was triturated with dichloromethane and the solid formed was filtered. The filtrate was concentrated in vacuo and the residue was purified by flash chromatography (50 g silica column, from 0% EtOAc, 100% cyclohexane to 20% EtOAc, 80% cyclohexane). The relevant fractions were combined and concentrated in vacuo. The residue was further purified by flash chromatography (100 g silica column, from 0% EtOAc, 100% cyclohexane to 20% EtOAc, 80% cyclohexane). The relevant fractions were combined and concentrated in vacuo to give 4.74 g of intermediate 3 (79% yield, pale yellow oil).

Preparation of Intermediate 10:

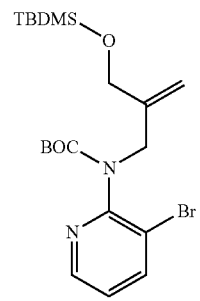

A solution of intermediate 2 (138 g, 505.26 mmol) and intermediate 9 (138.5 g, 493.84 mmol) in DMF (1250 mL) was treated with Cs$_2$CO$_3$ (322 g, 988.28 mmol) and the mixture was heated to 55° C. and stirred mechanically overnight. The mixture was partitioned between diethyl ether and water and the organic layer was washed with water (three times) and brine, dried over Na$_2$SO$_4$ and evaporated. The residue was dissolved in petroleum ether 40-60° C. and treated with flash silica gel. The mixture was filtered through a plug of silica gel and washed with 10% diethyl ether in petroleum ether. The filtrate was evaporated to give 166.5 g of intermediate 10 (74% yield, pale yellow oil) which was used in the next step without further purification.

Example A3

Preparation of Intermediate 4:

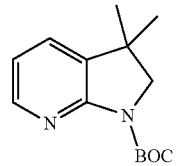 [SMILES: CC(C)(C)OC(=O)N1CC(C)(C)c2cccnc21]

A suspension of intermediate 3 (4.74 g, 14.49 mmol), NaOAc (3.09, 37.66 mmol), sodium formate (2.56 g, 37.66 mmol), TEAC (3.00 g, 18.11 mmol) and Pd(OAc)$_2$ (163.00 mg, 0.72 mmol) in DMF (50 mL) was degassed with argon and stirred at 85° C. for 18 h. The reaction mixture was filtered through Celite® and the pad was washed with DCM. DCM was removed in vacuo and the solution was diluted with EtOAc, washed with water and brine and the organic layer was dried over Na$_2$SO$_4$ and concentrated in vacuo. The residue was purified by flash chromatography (100 g silica column, from 0% EtOAc, 100% cyclohexane to 30% EtOAc, 70% cyclohexane). The relevant fractions were combined and concentrated in vacuo to give 2.68 g of intermediate 4 (75% yield, white solid).

Preparation of Intermediate 11:

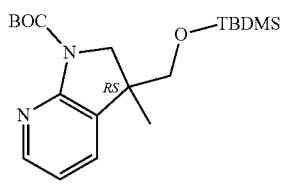

A solution of intermediate 10 (166.00 g, 362.86 mmol) in N,N-dimethylacetamide (750 mL) was treated with N,N- dicyclohexylmethylamine (106.30 g, 544.17 mmol), sodium formate (61.80 g, 908.73 mmol), TEAC (83.00 g, 500.89 mmol) and finally Pd(OAc)$_2$ (4.00 g, 17.82 mmol) and the mixture was evacuated and purged with nitrogen (three times) and heated to 100° C. The reaction mixture was stirred at 100° C. for 12 h and the mixture was cooled to rt and partitioned between ethyl acetate and 1M citric acid solution. The mixture was filtered through Celite® and the two layers of the filtrate were separated and the organic layer was washed with water, saturated NaHCO$_3$ solution, water and brine, dried over Na$_2$SO$_4$ and evaporated under vacuum. The residue was purified by silica gel plug (from 0% acetone, 100% DCM to 10% acetone, 90% DCM) to give 119.5 g of intermediate 11 (87% yield, straw-colored oil).

Example A4

Preparation of Intermediate 5:

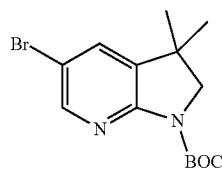 [SMILES: CC(C)(C)OC(=O)N1CC(C)(C)c2cc(Br)cnc21]

To a solution of intermediate 4 (2.68 g, 10.79 mmol) in C$_3$CN (45 mL) was added portionwise NBS (2.11 g, 11.87 mmol) and the reaction mixture was stirred at 40° C. for 18 h. CH$_3$CN was removed in vacuo and the solution was diluted with EtOAc, washed with a saturated solution of NaHCO$_3$ and brine and the organic layer was dried over Na$_2$SO$_4$ and concentrated in vacuo. The residue was purified by flash chromatography (50 g silica column, from 0% EtOAc, 100% cyclohexane to 20% EtOAc, 80% cyclohexane). The relevant fractions were combined and concentrated in vacuo to give 3.37 g of intermediate 5 (95% yield, white solid).

Preparation of Intermediate 12:

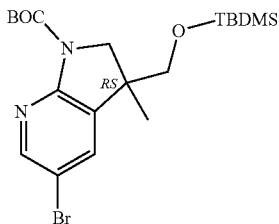

A solution of intermediate 11 (119.5 g, 315.65 mmol) in CH$_3$CN (750 mL) was treated with NBS (67.5 g, 379.25 mmol) and the solution was stirred and heated to 45° C. (block temp) for 4 h. The solution was cooled and evaporated under vacuum and the residue was partitioned between ethyl acetate and aqueous sodium thiosulfate solution. The organic layer was washed with water, aqueous K$_2$CO$_3$ solution, water, 0.5M citric acid solution, water and brine, dried over Na$_2$SO$_4$ and evaporated. The residue was dissolved in CH$_2$Cl$_2$, stirred with flash silica gel and filtered. The cake was eluted with CH$_2$Cl$_2$ and 10% EtOAc/CH$_2$Cl$_2$ and the filtrate was evaporated to give 127.8 g of intermediate 12 (84% yield, brown syrup).

Example A5

Preparation of Intermediate 12S and Intermediate 12R:

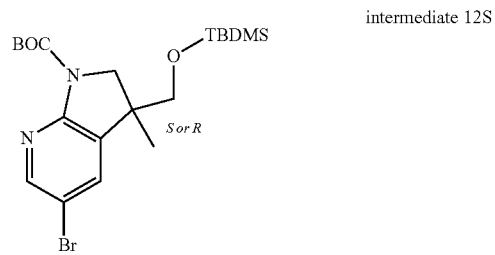

intermediate 12S

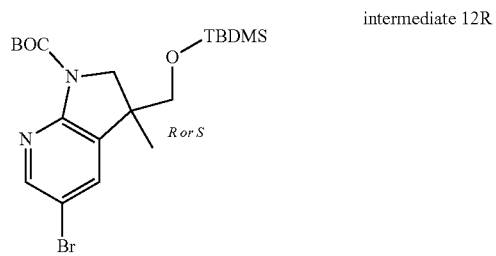

intermediate 12R

Intermediate 12 (50 g) was separated via chiral SFC (Stationary phase: CHIRALPAK IC 5 μm 250×30 mm, Mobile phase: 60% CO$_2$, 40% iPrOH) to give 21 g of intermediate 12S (42% yield) and 20.7 g of intermediate 12R (41% yield).

Example A6

Preparation of Intermediate 6:

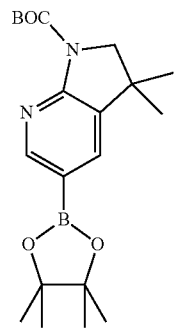

To a solution of intermediate 5 (3.37 g, 10.31 mmol), bis(pinacolato)diboron (3.27 g, 12.89 mmol), and KOAc (3.04 g, 30.93 mmol) in 1,4-dioxane (75 mL) was added Pd(dppf)Cl$_2$.CH$_2$Cl$_2$ (421.00 mg, 0.52 mmol) and the reaction mixture was heated for 3 h at 85° C. The reaction mixture was diluted with EtOAc, filtered through a pad of Celite® and the filtrate was washed with water, dried over Na$_2$SO$_4$ and concentrated in vacuo. The residue was purified by flash chromatography (100 g silica column, from 0% EtOAc, 100% cyclohexane to 35% EtOAc, 65% cyclohexane). The relevant fractions were combined and concentrated in vacuo to give 2.84 g of intermediate 6 (74% yield, light brown oil).

Preparation of Intermediate 13:

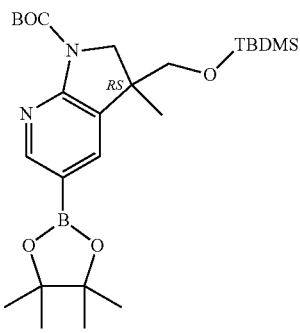

A solution of intermediate 12 (127.80 g, 388.82 mmol) in 1,4-dioxane (1250 mL) was treated with Bis(pinacolato)diboron (107.20 g, 422.15 mmol), potassium acetate (99.70 g, 1015.9 mmol) and finally Pd(dppf)Cl$_2$.CH$_2$Cl$_2$ (13.80 g, 16.9 mmol). The flask was evacuated and purged with nitrogen (three times) and the mixture was heated to 85° C. (block temp) and stirred overnight. The reaction mixture was cooled and evaporated and the residue was partitioned between ethyl acetate and water and the mixture was filtered through celite. The filtrate was separated and the organic layer was washed with water (two times) and brine, dried over Na$_2$SO$_4$ and evaporated to give 170.94 g of intermediate 13 (quant. yield, dark brown gum) which was used in the next step without further treatment.

Example A7

Preparation of Intermediate 7:

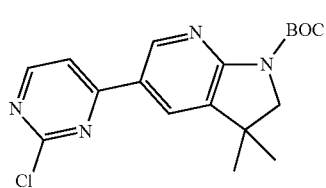 [SMILES: CC(C)(C)OC(=O)N1CC(C)(C)c2cc(-c3ccnc(Cl)n3)cnc21]

To a solution of intermediate 6 (2.84 g, 7.59 mmol), 2,4-dichloropyrimidine (1.24 g, 8.35 mmol) and Na$_2$CO$_3$ (3.22 g, 30.35 mmol) in 1,4-dioxane (50 mL) and water (5 mL) was added Pd(PPh$_3$)$_4$ (438 mg, 0.38 mmol) and the reaction mixture was heated for 5 h at 95° C. The reaction mixture was then diluted with EtOAc, filtered through a pad of Celite® and the filtrate was washed with water, dried over Na$_2$SO$_4$ and concentrated in vacuo. The residue was triturated with diethyl ether and the solid formed was collected by filtration and dried in vacuo to give 1.19 g of intermediate 7 (44% yield, off-white solid).

Preparation of Intermediate 14:

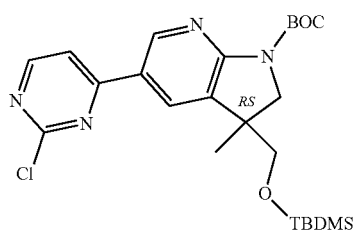

A solution of intermediate 13 (170.94 g, 338.80 mmol) in 1,4-dioxane (1250 mL) was treated with 2,4-dichloropyrimidine (75.30 g, 505.44 mmol) and a solution of sodium carbonate (107.90 g, 1018.04 mmol) in water (420 mL) was added followed by Pd(PPh$_3$)$_4$ (19.50 g, 16.88 mmol). The mixture was purged with nitrogen (three times) and then heated to 85° C. (block temp) and stirred overnight. The mixture was cooled and evaporated and the residue was partitioned between EtOAc and water and was filtered through celite. The filtrate was transferred to a separating funnel and organic layer was washed with water and brine, dried over Na$_2$SO$_4$ and evaporated. The residue was dissolved in 10% acetone in CH$_2$Cl$_2$ and stirred with flash silica gel and the mixture was filtered, washing through with acetone/DCM solution (1/9, v/v). The filtrate was evaporated and the residue was triturated with 10% diethyl ether in petrol and filtrated to give 112 g of a first batch of intermediate 14. The liquors were evaporated and the residue was purified by silica gel plug (20-50% EtOAc in 40/60 petrol) to give a pale yellow gum which was triturated with petroleum ether 40-60° C. to give 12.7 g of a second batch of intermediate 14. The two batches were mixed to a single batch to give 124.7 g of intermediate 14 (75% yield).

Preparation of Intermediate 15:

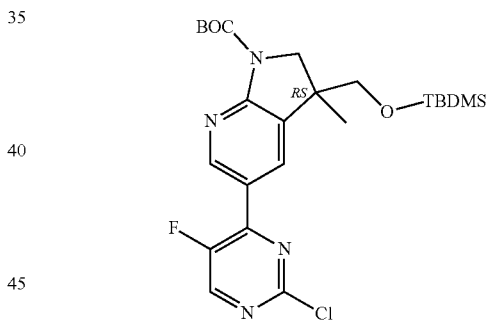

To a solution of intermediate 13 (0.50 g, 0.99 mmol), 5-fluoro-2,4-dichloropyrimidine (215.00 mg, 1.29 mmol) and Cs$_2$CO$_3$ (0.97 g, 2.97 mmol) in 1,4-dioxane (5 mL) and water (0.5 mL) was added Pd(PPh$_3$)$_4$ (0.06 g, 0.052 mmol) and the reaction mixture was heated for 2 h at 95° C. The reaction mixture was left stirring for a further 1 h. The reaction mixture was diluted with ethyl acetate and the solution was washed with water. The organic layer was dried with sodium sulfate and concentrated in vacuo. The residue was purified by flash chromatography (50 g silica column, 0% to 5% methanol in dichloromethane). The relevant fractions were joined and concentrated in vacuo yielding to yellow foam. The residue was further purified by flash chromatography (25 g silica column, 0% to 5% methanol in dichloromethane). The relevant fractions were joined and concentrated in vacuo to give 300 mg of intermediate 15 (59% yield, yellow oil).

Example A8

Preparation of Intermediate 14R and 14S

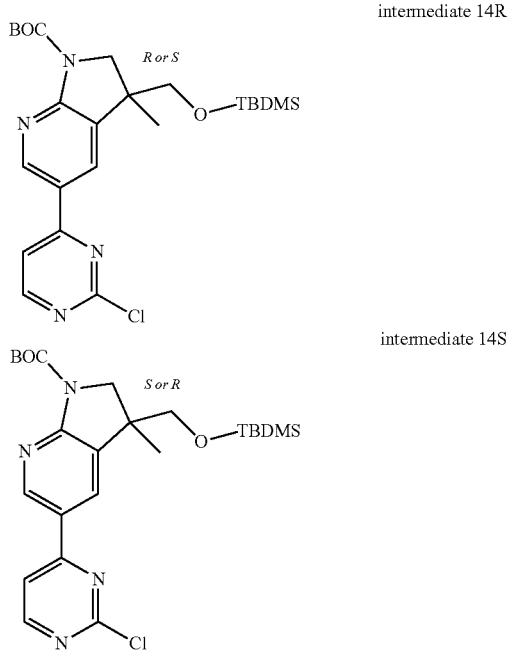

Intermediate 14 (50 g) was separated by chiral SFC (Stationary phase: Chiralpak AD-H 5 μm 250*30 mm, mobile phase: 80% CO₂, 20% iPrOH) to give 23.1 g of intermediate 14R (46% yield) and 23.4 g of intermediate 14S (47% yield).

Example A9

Method A1:
Preparation of Intermediate 18:

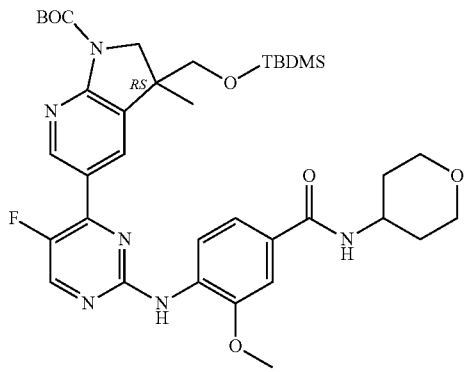

To a solution of intermediate 15 (100 mg, 0.20 mmol), intermediate 17 (54.80 mg, 0.22 mmol), BINAP (11.80 mg, 0.019 mmol) and Cs₂CO₃ (179.00 mg, 0.55 mmol) in 1,4-dioxane (3 mL) was added Pd(OAc)₂ (4.27 mg, 0.019 mmol) and the reaction mixture was heated for 0.5 h at 95° C. The reaction mixture was diluted with ethyl acetate and washed with water and brine. The layers were separated and the organic layer was dried over Na₂SO₄ and concentrated under vacuum to give 142 mg of intermediate 18 (yellow oil) which was used in the next step without further purification.

Preparation of Intermediate 21:

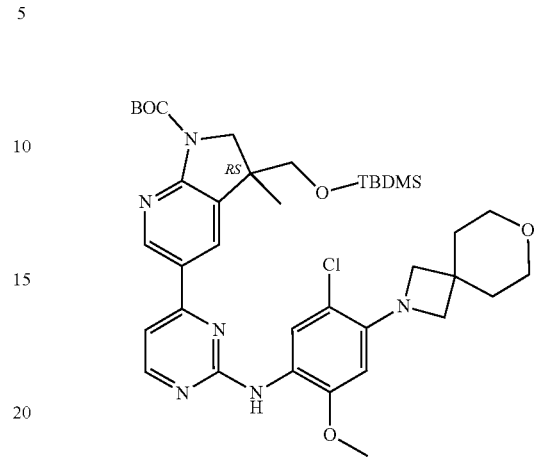

To a solution of intermediate 14 (150 mg, 0.31 mmol), intermediate 20 (99.30 mg, 0.35 mmol), BINAP (193 mg, 0.031 mmol) and Cs₂CO₃ (298 mg, 0.91 mmol) in 1,4-dioxane (3 mL) was added Pd(OAc)₂ (6.96 mg, 0.031 mmol) and the reaction mixture was heated for 1 h at 95° C. The reaction mixture was then diluted with ethyl acetate and washed with water and brine. The layers were separated and the organic layer was dried with sodium sulfate and concentrated in vacuo to give 255 mg of intermediate 21 (orange oil) which was used in the next step without further purification.

Preparation of Intermediate 25:

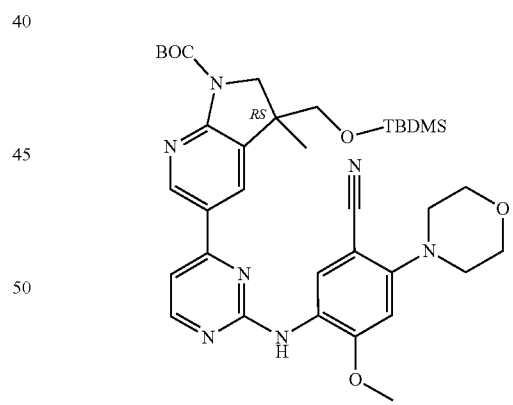

To a solution of intermediate 14 (150 mg, 0.31 mmol), intermediate 24 (86.20 mg, 0.36 mmol based on 95% purity determined by LC/MS), Pd(OAc)₂ (6.96 mg, 0.031 mmol) and Cs₂CO₃ (298 mg, 0.92 mmol) in 1,4-dioxane (3 mL) was added BINAP (19.30 mg, 0.031 mmol) and the reaction mixture was heated for 0.5 h at 95° C. The reaction mixture was then diluted with ethyl acetate and washed with water and brine. The layers were separated and the organic layer was dried with sodium sulfate and concentrated in vacuo to give 289 mg of intermediate 25 (orange oil) which was used as it in the next step.

Preparation of Intermediate 28:

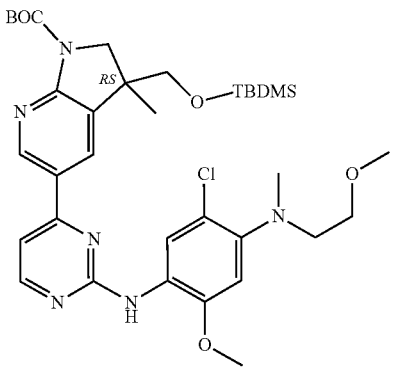

To a solution of intermediate 14 (150 mg, 0.31 mmol), intermediate 27 (85.90 mg, 0.36 mmol based on 95% purity determined by LC/MS), Pd(OAc)$_2$ (6.96 mg, 0.031 mmol) and Cs$_2$CO$_3$ (298 mg, 0.92 mmol) in 1,4-dioxane (3 mL) was added BINAP (19.30 mg, 0.031 mmol) and the reaction mixture was heated for 1 h at 95° C. The reaction mixture was then diluted with ethyl acetate and washed with water and brine. The layers were separated and the organic layer was dried with sodium sulfate and concentrated in vacuo to give 240 mg of intermediate 28 (dark oil) which was used in the next step without further purification.

Preparation of Intermediate 31:

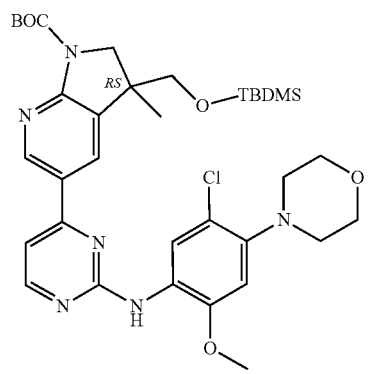

To a solution of intermediate 14 (150 mg, 0.31 mmol), intermediate 30 (85.20 mg, 0.36 mmol based on 95% purity determined by LC/MS), Pd(OAc)$_2$ (6.96 mg, 0.031 mmol) and Cs$_2$CO$_3$ (298 mg, 0.92 mmol) in 1,4-dioxane (3 mL) was added BINAP (19.30 mg, 0.031 mmol) and the reaction mixture was heated for 3 h at 95° C. The reaction mixture was then diluted with ethyl acetate and washed with water and brine. The layers were separated and the organic layer was dried with sodium sulfate and concentrated in vacuo to give 259 mg of intermediate 31 (orange oil) which was used in the next step without further purification.

Preparation of Intermediate 34:

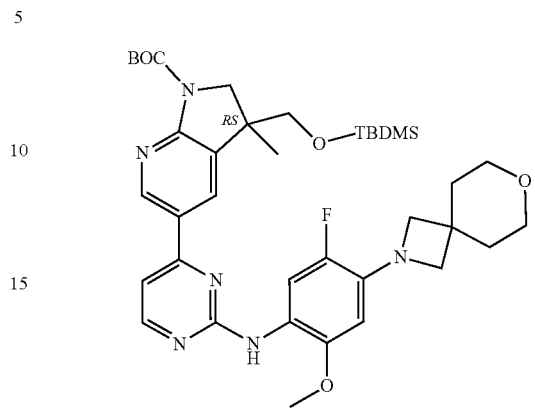

A degassed suspension of intermediate 14 (638.43 mg, 1.30 mmol), intermediate 33 (382 mg, 1.43 mmol), Pd(OAc)$_2$ (29.18 mg, 0.13 mmol), BINAP (80.95 mg, 0.13 mmol) and Cs$_2$CO$_3$ (1.27 g, 3.90 mmol) in 1,4-dioxane (15 mL) was heated at 75° C. for 30 min. The reaction mixture was partitioned between EtOAc and NaHCO$_3$ solution and the organic layer was washed with brine, dried over Na$_2$SO$_4$ and concentrated in vacuo to give 937 mg of intermediate 34 which was used in the next step without further purification.

Preparation of Intermediate 39:

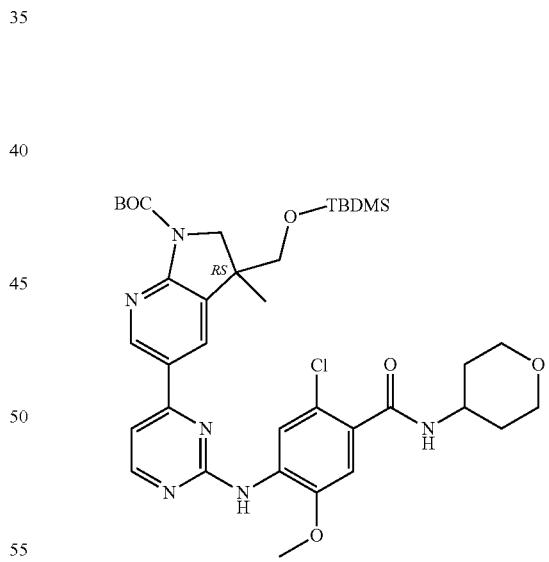

A degassed suspension of intermediate 14 (100.18 mg, 0.20 mmol), intermediate 38 (64 mg, 0.23 mmol), Pd(OAc)$_2$ (4.49 mg, 0.02 mmol), BINAP (12.45 mg, 0.02 mmol) and Cs$_2$CO$_3$ (231.98 mg, 0.71 mmol) in 1,4-dioxane (2 mL) was heated at 85° C. for 1 h. The reaction mixture was partitioned between EtOAc and NaHCO$_3$ solution and the organic layer was washed with brine, dried over Na$_2$SO$_4$ and concentrated in vacuo to give 148 mg of intermediate 39 which was used in the next step without further purification.

Preparation of Intermediate 42:

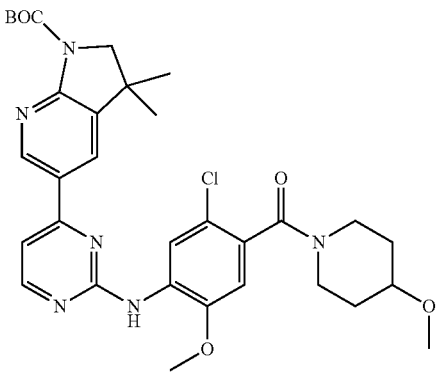 [SMILES: COc1cc(C(=O)N2CCC(OC)CC2)c(Cl)cc1Nc1nccc(-c2cnc3c(c2)C(C)(C)CN3C(=O)OC(C)(C)C)n1]

A degassed suspension of intermediate 7 (131.71 mg, 0.36 mmol), intermediate 41 (120 mg, 0.40 mmol), Pd(OAc)$_2$ (8.31 mg, 0.04 mmol), BINAP (23.04 mg, 0.04 mmol) and Cs$_2$CO$_3$ (356.77 mg, 1.10 mmol) in 1,4-dioxane (4 mL) was heated at 85° C. for 1 h. The reaction mixture was partitioned between EtOAc and NaHCO$_3$ solution and the organic layer was washed with brine, dried over Na$_2$SO$_4$ and concentrated in vacuo to give 231 mg of intermediate 42 which was used in the next step without further purification.

Preparation of Intermediate 49:

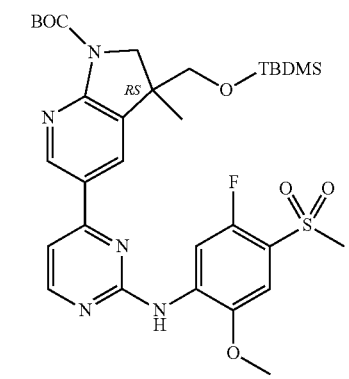

Intermediate 14 (386.99 mg, 0.79 mmol), intermediate 48 (198.62 mg, 0.91 mmol), Pd(OAc)$_2$ (17.69 mg, 0.08 mmol), BINAP (49.19 mg, 0.08 mmol) and Cs$_2$CO$_3$ (770.24 mg, 2.36 mmol) were added together in 1,4-dioxane (7.9 mL) and the resulting mixture was heated at 95° C. under nitrogen for 1.5 h. The reaction was allowed to cool to room temperature, diluted with water and extracted with ethyl acetate (three times). Organic layers were separated, combined, dried over sodium sulfate and evaporated under reduced pressure. The crude residue was purified by column chromatography (40 g silica) eluting with a gradient: from 100% pentane, 0% EtOAC to 0% pentane, 100% EtOAc. Fractions containing product were combined and evaporated under reduced pressure to give 203 mg of intermediate 49 (38% yield, yellow oil) which was used in the next step without any further purification.

Preparation of Intermediate 56:

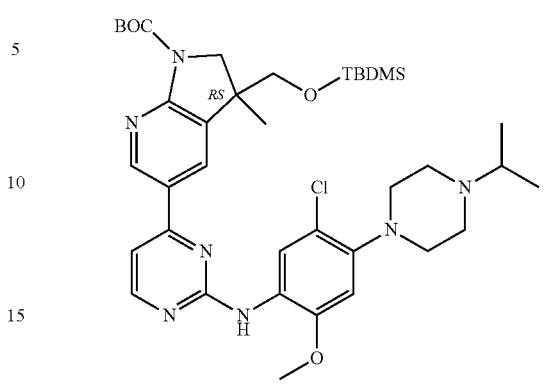

Intermediate 14 (337.38 mg, 0.69 mmol), intermediate 55 (195.00 mg, 0.69 mmol), Pd(OAc)$_2$ (15.42 mg, 0.069 mmol), BINAP (42.78 mg, 0.069 mmol) and Cs$_2$CO$_3$ (671.52 mg, 2.06 mmol) were added together in 1,4-dioxane (6.0 mL) and the resulting mixture was heated at 95° C. under nitrogen for 1 h. The reaction was allowed to cool to rt, diluted with water and extracted with ethyl acetate. The organic layers were separated, combined, dried over magnesium sulfate and evaporated under reduced pressure. The crude residue was purified by flash chromatography (12 g silica column, mobile phase gradient: from 100% DCM to 92% DCM, 8% 2M NH$_3$ in MeOH) to give 328 mg of intermediate 56 (65% yield, orange solid).

Preparation of Intermediate 59:

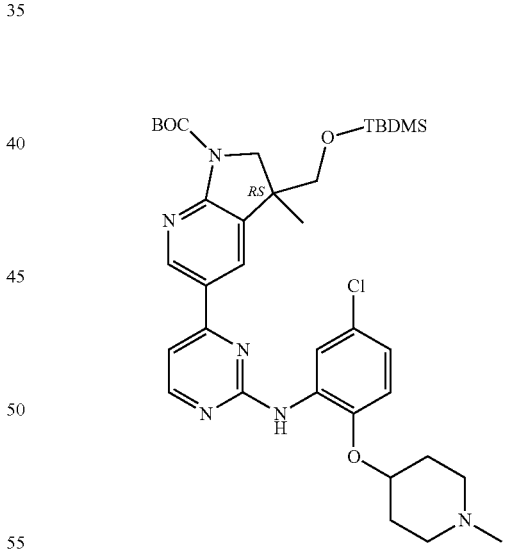

A degassed suspension of intermediate 14 (245.55 mg, 0.50 mmol), intermediate 58 (132.40 mg, 0.55 mmol), Pd(OAc)$_2$ (11.23 mg, 0.05 mmol), BINAP (31.13 mg, 0.05 mmol) and Cs$_2$CO$_3$ (488.73 mg, 1.50 mmol) in 1,4-dioxane (5 mL) was heated to 85° C. for 30 min. The reaction mixture was partitioned between DCM and NaHCO$_3$ solution and the organic layer was washed with brine, dried over Na$_2$SO$_4$ and concentrated in vacuo to give 348 mg of intermediate 59 (quant. yield) which was used in the next reaction without further purification.

Preparation of Intermediate 62:

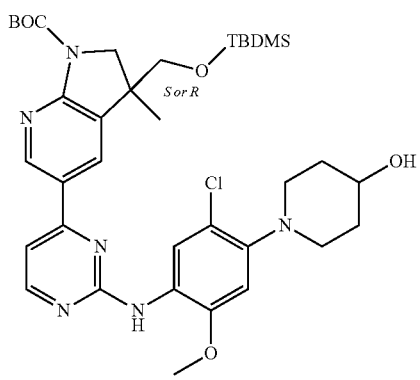

A stirred suspension of intermediate 14S (150.00 mg, 0.31 mmol), intermediate 61 (80.25 mg, 0.31 mmol), Pd(OAc)$_2$ (6.40 mg, 0.029 mmol), BINAP (18.40 mg, 0.030 mmol) and Cs$_2$CO$_3$ (279.00 mg, 0.86 mmol) in 1,4-dioxane (6 mL) in sealed RB flask was degassed, flushed with argon and heated at 85±5° C. for 3 h. The mixture was cooled and diluted with EtOAc and water. The organic layer was separated, washed with brine, dried over Na$_2$SO$_4$ and concentrated in vacuo. The crude residue was purified by column chromatography (12 g silica, mobile phase gradient: from 100% pentane, 0% EtOAC to 0% pentane, 100% EtOAc). Relevant fractions were combined and evaporated to give 133 mg of intermediate 62 (60% yield, yellow solid).

Method A2:
Preparation of Intermediate 123:

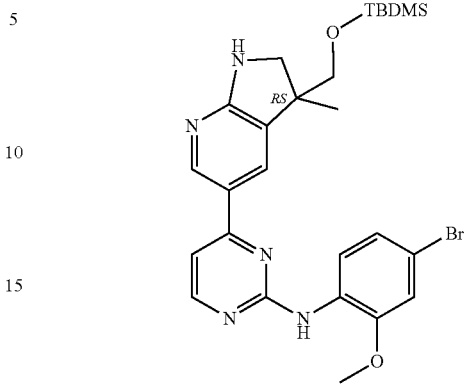

Intermediate 14 (2 g, 4.07 mmol), 4-bromo-2-methoxy aniline (906 mg, 4.48 mmol), APTS (39 mg, 0.23 mmol) and isopropanol (15 mL) were combined in a microwave tube and heated at 140° C. for 3 hours. The reaction was heated for a further 90 min at 150° C. The reaction was concentrated in vacuo, dissolved in DCM, washed with water and brine, dried over sodium sulfate, filtered and concentrated in vacuo. The crude reaction mixture was purified by column chromatography using cyclohexane:EtOAc (0-100%) as eluent. Product containing fractions were concentrated in vacuo to give 395 mg of intermediate 123 (17% yield).

The intermediates in the Table below were prepared by using an analogous method as described in method A1, starting from the respective starting materials.

| Intermediate no. | Structure | Method |
|---|---|---|
| Intermediate 65 (from intermediates 7 and 64) | 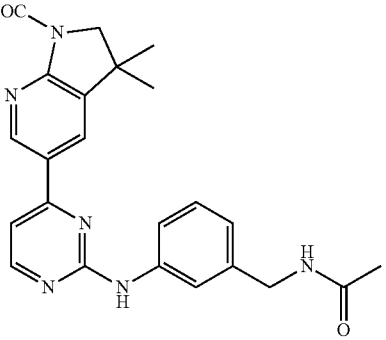 | A1 |
| Intermediate 74 (from intermediate 14 and 3,4,5-trimethoxyaniline) | 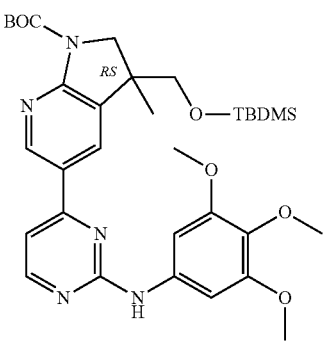 | A1 |

-continued
| Intermediate no. | Structure | Method |
|---|---|---|
| Intermediate 78 (from intermediates 7 and 77) | 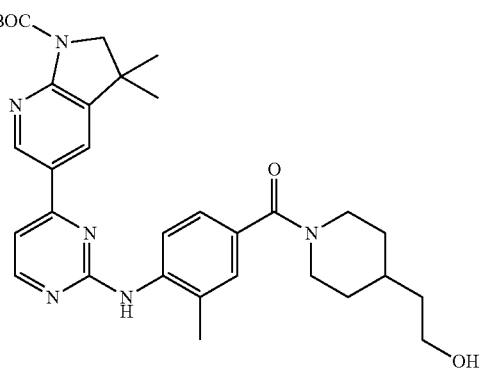 | A1 |
| Intermediate 91 (from intermediates 7 and 90) | 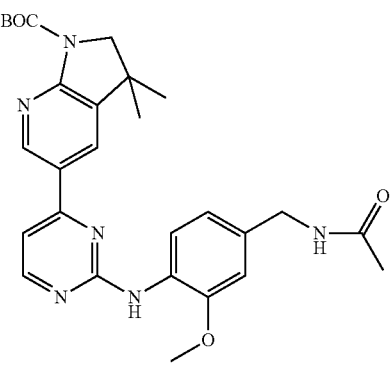 [SMILES: COc1cc(CNC(C)=O)ccc1Nc1nccc(-c2cnc3c(c2)C(C)(C)CN3C(=O)OC(C)(C)C)n1] | A1 |
| Intermediate 100 (from intermediates 7 and 99) | 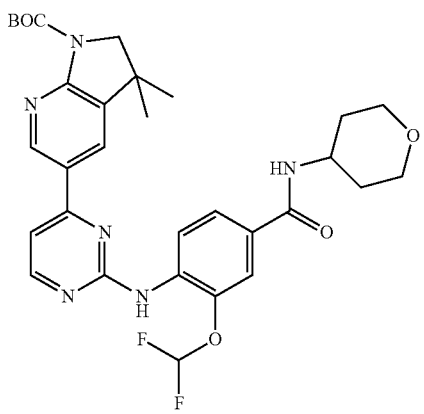 [SMILES: CC(C)(C)OC(=O)N1CC(C)(C)c2cc(-c3ccnc(Nc4ccc(C(=O)NC5CCOCC5)cc4OC(F)F)n3)cnc21] | A1 |
| Intermediate 102 (from intermediates 7 and 101) | 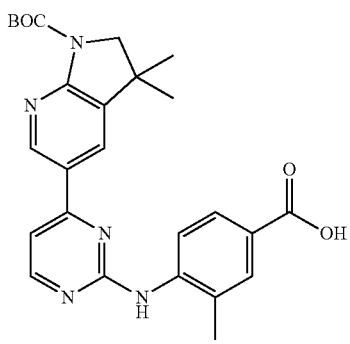 [SMILES: Cc1cc(C(=O)O)ccc1Nc1nccc(-c2cnc3c(c2)C(C)(C)CN3C(=O)OC(C)(C)C)n1] | A1 |

-continued
| Intermediate no. | Structure | Method |
|---|---|---|
| Intermediate 114 (from intermediate 14 and 4-amino-3-methoxy-benzoic acid) | 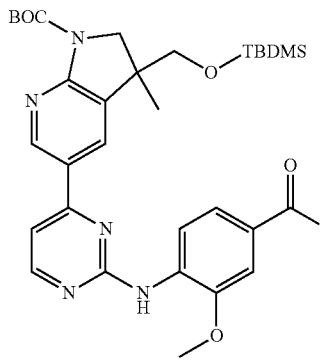 | A1 |
| Intermediate 119 (from intermediate 14 and methyl 4-amino-3-methoxybenzoate) | 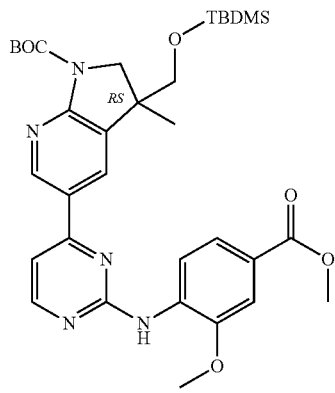 | A1 |
| Intermediate 128 (from intermediates 14 and 127) | 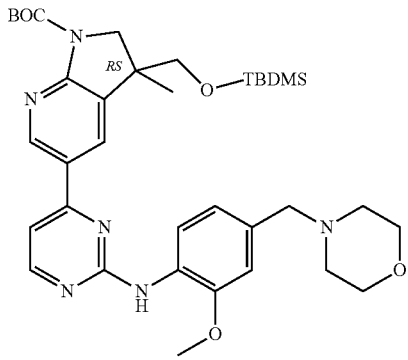 | A1 |
| Intermediate 131 (from intermediates 14 and 130) | 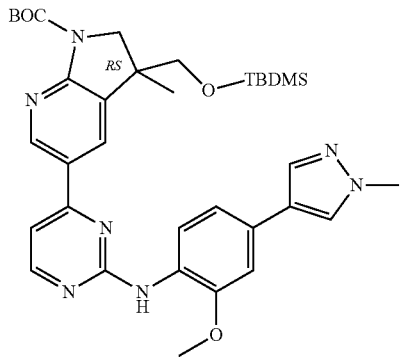 | A1 |

-continued
| Intermediate no. | Structure | Method |
|---|---|---|
| Intermediate 135 (from intermediates 14 and 134) | 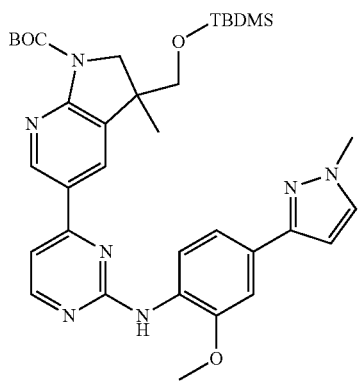 | A1 |
| Intermediate 138 (from intermediates 14 and 137) | 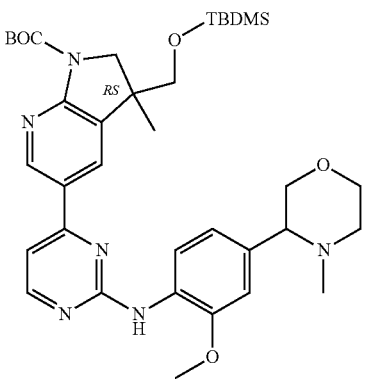 | A1 |
| Intermediate 141 (from intermediates 14 and 140) | 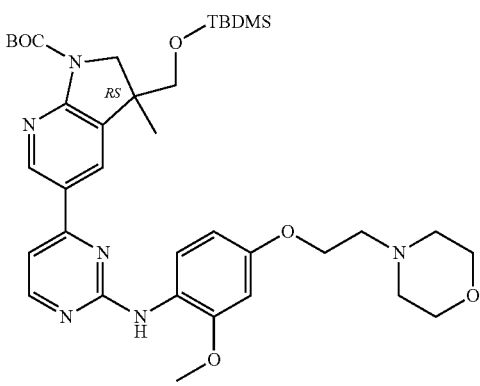 | A1 |
| Intermediate 146 (from intermediates 14 and 145) | 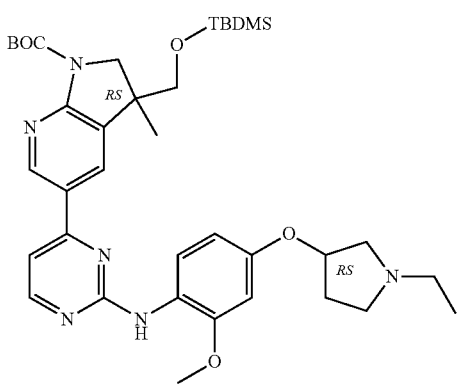 | A1 |

-continued
| Intermediate no. | Structure | Method |
|---|---|---|
| Intermediate 149 (from intermediates and 148) | 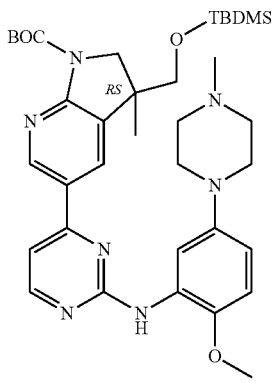 | A1 |
| Intermediate 156 (from intermediates 14 and 155) | 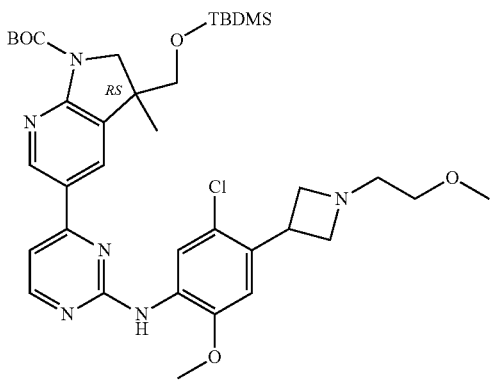 | A1 |
| Intermediate 159 (from intermediates 14 and 158) | 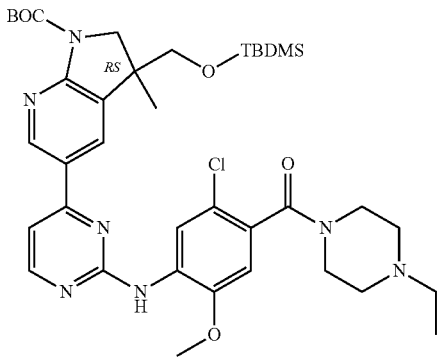 | A1 |
| Intermediate 162 (from intermediates 14 and 161) | 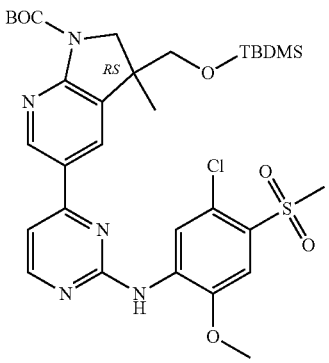 | A1 |

| Intermediate no. | Structure | Method |
|---|---|---|
| Intermediate 166 (from intermediates 14 and 165) | (structure shown) | A1 |
| Intermediate 172 (from intermediates 14S and 171) | (structure shown) | A1 |

Example A11

Preparation of Intermediate 75:

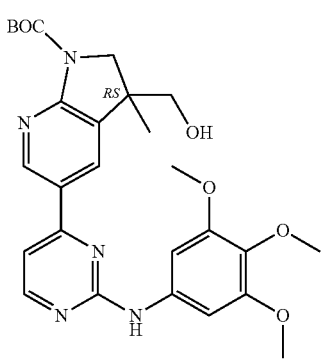 [SMILES: COc1cc(Nc2nccc(-c3cnc4c(c3)C(C)(CO)CN4C(=O)OC(C)(C)C)n2)cc(OC)c1OC]

Intermediate 74 (252 mg, 0.40 mmol) was dissolved in THF (5 mL) and TBAF (1.0 M in THF) (0.80 mL, 0.80 mmol) was added dropwise. The reaction mixture was stirred at rt for 2 hours. The reaction was quenched by addition of water (20 mL) and extracted with DCM (2×25 mL). The combined organics layers were washed with brine (1×30 mL), dried over sodium sulphate, filtered and the filtrate was evaporated in vacuo to an orange-brown oil. The crude material was purified by silica column chromatography (24 g, mobile phase gradient: from 100% DCM to 93% DCM, 7% MeOH). Appropriate fractions were combined and evaporated to give 130 mg of intermediate 75 (63% yield, beige solid).

The intermediate in the Table below was prepared by using an analogous method, starting from the respective starting materials.

| Intermediate number | Structure |
|---|---|
| Intermediate 120 (from intermediate 119) | (structure shown) |

Example A12

Preparation of Intermediate 121:

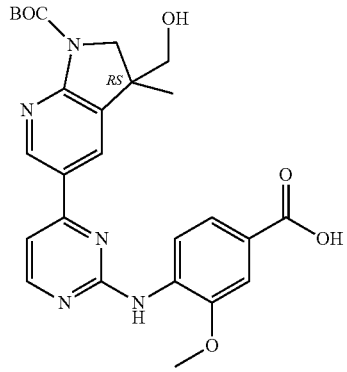 [SMILES: COc1cc(C(=O)O)ccc1Nc1nccc(-c2cnc3c(c2)C(C)(CO)CN3C(=O)OC(C)(C)C)n1]

To a stirred solution of intermediate 120 (274 mg; 0.525 mmol) in methanol (5 mL) at room temperature was added 2M aqueous lithium hydroxide (4 mL) and the reaction stirred for 2 hours. Then, the reaction was warmed to 50° C. and stirred for an additional 3 hours. The methanol was removed in vacuo and the pH of the solution adjusted to 6.0. The reaction was extracted with 3:1 mixture of DCM:MeOH but the product stayed in the aqueous phase. The aqueous phase was concentrated in vacuo and then, stirred in methanol (10 mL) for 5 minutes. The suspension was filtered and the filtrate concentrated in vacuo to afford 214 mg of intermediate 121 used in the next step without any further purification.

Example A13

Preparation of Intermediate 103:

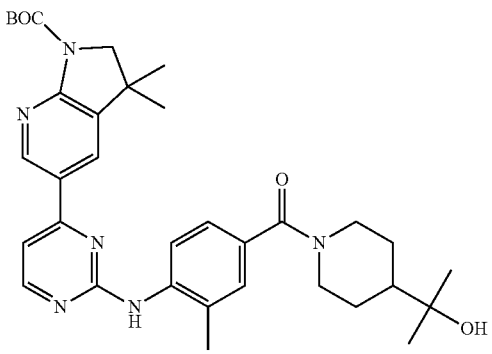 [SMILES: Cc1cc(C(=O)N2CCC(C(C)(C)O)CC2)ccc1Nc1nccc(-c2cnc3c(c2)C(C)(C)CN3C(=O)OC(C)(C)C)n1]

To a solution of intermediate 102 (75 mg, 0.16 mmol) and HATU (77.90 mg, 0.21 mmol) in DIPEA (82.40 µL, 0.082 mmol) and DMF (3 mL) was added 2-(4-piperidyl)-2-propanol (24.90 mg, 0.17 mmol) and the reaction mixture was stirred at ambient temperature for 1 h. The residue was then diluted with ethyl acetate, washed with water and the organic layer was dried with sodium sulfate and concentrated in vacuo to give 92 mg of intermediate 103 (colorless oil).

Example A14

Preparation of Intermediate 124:

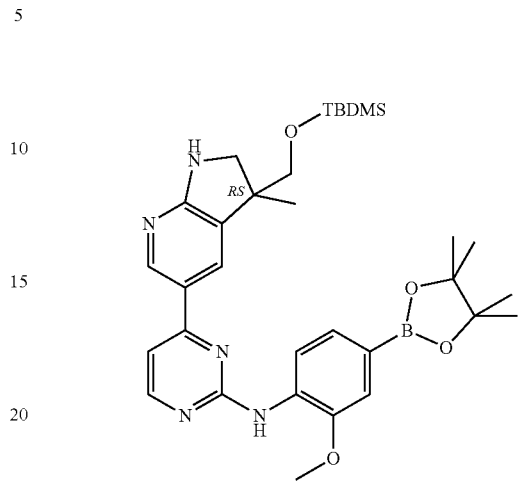

A stirred solution of intermediate 123 (289 mg, 0.52 mmol) in DME (4 mL) was degassed with argon for 5 minutes before Bis(pinacolato)diboron (198.00 mg, 0.78 mmol), KOAc (153 mg, 1.56 mmol) and Pd(dppf)Cl$_2$ (19 mg, 0.026 mmol) were added and the vial capped. The reaction was heated at 100° C. for 3 hours. The reaction was filtered and concentrated in vacuo. The crude material was purified by column chromatography using cyclohexane:EtOAc (0-50%) as eluent to give 300 mg of intermediate 124 (89% yield, yellow gum).

Example A15

Preparation of Intermediate 163:

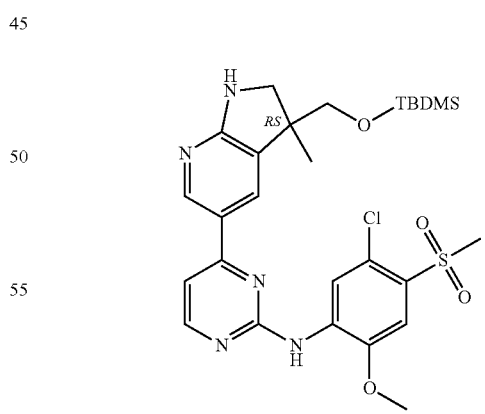

A solution of intermediate 162 (0.30 g, 0.43 mmol) in TFA (5.0 mL) under a nitrogen atmosphere at rt was stirred for 2 hours. The mixture was diluted with toluene and concentrated in vacuo to afford 252 mg of intermediate 163 (yellow oil) which was used in the next step without further purification.

Example A16

Method A3:
Preparation of Intermediate 16:

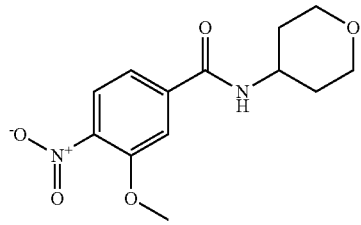

To a solution of 3-methoxy-4-nitrobenzoic acid (500 mg, 2.54 mmol) and HATU (1.25 g, 3.30 mmol) in DIPEA (1.32 mL, 7.61 mmol) and DCM (10 mL) was added 4-aminotetrahydropyran (257 mg, 2.54 mmol) and the reaction mixture was stirred at room temperature for 2 h. The reaction mixture was diluted with dichloromethane, washed with water and the organic layer was dried with sodium sulfate and concentrated in vacuo. The residue was triturated in a minimum amount of DCM and the solid formed was recovered by filtration and dried in vacuo to give 352 mg of intermediate 16 (50% yield, pale yellow solid).

Preparation of Intermediate 37:

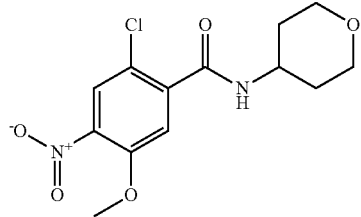

HATU (621.30 mg, 1.63 mmol) was added to a solution of intermediate 36 (291 mg, 1.26 mmol), 4-aminotetrahydropyran (139.89 mg, 1.38 mmol) and DIPEA (656.9 µL, 3.77 mmol) in DMF (5 mL) and the mixture was stirred at rt for 45 min. The reaction mixture was partitioned between EtOAc and a diluted aqueous solution of NaHCO₃. The organic layer was washed with brine, dried over Na₂SO₄ and concentrated in vacuo. The residue was purified by flash chromatography (40 g Si-PPC, DCM/EtOAc, 0-70%) to give 370 mg of intermediate 37 (94% yield, white foam).

Preparation of Intermediate 40:

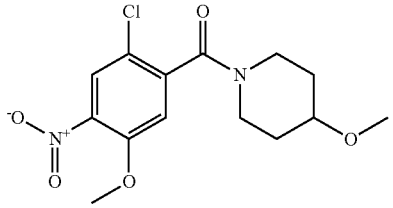

HATU (621.30 mg, 1.63 mmol) was added to a solution of intermediate 36 (291 mg, 1.26 mmol), 4-methoxypiperidine (159.29 mg, 1.38 mmol) and DIPEA (656.88 µL, 3.77 mmol) in DMF (5 mL) and the mixture was stirred at rt for 45 min. The reaction mixture was partitioned between EtOAc and a diluted aqueous solution of NaHCO₃ The organic layer was washed with brine, dried over Na₂SO₄ and concentrated in vacuo. The residue was purified by flash chromatography (40 g Si-PPC, DCM/EtOAc, 0-70%) to give 356 mg of intermediate 40 (86% yield, white solid).

The intermediates in the Table below were prepared by using an analogous method as described in method A3, starting from the respective starting materials.

| Intermediate number | Structure | Method |
|---|---|---|
| Intermediate 98 (from intermediate 97) | 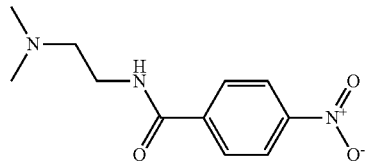 [SMILES: CN(C)CCNC(=O)c1ccc([N+](=O)[O-])cc1] | A3 |

Method A4:
Preparation of Intermediate 66:

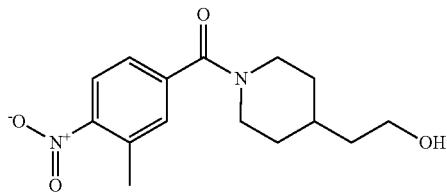

A mixture of 4-nitrobenzoic acid (2.00 g, 11.97 mmol), N,N-dimethylethylenediamine (1.45 mL, 13.16 mmol), EDC (2.52 g, 13.16 mmol) and HOBt (1.78 g, 13.16 mmol) in DCM (25 mL) was stirred at room temperature for 12 h. H₂O was added and the mixture was extracted with CH₂Cl₂. The organic layer was separated, dried over magnesium sulfate, filtered, and the solvent was evaporated to give 1.5 g of intermediate 66 (53% yield).

Method A5:
Preparation of Intermediate 76:

A stirred solution of 3-methyl-4-nitrobenzoic acid (1 g, 5.52 mmol) in DMF (15 mL) was treated successively with EDC (1.27 g, 6.62 mmol), HOAt (902.00 mg, 6.62 mmol) and finally 4-piperidine ethanol (1.07 g, 8.28 mmol) and the reaction mixture was stirred at ambient temperature for 24 h. The reaction mixture was diluted with ethyl acetate and washed with water and brine. The organic layer was dried with sodium sulfate, filtered and concentrated in vacuo. The residue was sonicated with diethyl ether, and the white solid formed was collected by filtration and dried in vacuo to give 1.17 g of intermediate 76 (72% yield) which was used in the next step without further purification.

Method A6:

Preparation of Intermediate 147:

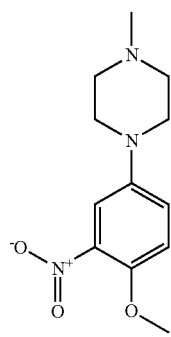

To a solution of 4-bromo-1-methoxy-2-nitrobenzene (1 g, 4.31 mmol), N-methyl piperazine (956 μL, 8.62 mmol), Xantphos (748 mg, 1.29 mmol) and Cs$_2$CO$_3$ (2.81 g, 8.62 mmol) in 1,4-dioxane (10 mL) was added Pd$_2$(dba)$_3$ (788.00 mg, 0.86 mmol) and the reaction mixture was stirred at 90° C. for 21 h. The reaction mixture was diluted with ethyl acetate, washed with water and the organic layer was dried over sodium sulfate and concentrated in vacuo to give 638 mg of intermediate 147 (59% yield, orange oil) which was used in the next step without further purification.

Method A7:

Preparation of Intermediate 152:

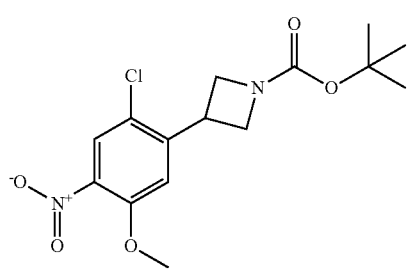

TMSCl (129 μL, 1.01 mmol) was added to a suspension of zinc dust (530 mg, 8.11 mmol) in dimethyl acetamide (4 mL) at 65° C. under nitrogen. 1,2 bromoethane (86 μL, 1 mmol) was then added and the mixture was stirred for 40 min. 3-iodo-N-boc azetidine (1.43 g, 5.06 mmol) in dimethyl acetamide (2 mL) was then added dropwise over 1 min and the mixture was stirred for 30 min at 65° C. 5-bromo-4-chloro-2-nitroanisole (1.00 g, 3.75 mmol) in dimethyl acetamide (4 mL) was then added followed by Pd(dppf)Cl$_2$.CH$_2$Cl$_2$ (91 mg, 0.11 mmol) and CuI (44 mg, 0.23 mmol) and the mixture was stirred at 85° C. for 1.5 h. The cooled mixture was partitioned between a saturated aqueous solution of ammonium chloride (30 mL) and ethyl acetate (3×30 mL). The combined organic extracts were washed with brine (40 mL) and dried over Na$_2$SO$_4$. The solvent was evaporated and the residue was purified by flash column chromatography (mobile phase gradient: from 100% pentane to 50% pentane, 50% EtOAc) to give 1.14 g of intermediate 152 (89% yield, pale yellow gum).

Method A8:

Preparation of Intermediate 157:

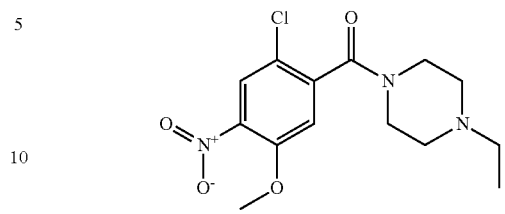

A mixture of 1-bromo-2-chloro-5-methoxy-nitrobenzene (0.35 g, 1.31 mmol), N-ethyl piperazine (0.22 mL, 1.75 mmol), Mo(CO)$_6$ (0.17 g, 0.66 mmol), Herrmann's catalyst (0.12 g, 0.131 mmol), DBU (0.13 mL, 0.88 mmol), tris-(tert-butyl))phosphonium tetrafluoroborate (0.095 g, 0.327 mmol) and anhydrous THF (5.2 mL) in a 20 mL vial under Argon atmosphere was heated by microwave irradiation at 125° C. for 6 min. The mixture was concentrated in vacuo and the residue was purified by column chromatography (eluting with a mixture of DCM and 2 M ammonia in MeOH (1:0 to 19:1)) to give 221 mg of intermediate 157 (51% yield, pale yellow foam).

Example A17

Method A9:

Preparation of Intermediate 19:

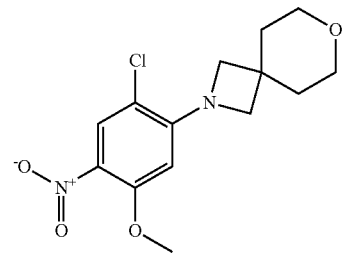

A suspension of 1-bromo-2-chloro-5-methoxy-4-nitrobenzene (250 mg, 0.94 mmol), 7-oxa-2-azaspiro[3,5]nonane oxalate (224 mg, 1.03 mmol) and K$_2$CO$_3$ (389 mg, 2.81 mmol) in DMF (3 mL) was stirred at 80° C. for 18 h. The reaction mixture was diluted with ethyl acetate, washed with water and brine and the organic layer was dried with sodium sulfate and concentrated in vacuo. The residue was triturated with diethyl ether and the yellow solid formed was collected by filtration and dried in vacuo to give 136.5 mg of intermediate 19 (46% yield, yellow solid) which was used in the next step without further purification.

Preparation of Intermediate 23:

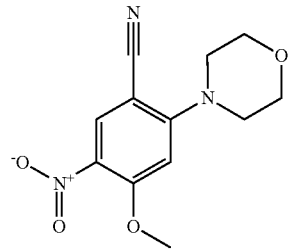

A solution of intermediate 22 (1.19 g, 5.76 mmol), morpholine (577 µL, 6.67 mmol) and K₂CO₃ (1.68 g, 12.12 mmol) in DMF (10 mL) was stirred at 80° C. for 1 h. The reaction mixture was diluted with ethyl acetate, washed with water and the organic layer was dried with sodium sulfate and concentrated in vacuo to give 1.24 g of intermediate 23 (78% yield, 95% purity based on LC/MS, yellow solid).

Preparation of Intermediate 26:

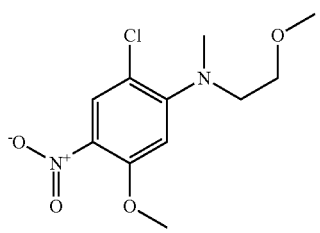

A solution of 1-bromo-2-chloro-5-methoxy-4-nitrobenzene (250 mg, 0.94 mmol), N-(2-methoxyethyl)-N-methylamine (112 µL, 1.03 mmol) and K₂CO₃ (259 mg, 1.88 mmol) in DMF (2 mL) was stirred at 80° C. for 72 h. The reaction mixture was diluted with ethyl acetate, washed with water and the organic layer was dried with sodium sulfate and concentrated in vacuo to give 258 mg of intermediate 26 (quant. yield, orange solid) which was used in the next step without further purification.

Preparation of Intermediate 29:

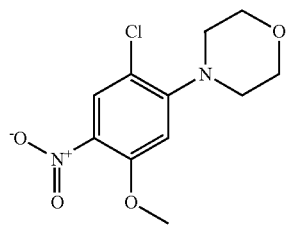

A solution of 1-bromo-2-chloro-5-methoxy-4-nitrobenzene (200 mg, 0.75 mmol), morpholine (71.50 µL, 0.83 mmol) and K₂CO₃ (208 mg, 1.50 mmol) in DMF (2 mL) was stirred at 80° C. for 22 h. The reaction mixture was diluted with ethyl acetate, washed with water and the organic layer was dried with sodium sulfate and concentrated in vacuo to give 143 mg of intermediate 29 (70% yield, purple solid).

Method 10:

Preparation of Intermediate 32:

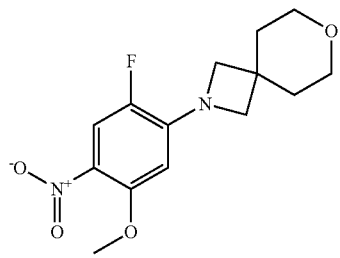

A suspension of 1,2-difluoro-4-methoxy-5-nitrobenzene (300 mg, 1.59 mmol), 7-oxa-2-azaspiro[3,5]nonane oxalate (361.67 mg, 1.67 mmol) and Cs₂CO₃ (1.55 g, 4.77 mmol) in DMF (5 mL) was heated to 80° C. for 15 min. The reaction mixture was poured onto ice and the resultant precipitate was collected by filtration, washed with water and diethyl ether and dried under vacuo to give 435 mg of intermediate 32 (93% yield, yellow solid).

Preparation of Intermediate 54:

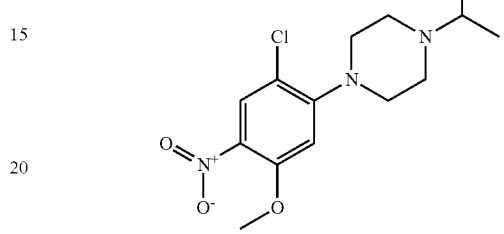

1-bromo-2-chloro-5-methoxy-4-nitrobenzene (375.00 mg, 1.41 mmol), N-isopropyl piperazine (198.73 mg, 1.55 mmol) and Cs₂CO₃ (1.37 g, 4.22 mmol) were added together in DMF (7 mL) and the resulting mixture was heated at 85° C. under nitrogen for 4 h. The reaction was diluted with water and extracted with ethyl acetate. The organic layers were combined, dried over sodium sulfate and evaporated under reduced pressure. The crude product was purified by flash chromatography (12 g, mobile phase gradient: from 100% DCM to 90% DCM, 10% MeOH) to give 160 mg of intermediate 54 (36% yield, yellow solid).

Preparation of Intermediate 60:

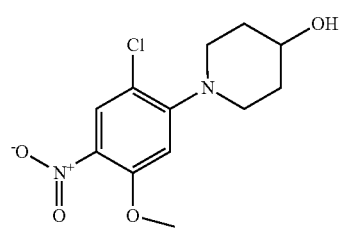

A suspension of 1-bromo-2-chloro-5-methoxy-4-nitrobenzene (1.50 g, 5.63 mmol), 4-hydroxypiperidine (507 mg, 5.63 mmol) and Cs₂CO₃ (5.50 g, 16.89 mmol) in DMF (15 mL) was stirred at 80° C. for 2 h. Another equivalent of 4-hydroxypiperidine (507.00 mg, 5.63 mmol) was added and the reaction mixture was stirred at 80° C. for another 18 h. The reaction mixture was diluted with ethyl acetate, washed with water and brine and the organic layer was dried with sodium sulfate and concentrated in vacuo. The residue was dissolved in ethyl acetate (2 mL) and cyclohexane was added until a precipitate was formed. The solid was recovered by filtration, washed with cyclohexane and dried in vacuo to give 1 g of intermediate 60 (62% yield, yellow solid) which was used in the next step without further purification.

Method A11:
Preparation of Intermediate 57:

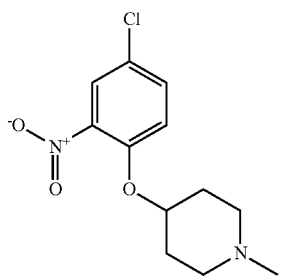

NaH (60% dispersion in mineral oil) (407.60 mg, 10.19 mmol) was added to a solution of 4-hydroxy-1-methylpiperidine (1.08 g, 9.34 mmol) in DMF (9 mL) at 0° C. and the mixture was warmed to rt for 15 min. 5-chloro-2-fluoronitrobenzene (1.49 g, 8.49 mmol) was added and the mixture was stirred at rt for a further 2 h. The reaction mixture was partitioned between EtOAc and saturated aqueous solution of NaHCO₃. The organic layer was washed with brine, dried over Na₂SO₄ and concentrated in vacuo. The crude residue was purified by flash chromatography (40 g Si-PPC, mobile phase gradient: from 100% DCM to 90% DCM, 10% 2M ammonia in MeOH) to give 1.69 g of intermediate 57 (74% yield, yellow oil).

Method A12:
Preparation of Intermediate 63:

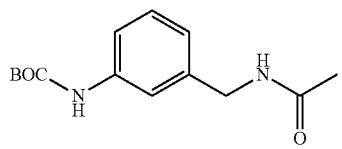 [SMILES: CC(=O)NCc1cccc(NC(=O)OC(C)(C)C)c1]

To a solution of 3-(aminomethyl)-1-N-Boc-aniline (1 g, 4.50 mmol) in TEA (911 mg, 9 mmol) and DCM (10 mL) was added acetyl chloride (424.00 mg, 5.40 mmol) and the reaction mixture was stirred at ambient temperature for 1 h. The reaction mixture was partitioned between dichloromethane and brine. The organic layer was dried with sodium sulfate, filtered and concentrated in vacuo to give 1.19 g of intermediate 63 (orange oil).

Method A13:
Preparation of Intermediate 94:

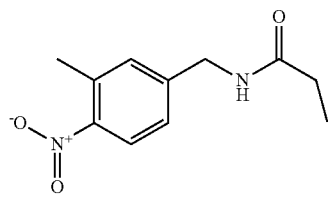

To a solution of intermediate 93 (350.00 mg, 2.1 mmol) in pyridine (4 mL) was added propionyl chloride (0.7 mL, 8 mmol) and the reaction mixture was stirred at room temperature for 1 hour. The solution was diluted to 20 mL with DCM and washed 3 times with water. The combined aqueous extracts were washed with 5 mL of DCM. The organics layers were combined and washed with an aqueous solution of CuSO₄. The organic layer was isolated and evaporated to dryness. The crude residue was purified by flash chromatography (25 g Si cartridge, mobile phase gradient: from 100% DCM to 60% DCM, 40% EtOAc) to give 500 mg of intermediate 94 (yellow solid).

Method A14:
Preparation of Intermediate 139:

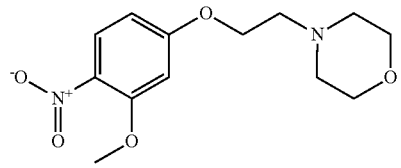

A mixture of 4-fluoro-2-methoxynitrobenzene (1.00 g, 5.84 mmol), 2-morpholino-ethanol (1.50 g, 11.4 mmol) and tetrabutylammonium bromide (375.00 mg, 1.16 mmol) in KOH (5M in water) (5 mL) and toluene (5 mL) was heated at 60° C. for 18 h. The resulting yellow mixture was poured into water (30 mL) extracted with ethyl acetate (3×30 mL), filtered through a phase separator and solvent was evaporated under reduced pressure to give a yellow oil. The crude material was purified by flash chromatography column on silica (100 g, mobile phase gradient: from 100% DCM to 80% DCM, 20% MeOH, over 30 minutes). Fractions containing product were combined and solvent was evaporated to give 1.62 g of intermediate 139 (98% yield, yellow oil).

Method A15:
Preparation of Intermediate 154:

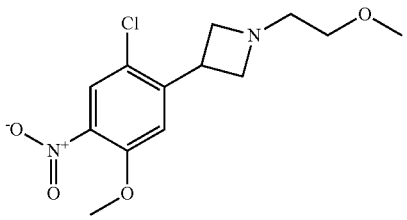

A mixture of intermediate 153 (300 mg, 1.24 mmol), 2-bromo-methoxyethane (233 µL, 2.48 mmol) and DIPEA (883 µL, 4.96 mmol) in DMF (5 mL) was stirred at 45° C. for 18 h. The mixture was purified by SCX-2 (elution with methanol followed by methanolic ammonia (2M)) to give after evaporation a colorless gum. The crude residue was purified further by flash chromatography column (mobile phase gradient: from 100% DCM to 100% DCM-methanolic ammonia (2M, 20:1) mixture) to give 118 mg of intermediate 154 (32% yield, pale yellow gum).

Method A16:
Preparation of Intermediate 170:

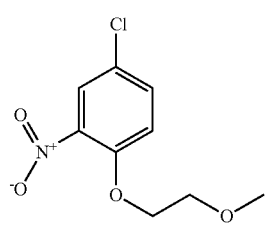

5-chloro-2-fluoronitrobenzene (335 μL, 2.85 mmol) and 2-methoxyethanol (0.25 mL, 3.14 mmol) were dissolved in distilled THF (3.48 mL) (to give a 0.1-0.2 M solution) under Ar and cooled to 0° C. KHMDS (3.14 mL, 3.14 mmol) dissolved in distilled THF (3.14 mL) (to give 0.5 M solution) was added dropwise, resulting in a color change from colorless to dark orange. This solution was stirred from 0° C. to room temperature over 2 h and then diluted with $CH_2Cl_2$ and washed with a saturated aqueous solution of $NH_4Cl$. The aqueous layer was extracted once with $CH_2Cl_2$. The organic layers were combined, dried over $MgSO_4$ and concentrated under reduced pressure. The crude residue was purified on silica gel (irregular SiOH, 24 g; mobile phase gradient: from 0% EtOAc, 100% heptane to 30% EtOAc, 70% heptane). Fractions containing product were collected and evaporated to dryness to give 711 mg of intermediate 170 (quant. yield, orange oil).

The intermediates in the Table below were prepared by using an analogous method as describes in methods A13 to A20, starting from the respective starting materials.

| Intermediate number | Structure | Method |
|---|---|---|
| Intermediate 89 (from intermediate 88 and acetyl chloride) | 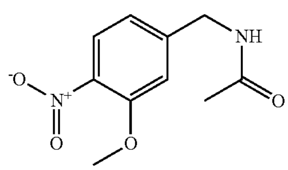 | A12 |
| Intermediate number Intermediate 117 (from intermediate 116 and acetyl chloride) | 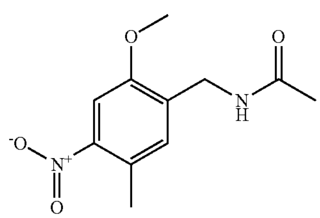 | A12 |
| Intermediate 126 (from intermediate 125 and morpholine) | 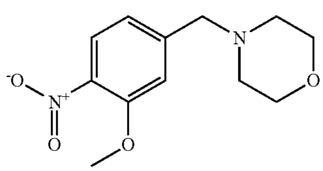 | A12 |
| Intermediate 142 (from 4-fluoro-2-methoxynitrobenzene and 1-Boc-3-pyrrolidinol) | | A14 |
| Intermediate 150 (from 1-bromo-2-chloro-5-methoxy-4-nitrobenzene and azetidin-3-yl-dimethyl-amine.HCl) | 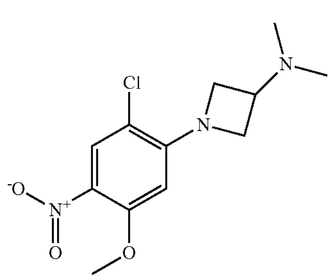 | A9 |

Example A18

Method A17:
Preparation of Intermediate 17:

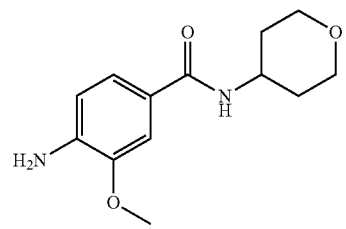 [SMILES: COc1cc(C(=O)NC2CCOCC2)ccc1N]

A suspension of intermediate 16 (352 mg, 1.26 mmol), Pd/C (10% wt, 150 mg) and ammonium formate (792.00 mg, 12.56 mmol) in EtOH (30 mL) was stirred for 2 h at 80° C. The reaction mixture was filtered through Celite® and the solution was concentrated in vacuo. The residue was loaded onto an Isolute® SCX-2 cartridge which was washed with methanol and then the product was eluted with 2M $NH_3$ in methanol. The 2M $NH_3$ in methanol solution was concentrated in vacuo to give 293 mg of intermediate 17 (93% yield, off-white solid).

Method A18:
Preparation of Intermediate 20:

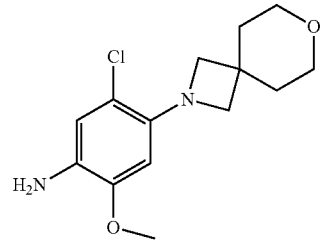 [SMILES: COc1cc(N2CC3(CCOCC3)C2)c(Cl)cc1N]

A suspension of intermediate 19 (136 mg, 0.44 mmol), $NH_4Cl$ (93 mg, 1.74 mmol) and iron powder (121 mg, 2.17 mmol) in EtOH (1 mL) and water (1.5 mL) was heated to 75° C. for 1 h. The reaction mixture was filtered through Celite® and the filtrate was concentrated in vacuo. The residue was partitioned between dichloromethane and a diluted aqueous solution of $NaHCO_3$. The organic layer was dried with sodium sulfate and concentrated in vacuo to give 109 mg of intermediate 20 (89% yield, grey solid).

Preparation of Intermediate 27:

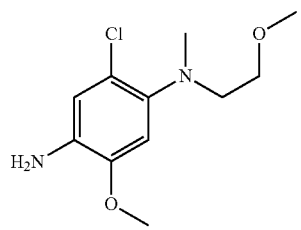 [SMILES: COCCN(C)c1cc(OC)c(N)cc1Cl]

A suspension of intermediate 26 (258 mg, 0.94 mmol), $NH_4Cl$ (201 mg, 3.75 mmol) and iron powder (262 mg, 4.69 mmol) in EtOH (2 mL) and water (3 mL) was heated to 80° C. for 0.5 h. The reaction mixture was filtered through Celite® and the filtrate was concentrated in vacuo. The residue was partitioned between dichloromethane and a diluted aqueous solution of NaHCO₃. The organic layer was dried with sodium sulfate and concentrated in vacuo to give 124 mg of intermediate 27 (50% yield, 92% purity based on LC/MS, dark oil) which was used in the next step without further purification.

Preparation of Intermediate 30:

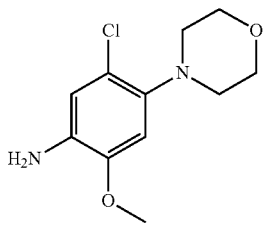 [SMILES: COc1cc(N2CCOCC2)c(Cl)cc1N]

A suspension of intermediate 29 (175 mg, 0.64 mmol), NH₄Cl (137 mg, 2.57 mmol) and iron powder (179 mg, 3.21 mmol) in EtOH (2 mL) and water (3 mL) was heated at 75° C. for 3 h. The reaction mixture was filtered through Celite® and the filtrate was concentrated in vacuo. The residue was partitioned between dichloromethane and a diluted aqueous solution of NaHCO₃. The organic layer was dried with sodium sulfate and concentrated in vacuo to give 153 mg of intermediate 30 (quant. yield, dark purple solid) which was used in the next step without further purification.

Preparation of Intermediate 33:

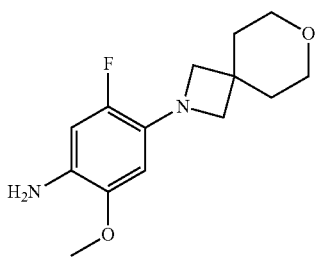 [SMILES: COc1cc(N2CC3(CCOCC3)C2)c(F)cc1N]

A suspension of intermediate 32 (435 mg, 1.47 mmol), NH₄Cl (314.52 mg, 5.88 mmol) and iron powder (410.46 mg, 7.35 mmol) in EtOH (10 ML) and water (10 ML) was heated at 75° C. for 0.5 h. The reaction mixture was filtered through Celite® and the filtrate was concentrated in vacuo. The residue was partitioned between dichloromethane and a diluted aqueous solution of NaHCO₃. The organic layer was dried with sodium sulfate and concentrated in vacuo to give 382 mg of intermediate 33 (97% yield, purple solid) which was used in the next step without further purification.

Preparation of Intermediate 38:

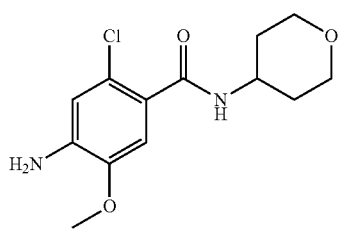 [SMILES: COc1cc(C(=O)NC2CCOCC2)c(Cl)cc1N]

A suspension of intermediate 37 (370 mg, 1.18 mmol), NH₄Cl (251.40 mg, 4.70 mmol) and iron powder (328.37 mg, 5.88 mmol) in EtOH (8 mL) and water (8 mL) was heated at 80° C. for 0.5 h. The reaction mixture was filtered through Celite® and the filtrate was concentrated in vacuo. The residue was partitioned between dichloromethane and a diluted aqueous solution of NaHCO₃. The organic layer was dried with sodium sulfate and concentrated in vacuo to give 96 mg of intermediate 38 (29% yield, white solid) which was used in the next step without further purification.

Preparation of Intermediate 41:

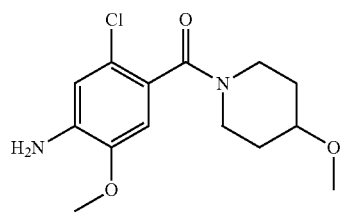 [SMILES: COc1cc(C(=O)N2CCC(OC)CC2)c(Cl)cc1N]

A suspension of intermediate 40 (356 mg, 1.08 mmol), NH₄Cl (231.61 mg, 4.33 mmol) and iron powder (302.68 mg, 5.42 mmol) in EtOH (8 mL) and water (8 mL) was heated at 80° C. for 0.5 h. The reaction mixture was filtered through Celite® and the filtrate was concentrated in vacuo. The residue was partitioned between dichloromethane and a diluted aqueous solution of NaHCO₃ solution. The organic layer was dried with sodium sulfate and concentrated in vacuo to give 323 mg of intermediate 41 (white solid) which was used in the next step without further purification.

Preparation of Intermediate 55:

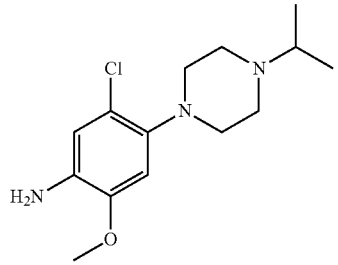 [SMILES: COc1cc(N2CCN(C(C)C)CC2)c(Cl)cc1N]

Intermediate 54 (240 mg, 0.76 mmol), NH₄Cl (163.68 mg, 3.06 mmol) and iron powder (213.35 mg, 3.82 mmol) were added together in EtOH (1.2 mL) and water (3.6 mL) and the resulting mixture was heated at 75° C. under nitrogen for 1.5 hours. The reaction mixture was filtered through Celite® and the filtrate was concentrated in vacuo. The residue was partitioned between ethyl acetate and water. The organic layer was dried with sodium sulfate and concentrated in vacuo to give 195 mg of intermediate 55 (90% yield) which was used in the next step without further purification.

Preparation of intermediate 58:

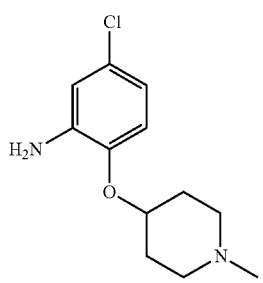 [SMILES: CN1CCC(Oc2ccc(Cl)cc2N)CC1]

A suspension of intermediate 57 (1.69 g, 6.24 mmol), NH₄Cl (1.33 g, 24.96 mmol) and iron powder (1.74 g, 31.2 mmol) in EtOH (18 mL) and water (18 mL) was heated to 85° C. for 1 h. The reaction mixture was filtered through Celite® and the filtrate was concentrated in vacuo. The residue was partitioned between dichloromethane and a diluted aqueous solution of NaHCO₃. The organic layer was dried with sodium sulfate and concentrated in vacuo to give 1.28 g of intermediate 58 (85% yield, off-white solid) which was used in the next step without further purification.

Method A19:

Preparation of Intermediate 24:

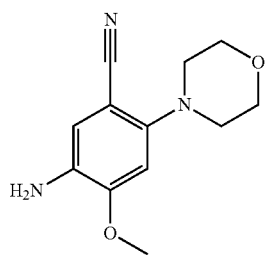

A suspension of intermediate 23 (1.24 g, 4.71 mmol) and tin (II) chloride dihydrate (7.44 g, 32.97 mmol) in EtOH (50 mL) was heated at reflux for 1 h. Aqueous sodium bicarbonate and dichloromethane were added and the organic layer was isolated, dried with sodium sulfate, filtered and concentrated in vacuo to give 573 mg of intermediate 24 (50% yield, 95% purity based on LC/MS).

Method A20:

Preparation of Intermediate 48:

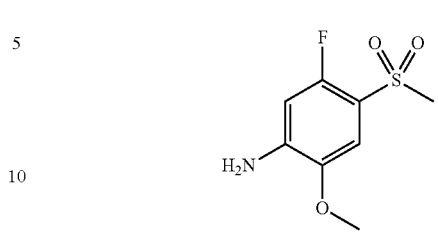

To a solution of intermediate 47 (492 mg, 1.97 mmol) in EtOH (50 mL) was added Pd/C (10% wt., 50 mg) and the resulting mixture was stirred under hydrogen (1 atm.) at room temperature for 6 h. The reaction was filtered through Celite® and the filtrate was evaporated under reduced pressure. The residue was purified by column chromatography (25 g silica, mobile phase gradient: from 100% cyclohexane to 30% cyclohexane, 70% EtOAc). Product containing fractions were combined and evaporated under reduced pressure to give 412 mg of intermediate 48 (95% yield, pale yellow oil).

Method A21:

Preparation of Intermediate 61:

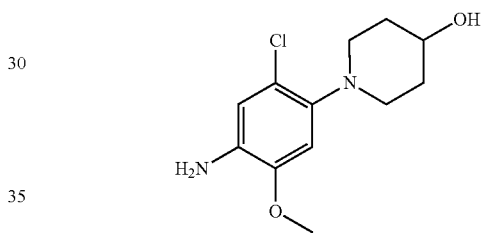

To a solution of intermediate 60 (1 g, 3.49 mmol) in EtOH (40 mL) was added under nitrogen PtO₂ (79.50 mg, 0.35 mmol). The reaction mixture was placed under 1 atm. hydrogen and stirred for 1 h at ambient temperature. Another portion of PtO₂ (79.50 mg, 0.35 mmol) was added and the reaction mixture was stirred for a further 18 h. The reaction mixture was filtered through Celite® and the filtrate was concentrated in vacuo to give 809 mg of intermediate 61 (90% yield, purple oil).

The intermediates in the Table below were prepared by using an analogous method as described in methods A17 to A21, starting from the respective starting materials.

| Intermediate number | Structure | Method |
| --- | --- | --- |
| Intermediate 77 (from intermediate 76) | 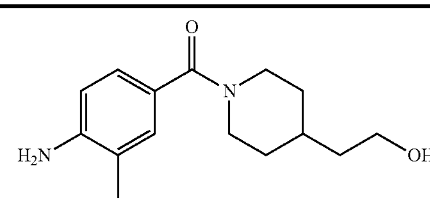 | A17 |
| Intermediate 90 (from intermediate 89) | 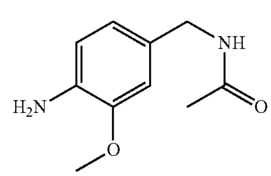 | A17 |

-continued
| Intermediate number | Structure | Method |
|---|---|---|
| Intermediate 95 (from intermediate 94) | 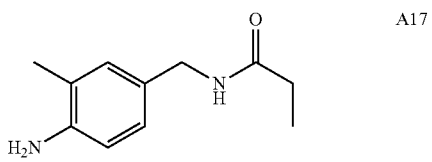 | A17 |
| Intermediate 99 (from intermediate 98) | 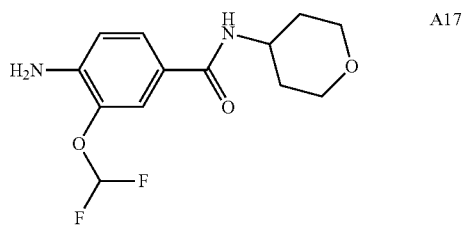 | A17 |
| Intermediate 101 (from 3-methyl-4-nitrobenzoic acid) | 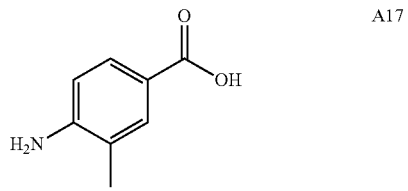 | A17 |
| Intermediate 118 (from intermediate 117) | 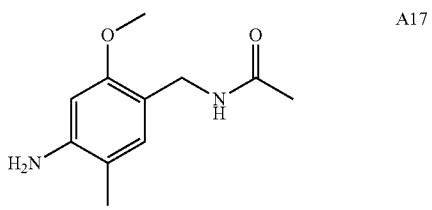 | A17 |
| Intermediate 127 (from intermediate 126) | 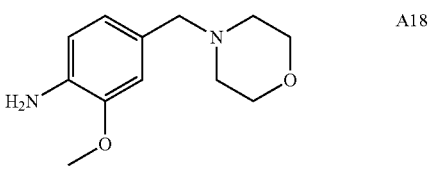 | A18 |
| Intermediate 130 (from intermediate 129) | 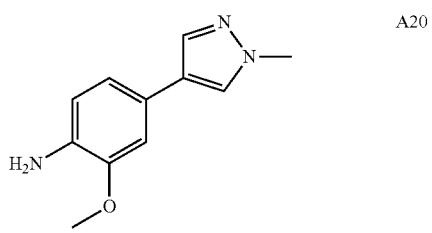 | A20 |
| Intermediate 134 (from intermediate 133) | 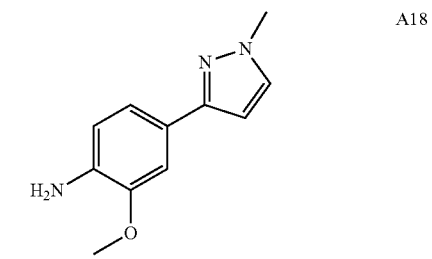 | A18 |

-continued
| Intermediate number | Structure | Method |
|---|---|---|
| Intermediate 137 (from intermediate 136) | 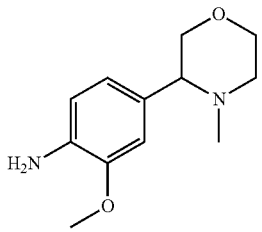 [SMILES: COc1cc(C2COCCN2C)ccc1N] | A18 |
| Intermediate 140 (from intermediate 139) | 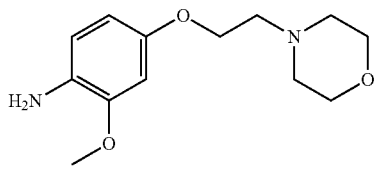 [SMILES: COc1cc(OCCN2CCOCC2)ccc1N] | A20 |
| Intermediate 145 (from intermediate 144) | 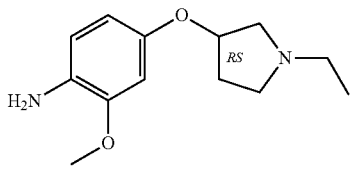 [SMILES: CCN1CCC(Oc2ccc(N)c(OC)c2)C1] | A20 |
| Intermediate 148 (from intermediate 147) | 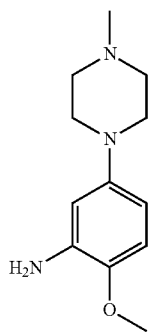 | A20 |
| Intermediate 151 (from intermediate 150) | 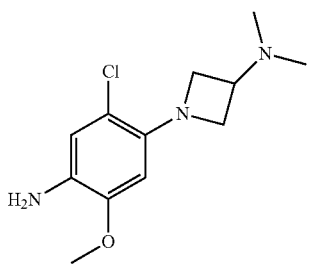 [SMILES: COc1cc(N2CC(N(C)C)C2)c(Cl)cc1N] | A18 |
| Intermediate 155 (from intermediate 154) | 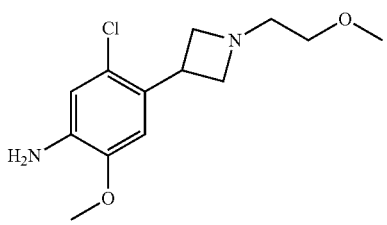 [SMILES: COCCN1CC(c2cc(OC)c(N)cc2Cl)C1] | A21 |

-continued

| Intermediate number | Structure | Method |
|---|---|---|
| Intermediate 158 (from intermediate 157) | ![structure] | A18 |
| Intermediate 161 (from intermediate 160) | ![structure] | A18 |
| Intermediate 165 (from intermediate 164) | ![structure] | A18 |
| Intermediate 171 (from intermediate 170) | ![structure] | A18 |

Example A19

Preparation of Intermediate 22:

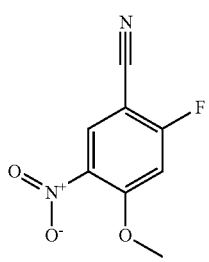

2-fluoro-4-methoxy benzonitrile (1 g, 6.62 mmol) was added to a stirred mixture of KNO₃ (736 mg, 7.28 mmol) in concentrated H₂SO₄ (6.5 mL) at 0° C. and the reaction mixture was stirred at this temperature for 1 h. The reaction mixture was then carefully poured onto a saturated solution of sodium hydrogenocarbonate at 0° C. under stirring. The resulting mixture was extracted with dichloromethane and the organic layer was dried with sodium sulfate and concentrated in vacuo to give 1.19 g of intermediate 22 (87% yield, 95% purity based on LC/MS, orange oil) which was used in the next step without further purification.

Example A20

Preparation of Intermediate 35:

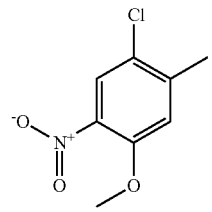

NaH (60% dispersion in mineral oil) (1.28 g, 31.99 mmol) was added portionwise to a solution of 4-chloro-3-methyl-6-nitrophenol (5 g, 26.66 mmol) in DMF (60 mL) at 0° C., and the mixture was stirred for 15 min at this temperature. MeI (1.83 mL, 29.33 mmol) was added and the mixture was warmed to rt and stirred for 24 h. The reaction mixture was partitioned between EtOAc and water and the organic layer was washed with brine, dried over Na₂SO₄ and concentrated in vacuo. The crude residue was purified by flash chromatography (80 g Si-PPC, mobile phase gradient: from 100% cyclohexane to 80% cyclohexane, 20% EtOAc) to give 4.09 g of intermediate 35 (76% yield, pale yellow solid).

Preparation of Intermediate 133:

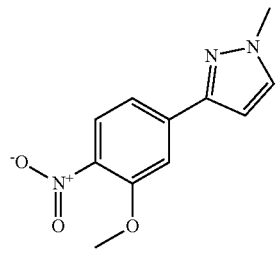

Cs$_2$CO$_3$ (612 mg, 1.88 mmol) and MeI (466 mg, 3.28 mmol) were added to a solution of intermediate 132 (343.00 mg, 1.56 mmol) in DMF (5 mL) at rt under Ar. The mixture was stirred for 48 h. The resulting yellow mixture was poured into brine (30 mL) and extracted with ethyl acetate (3×20 mL). The combined organic layers were filtered through a phase separator and solvent was evaporated under reduced pressure. The crude material was purified by flash column chromatography on silica (80 g) eluting with cyclohexane/ethyl acetate (0 to 40%) over 35 minutes. Fractions containing product were combined and solvent was evaporated under reduced pressure to give 300 mg of intermediate 133 (82% yield, pale yellow solid).

Preparation of Intermediate 136:

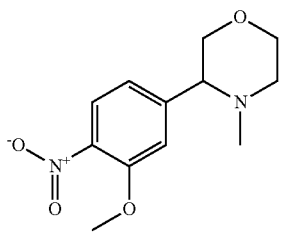

A mixture of 2-methoxy-4-morpholin-3-yl-1-nitrobenzene hydrochloride (500 mg, 1.82 mmol) and paraformaldehyde (1.60 g, 17.80 mmol) in formic acid (5 mL) was heated at 45° C. for 16 h and 100° C. for 6 h. Solvent was evaporated under reduced pressure and the compound was purified by an SCX column (50 g) eluting with a 2M solution of ammonia in methanol. The crude material was purified by flash column chromatography on silica (80 g) eluting with dichloromethane/methanol (0 to 10%) over 30 minutes. Fractions containing product were combined and solvent was evaporated under reduced pressure to give 478 mg of intermediate 136 (99% yield, pale yellow solid).

Preparation of Intermediate 144:

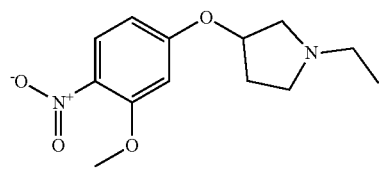

A solution of intermediate 143 (266 mg, 1 mmol based on 90% purity determined by LC/MS), Iodoethane (72.70 µL, 0.90 mmol) and TEA (420 µL, 3.01 mmol) in THF (5 mL) was stirred at rt for 16 h. The resulting yellow mixture was poured into water (30 mL) and extracted with ethyl acetate (3×30 mL), filtered through a phase separator and solvent was evaporated under reduced pressure to give a yellow oil. The crude material was purified by flash column chromatography on silica (80 g) eluting with dichloromethane/methanol (0 to 15%) over 30 minutes. Fractions containing product were combined and solvent was evaporated to give 201 mg of intermediate 144 (75% yield, pale yellow oil).

Example A21

Preparation of Intermediate 36:

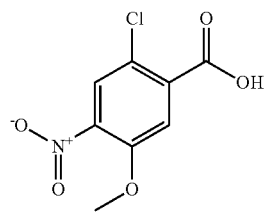

A suspension of intermediate 35 (4.09 g, 20.29 mmol) and KMnO$_4$ (12.83 g, 81.16 mmol) in water (150 mL) was heated at reflux for 24 h. A second portion of KMnO$_4$ (6.42 g, 40.60 mmol) was added and the reaction mixture was refluxed for a further 24 h. The cooled reaction mixture was acidified to pH 2 with a concentrated hydrogen chloride solution and extracted several times with EtOAc. The organic layers were dried over Na$_2$SO$_4$, filtered and concentrated in vacuo. The product was triturated with cold DCM and filtered to give 873 mg of intermediate 36 (17% yield, off-white solid).

Example A22

Preparation of Intermediate 46:

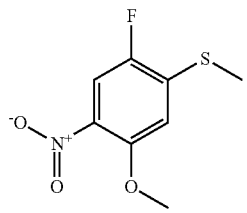

To a solution of 1,2-difluoro-4-methoxy-5-nitrobenzene (720 mg, 3.81 mmol) in EtOH (100 mL) was added dropwise a solution of sodium thiomethoxide (300 mg, 4.22 mmol) in water (1 mL) and the resulting mixture was refluxed under nitrogen for 4 hours. A further amount of sodium thiomethoxide (350 mg, 4.92 mmol) in water (1 mL) was added and the resulting mixture was refluxed for 18 hours. The reaction was allowed to cool to room temperature and the solvent was removed under reduced pressure. The residue was purified by column chromatography (80 g silica, mobile phase gradient: from 100% cyclohexane to 50% cyclohexane, 50% EtOAc). Fractions containing the product were combined and evaporated under reduced pressure to give 491 mg of intermediate 46 (59% yield, pale yellow solid).

157

Preparation of Intermediate 47:

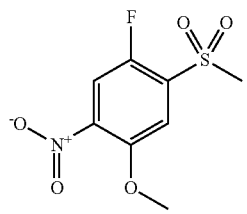

Intermediate 46 (491 mg, 2.26 mmol) was dissolved in DCM (20 mL), treated with mCPBA (658.45 mg, 2.94 mmol based on 77% purity) and the resulting mixture was stirred at room temperature under nitrogen for 18 h. A further amount of mCPBA (658.45 mg, 2.94 mmol based on 77% purity) was added and the resulting mixture was stirred at room temperature under nitrogen for 5 h. The solvent was removed under reduced pressure and the residue was taken up in dichloromethane. The solid was collected by filtration and discarded. The filtrate was purified by column chromatography (80 g silica, mobile phase gradient: from 100% cyclohexane to 50% cyclohexane, 50% EtOAc). Product containing fractions were combined and evaporated under reduced pressure to give 492 mg of intermediate 47 (87% yield, off-white solid).

The intermediate in the Table below was prepared by using an analogous method, starting from the respective starting materials.

| Intermediate number | Structure |
|---|---|
| Intermediate 160 (from chloro-2-fluoro-4-methoxy-5-nitrobenzene) | 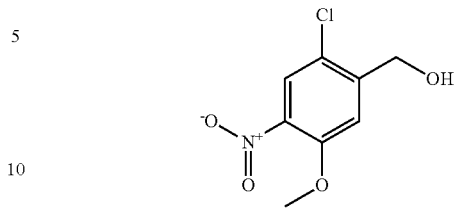 |

Example A23

Preparation of Intermediate 125:

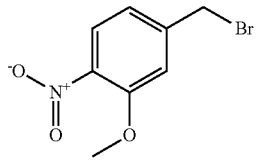

CBr$_4$ (1.36 g, 4.10 mmol) was added to a stirred solution of 3-methoxy-4-nitrobenzyl alcohol (500.00 mg, 2.73 mmol) and PPh$_3$ (1.07 g, 4.10 mmol) in THF (10 mL) and the mixture was stirred at rt for 24 h. The reaction mixture was concentrated in vacuo and the residue was purified by flash chromatography (40 g Si-PPC, mobile phase gradient: from 100% cyclohexane to 20% cyclohexane, 80% EtOAc) to give 617 mg of intermediate 125 (92% yield, pale yellow solid).

158

Preparation of Intermediate 164:

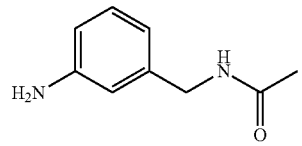

A suspension of 4-nitro-3-methoxybenzylalcohol (500 mg, 2.73 mmol) and NCS (400.60, 3 mmol) in MeCN (5 mL) was heated at purified by flash chromatography (40 g Si-PPC, mobile phase gradient: from 100% cyclohexane to 20% cyclohexane, 80% EtOAc) to give 460 mg of intermediate 164 (77% yield, yellow solid).

Example A25

Preparation of Intermediate 64:

To a solution of intermediate 63 (1.19 g, 4.27 mmol) in DCM (5 mL) was added TFA (5 mL) and the reaction mixture was stirred at ambient temperature for 1 h. The solution was then loaded onto an Isolute® SCX-2 cartridge which was washed with methanol and then the product was eluted with 2M NH$_3$ in methanol. The 2M NH$_3$ in methanol solution was concentrated in vacuo to give 700 mg of intermediate 64 (quant. yield, orange oil). The intermediates in the Table below were prepared by using an analogous method, starting from the respective starting materials.

| Intermediate number | Structure |
|---|---|
| Intermediate 143 (from intermediate 142) | 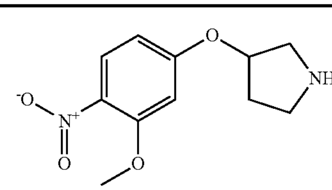 |
| Intermediate 153 (from intermediate 152) | 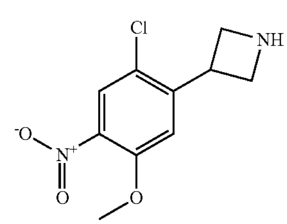 |

Example A26

Preparation of Intermediate 92:

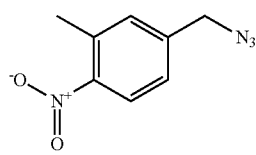

To a suspension of 3-Methyl-4-nitrobenzyl bromide (2.53 g; 11.0 mmol) in DMF (10 mL) was added sodium azide (715 mg; 11.0 mmol) and the reaction mixture was stirred at room temperature for 18 h. The reaction was poured into water (50 mL) and extracted with ethyl acetate (2×50 mL). The combined organic layers were washed with water (25 mL), then brine (25 mL), dried ($Na_2SO_4$) and evaporated in-vacuo to afford 2.26 g of intermediate 92 used in the next step without purification.

Preparation of Intermediate 93:

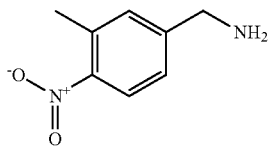

To a solution of two-phase mixture of intermediate 92 (2.2 g; 11.5 mmol) in THF (25 ml) and water (25 ml) was added $PPh_3$ (3 g; 11.5 mmol) at room temperature and left to stir overnight. The reaction mixture was then passed through a 50 g SCX-2 cartridge which was washed with $CH_3CN$, MeOH and then eluted off with 2M ammonia in methanol. The filtrate was concentrated to afford 1.53 g of intermediate 93 as an orange oil

Example A27

Preparation of Intermediate 88:

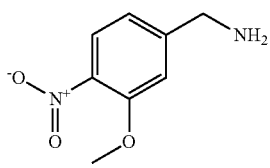

To a solution of 3-methoxy-4-nitrobenzamide (1.50 g, 7.65 mmol) in THF (35 mL) at ambient temperature was added dropwise Borane-THF complex 1M (15.28 mL, 15.28 mmol) over 10 min. The reaction mixture was refluxed for 4 h under Argon, then allowed to stirred at rt over 72 h and further stirring at 70° C. for 3 h. The reaction mixture was allowed to cool to rt and was carefully loaded onto an Isolute® SCX-2 cartridge, 70 g which was washed with DCM/methanol and then the product was eluted with a mixture of DCM/2M $NH_3$ in methanol (1:1 to 0:100). The 2M $NH_3$ in methanol solution was concentrated in vacuo. The crude product was purified by silica column chromatography (companion 40 g, mobile phase gradient: from 100% DCM to 90% DCM, 10% 2N $NH_3$ in MeOH) to give 892 mg of intermediate 88 (91% yield, 95% purity based on LC/MS, white solid).

The intermediate in the Table below was prepared by using an analogous method, starting from the respective starting materials.

| Intermediate number | Structure |
|---|---|
| Intermediate 116 (from intermediate 115) | 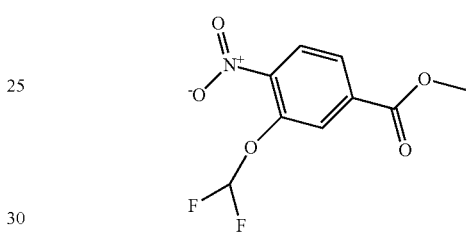 |

Example A28

Preparation of Intermediate 96:

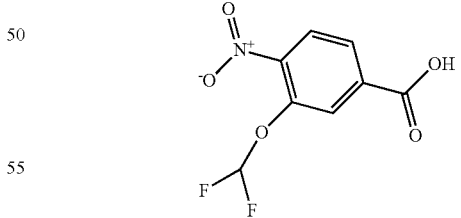

To a solution of methyl 3-hydroxy-4-nitrobenzoate (2.50 g, 12.68 mmol) in DMF (25 mL) under Ar was added $K_2CO_3$ (2.01 mL, 19.02 mmol) and methyl 2-chloro-2,2-difluoro-acetate (2.63 g, 19.02 mmol). After 10 min, the reaction mixture was warmed to 100° C. for 18 h. The reaction mixture was allowed to cool to rt. Water was added and the reaction was extracted with $Et_2O$. The organic phase was washed with water and brine, dried over $Na_2SO_4$ and concentrated in vacuo. The crude product was purified by silica column chromatography (companion 240 g Si, mobile phase gradient: from 100% pentane to 40% pentane, 60% $Et_2O$) to give 923 mg of intermediate 96 (28%, 95% purity based on LC/MS, yellowish solid).

Preparation of Intermediate 97:

Intermediate 96 (923 mg, 3.74 mmol) was suspended in a mixture of THF (60 mL) and MeOH (40 mL) and the resulting mixture was treated with LiOH 2N (9.34 mL, 18.68 mmol) and heated at 45° C. under reflux for 3 h. The reaction mixture was allowed to cool to room temperature and was partially evaporated under reduced pressure. The residue was taken up in water, acidified to pH 5 with 1N HCl and extracted three times with EtOAc. The combined organic fractions were further washed with water and brine, dried over Na₂SO₄, filtered and concentrated in vacuo to give 841 mg of intermediate 97 (92% yield, 95% purity based on LC/MS, yellowish solid).

Example A29

Preparation of Intermediate 115:

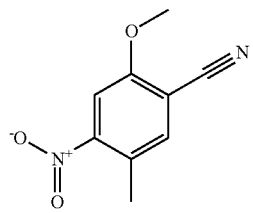

The reagents were divided equally across four 20 ml microwave vials (5. mmol of 1-bromo-2-methoxy-5-methyl-4-nitrobenzene (1 g; 5 mmol), zinc cyanide (1.2 g; 10.16 mmol), Pd(PPh₃)₄ (231 mg; 0.05 mmol and DMF (15 ml) in each), degassed under nitrogen and irradiated under microwaves at 170° C. for 20 minutes. The 4 reaction mixtures were then combined for the work up by pouring into an aqueous solution of NaHCO₃ and extracting with EtOAc (twice). The combined organic lasers were dried and concentrated in vacuo. Then, the residue was purified by silica gel chromatography with 0-75% EtOAc in cyclohexane (holding the gradient at 20% until elution unreacted 1-brom-2-methoxy-5-methyl-4-nitrobenzene) to afford 1.2 g of intermediate 115 as a pale yellow solid.

Example A32

Preparation of Intermediate 129:

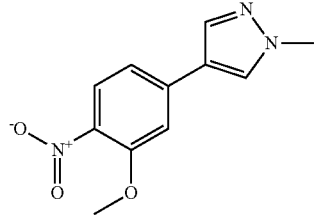

A degassed solution of 5-bromo-2-nitroanisole (200.00 mg, 0.86 mmol), 1-methylpyrazole-4-boronic acid pinacol ester (197.25 mg, 0.95 mmol), Pd(dppf)Cl₂ (35.12 mg, 0.043 mmol) and Cs₂CO₃ (843.87 mg, 2.59 mmol) in 1,4-dioxane (4 mL) and water (1 mL) was heated to 100° C. for 1 h. The reaction mixture was partitioned between EtOAc and water and the organic layer was washed with brine, dried over Na₂SO₄ and concentrated in vacuo. The crude product was purified by flash chromatography (25 g Si-PPC, mobile phase gradient: from 100% DCM to 60% DCM, 40% EtOAc) to give 168 mg of intermediate 129 (84% yield, pale yellow solid).

Example A33

Preparation of Intermediate 132:

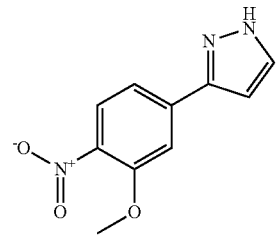

3-methoxy-4-nitroacetophenone (1 g, 5.12 mmol) and N,N-dimethylformamide dimethylacetal (12.20 g, 102.38 mmol) were heated at 80° C. for 3 h. The resulting yellow mixture was filtered at rt and subsequently dried under a stream of air. EtOH (20 mL) and methylhydrazine (1.25 g, 27.1 mmol) were added to the yellow solid and the mixture was stirred at 60° C. for 3 h and at rt for 16 h. Solvent was evaporated under reduced and the crude material was purified by flash column chromatography on silica (80 g) eluting with dichloromethane/methanol (0 to 10%) over 30 minutes. Fractions containing the product were combined and the solvent was evaporated. The residue was further purified by flash column chromatography on silica (80 g) eluting with cyclohexane/ethyl acetate (0 to 50%) over 30 minutes. Fractions containing product were combined and the solvent was evaporated to give 343 mg of intermediate 132 (31% yield, yellow solid).

Example A34

Preparation of Intermediate 8:

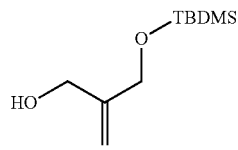

NaH (60% dispersion in mineral oil) (94.89 g, 2372.17 mmol) was charged in a 3-necked round bottom flask. Dry THF (800 mL) was added and the resulting suspension was cooled to 0° C. A solution of 2-methylene-1,3-propanediol (190.00 g, 2156.52 mmol) in THF (300 mL) was added and stirred at 0° C. for 45 min. A solution of TBDMSCl (357.54 g, 2372.17 mmol) in THF (400 mL) was then added dropwise at 0° C. and the mixture was stirred for 3 h at room temperature. The reaction was quenched by addition of water (2 L) and aqueous layer was extracted with EtOAc (1.5 L). The organic layer was dried over MgSO₄, filtered and concentrated under reduced pressure. The crude residue was purified by column chromatography (eluent: from 95% Petroleum ether, 5% EtOAc to 86% Petroleum ether, 14% EtOAc). Fractions containing the product were collected and evaporated in vacuum to give 280 g of intermediate 8 (64% yield, clear oil).

163
Preparation of Intermediate 9:

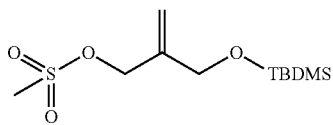

A solution of intermediate 8 (100 g, 494.15 mmol) in DCM (1 L) was treated with TEA (104 mL, 746.16 mmol) and the solution was cooled to 0° C. MsCl (62.4 g, 544.74 mmol) was added and the mixture was stirred for 30 min. The reaction mixture was transferred into a separating funnel and washed with dilute citric acid solution. Layers were separated and the organic layer was dried over Na₂SO₄, filtered and evaporated to give 138.6 g of intermediate 9 (quant. yield, pale yellow oil).

Example A35

Preparation of Intermediate 173

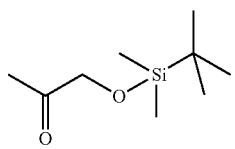

1-Hydroxy-2-propanone (3 g, 36.5 mmol) was dissolved in DCM (30 ml) and cooled under nitrogen to 0° C. Triethylamine (6.8 mL, 48.6 mmol) and DMAP (0.25 g, 2.02 mmol) were added at 0° C. Tert-Butyldimethylsilyl chloride (6.8 mL, 45 mmol) was added in one portion and the reaction was stirred for 2 hours at room temperature. The reaction was quenched by addition of water (40 ml). The aqueous layer was extracted with DCM (3×25 ml) and the combined organic layers were dried over sodium sulphate, filtered and evaporated in vacuo to give a brown oil. The crude material was purified by silica gel chromatography (50 g) eluting with cyclohexane followed by 5% EtOAc/cyclohexane to give 3.7 g (54% yield) of intermediate 173 as a clear oil.

Preparation of Intermediate 174:

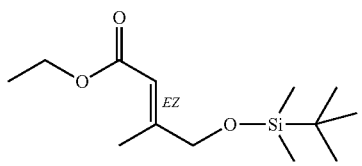 [SMILES: CCOC(=O)/C=C(\C)CO[Si](C)(C)C(C)(C)C]

Sodium hydride (60% in oil) (792 mg, 19.8 mmol) was suspended in THF (25 ml) and the suspension was cooled to 0° C. under nitrogen. Triethyl phosphonoacetate (3.6 mL, 18 mmol) was added dropwise and the reaction was stirred at 0° C. for 1 hour. Intermediate 173 (2.83 g, 15 mmol) was added dropwise and the reaction mixture stirred at 0° C. for 30 minutes. The reaction mixture was warmed to room temperature and stirred for 16 hours. Water (15 ml) was added and the mixture extracted with diethyl ether (3×25 ml). The combined organic layers were washed with brine (1×30 ml), dried over sodium sulphate, filtered and evaporated to give 4.09 g of intermediate 174 as a pale yellow oil.

164
Preparation of Intermediate 175:

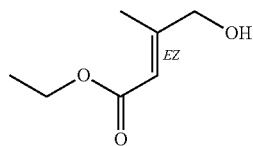

Intermediate 174 (3.9 g, 15 mmol) was dissolved in THF (30 ml) and TBAF (1M in THF) (22.5 mL, 22.5 mmol) was added dropwise. The reaction mixture was stirred at room temperature for 2 hours. The reaction was quenched by addition of water (20 ml) and extracted with EtOAc (3×25 ml). The combined organic layers were washed with saturated sodium bicarbonate (1×25 ml), brine (1×25 ml), dried over sodium sulphate, filtered and the solvent evaporated in vacuo to give a brownish oil. The crude material was purified by silica column chromatography (50 g) eluting with pentane, 10% and 25% EtOAc/pentane to give 1.39 g (64% yield) of intermediate 175 as a clear pale yellow syrup.

Preparation of Intermediate 176:

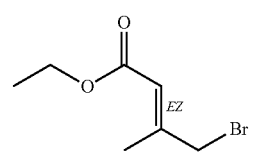

Intermediate 175 (1.39 g, 9.64 mmol) was dissolved in DCM (100 ml) and cooled to 0° C. under nitrogen. Imidazole (0.92 g, 13.5 mmol) and reagent triphenylphosphine (3.8 g, 14.46 mmol) were added followed by carbon tetrabromide (4.48 g, 13.5 mmol). The reaction mixture was stirred at 0° C. for 1 hour, then quenched with 2 g Na₂S₂O₃ in 50 ml water. The organic layer was washed with water (1×50 ml), brine (1×50 ml), dried over sodium sulphate, filtered and the filtrate evaporated in vacuo to give a brownish oil. The crude material was purified by silica column chromatography (50 g) eluting with pentane, 5% and 10% EtOAc/pentane to give 1.34 g (67% yield) of intermediate 176 as a colourless oil.

Preparation of Intermediate 177:

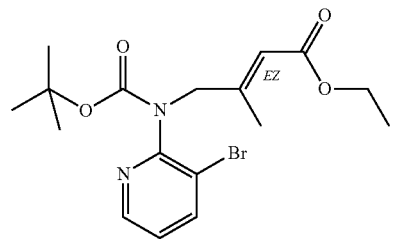 [SMILES: CCOC(=O)/C=C(\C)CN(C(=O)OC(C)(C)C)c1ncccc1Br]

Intermediate 2 (0.546 g, 2 mmol) was dissolved in DMF (10 ml) and cooled to 0° C. under nitrogen. NaH (60% in oil) (96 mg, 2.4 mmol) was added portionwise and the reaction mixture was stirred at 0° C. for 5 min followed by stirring at room temperature for 25 minutes. Intermediate 176 (538 mg, 2.6 mmol) in DMF (2 ml) was added and the reaction was stirred at room temperature for 16 hours. 40 ml of water was added and the mixture was extracted with EtOAc (3×30 ml). The combined organic layers were washed with brine (2×25 ml), dried over sodium sulphate, filtered and the filtrate evaporated in vacuo to give a clear syrup. The crude material was purified by silica gel chromatography (40 g) eluting with 0-30% EtOAc/cyclohexane to give 670 mg (84% yield) of intermediate 177 a clear syrup.

Preparation of Intermediate 178:

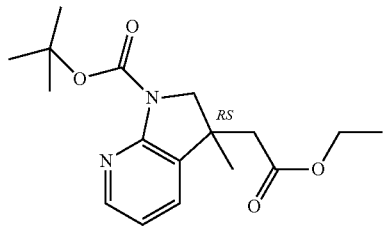 [SMILES: CCOC(=O)CC1(C)CN(C(=O)OC(C)(C)C)c2ncccc21]

Intermediate 177 (670 mg, 1.68 mmol), sodium acetate (358 mg, 4.37 mmol), sodium formate (297 mg, 4.37 mmol), tetraethyl ammonium chloride (348 mg, 2.1 mmol) and Pd(OAc)$_2$ (18.8 mg, 0.084 mmol) were suspended in DMF (20 ml) and purged with argon for 10 minutes. The reaction mixture was heated at 85° C. for 2.5 hours. Water (40 ml) was added followed by EtOAc (40 ml). The solids were removed from the mixture by filtration through a pad of celite. The layers from the filtrate were separated and the aqueous layer was extracted with further EtOAc (2×25 ml). The combined organic layers were washed with brine (50 ml), dried over sodium sulphate, filtered and the filtrate evaporated in vacuo to give a yellowish syrup. The crude material was purified by silica gel chromatography (20 g) eluting with 0-40% EtOAc/cyclohexane to give 440 mg of intermediate 178 (82% yield) as a clear yellowish syrup.

Preparation of Intermediate 179:

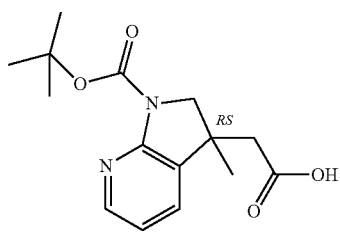 [SMILES: CC(C)(C)OC(=O)N1CC(C)(CC(=O)O)c2cccnc21]

Intermediate 178 (1.05 g, 3.3 mmol) was dissolved in THF (5 ml) and water (5 ml). Lithium hydroxide (395 mg, 9.42 mmol) was added and the reaction stirred at room temperature for 90 minutes. The pH was adjusted to 4.0 by addition of 5% aqueous solution of potassium hydrogen sulphate. The aqueous layer was extracted with EtOAc (3×25 ml). The combined organic layers were washed with brine (1×25 ml), dried over sodium sulphate, filtered and evaporated in vacuo to give 673 mg (93% yield) of intermediate 179 as an off-white solid.

Preparation of Intermediate 180:

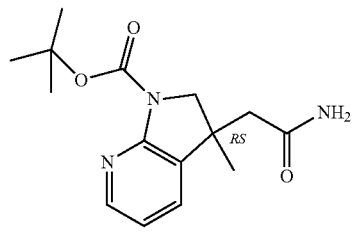 [SMILES: CC(C)(C)OC(=O)N1CC(C)(CC(N)=O)c2cccnc21]

Intermediate 179 (450 mg, 1.54 mmol) was dissolved in a mixture of DCM (10 ml) and DIPEA (411 μL, 2.36 mmol) and cooled to 0° C. HATU (644 mg, 1.69 mmol) was added and the reaction stirred at 0° C. for 30 minutes. Ammonia in MeOH (7 M) (660 μL, 4.62 mmol) was added. The reaction mixture warmed to room temperature and stirred for 16 hours. DCM (15 ml) was added. The organic layer was washed with water (15 ml), 5% aqueous solution of citric acid (15 ml), brine (20 ml), dried over sodium sulphate, filtered and evaporated in vacuo to give 574 mg of a yellowish gum. The crude compound was purified by silica column chromatography (20 g) eluting with 0-8% MeOH/DCM to give 310 mg (69% yield) of intermediate 180 as a white foam.

Preparation of Intermediate 181:

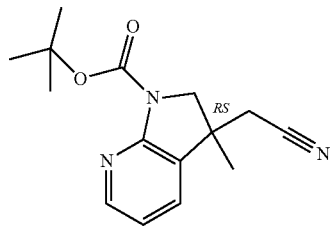 [SMILES: CC(C)(C)OC(=O)N1CC(C)(CC#N)c2cccnc21]

Intermediate 180 (310 mg, 1.06 mmol) and imidazole (144 mg, 2.12 mmol) were dissolved in pyridine (8 ml) and the reaction mixture was cooled to 0° C. under nitrogen. POCl$_3$ (198 μL, 2.12 mmol) in DCM (2 ml) was added dropwise and the reaction was stirred at 0° C. for 1 hour. Water (25 ml) was added to the reaction mixture and the aqueous layer was extracted with EtOAC (3×30 ml). The combined organic layers were washed with brine (1×30 ml), dried over sodium sulphate, filtered and the filtrate evaporated in vacuo to an oil. The crude material was purified by silica column chromatography (20 g) eluting with 0-6% MeOH/DCM to give 266 mg (92%, yield) of intermediate 181 as a clear glass.

Preparation of Intermediate 182:

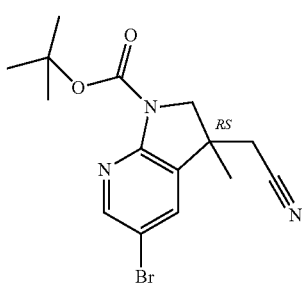 [SMILES: CC(C)(C)OC(=O)N1CC(C)(CC#N)c2cc(Br)cnc21]

Intermediate 181 (265 mg, 0.97 mmol) was dissolved in ACN (20 ml). NBS (206 mg, 1.16 mmol) was added and the reaction mixture was stirred at 40° C. for 16 hours. Tan, the solvent was evaporated and the residue was dissolved in EtOAc (30 ml). The organic layer was washed with saturated sodium bicarbonate (15 ml), brine (15 ml), dried over sodium sulphate, filtered and evaporated in vacuo to give a golden syrup. The crude material was purified by silica column chromatography (20 g) eluting with 0-40% EtOAc/cyclohexane to give 300 mg (88% yield) of intermediate 182 as a clear glass.

Preparation of Intermediate 183:

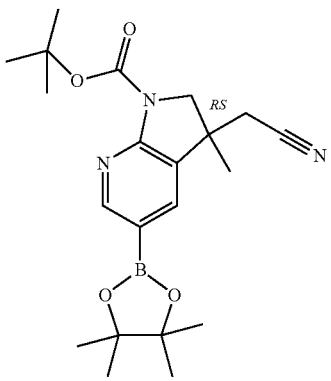 [SMILES: CC(C)(C)OC(=O)N1CC(C)(CC#N)c2cc(B3OC(C)(C)C(C)(C)O3)cnc21]

Intermediate 182 (300 mg, 0.85 mmol), bis(pinacolato)diboron (269 mg, 1.06 mmol) and potassium acetate (250 mg, 2.55 mmol) were suspended in 1,2-dimethoxyethane (3 ml) and the reaction mixture was degassed (argon) for 5 minutes. 1,1'-bis(diphenyl-phosphino)ferrocene]dichloropalladium(II) (31 mg, 0.042 mmol) was added and the reaction mixture was degassed (argon) for a further 5 minutes. The reaction was heated at 85° C. for 20 hours, then cooled, filtered through a pad of Celite® which was washed with EtOAc and DCM. The filtrate was evaporated in vacuo to give 528 mg of intermediate 183 as a brown oil which was directly used in the next step without any further purification.

Preparation of Intermediate 184:

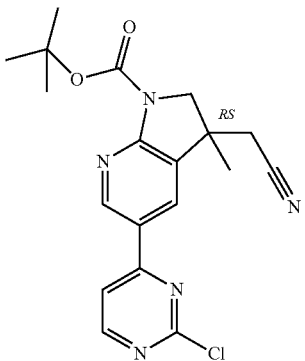 [SMILES: CC(C)(C)OC(=O)N1CC(C)(CC#N)c2cc(-c3ccnc(Cl)n3)cnc21]

Intermediate 183 (340 mg, 0.85 mmol), 2,4-dichloropyrimidine (190 mg, 1.275 mmol) and Na$_2$CO$_3$ (360 mg, 3.4 mmol) were suspended in 1,4-dioxane (15 ml) and water (3 ml). The reaction mixture was degassed with argon (5 minutes). Then, Pd(PPh$_3$)$_4$ (49 mg, 0.042 mmol) was added and the reaction mixture was degassed with argon (5 minutes). The reaction mixture was heated at 85° C. for 16 hours, then, cooled and filtered through a pad of Celite® which was washed with EtOAc, DCM. The filtrate was evaporated in vacuo to give a brown oil. The crude material was purified by silica gel chromatography (40 g) eluting with 0-5% MeOH/DCM to give 150 mg (46% yield) of intermediate 184 as an off-white foam.

Example A36

Preparation of Intermediate 185:

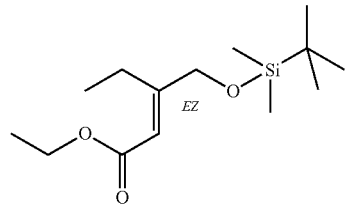 [SMILES: CCOC(=O)/C=C(\CC)CO[Si](C)(C)C(C)(C)C]

Sodium hydride (60% in oil) (2.09 g, 52.3 mmol) was suspended in THF (70 ml) and the suspension was cooled to 0° C. under nitrogen. Triethyl phosphonoacetate (9.4 mL, 47.5 mmol) was added dropwise and the reaction was stirred at 0° C. for 1 hour. 1-[[(1,1-Dimethylethyl)dimethylsilyl]oxy]-2-butanone (8 g, 39.5 mmol) was added dropwise and the reaction mixture stirred at 0° C. for 30 minutes. The reaction mixture was warmed to room temperature and stirred for 16 hours. Water (15 ml) was added and the mixture was extracted with diethyl ether (3×25 ml). The combined organic layers were washed with brine (1×30 ml), dried over sodium sulphate, filtered and the filtrate evaporated to give 11.1 g of intermediate 185 as a pale yellow oil.

Preparation of Intermediate 186:

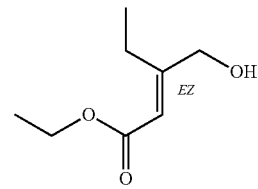

Intermediate 185 (11 g, 40.4 mmol) was dissolved in THF (50 ml) and TBAF (1M in THF) (60.7 ml, 60.7 mmol) was added dropwise. The reaction mixture was stirred at room temperature overnight. The reaction was quenched by addition of water (20 ml) and extracted with EtOAc (3×25 ml). The combined organic layers were washed with saturated sodium bicarbonate (1×25 ml), brine (1×25 ml), dried over sodium sulphate, filtered and the solvent was evaporated in vacuo to give a brownish oil. The crude material was purified by silica gel chromatography (50 g) eluting with pentane, 10% and 25% EtOAc/pentane to give 3.7 g (59% yield) of intermediate 186 as a pale yellow syrup.

Preparation of Intermediate 187:

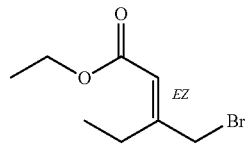

Intermediate 187 was prepared accordingly to intermediate 176 starting from intermediate 186 (2.5 g; 51%).

Preparation of Intermediate 188:

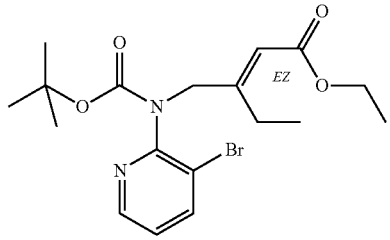 [SMILES: CCOC(=O)/C=C(\CC)CN(C(=O)OC(C)(C)C)c1ncccc1Br]

Intermediate 188 was prepared accordingly to intermediate 177 starting from intermediate 187 (3.2 g; 84%).

Preparation of Intermediate 189:

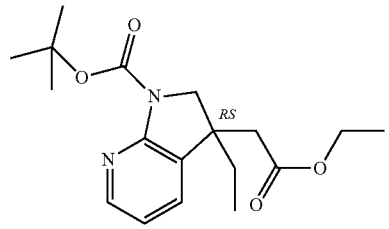

Intermediate 189 was prepared accordingly to intermediate 178 starting from intermediate 188 (2.47 g; 97%).

Preparation of Intermediate 190:

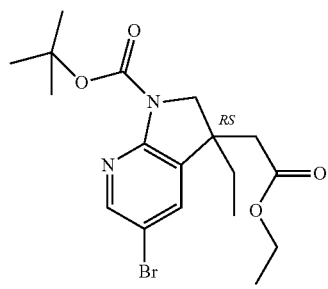 [SMILES: CCOC(=O)CC1(CC)CN(C(=O)OC(C)(C)C)c2ncc(Br)cc21]

Intermediate 190 was prepared accordingly to intermediate 182 starting from intermediate 189 (2.95 g; 98%).

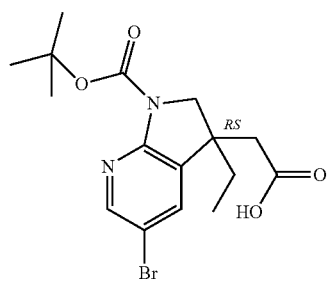 [SMILES: CCC1(CC(=O)O)CN(C(=O)OC(C)(C)C)c2ncc(Br)cc21]

Preparation of Intermediate 191:

Intermediate 191 was prepared accordingly to intermediate 179 starting from intermediate 189 (1.26 g; 87%).

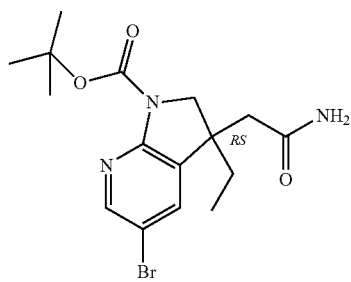 [SMILES: CCC1(CC(N)=O)CN(C(=O)OC(C)(C)C)c2ncc(Br)cc21]

Preparation of Intermediate 192:

Intermediate 192 was prepared accordingly to intermediate 180 starting from intermediate 191 (1.26 g).

Preparation of Intermediate 193:

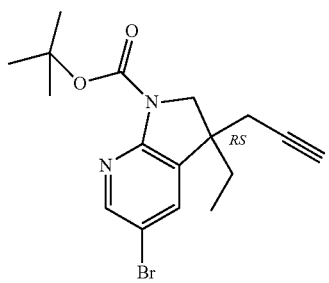 [SMILES: C#CCC1(CC)CN(C(=O)OC(C)(C)C)c2ncc(Br)cc21]

Intermediate 193 was prepared accordingly to intermediate 181 starting from intermediate 192 (819 mg; 68%).

Preparation of Intermediate 194:

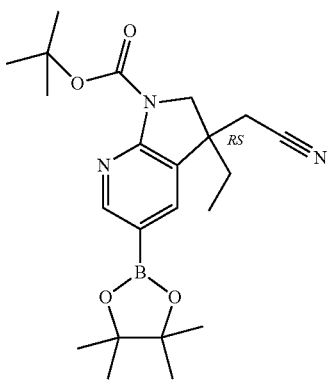 [SMILES: CCC1(CC#N)CN(C(=O)OC(C)(C)C)c2ncc(B3OC(C)(C)C(C)(C)O3)cc21]

Intermediate 194 was prepared accordingly to intermediate 183 starting from intermediate 193.

Preparation of Intermediate 195:

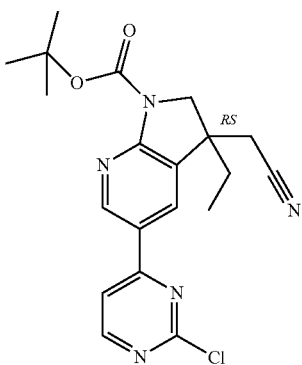 [SMILES: CCC1(CC#N)CN(C(=O)OC(C)(C)C)c2ncc(-c3ccnc(Cl)n3)cc21]

Intermediate 195 was prepared accordingly to intermediate 184 starting rom intermediate 194 (430 mg; 94%).

Example A37

Preparation of Intermediate 196:

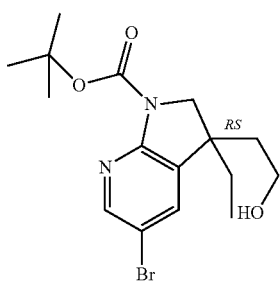 [SMILES: CCC1(CCO)CN(C(=O)OC(C)(C)C)c2ncc(Br)cc21]

To a stirred solution of intermediate 190 (1.4 g, 3.39 mmol) in THF (12 mL) and MeOH (4 mL) at room temperature was added sodium borohydride (256 mg, 6.77 mmol) portionwise. The reaction was stirred at room temperature for 4 hours. The reaction was heated to 50° C. and stirred overnight. Additional sodium borohydride (256 mg, 6.77 mmol) was added and the reaction was refluxed and stirred for 4 hours. The reaction was cooled, quenched with water, extracted with EtOAc (3×30 mL), washed with brine, dried over sodium sulfate, filtered and concentrated in vacuo. The crude product was purified by column chromatography using cycloxexane:EtOAc (0-50%) as eluent to give 613 mg (49% yield) of intermediate 196.

Preparation of Intermediate 197:

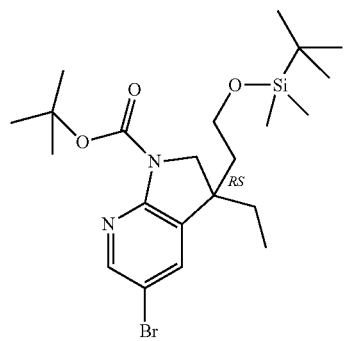 [SMILES: CCC1(CCO[Si](C)(C)C(C)(C)C)CN(C(=O)OC(C)(C)C)c2ncc(Br)cc21]

To a solution of intermediate 196 (610 mg, 1.64 mmol), TEA (199 mg, 1.97 mmol) and DMAP (10 mg, 0.082 mmol) in DCM (10 mL) at 0° C. was added tert-butyldimethylsilyl chloride (273 mg, 1.81 mmol) in one portion. The cooling bath was removed and the reaction left to warm to room temperature and stirred for 2 hours. The reaction was quenched with water (50 mL). The layers were separated and the aqueous layer was extracted with DCM (×2). The organic layer was dried over sodium sulfate, filtered and concentrated in vacuo to give a crude residue (0.858 g) which was purified by column chromatography using DCM:MeOH (0-5%) as eluent. The fractions containing the product were combined and concentrated in vacuo to give 535 mg (67% yield) of intermediate 197 as a colourless oil.

Preparation of Intermediate 198:

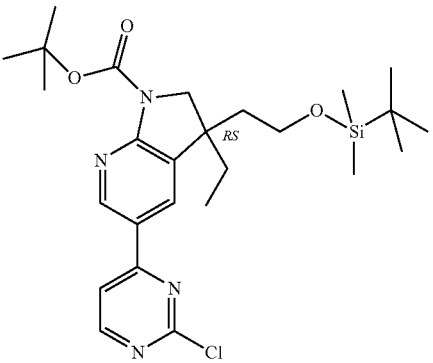 [SMILES: CCC1(CCO[Si](C)(C)C(C)(C)C)CN(C(=O)OC(C)(C)C)c2ncc(-c3ccnc(Cl)n3)cc21]

Intermediate 198 was prepared accordingly to intermediate 183 starting from intermediate 197

Preparation of Intermediate 199:

Intermediate 199 was prepared accordingly to intermediate 184 starting from intermediate 198 (186 mg; 78%).

Example A38

Preparation of Intermediate 200:

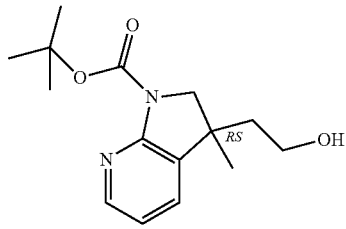 [SMILES: CC(C)(C)OC(=O)N1CC(C)(CCO)c2cccnc21]

Intermediate 179 (200 mg, 0.684 mmol) and TEA (100 µL, 0.72 mmol) were dissolved in THF (3 ml) and cooled to 0° C. under nitrogen. Ethyl chloroformate (69 µL, 0.72 mmol) was added slowly at 0° C. and the reaction mixture was stirred for 30 minutes. Sodium borohydride (39 mg, 1.03 mmol) was added followed by slow addition of IMS (5 ml). The reaction was stirred at 10° C. for 1 hour. The reaction was quenched by addition of 5% aqueous solution of potassium hydrogen sulphate (to pH 4) and extracted with DCM (3×25 ml). The combined organic layers were washed with brine (25 ml), dried over sodium sulphate, filtered and the filtrate evaporated in vacuo to give a syrup. The crude material was purified by silica column chromatography (25 g) eluting with 0-6% MeOH/DCM to give 68 mg (36% yield) of intermediate 200.

Preparation of Intermediate 201:

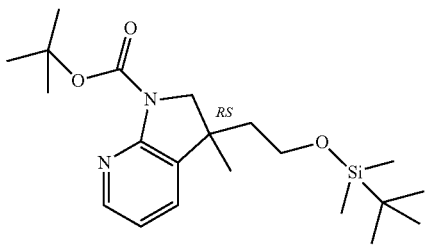 [SMILES: CC(C)(C)OC(=O)N1CC(C)(CCO[Si](C)(C)C(C)(C)C)c2cccnc21]

Intermediate 201 was prepared accordingly to intermediate 197 starting from intermediate 200 (100 mg)

Preparation of Intermediate 202:

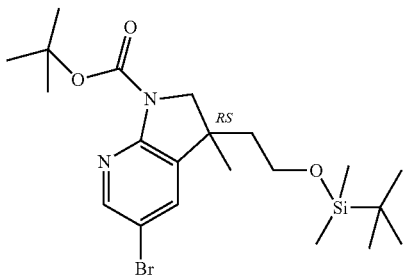 [SMILES: CC(C)(C)OC(=O)N1CC(C)(CCO[Si](C)(C)C(C)(C)C)c2cc(Br)cnc21]

Intermediate 202 was prepared accordingly to intermediate 181 starting from intermediate 201 (79.5 mg; 70%).

Preparation of Intermediate 203

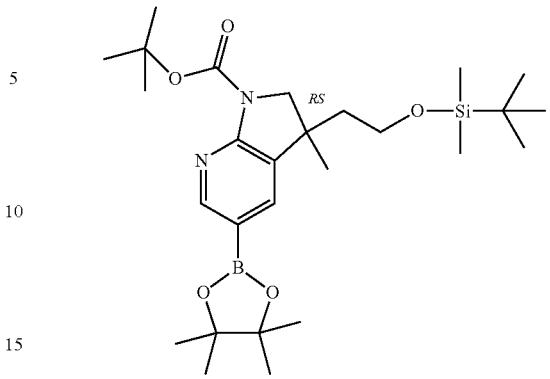

Intermediate 203 was prepared accordingly to intermediate 183 starting from intermediate 202.

Preparation of Intermediate 204:

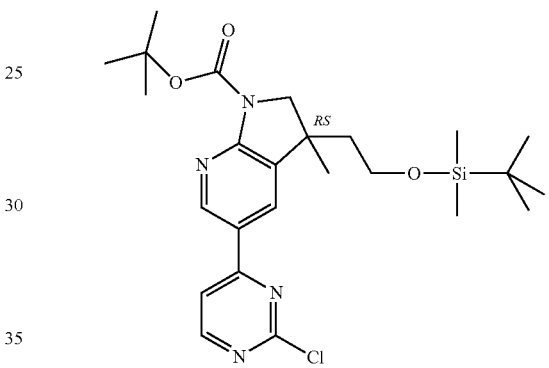

Intermediate 204 was prepared accordingly to intermediate 184 starting from intermediate 203 (55 mg; 72%).

B. Preparation of the Final Compounds

Example B1

Method B1:
Preparation of Compound 1:

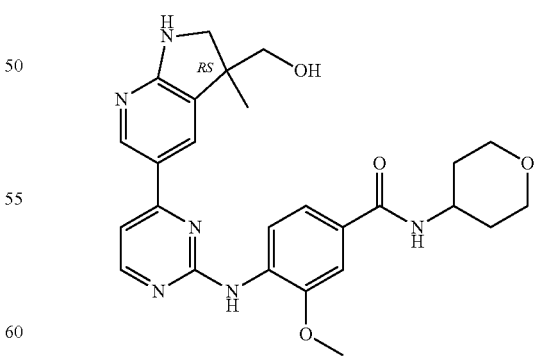

A solution of intermediate 14 (125 mg, 0.26 mmol) in 1,4-dioxane (3.50 mL) was added to intermediate 17 (63.83 mg, 0.26 mmol), BINAP (16.19 mg, 0.026 mmol), Pd(OAc)$_2$ (5.84 mg, 0.026 mmol) and Cs$_2$CO$_3$ (249.25 mg, 0.77 mmol) and placed under vacuum before to be purged by argon and heated to 95° C. for 2 h. The mixture was then partitioned between DCM and water. The DCM was isolated and evaporated to dryness. The residue was then dissolved into THF (4 mL), treated with TBAF (1M in THF) (0.50 mL, 0.50 mmol) and stirred at room temperature for 3 h. The mixture was diluted with DCM, washed with water, dried over MgSO₄ and evaporated to dryness. The residue was dissolved in DCM (2 mL), treated with TFA (2 mL) and stirred at room temperature for 2 h. The mixture was evaporated to dryness and then loaded onto a 10 g SCX-2 cartridge, washed with acetonitrile, methanol and eluted off with 2M ammonia in methanol. The filtrate was evaporated to give 130 mg of a golden residue. This residue was purified by MDAP to afford 74 mg of compound 1 (60% yield, 99.8% purity based on LC/MS, colorless crystal).

Method B2:
Preparation of Compound 74:

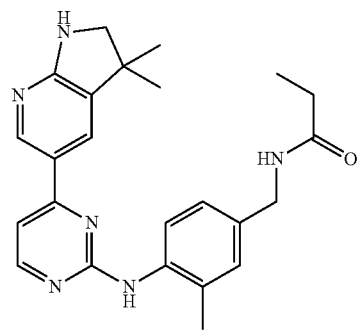 [SMILES: CCC(=O)NCc1ccc(Nc2nccc(-c3cnc4c(c3)C(C)(C)CN4)n2)c(C)c1]

A solution of intermediate 7 (100 mg; 0.2 mmol) and intermediate 95 (64 mg; 0.333 mmol) in dioxane (2 mL) was added to BINAP (17.4 mg; 0.028 mmol), Pd(OAc)₂ (6.3 mg; 0.028 mmol) and Cs₂CO₃ (270.7 mg; 0.831 mmol). The vial was then sealed, flushed with Ar and then, heated at 95° C. for 2 hrs. The mixture was then partitioned between DCM and water. The DCM layer was isolated, evaporated to dryness and then, dissolved into 2 ml of DCM, treated with 2 ml of TFA and stirred at room temperature for 3 hr. The mixture was evaporated to dryness and loaded onto an 10 g SCX-2 cartridge which was washed with acetonitrile, methanol and eluted off with 2M ammonia in methanol. The filtrate was evaporated to give a golden residue which was purified by MDAP to afford 69 mg (60%) of compound 74.

Method B3:
Preparation of Compound 289:

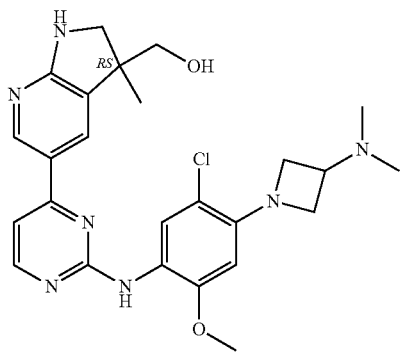 [SMILES: COc1cc(N2CC(N(C)C)C2)c(Cl)cc1Nc1nccc(-c2cnc3c(c2)C(C)(CO)CN3)n1]

Intermediate 14 (333 mg, 0.68 mmol), intermediate 151 (199.50 mg, 0.78 mmol), Pd(OAc)₂ (15.27 mg, 0.068 mmol), BINAP (42.34 mg, 0.068 mmol) and Cs₂CO₃ (663.04 mg, 2.04 mmol) were added together in 1,4-dioxane (7.0 mL) and the resulting mixture was heated at 95° C. under nitrogen for 1 hour. The reaction was cooled to room temperature, diluted with water and extracted with ethyl acetate (three times). The organic phase was dried over sodium sulfate and evaporated under reduced pressure to give a brown solid. The crude residue was purified by column chromatography (40 g silica) eluting with a mixture of MeOH in DCM (0 to 3%). Fractions containing the product were combined and evaporated under reduced pressure. Further purification by column chromatography (40 g silica) eluting with EtOAc first and then with a mixture of MeOH in DCM (0 to 5%) was performed. The crude sample was dissolved in DMSO then loaded on a SCX-2 cartridge (25 g), retained for 1 hour and eluted with DCM, MeOH and finally 2N ammonia solution in MeOH. Basic fractions were concentrated in vacuo and the crude residue was purified by MDAP under acidic condition. The fractions containing the product were mixed and concentrated to afford an impure fraction (165 mg) which was finally purified by MDAP under basic conditions to give after freeze drying 112 mg of compound 289 (33% yield, yellow solid).

The compounds in the Table below were prepared by using an analogous method described in methods B1 to B3, starting from the respective starting materials.

| Compound number | Structure | Method |
|---|---|---|
| Compound 74 | (structure) | B2 |

-continued
| Compound number | Structure | Method |
|---|---|---|
| Compound 75 | 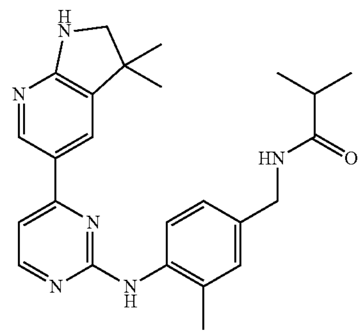 [SMILES: Cc1cc(CNC(=O)C(C)C)ccc1Nc1nccc(-c2cnc3c(c2)C(C)(C)CN3)n1] | B2 |
| Compound 76 | 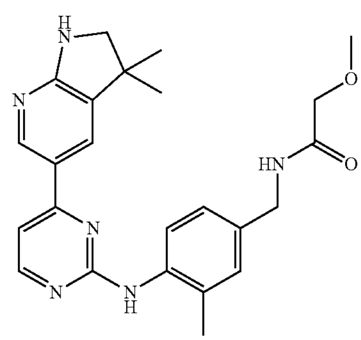 [SMILES: COCC(=O)NCc1ccc(Nc2nccc(-c3cnc4c(c3)C(C)(C)CN4)n2)c(C)c1] | B2 |
| Compound 84 | 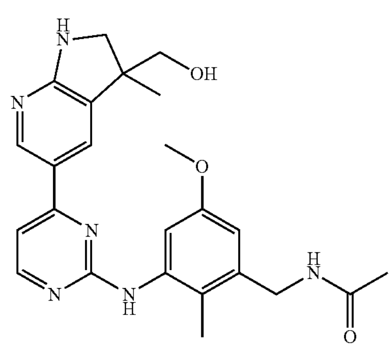 [SMILES: COc1cc(CNC(C)=O)c(C)c(Nc2nccc(-c3cnc4c(c3)C(C)(CO)CN4)n2)c1] | B1 |
| Compound 86 | 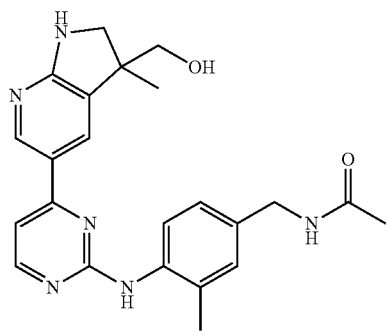 [SMILES: CC(=O)NCc1ccc(Nc2nccc(-c3cnc4c(c3)C(C)(CO)CN4)n2)c(C)c1] | B2 |

-continued
| Compound number | Structure | Method |
|---|---|---|
| Compound 87 | 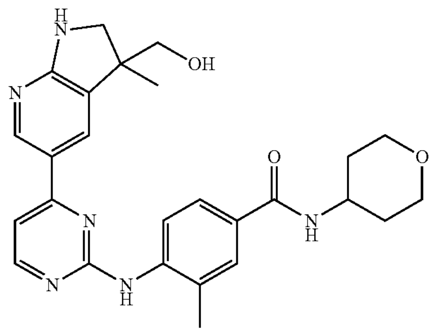 [SMILES: Cc1cc(C(=O)NC2CCOCC2)ccc1Nc1nccc(-c2cnc3c(c2)C(C)(CO)CN3)n1] | B2 |
| Compound 89 | 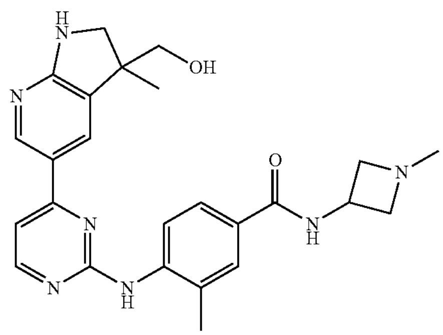 [SMILES: Cc1cc(C(=O)NC2CN(C)C2)ccc1Nc1nccc(-c2cnc3c(c2)C(C)(CO)CN3)n1] | B1 |
| Compound 90 | 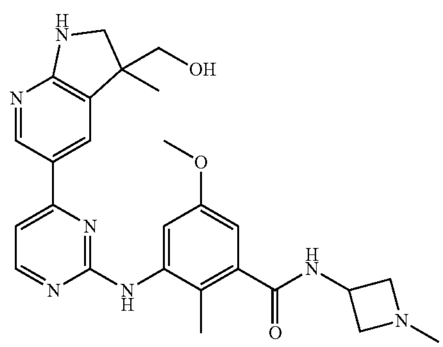 [SMILES: COc1cc(Nc2nccc(-c3cnc4c(c3)C(C)(CO)CN4)n2)c(C)c(C(=O)NC2CN(C)C2)c1] | B1 |
| Compound 105 | 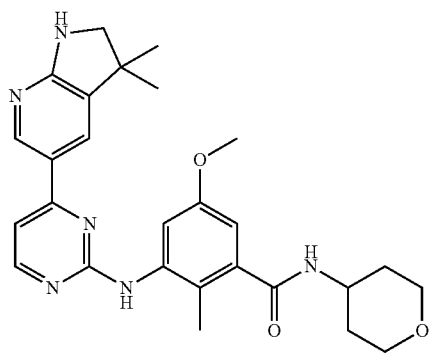 [SMILES: COc1cc(Nc2nccc(-c3cnc4c(c3)C(C)(C)CN4)n2)c(C)c(C(=O)NC2CCOCC2)c1] | B2 |

| Compound number | Structure | Method |
|---|---|---|
| Compound 106 | 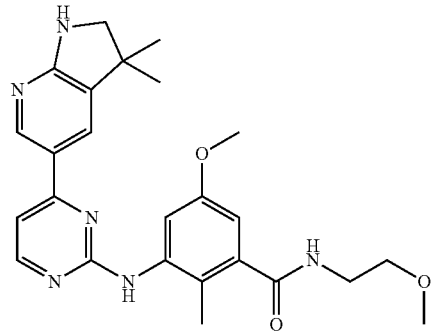 [SMILES: COCCNC(=O)c1cc(OC)cc(Nc2nccc(-c3cnc4c(c3)C(C)(C)CN4)n2)c1C] | B2 |
| Compound 107 | 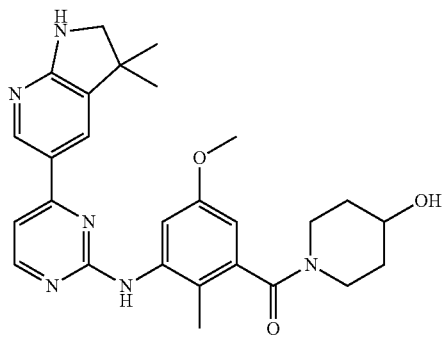 [SMILES: COc1cc(Nc2nccc(-c3cnc4c(c3)C(C)(C)CN4)n2)c(C)c(C(=O)N2CCC(O)CC2)c1] | B2 |
| Compound 108 | 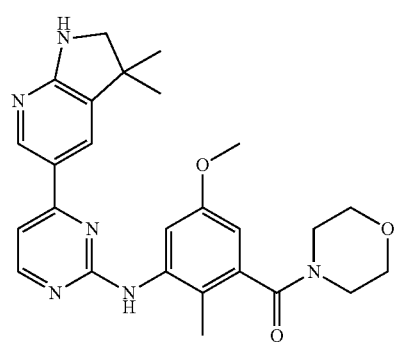 [SMILES: COc1cc(Nc2nccc(-c3cnc4c(c3)C(C)(C)CN4)n2)c(C)c(C(=O)N2CCOCC2)c1] | B2 |
| Compound 109 | 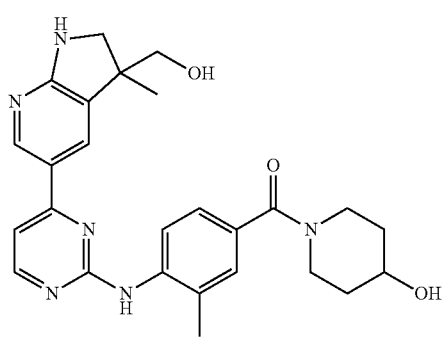 [SMILES: Cc1cc(C(=O)N2CCC(O)CC2)ccc1Nc1nccc(-c2cnc3c(c2)C(C)(CO)CN3)n1] | B1 |

-continued

| Compound number | Structure | Method |
|---|---|---|
| Compound 120 | 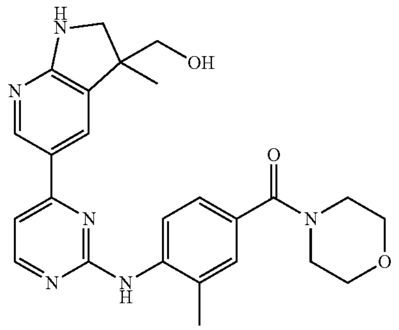 [SMILES: Cc1cc(C(=O)N2CCOCC2)ccc1Nc1nccc(-c2cnc3c(c2)C(C)(CO)CN3)n1] | B2 |
| Compound 121 | 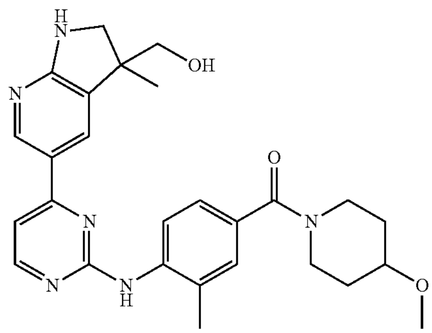 [SMILES: COC1CCN(C(=O)c2ccc(Nc3nccc(-c4cnc5c(c4)C(C)(CO)CN5)n3)c(C)c2)CC1] | B2 |
| Compound 135 (from intermediates 7 and 118) | 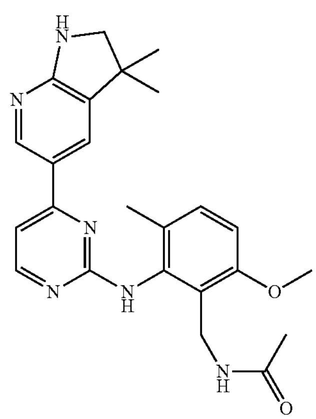 [SMILES: COc1ccc(C)c(Nc2nccc(-c3cnc4c(c3)C(C)(C)CN4)n2)c1CNC(C)=O] | B2 |
| Compound 140 | 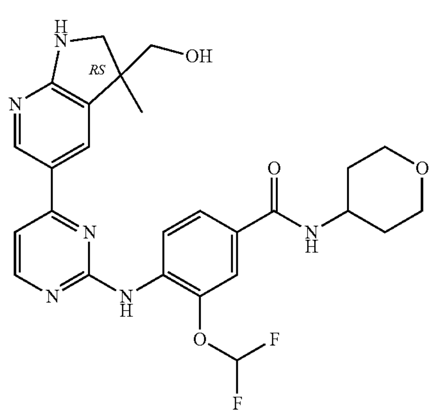 [SMILES: CC1(CO)CNc2ncc(-c3ccnc(Nc4ccc(C(=O)NC5CCOCC5)cc4OC(F)F)n3)cc21] | B2 |

| Compound number | Structure | Method |
|---|---|---|
| Compound 147 prepared in 2 steps from intermediate 184 | 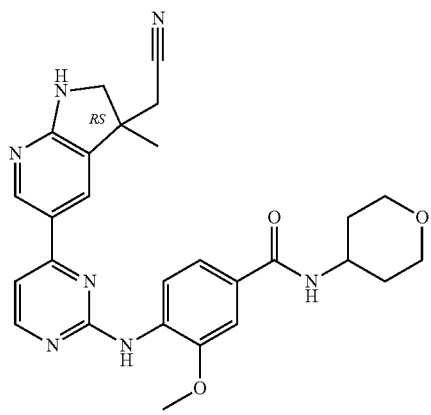 [SMILES: COc1cc(C(=O)NC2CCOCC2)ccc1Nc1nccc(-c2cnc3c(c2)C(C)(CC#N)CN3)n1] | B2 |
| Compound 148 prepared in 2 steps from intermediate 184 | 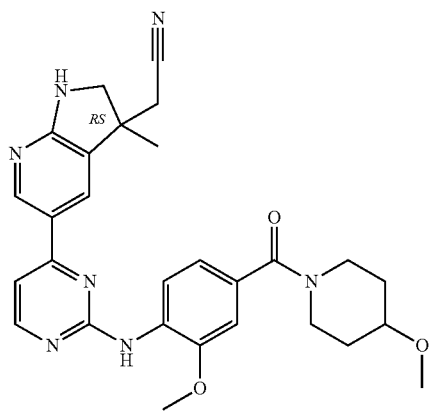 [SMILES: COc1cc(C(=O)N2CCC(OC)CC2)ccc1Nc1nccc(-c2cnc3c(c2)C(C)(CC#N)CN3)n1] | B2 |
| Compound 151 | 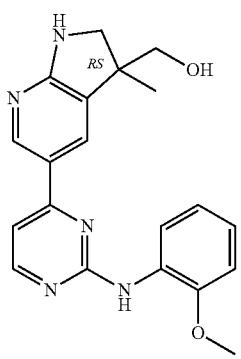 [SMILES: COc1ccccc1Nc1nccc(-c2cnc3c(c2)C(C)(CO)CN3)n1] | B2 |
| Compound 158 prepared in 2 to 3 steps from intermediate 199 | 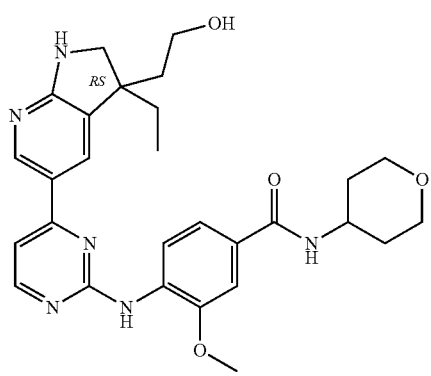 [SMILES: CCC1(CCO)CNc2ncc(-c3ccnc(Nc4ccc(C(=O)NC5CCOCC5)cc4OC)n3)cc21] | B2 |

| Compound number | Structure | Method |
|---|---|---|
| Compound 159 prepared in 2 to 3 steps from intermediate 199 | 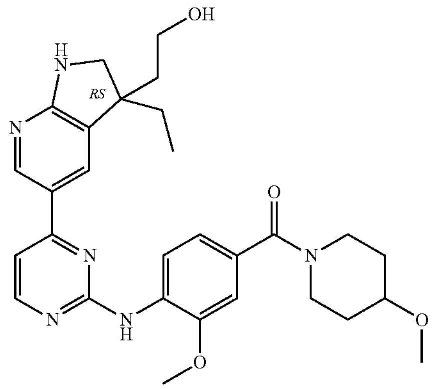 [SMILES: CCC1(CCO)CNc2ncc(-c3ccnc(Nc4ccc(C(=O)N5CCC(OC)CC5)cc4OC)n3)cc21] | B2 |
| Compound 360 | 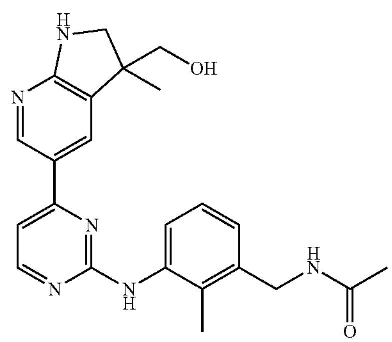 [SMILES: CC(=O)NCc1cccc(Nc2nccc(-c3cnc4c(c3)C(C)(CO)CN4)n2)c1C] | B1 |

Example B2

Preparation of Compound 2:

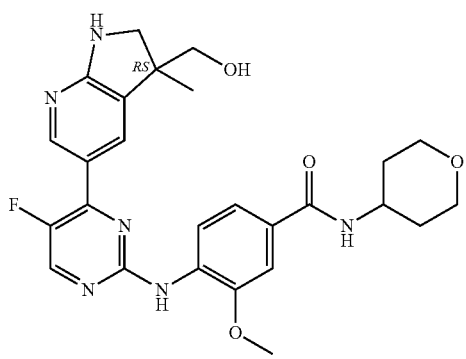 [SMILES: COc1cc(C(=O)NC2CCOCC2)ccc1Nc1ncc(F)c(-c2cnc3c(c2)C(C)(CO)CN3)n1]

Intermediate 18 (142.00 mg, 0.20 mmol) was dissolved in DCM (5 mL) and TFA (5 mL) was added. The reaction mixture was stirred at rt for 7 h. The reaction mixture was concentrated in vacuo and the residue was dissolved in neat TFA (3 mL) and left stirring for 1 h. The solution was diluted with dichloromethane and loaded onto an Isolute® SCX-2 cartridge which was washed with dichloromethane followed by methanol and then the product was eluted with 2M ammonia in methanol. The 2M ammonia in methanol solution was concentrated in vacuo and the residue was purified by MDAP to give 53 mg of compound 2 (53% yield).

Preparation of Compound 9:

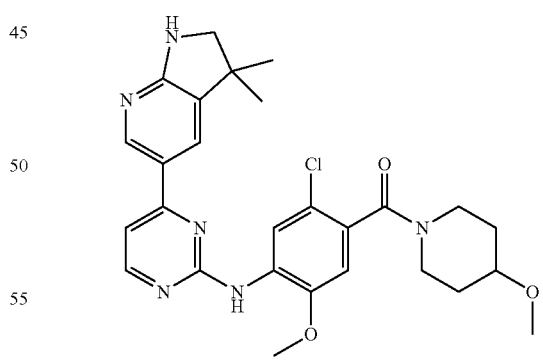

TFA (3 mL) was added to a solution of intermediate 42 (230.56 mg, 0.37 mmol) in DCM (3 mL) and the mixture was stirred for 2 h at rt. The reaction mixture was diluted with DCM and loaded onto a 5 g SCX-2 cartridge which was washed with DCM, then MeOH and eluted with 2 M ammonia in MeOH. The basic fraction was concentrated in vacuo and the residue was triturated with warm DMSO to give 114 mg of compound 9 (59% yield, pale yellow solid).

Method B5:
Preparation of Compound 3:

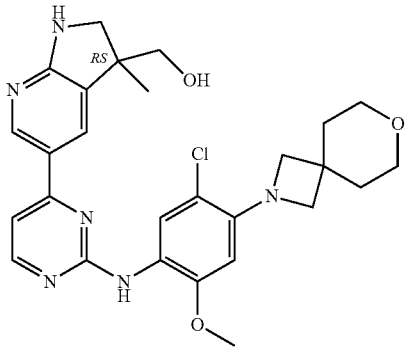 [SMILES: COc1cc(N2CC3(CCOCC3)C2)c(Cl)cc1Nc1nccc(-c2cnc3c(c2)C(C)(CO)CN3)n1]

A solution of intermediate 21 (255 mg, 0.31 mmol based on 88% purity determined by LC/MS) in TFA (3 mL) was stirred at ambient temperature for 18 h. The reaction mixture was loaded onto an Isolute® SCX-2 cartridge which was washed with methanol and then the product was eluted with 2M ammonia in methanol. The 2M ammonia in methanol solution was concentrated in vacuo. The residue was purified by MDAP (basic column) to give 75 mg of compound 3 (47% yield, yellow foam).

Preparation of Compound 5:

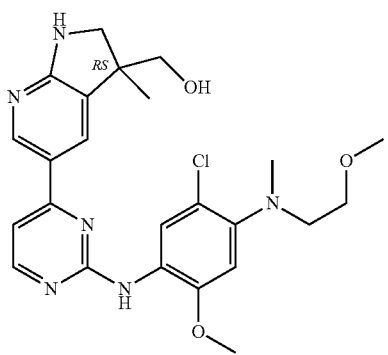 [SMILES: COCCN(C)c1cc(OC)c(Nc2nccc(-c3cnc4c(c3)C(C)(CO)CN4)n2)cc1Cl]

A solution of intermediate 28 (240 mg, 0.31 mmol based on 89% purity determined by LC/MS) in TFA (3 mL) was stirred at ambient temperature for 18 h. The reaction mixture was loaded onto an Isolute® SCX-2 cartridge which was washed with methanol and then the product was eluted with 2M ammonia in methanol. The 2M ammonia in methanol solution was concentrated in vacuo. The residue was purified by MDAP (basic column) to give 53 mg of compound 5 (36% yield).

Preparation of Compound 6:

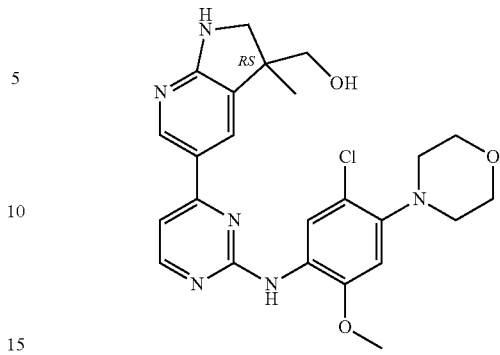

A solution of intermediate 31 (259 mg, 0.31 mmol based on 82% purity determined by LC/MS) in TFA (3 mL) was stirred at ambient temperature for 18 h. The reaction mixture was loaded onto an Isolute® SCX-2 cartridge which was washed with methanol and then, the product was eluted with 2M ammonia in methanol. The 2M ammonia in methanol solution was concentrated in vacuo. The residue was purified by MDAP (basic column) to give 76 mg of compound 6 (52% yield).

Preparation of Compound 7:

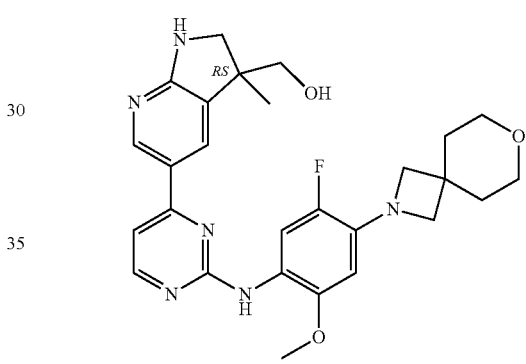

A solution of intermediate 34 (937.23 mg, 1.30 mmol) in TFA (9 mL) was stirred at ambient temperature for 18 h. The reaction mixture was diluted with DCM and loaded onto a 20 g SCX-2 cartridge which was washed with DCM, then methanol and then, the product was eluted with 2M ammonia in methanol. The basic fraction was concentrated in vacuo. The residue was purified by MDAP (basic column) to give 456 mg of compound 7 (69% yield, yellow solid).

Preparation of Compound 8:

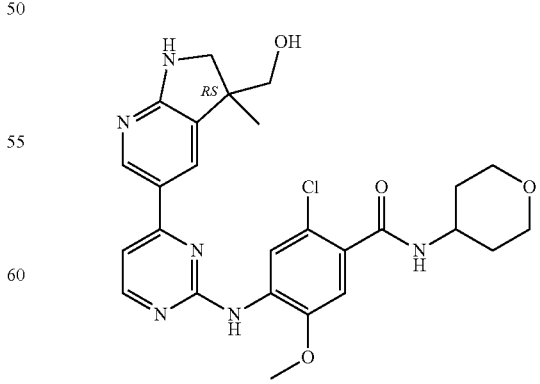

A solution of intermediate 39 (148.88 mg, 0.20 mmol) in TFA (2 mL) was stirred at ambient temperature for 15 h. The reaction mixture was diluted with DCM and loaded onto a 5 g SCX-2 cartridge which was washed with DCM. Then, methanol and then the product was eluted with 2M ammonia in methanol. The basic fraction was concentrated in vacuo. The residue was purified by MDAP (basic column) to give 65 mg of compound 8 (62% yield, pale yellow solid).

Preparation of Compound 12:

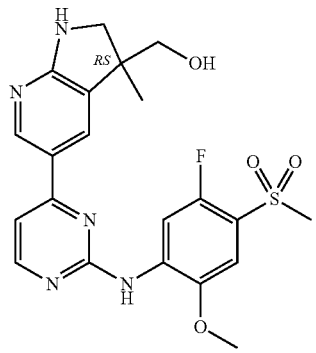 [SMILES: COc1cc(S(C)(=O)=O)c(F)cc1Nc1nccc(-c2cnc3c(c2)C(C)(CO)CN3)n1]

Intermediate 49 (203 mg, 0.30 mmol) was dissolved in TFA (3 mL) and the resulting mixture was stirred at room temperature for 18 h. The reaction was diluted with methanol and placed on a 10 g SCX column eluting with methanol, followed by 2M ammonia in MeOH. Basic fractions containing product were combined and evaporated under reduced pressure. The crude residue was purified by column chromatography (25 g silica) eluting with a gradient of 0-5% 2M ammonia in MeOH and DCM. Product containing fractions were combined and evaporated under reduced pressure to give an off-white solid which was dried under high vacuum at 50° C. for 18 hours to give 56 mg of compound 12 (41% yield, off-white solid).

Preparation of Compound 14:

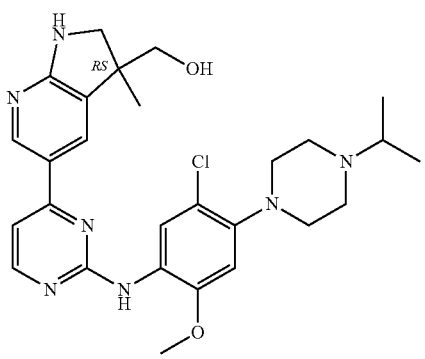 [SMILES: COc1cc(N2CCN(C(C)C)CC2)c(Cl)cc1Nc1nccc(-c2cnc3c(c2)C(C)(CO)CN3)n1]

Intermediate 56 (328 mg, 0.44 mmol) was dissolved in TFA (5 mL) and the resulting mixture was stirred at rt under N₂ for 2.5 h. The reaction was diluted with methanol and passed down a 10 g SCX column eluting with methanol, left inside the column for 10 min and then washed with 2M ammonia/methanol solution. The basic fractions were combined and evaporated under reduced pressure to give a pale beige solid. This solid was treated with TFA (3 mL) for 3 h, then diluted with methanol and passed down a 10 g SCX column eluting with methanol, left inside the column for 10 min and then washed with 2M ammonia/methanol solution. The basic fractions were combined and evaporated under reduced pressure to give a pale beige solid. The product was dissolved in a mixture of acetonitrile/water and freeze dried to give 160 mg of compound 14 (68% yield, pale yellow solid).

Preparation of Compound 15:

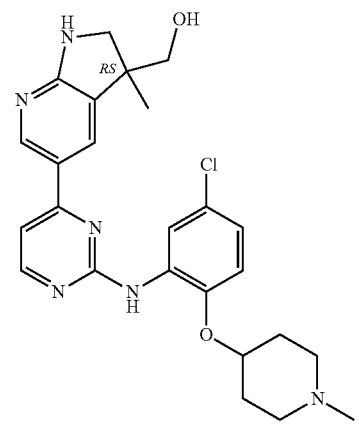 [SMILES: CN1CCC(Oc2ccc(Cl)cc2Nc2nccc(-c3cnc4c(c3)C(C)(CO)CN4)n2)CC1]

A solution of intermediate 59 (347.68 mg, 0.50 mmol) in TFA (3 mL) was stirred for 4 h at rt. The reaction mixture was diluted with DCM and loaded onto a 5 g SCX-2 cartridge, washed with DCM, then MeOH and eluted with 2 M ammonia in MeOH. The basic fraction was concentrated in vacuo and the product was purified with MDAP (basic column) to give 136 mg of compound 15 (57% yield, yellow solid).

Preparation of Compound 16:

Intermediate 62 (133.00 mg, 0.19 mmol) was dissolved in TFA (5 mL) and the resulting mixture was stirred at rt under N₂ for 5 h. Then the reaction was diluted with methanol and passed down a 10 g SCX column eluting with methanol, and then washed with 2M ammonia/methanol solution. Basic fractions were combined and evaporated under reduced pressure to give a pale yellow solid which was purified by flash silica chromatography (12 g) eluted with 0-5% 2M ammonia/methanol in DCM. The residue was dissolved in a mixture of acetonitrile/water and was freeze dried to give 40 mg of compound 16 (42% yield, off-white solid).

Method B16:
Preparation of Compound 4:

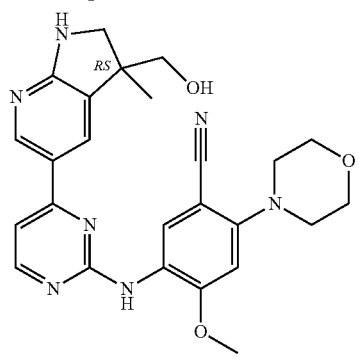

A solution of intermediate 25 (289.00 mg, 0.30 mmol based on 72% purity determined by LC/MS) in TFA (3 mL) was stirred at ambient temperature for 18 h. The reaction mixture was concentrated in vacuo and the residue was treated with $K_2CO_3$ (253.00 mg, 1.83 mmol) in DCM (2 mL) for 2 h at 50° C. The reaction mixture was partitioned between ethyl acetate and water and the organic layer was dried with sodium sulfate and concentrated in vacuo. The residue was purified by MDAP (basic column) to give 55 mg of compound 4 (38% yield).

Method B7:
Alternative Preparation of Compound 16:

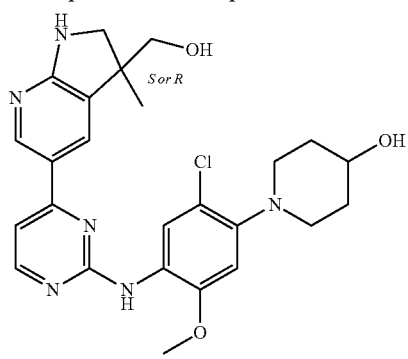

HCl (3M in $H_2O$) (2.03 mL, 6.09 mmol) was added to a solution of intermediate 62 (628 mg, 0.61 mmol) in MeOH (9.33 mL) and the reaction mixture was stirred for 5 h at reflux. The reaction mixture was cooled down to room temperature and neutralized with a saturated solution of $NaHCO_3$. The reaction mixture was partitioned between DCM/MeOH (9/1) and a saturated solution of $NaHCO_3$ and was filtered to remove the precipitate. The solid was taken up with 100 mL of DCM/MeOH (1/1). The precipitate was filtered and the filtrate was concentrated under vacuo. The resulting residue was taken up with DCM/MeOH (8/2). The precipitate was filtered to afford a first batch of crude compound 16. The filtrate was concentrated and the resulting residue was taken up with DCM/MeOH (9/1). The precipitate was filtered, mixed with the first batch of crude compound 16 and the resulting solid was taken up with 20 mL of water, stirred at room temperature for 30 min, filtered and washed successively with $CH_3CN$ and $Et_2O$. The resulting precipitate was dried under vacuum to afford 193 mg of compound 16 (63% yield).

Method B8:
Preparation of Compound 53:

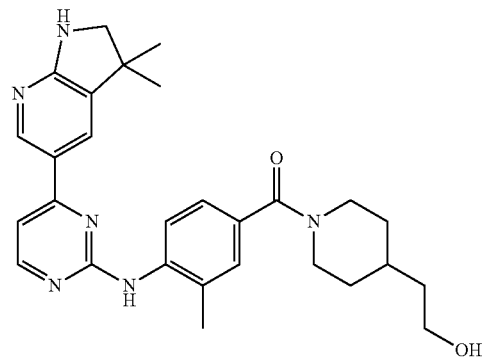 [SMILES: Cc1cc(C(=O)N2CCC(CCO)CC2)ccc1Nc1nccc(-c2cnc3c(c2)C(C)(C)CN3)n1]

To a solution of intermediate 78 (210 mg, 0.28 mmol) in DCM (5 mL) was added TFA (5 mL) and the reaction mixture was stirred at ambient temperature for 24 h. The solution was then concentrated in vacuo and the residue was dissolved in THF (5 mL) and NaOH 1N (5 mL) was added and the reaction mixture was stirred at ambient temperature for 1 h. The reaction mixture was acidified to pH-7 with 1M HCl and was extracted with ethyl acetate. The organic layer was dried with sodium sulfate, filtered and concentrated in vacuo. The residue was loaded onto an Isolute® SCX-2 cartridge which was washed with methanol and then the product was eluted with 2M $NH_3$ in methanol. The 2M $NH_3$ in methanol solution was concentrated in vacuo. The residue was purified by MDAP to give 48 mg of compound 53 (36% yield, yellow glass). The compounds in the Table below were prepared by using an analogous method as described in methods B4 to B8, starting from the respective starting materials.

| Compound number | Structure | Method |
|---|---|---|
| Compound 11 | 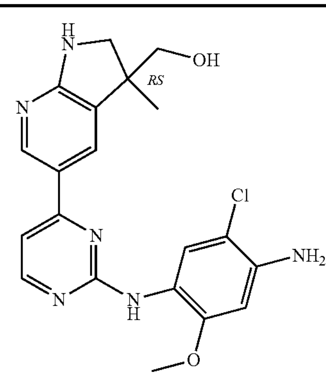 | B4 |

-continued
| Compound number | Structure | Method |
|---|---|---|
| Compound 17 (from intermediate 65) | 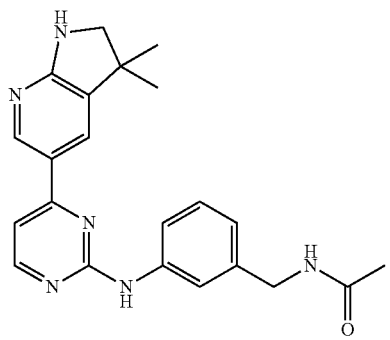 [SMILES: CC(=O)NCc1cccc(Nc2nccc(-c3cnc4c(c3)C(C)(C)CN4)n2)c1] | B4 |
| Compound 21 | 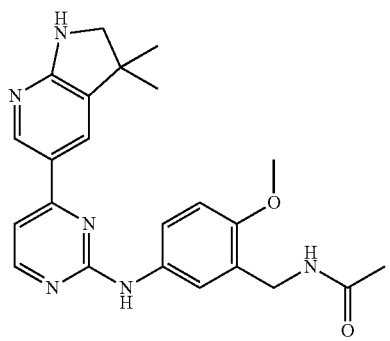 [SMILES: COc1ccc(Nc2nccc(-c3cnc4c(c3)C(C)(C)CN4)n2)cc1CNC(C)=O] | B4 |
| Compound 22 | 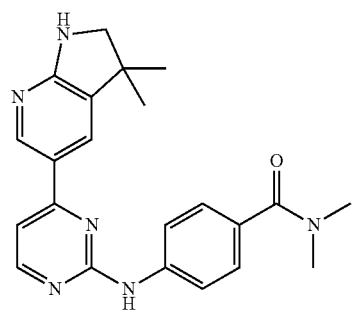 [SMILES: CN(C)C(=O)c1ccc(Nc2nccc(-c3cnc4c(c3)C(C)(C)CN4)n2)cc1] | B4 |
| Compound 24 | 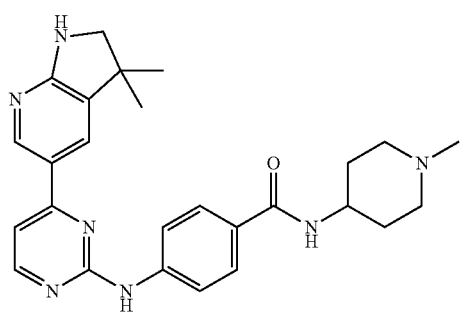 | B4 |

-continued

| Compound number | Structure | Method |
|---|---|---|
| Compound 28 | 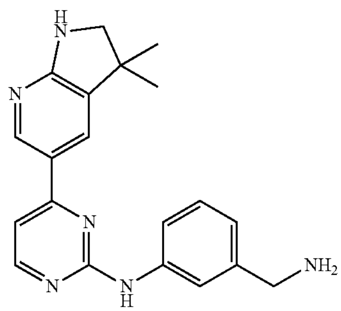 [SMILES: CC1(C)CNc2ncc(-c3ccnc(Nc4cccc(CN)c4)n3)cc21] | B4 |
| Compound 31 | 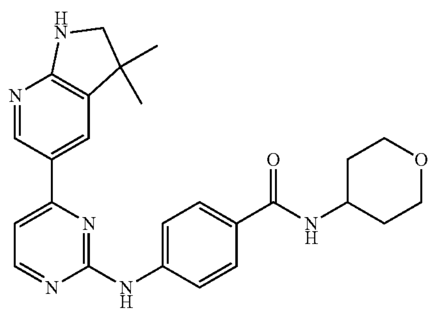 [SMILES: CC1(C)CNc2ncc(-c3ccnc(Nc4ccc(C(=O)NC5CCOCC5)cc4)n3)cc21] | B4 |
| Compound 32 | 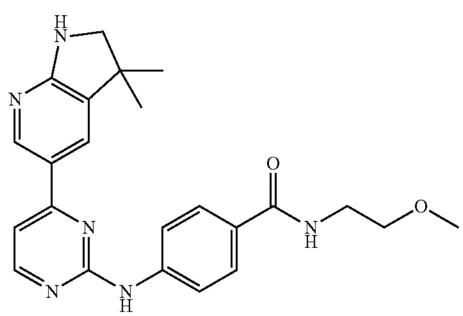 [SMILES: COCCNC(=O)c1ccc(Nc2nccc(-c3cnc4c(c3)C(C)(C)CN4)n2)cc1] | B4 |
| Compound 33 | 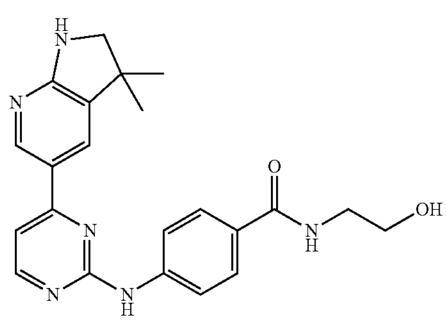 [SMILES: CC1(C)CNc2ncc(-c3ccnc(Nc4ccc(C(=O)NCCO)cc4)n3)cc21] | B4 |
| Compound 34 | 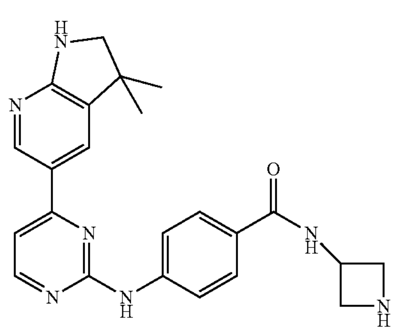 [SMILES: CC1(C)CNc2ncc(-c3ccnc(Nc4ccc(C(=O)NC5CNC5)cc4)n3)cc21] | B4 |

| Compound number | Structure | Method |
|---|---|---|
| Compound 35 | 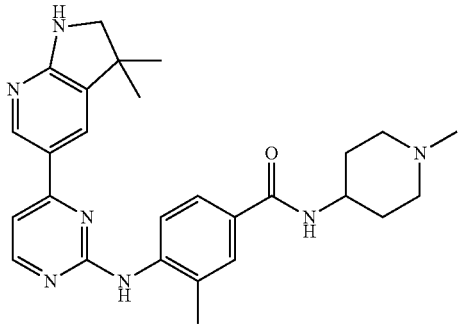 [SMILES: Cc1cc(C(=O)NC2CCN(C)CC2)ccc1Nc1nccc(-c2cnc3c(c2)C(C)(C)CN3)n1] | B4 |
| Compound 36 | 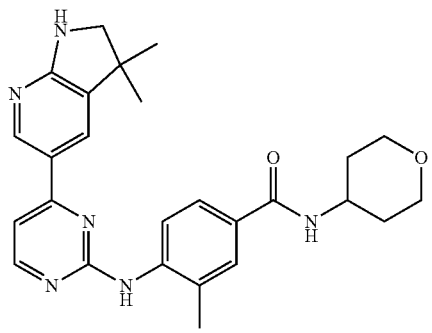 [SMILES: Cc1cc(C(=O)NC2CCOCC2)ccc1Nc1nccc(-c2cnc3c(c2)C(C)(C)CN3)n1] | B4 |
| Compound 42 | 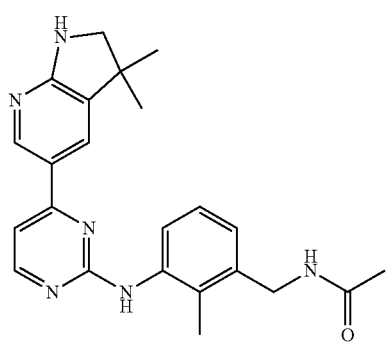 [SMILES: CC(=O)NCc1cccc(Nc2nccc(-c3cnc4c(c3)C(C)(C)CN4)n2)c1C] | B4 |
| Compound 43 | 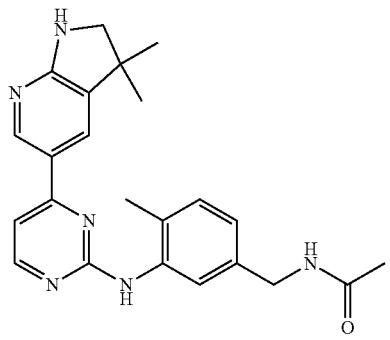 [SMILES: CC(=O)NCc1ccc(C)c(Nc2nccc(-c3cnc4c(c3)C(C)(C)CN4)n2)c1] | B4 |

-continued
| Compound number | Structure | Method |
|---|---|---|
| Compound 44 | 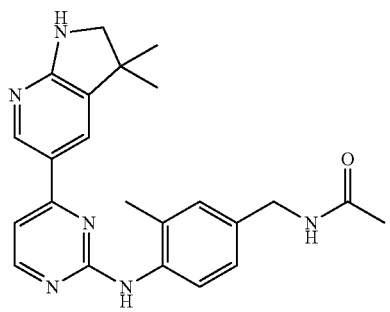 [SMILES: CC(=O)NCc1ccc(Nc2nccc(-c3cnc4c(c3)C(C)(C)CN4)n2)c(C)c1] | B4 |
| Compound 46 (from intermediate 75) | 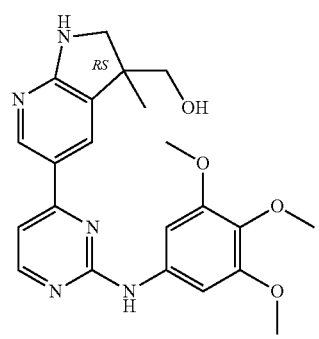 [SMILES: COc1cc(Nc2nccc(-c3cnc4c(c3)C(C)(CO)CN4)n2)cc(OC)c1OC] | B4 |
| Compound 49 | 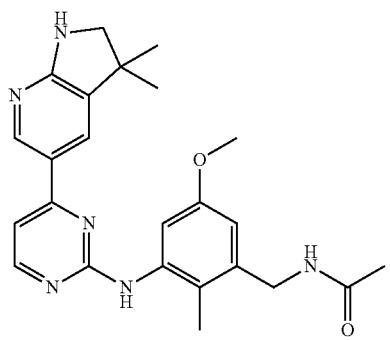 [SMILES: COc1cc(CNC(C)=O)c(C)c(Nc2nccc(-c3cnc4c(c3)C(C)(C)CN4)n2)c1] | B4 |
| Compound 50 | 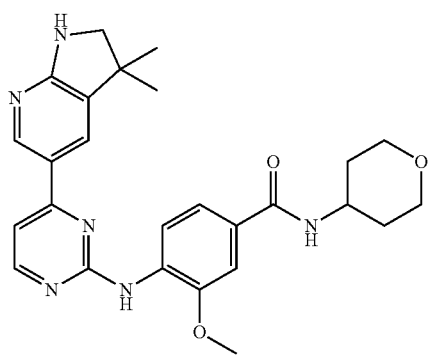 [SMILES: COc1cc(C(=O)NC2CCOCC2)ccc1Nc1nccc(-c2cnc3c(c2)C(C)(C)CN3)n1] | B4 |

-continued

| Compound number | Structure | Method |
|---|---|---|
| Compound 51 | 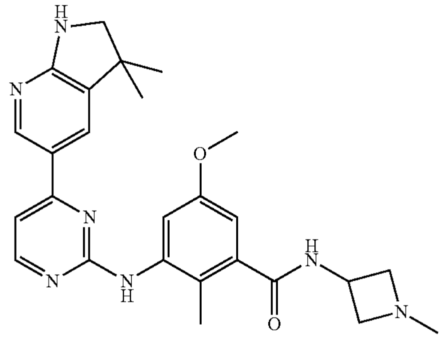 [SMILES: COc1cc(Nc2nccc(-c3cnc4c(c3)C(C)(C)CN4)n2)c(C)c(C(=O)NC2CN(C)C2)c1] | B4 |
| Compound 54 | 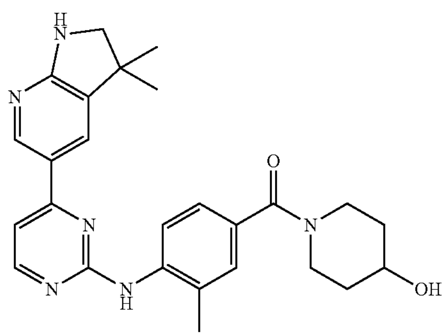 [SMILES: Cc1cc(C(=O)N2CCC(O)CC2)ccc1Nc1nccc(-c2cnc3c(c2)C(C)(C)CN3)n1] | B4 or B7 |
| Compound 55 | 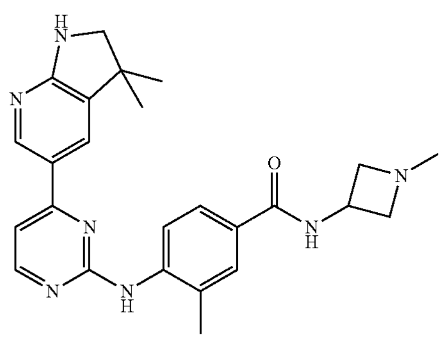 [SMILES: Cc1cc(C(=O)NC2CN(C)C2)ccc1Nc1nccc(-c2cnc3c(c2)C(C)(C)CN3)n1] | B4 |
| Compound 60 | 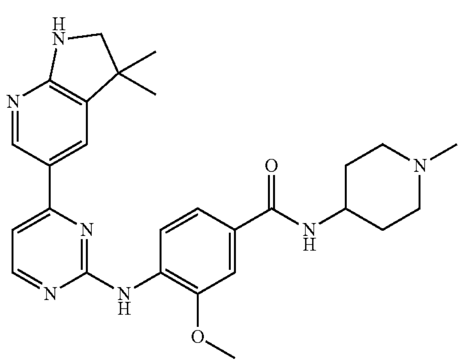 [SMILES: COc1cc(C(=O)NC2CCN(C)CC2)ccc1Nc1nccc(-c2cnc3c(c2)C(C)(C)CN3)n1] | B4 |

-continued
| Compound number | Structure | Method |
|---|---|---|
| Compound 62 (from intermediate 91) | 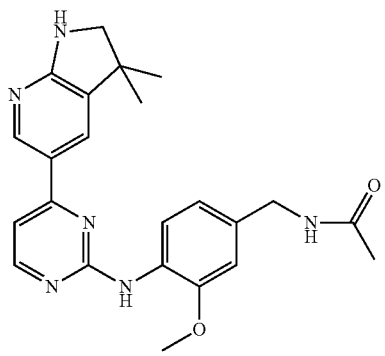 [SMILES: COc1cc(CNC(C)=O)ccc1Nc1nccc(-c2cnc3c(c2)C(C)(C)CN3)n1] | B4 |
| Compound 63 | 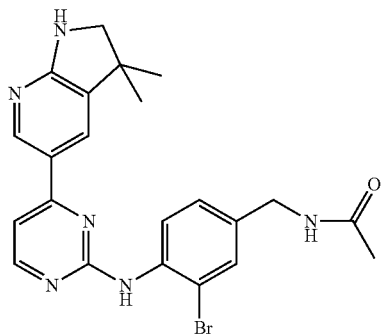 [SMILES: CC(=O)NCc1ccc(Nc2nccc(-c3cnc4c(c3)C(C)(C)CN4)n2)c(Br)c1] | B4 |
| Compound 64 | 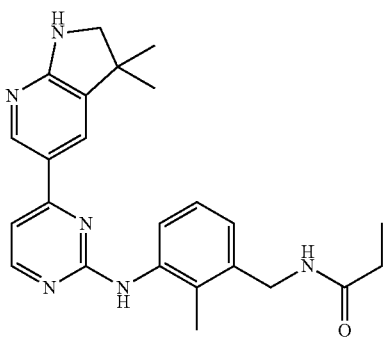 [SMILES: CCC(=O)NCc1cccc(Nc2nccc(-c3cnc4c(c3)C(C)(C)CN4)n2)c1C] | B4 |
| Compound 65 | 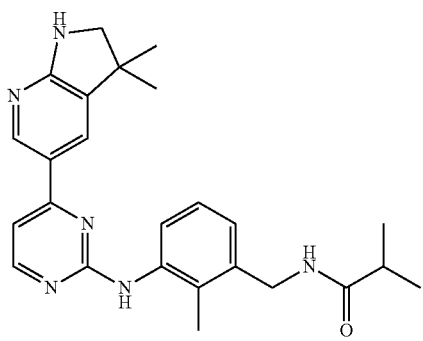 [SMILES: Cc1c(CNC(=O)C(C)C)cccc1Nc1nccc(-c2cnc3c(c2)C(C)(C)CN3)n1] | B4 |

| Compound number | Structure | Method |
|---|---|---|
| Compound 66 | 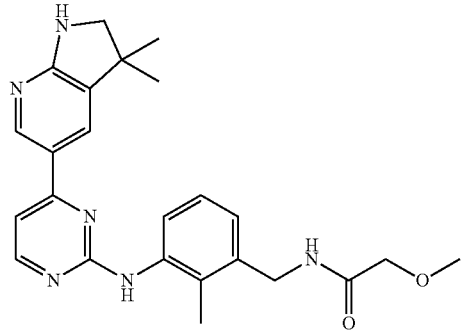 [SMILES: COCC(=O)NCc1cccc(Nc2nccc(-c3cnc4c(c3)C(C)(C)CN4)n2)c1C] | B4 |
| Compound 67 | 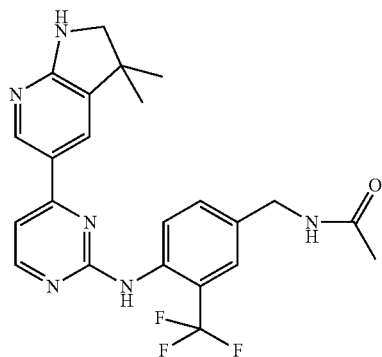 [SMILES: CC(=O)NCc1ccc(Nc2nccc(-c3cnc4c(c3)C(C)(C)CN4)n2)c(C(F)(F)F)c1] | B4 |
| Compound 72 | 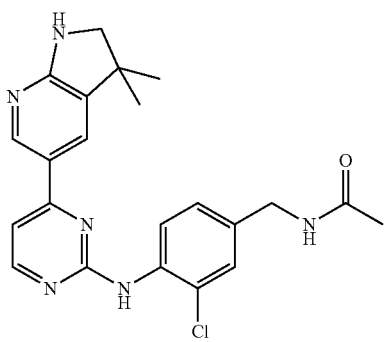 [SMILES: CC(=O)NCc1ccc(Nc2nccc(-c3cnc4c(c3)C(C)(C)CN4)n2)c(Cl)c1] | B4 |
| Compound 77 | 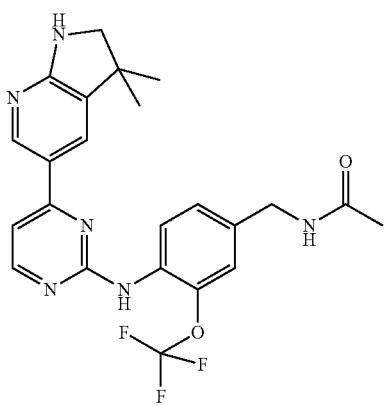 [SMILES: CC(=O)NCc1ccc(Nc2nccc(-c3cnc4c(c3)C(C)(C)CN4)n2)c(OC(F)(F)F)c1] | B4 |

-continued
| Compound number | Structure | Method |
|---|---|---|
| Compound 78 | 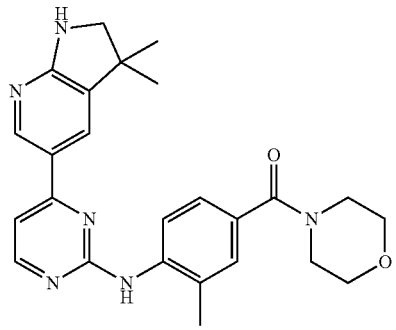 [SMILES: Cc1cc(C(=O)N2CCOCC2)ccc1Nc1nccc(-c2cnc3c(c2)C(C)(C)CN3)n1] | B4 |
| Compound 79 | 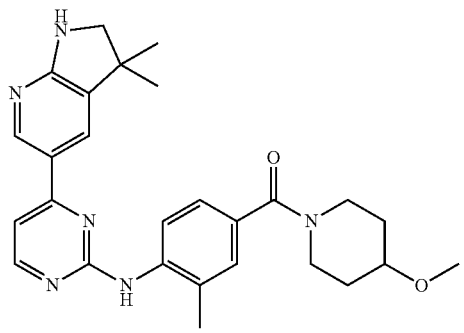 [SMILES: COC1CCN(C(=O)c2ccc(Nc3nccc(-c4cnc5c(c4)C(C)(C)CN5)n3)c(C)c2)CC1] | B4 |
| Compound 80 | 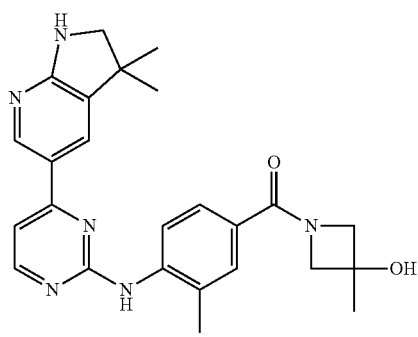 [SMILES: Cc1cc(C(=O)N2CC(C)(O)C2)ccc1Nc1nccc(-c2cnc3c(c2)C(C)(C)CN3)n1] | B4 |
| Compound 81 | 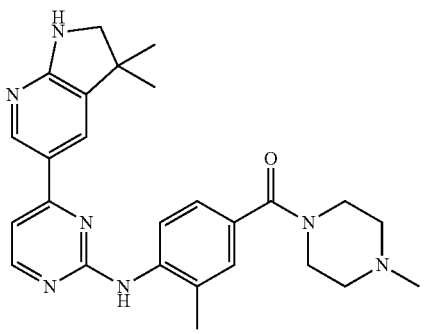 [SMILES: Cc1cc(C(=O)N2CCN(C)CC2)ccc1Nc1nccc(-c2cnc3c(c2)C(C)(C)CN3)n1] | B4 |

-continued
| Compound number | Structure | Method |
|---|---|---|
| Compound 82 (from intermediate 100) | 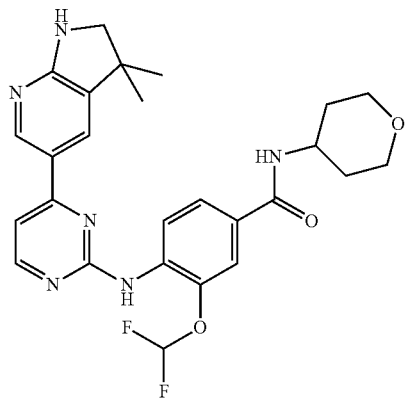 [SMILES: CC1(C)CNc2ncc(-c3ccnc(Nc4ccc(C(=O)NC5CCOCC5)cc4OC(F)F)n3)cc21] | B4 |
| Compound 83 | 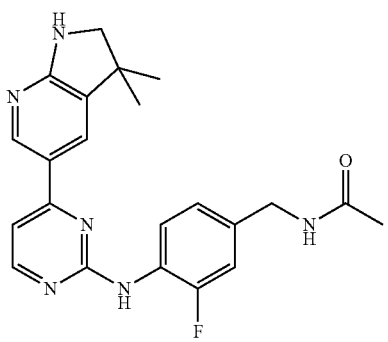 | B4 |
| Compound 85 | 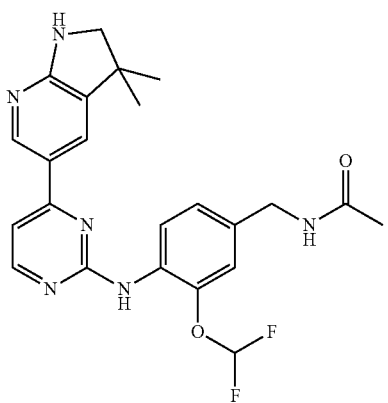 [SMILES: CC(=O)NCc1ccc(Nc2nccc(-c3cnc4c(c3)C(C)(C)CN4)n2)c(OC(F)F)c1] | B4 |
| Compound 91 | 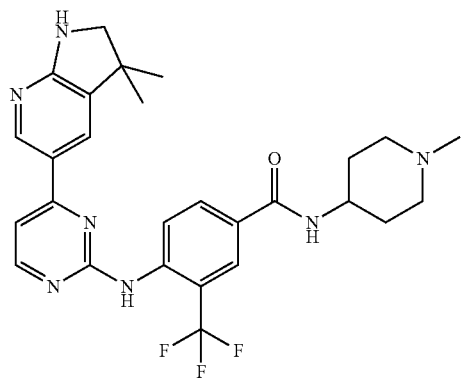 [SMILES: CN1CCC(NC(=O)c2ccc(Nc3nccc(-c4cnc5c(c4)C(C)(C)CN5)n3)c(C(F)(F)F)c2)CC1] | B4 |

-continued
| Compound number | Structure | Method |
|---|---|---|
| Compound 94 | 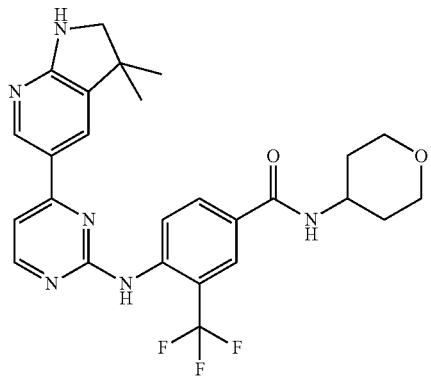 [SMILES: CC1(C)CNc2ncc(-c3ccnc(Nc4ccc(C(=O)NC5CCOCC5)cc4C(F)(F)F)n3)cc21] | B4 |
| Compound 96 | 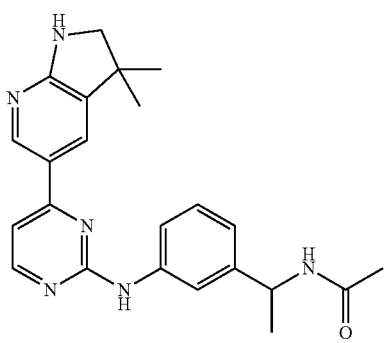 [SMILES: CC(=O)NC(C)c1cccc(Nc2nccc(-c3cnc4c(c3)C(C)(C)CN4)n2)c1] | B4 |
| Compound 97 | 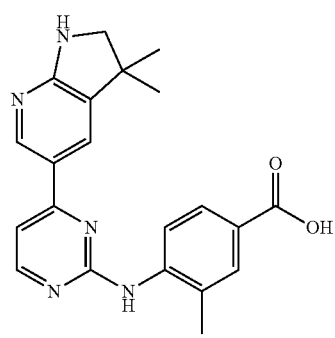 [SMILES: Cc1cc(C(=O)O)ccc1Nc1nccc(-c2cnc3c(c2)C(C)(C)CN3)n1] | B4 |
| Compound 98 (from intermediate 103) | 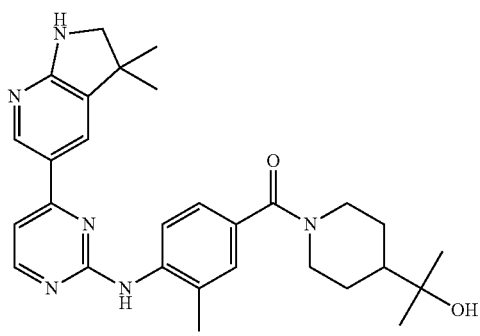 [SMILES: Cc1cc(C(=O)N2CCC(C(C)(C)O)CC2)ccc1Nc1nccc(-c2cnc3c(c2)C(C)(C)CN3)n1] | B4 |

-continued
| Compound number | Structure | Method |
|---|---|---|
| Compound 99 | 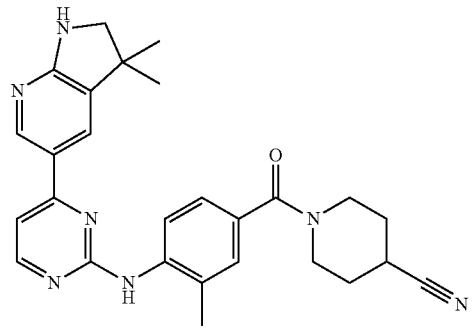 [SMILES: Cc1cc(C(=O)N2CCC(C#N)CC2)ccc1Nc1nccc(-c2cnc3c(c2)C(C)(C)CN3)n1] | B4 |
| Compound 100 | 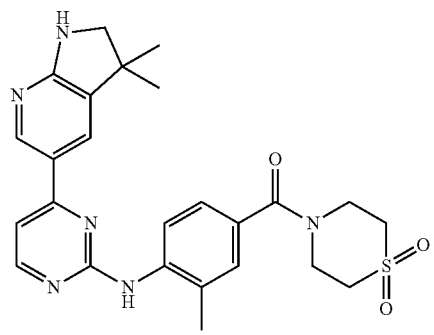 [SMILES: Cc1cc(C(=O)N2CCS(=O)(=O)CC2)ccc1Nc1nccc(-c2cnc3c(c2)C(C)(C)CN3)n1] | B4 |
| Compound 103 | 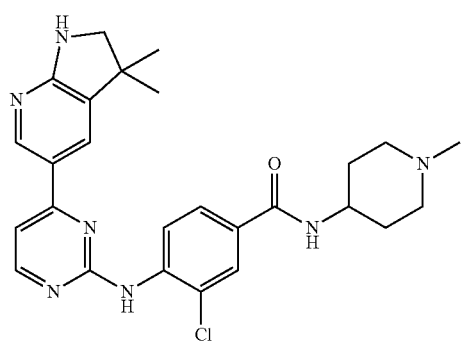 [SMILES: CN1CCC(NC(=O)c2ccc(Nc3nccc(-c4cnc5c(c4)C(C)(C)CN5)n3)c(Cl)c2)CC1] | B4 |
| Compound 104 | 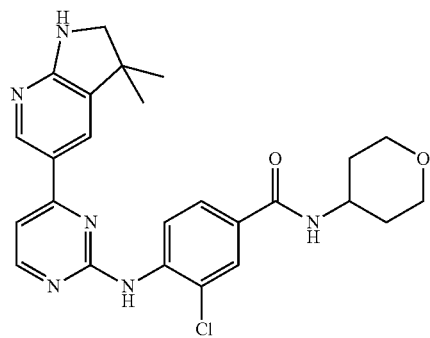 [SMILES: CC1(C)CNc2ncc(-c3ccnc(Nc4ccc(C(=O)NC5CCOCC5)cc4Cl)n3)cc21] | B4 |

| Compound number | Structure | Method |
|---|---|---|
| Compound 110 | 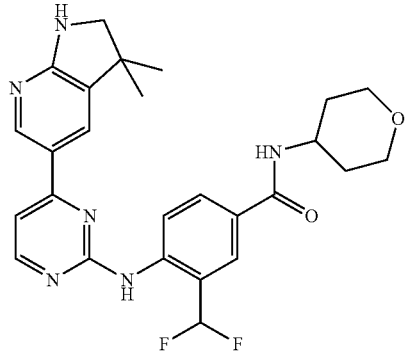 [SMILES: CC1(C)CNc2ncc(-c3ccnc(Nc4ccc(C(=O)NC5CCOCC5)cc4C(F)F)n3)cc21] | B4 |
| Compound 112 | 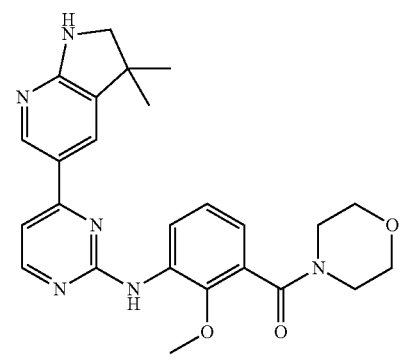 [SMILES: COc1c(Nc2nccc(-c3cnc4c(c3)C(C)(C)CN4)n2)cccc1C(=O)N1CCOCC1] | B4 |
| Compound 113 | 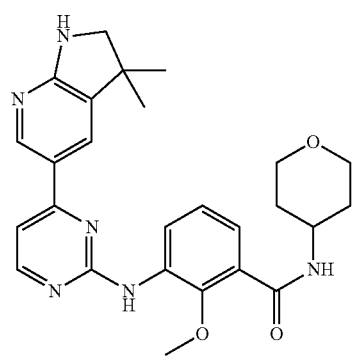 [SMILES: COc1c(Nc2nccc(-c3cnc4c(c3)C(C)(C)CN4)n2)cccc1C(=O)NC1CCOCC1] | B4 |
| Compound 114 | 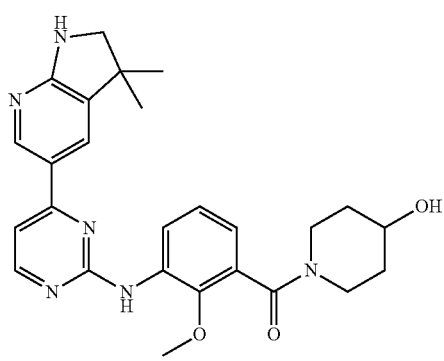 [SMILES: COc1c(Nc2nccc(-c3cnc4c(c3)C(C)(C)CN4)n2)cccc1C(=O)N1CCC(O)CC1] | B4 |

-continued
| Compound number | Structure | Method |
|---|---|---|
| Compound 115 | 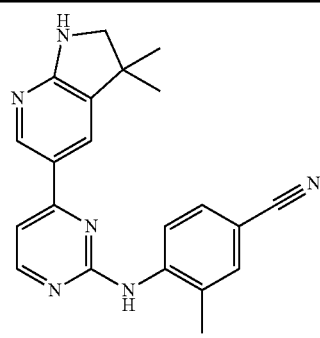 | B4 |
| Compound 116 | 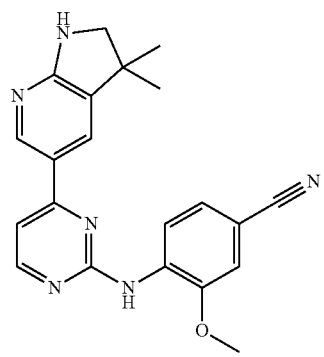 [SMILES: COc1cc(C#N)ccc1Nc1nccc(-c2cnc3c(c2)C(C)(C)CN3)n1] | B4 |
| Compound 117 | 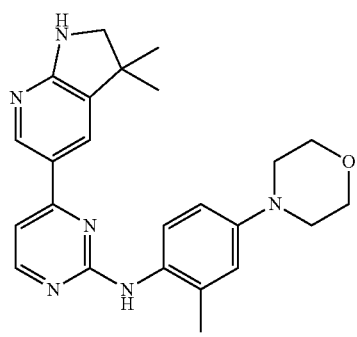 [SMILES: Cc1cc(N2CCOCC2)ccc1Nc1nccc(-c2cnc3c(c2)C(C)(C)CN3)n1] | B4 |
| Compound 119 | 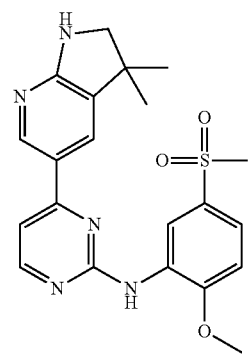 [SMILES: COc1ccc(S(C)(=O)=O)cc1Nc1nccc(-c2cnc3c(c2)C(C)(C)CN3)n1] | B4 |

-continued
| Compound number | Structure | Method |
|---|---|---|
| Compound 124 prepared in 2 to 3 steps from intermediate 204 | 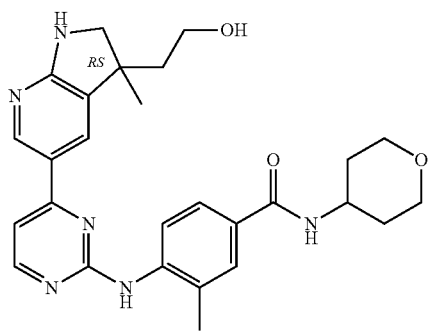 [SMILES: Cc1cc(C(=O)NC2CCOCC2)ccc1Nc1nccc(-c2cnc3c(c2)C(C)(CCO)CN3)n1] | B4 |
| Compound 126 prepared in 2 steps from intermediate 184 | 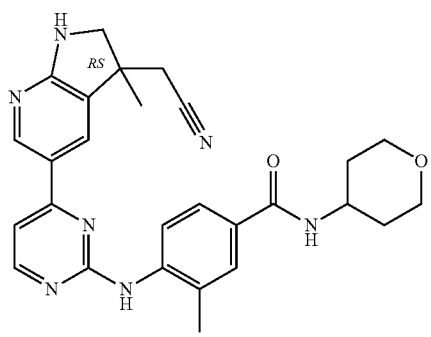 [SMILES: Cc1cc(C(=O)NC2CCOCC2)ccc1Nc1nccc(-c2cnc3c(c2)C(C)(CC#N)CN3)n1] | B4 |
| Compound 128 | 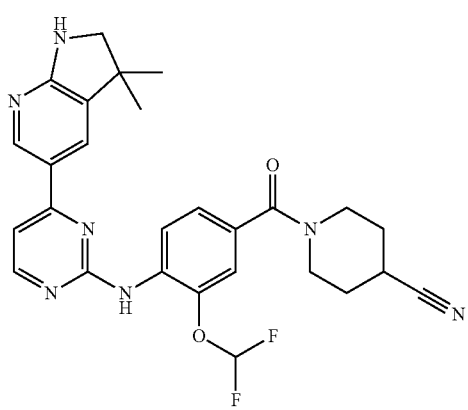 [SMILES: CC1(C)CNc2ncc(-c3ccnc(Nc4ccc(C(=O)N5CCC(C#N)CC5)cc4OC(F)F)n3)cc21] | B4 |
| Compound 129 | 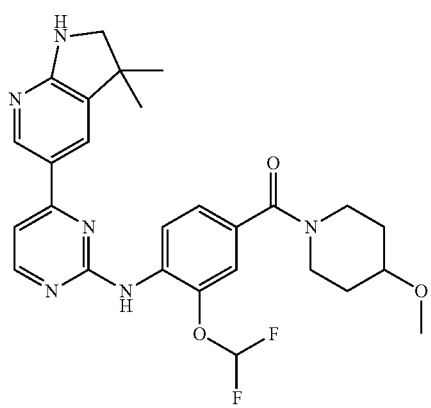 [SMILES: COC1CCN(C(=O)c2ccc(Nc3nccc(-c4cnc5c(c4)C(C)(C)CN5)n3)c(OC(F)F)c2)CC1] | B4 |

-continued
| Compound number | Structure | Method |
|---|---|---|
| Compound 145 | 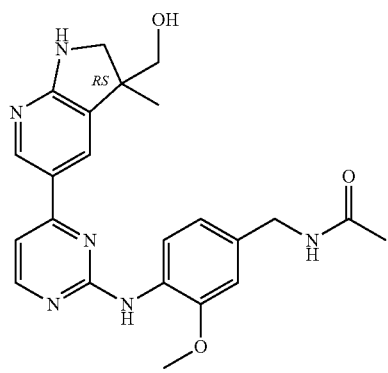 [SMILES: COc1cc(CNC(C)=O)ccc1Nc1nccc(-c2cnc3c(c2)C(C)(CO)CN3)n1] | B4 |
| Compound 154 prepared in 2 steps from intermediate 195 | 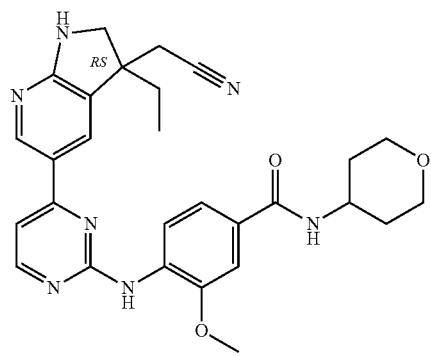 [SMILES: CCC1(CC#N)CNc2ncc(-c3ccnc(Nc4ccc(C(=O)NC5CCOCC5)cc4OC)n3)cc21] | B4 |
| Compound 155 prepared in 2 steps from intermediate 195 | 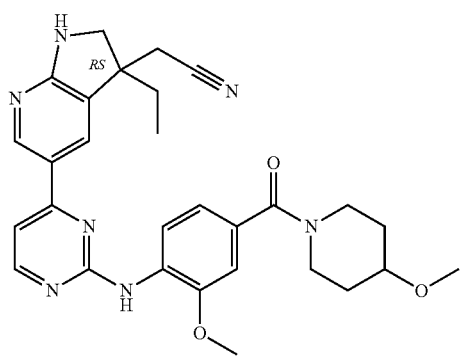 [SMILES: CCC1(CC#N)CNc2ncc(-c3ccnc(Nc4ccc(C(=O)N5CCC(OC)CC5)cc4OC)n3)cc21] | B4 |
| Compound 164 | 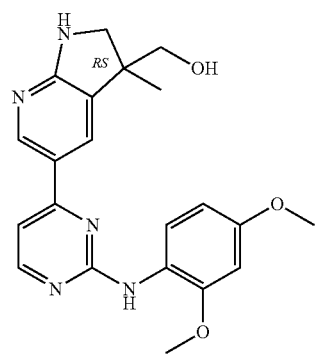 [SMILES: COc1ccc(Nc2nccc(-c3cnc4c(c3)C(C)(CO)CN4)n2)c(OC)c1] | B4 |

| Compound number | Structure | Method |
|---|---|---|
| Compound 165 (from intermediate 128) | 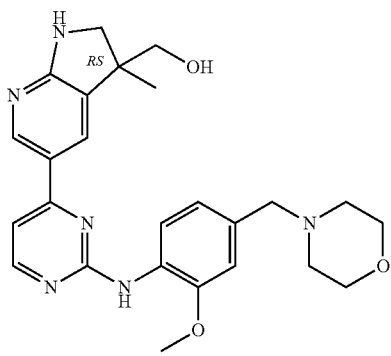 [SMILES: COc1cc(CN2CCOCC2)ccc1Nc1nccc(-c2cnc3c(c2)C(C)(CO)CN3)n1] | B5 |
| Compound 166 | 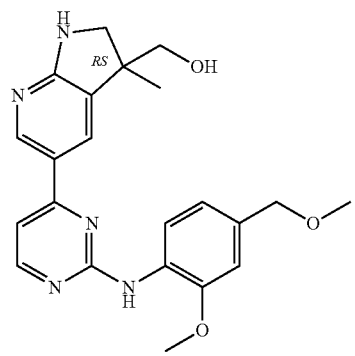 [SMILES: COCc1ccc(Nc2nccc(-c3cnc4c(c3)C(C)(CO)CN4)n2)c(OC)c1] | B4 |
| Compound 167 | 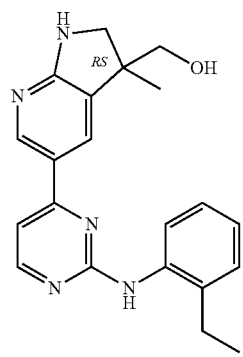 [SMILES: CCc1ccccc1Nc1nccc(-c2cnc3c(c2)C(C)(CO)CN3)n1] | B5 |
| Compound 168 | 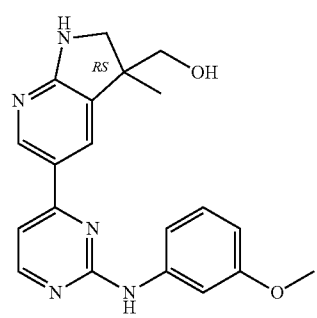 [SMILES: COc1cccc(Nc2nccc(-c3cnc4c(c3)C(C)(CO)CN4)n2)c1] | B5 |

-continued

| Compound number | Structure | Method |
|---|---|---|
| Compound 169 (from intermediate 131) | 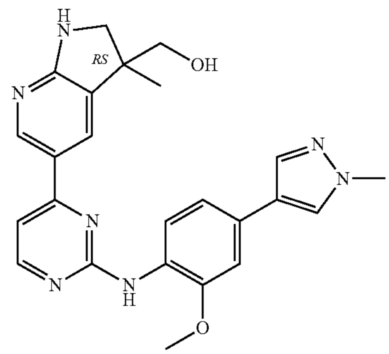 [SMILES: COc1cc(-c2cnn(C)c2)ccc1Nc1nccc(-c2cnc3c(c2)C(C)(CO)CN3)n1] | B5 |
| Compound 170 | 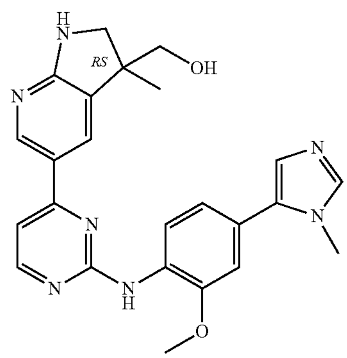 [SMILES: COc1cc(-c2cncn2C)ccc1Nc1nccc(-c2cnc3c(c2)C(C)(CO)CN3)n1] | B5 |
| Compound 171 | 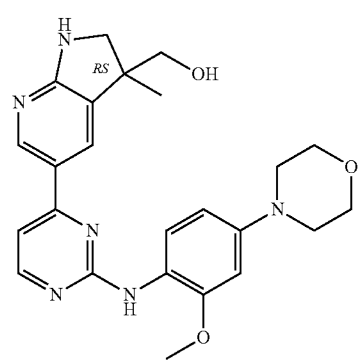 [SMILES: COc1cc(N2CCOCC2)ccc1Nc1nccc(-c2cnc3c(c2)C(C)(CO)CN3)n1] | B5 |
| Compound 172 | 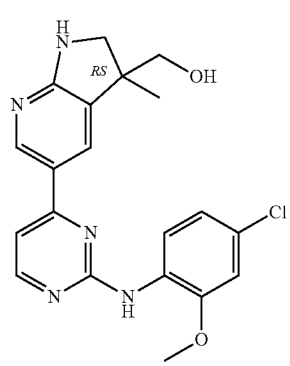 [SMILES: COc1cc(Cl)ccc1Nc1nccc(-c2cnc3c(c2)C(C)(CO)CN3)n1] | B5 |

-continued
| Compound number | Structure | Method |
|---|---|---|
| Compound 173 | 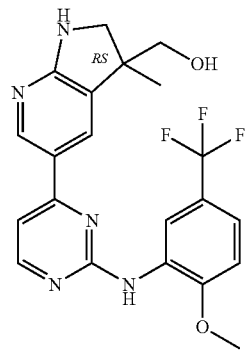 [SMILES: COc1ccc(C(F)(F)F)cc1Nc1nccc(-c2cnc3c(c2)C(C)(CO)CN3)n1] | B5 |
| Compound 174 | 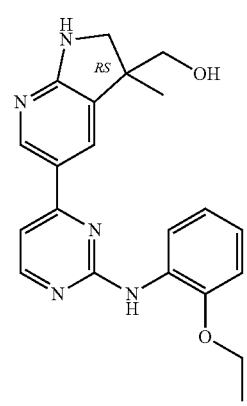 [SMILES: CCOc1ccccc1Nc1nccc(-c2cnc3c(c2)C(C)(CO)CN3)n1] | B5 |
| Compound 175 | 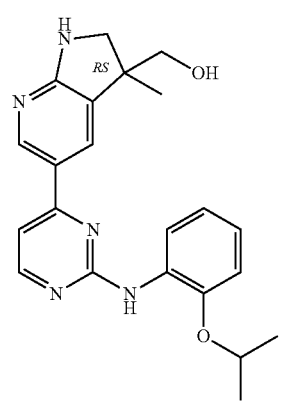 [SMILES: CC(C)Oc1ccccc1Nc1nccc(-c2cnc3c(c2)C(C)(CO)CN3)n1] | B5 |
| Compound 177 | 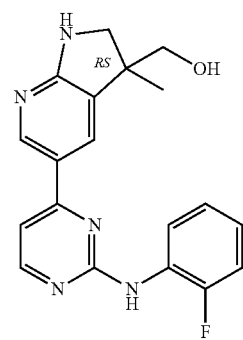 [SMILES: CC1(CO)CNc2ncc(-c3ccnc(Nc4ccccc4F)n3)cc21] | B5 |

-continued
| Compound number | Structure | Method |
|---|---|---|
| Compound 178 | 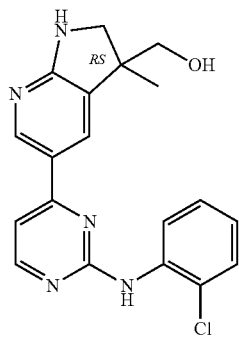 [SMILES: CC1(CO)CNc2ncc(-c3ccnc(Nc4ccccc4Cl)n3)cc21] | B5 |
| Compound 179 | 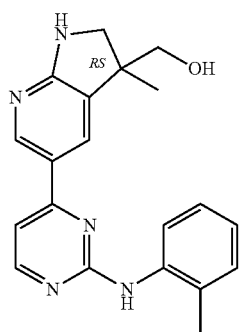 [SMILES: Cc1ccccc1Nc1nccc(-c2cnc3c(c2)C(C)(CO)CN3)n1] | B5 |
| Compound 180 | 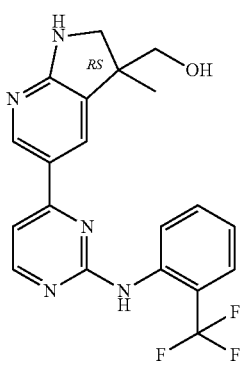 [SMILES: CC1(CO)CNc2ncc(-c3ccnc(Nc4ccccc4C(F)(F)F)n3)cc21] | B5 |
| Compound 186 | 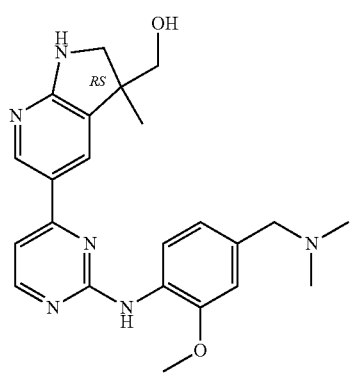 [SMILES: COc1cc(CN(C)C)ccc1Nc1nccc(-c2cnc3c(c2)C(C)(CO)CN3)n1] | B5 |

| Compound number | Structure | Method |
|---|---|---|
| Compound 189 | 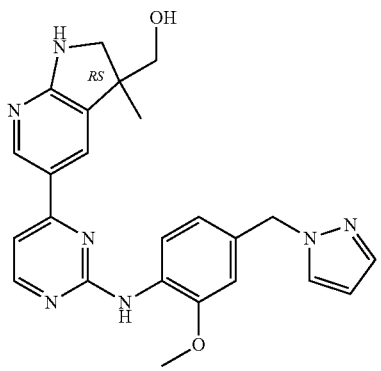 [SMILES: COc1cc(Cn2cccn2)ccc1Nc1nccc(-c2cnc3c(c2)C(C)(CO)CN3)n1] | B5 |
| Compound 190 | 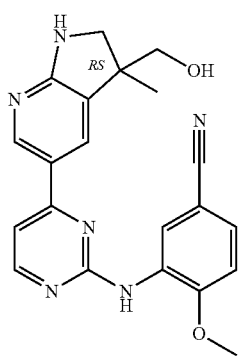 [SMILES: COc1ccc(C#N)cc1Nc1nccc(-c2cnc3c(c2)C(C)(CO)CN3)n1] | B6 |
| Compound 191 | 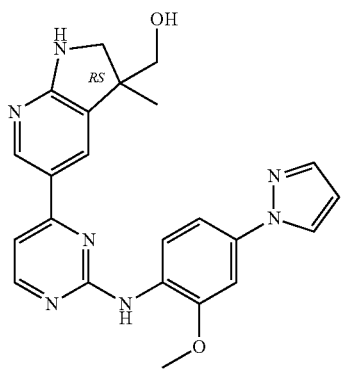 [SMILES: COc1cc(-n2cccn2)ccc1Nc1nccc(-c2cnc3c(c2)C(C)(CO)CN3)n1] | B5 |
| Compound 192 (from intermediate 135) | 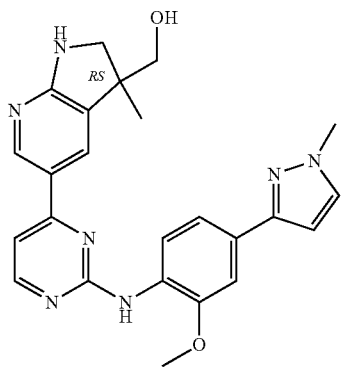 [SMILES: COc1cc(-c2ccn(C)n2)ccc1Nc1nccc(-c2cnc3c(c2)C(C)(CO)CN3)n1] | B5 |

-continued
| Compound number | Structure | Method |
|---|---|---|
| Compound 193 | 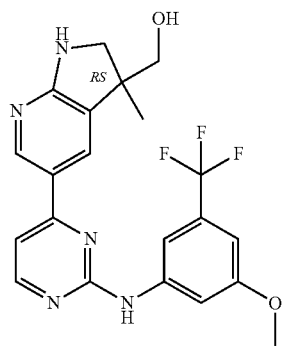 [SMILES: COc1cc(Nc2nccc(-c3cnc4c(c3)C(C)(CO)CN4)n2)cc(C(F)(F)F)c1] | B5 |
| Compound 194 | 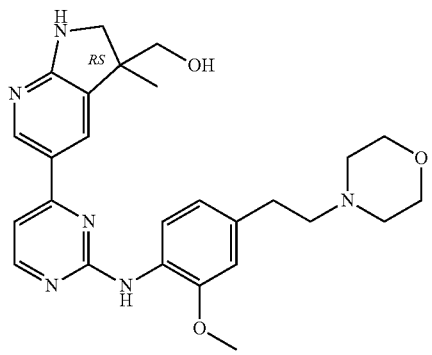 [SMILES: COc1cc(CCN2CCOCC2)ccc1Nc1nccc(-c2cnc3c(c2)C(C)(CO)CN3)n1] | B5 |
| Compound 195 | 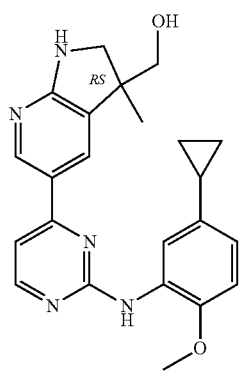 [SMILES: COc1ccc(C2CC2)cc1Nc1nccc(-c2cnc3c(c2)C(C)(CO)CN3)n1] | B5 |
| Compound 197 | 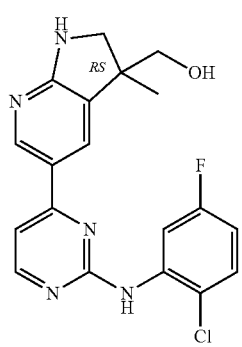 [SMILES: CC1(CO)CNc2ncc(-c3ccnc(Nc4cc(F)ccc4Cl)n3)cc21] | B5 |

-continued
| Compound number | Structure | Method |
|---|---|---|
| Compound 198 | 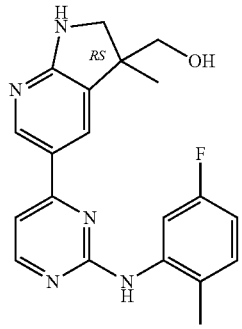 [SMILES: Cc1ccc(F)cc1Nc1nccc(-c2cnc3c(c2)C(C)(CO)CN3)n1] | B5 |
| Compound 199 | 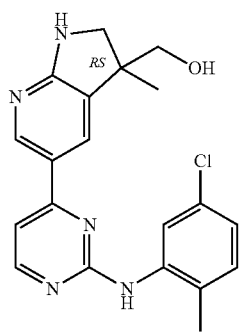 | B5 |
| Compound 200 (from intermediate 138) | 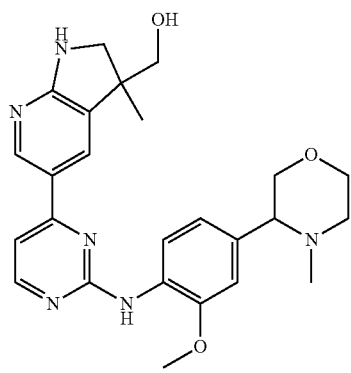 [SMILES: COc1cc(C2COCCN2C)ccc1Nc1nccc(-c2cnc3c(c2)C(C)(CO)CN3)n1] | B5 |
| Compound 202 | 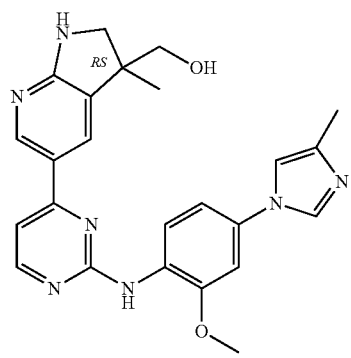 [SMILES: COc1cc(-n2cnc(C)c2)ccc1Nc1nccc(-c2cnc3c(c2)C(C)(CO)CN3)n1] | B5 |

| Compound number | Structure | Method |
|---|---|---|
| Compound 203 | 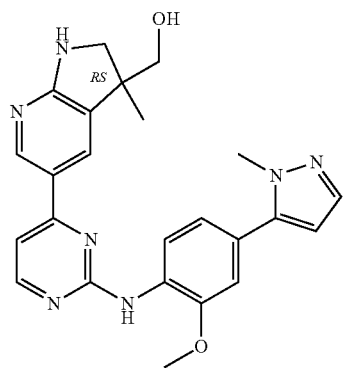 [SMILES: COc1cc(-c2ccnn2C)ccc1Nc1nccc(-c2cnc3c(c2)C(C)(CO)CN3)n1] | B5 |
| Compound 204 | 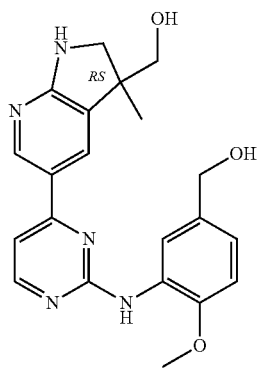 [SMILES: COc1ccc(CO)cc1Nc1nccc(-c2cnc3c(c2)C(C)(CO)CN3)n1] | B5 |
| Compound 205 | 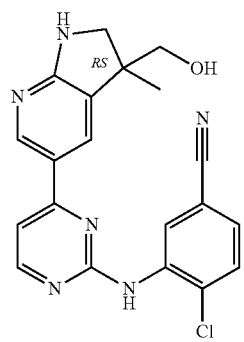 [SMILES: CC1(CO)CNc2ncc(-c3ccnc(Nc4cc(C#N)ccc4Cl)n3)cc21] | B6 |
| Compound 206 | 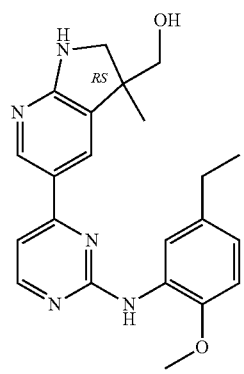 [SMILES: CCc1ccc(OC)c(Nc2nccc(-c3cnc4c(c3)C(C)(CO)CN4)n2)c1] | B5 |

| Compound number | Structure | Method |
|---|---|---|
| Compound 207 | 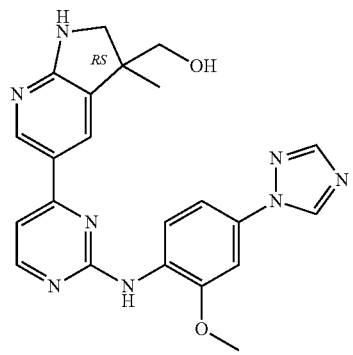 [SMILES: COc1cc(-n2cncn2)ccc1Nc1nccc(-c2cnc3c(c2)C(C)(CO)CN3)n1] | B5 |
| Compound 208 | 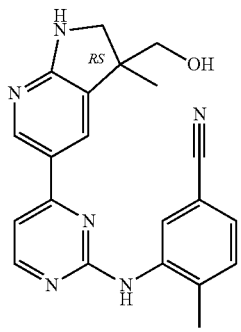 [SMILES: Cc1ccc(C#N)cc1Nc1nccc(-c2cnc3c(c2)C(C)(CO)CN3)n1] | B6 |
| Compound 209 | 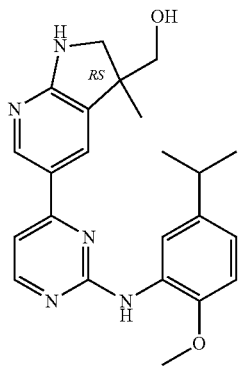 [SMILES: COc1ccc(C(C)C)cc1Nc1nccc(-c2cnc3c(c2)C(C)(CO)CN3)n1] | B5 |
| Compound 210 | 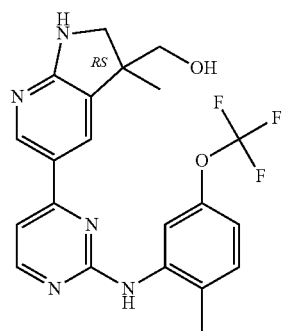 [SMILES: Cc1ccc(OC(F)(F)F)cc1Nc1nccc(-c2cnc3c(c2)C(C)(CO)CN3)n1] | B5 |

-continued
| Compound number | Structure | Method |
|---|---|---|
| Compound 211 | 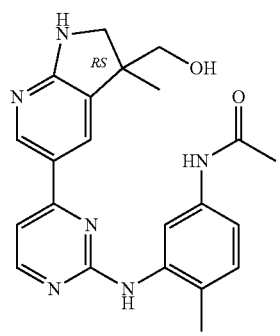 [SMILES: CC(=O)Nc1ccc(C)c(Nc2nccc(-c3cnc4c(c3)C(C)(CO)CN4)n2)c1] | B5 |
| Compound 212 | 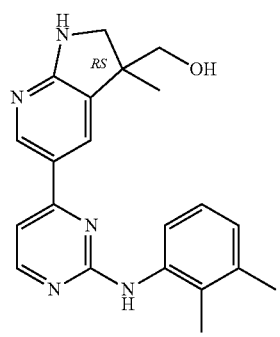 [SMILES: Cc1cccc(Nc2nccc(-c3cnc4c(c3)C(C)(CO)CN4)n2)c1C] | B5 |
| Compound 213 | 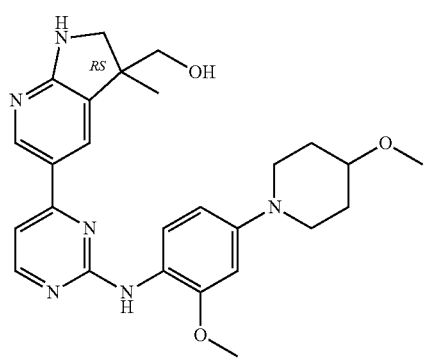 [SMILES: COc1cc(N2CCC(OC)CC2)ccc1Nc1nccc(-c2cnc3c(c2)C(C)(CO)CN3)n1] | B5 |
| Compound 214 | 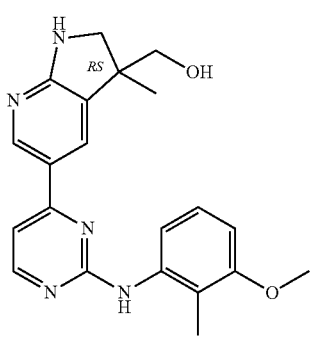 [SMILES: COc1cccc(Nc2nccc(-c3cnc4c(c3)C(C)(CO)CN4)n2)c1C] | B5 |

| Compound number | Structure | Method |
|---|---|---|
| Compound 215 | 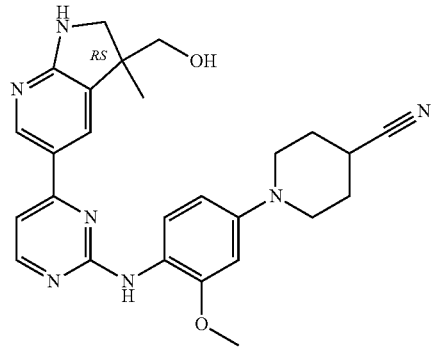 [SMILES: COc1cc(N2CCC(C#N)CC2)ccc1Nc1nccc(-c2cnc3c(c2)C(C)(CO)CN3)n1] | B6 |
| Compound 216 | 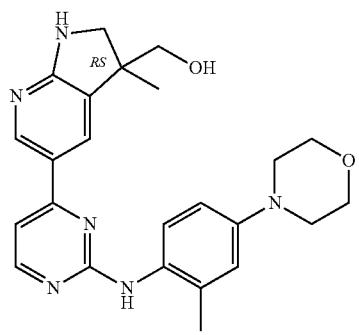 [SMILES: Cc1cc(N2CCOCC2)ccc1Nc1nccc(-c2cnc3c(c2)C(C)(CO)CN3)n1] | B5 |
| Compound 217 | 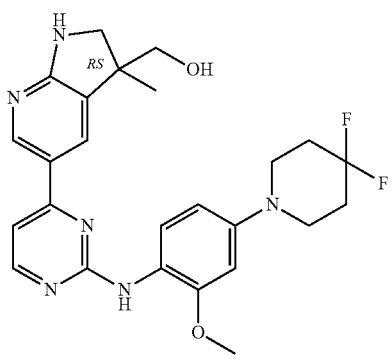 [SMILES: COc1cc(N2CCC(F)(F)CC2)ccc1Nc1nccc(-c2cnc3c(c2)C(C)(CO)CN3)n1] | B5 |
| Compound 218 (from intermediate 141) | 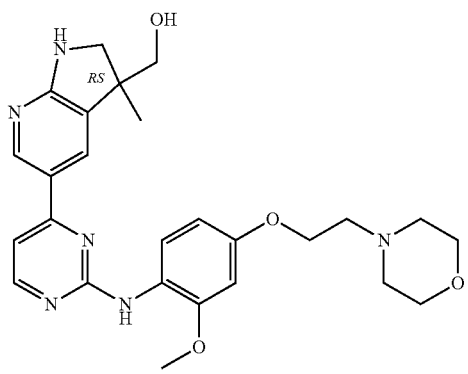 [SMILES: COc1cc(OCCN2CCOCC2)ccc1Nc1nccc(-c2cnc3c(c2)C(C)(CO)CN3)n1] | B5 |

-continued
| Compound number | Structure | Method |
|---|---|---|
| Compound 219 | 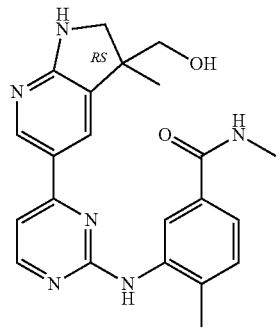 [SMILES: CNC(=O)c1ccc(C)c(Nc2nccc(-c3cnc4c(c3)C(C)(CO)CN4)n2)c1] | B5 |
| Compound 220 | 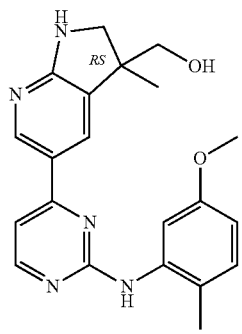 [SMILES: COc1ccc(C)c(Nc2nccc(-c3cnc4c(c3)C(C)(CO)CN4)n2)c1] | B5 |
| Compound 221 | 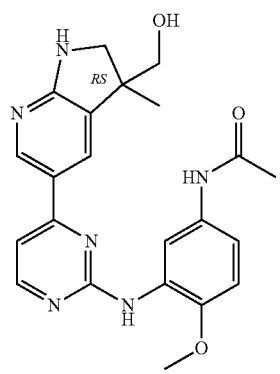 [SMILES: COc1ccc(NC(C)=O)cc1Nc1nccc(-c2cnc3c(c2)C(C)(CO)CN3)n1] | B5 |
| Compound 222 | 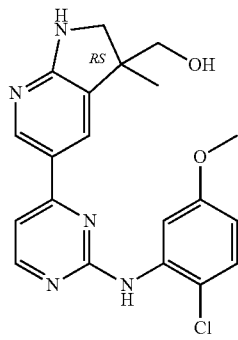 [SMILES: COc1ccc(Cl)c(Nc2nccc(-c3cnc4c(c3)C(C)(CO)CN4)n2)c1] | B5 |

-continued
| Compound number | Structure | Method |
|---|---|---|
| Compound 223 | 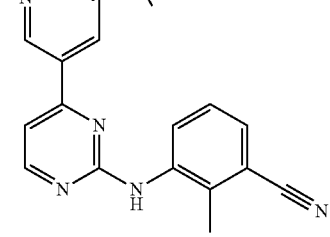 | B5 |
| Compound 224 | 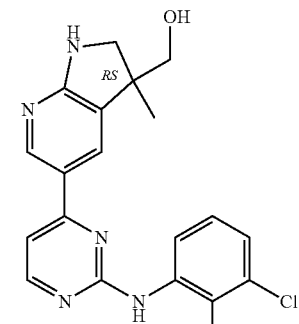 | B5 |
| Compound 225 | 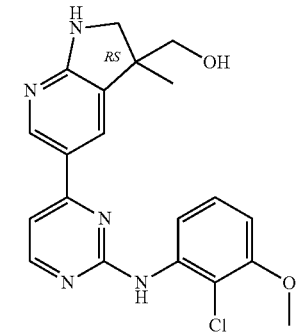 [SMILES: COc1cccc(Nc2nccc(-c3cnc4c(c3)C(C)(CO)CN4)n2)c1Cl] | B5 |
| Compound 226 | 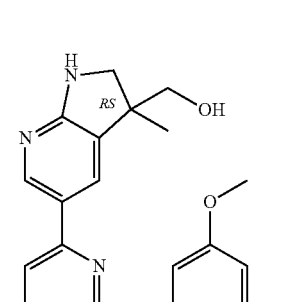 | B6 |

-continued
| Compound number | Structure | Method |
|---|---|---|
| Compound 227 | 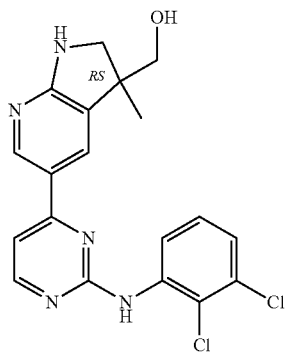 [SMILES: CC1(CO)CNc2ncc(-c3ccnc(Nc4cccc(Cl)c4Cl)n3)cc21] | B5 |
| Compound 228 | 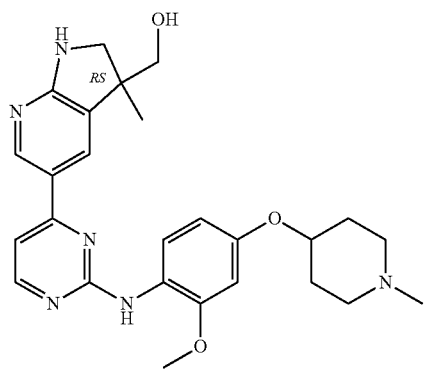 [SMILES: COc1cc(OC2CCN(C)CC2)ccc1Nc1nccc(-c2cnc3c(c2)C(C)(CO)CN3)n1] | B5 |
| Compound 229 | 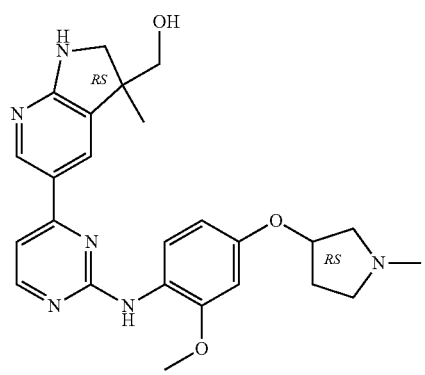 [SMILES: COc1cc(OC2CCN(C)C2)ccc1Nc1nccc(-c2cnc3c(c2)C(C)(CO)CN3)n1] | B5 |
| Compound 230 | 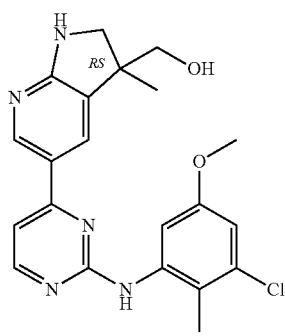 [SMILES: COc1cc(Cl)c(C)c(Nc2nccc(-c3cnc4c(c3)C(C)(CO)CN4)n2)c1] | B5 |

-continued
| Compound number | Structure | Method |
|---|---|---|
| Compound 233 (from intermediate 146) | 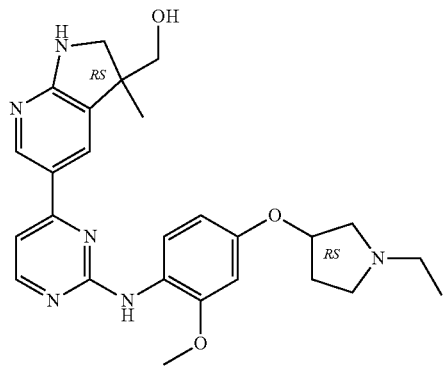 [SMILES: CCN1CCC(Oc2ccc(Nc3nccc(-c4cnc5c(c4)C(C)(CO)CN5)n3)c(OC)c2)C1] | B5 |
| Compound 234 | 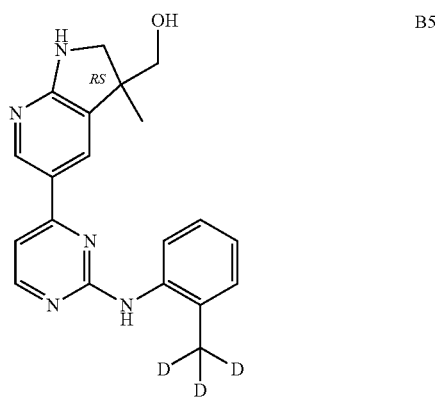 | B5 |
| Compound 238 (from intermediate 149 | 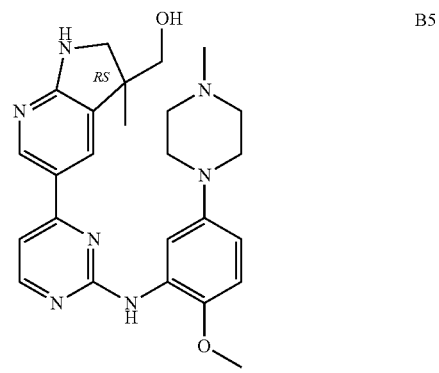 | B5 |
| Compound 239 | 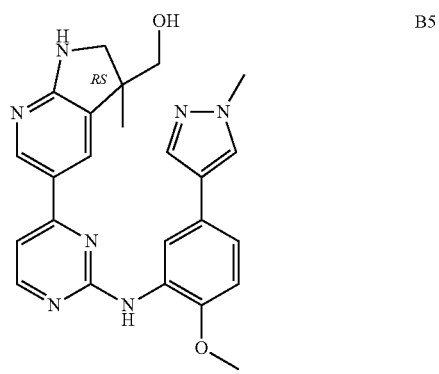 | B5 |

-continued
| Compound number | Structure | Method |
|---|---|---|
| Compound 241 | 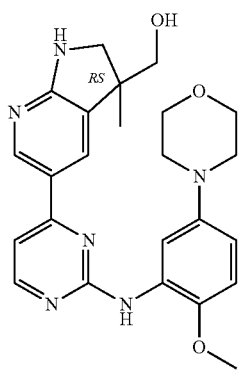 [SMILES: COc1ccc(N2CCOCC2)cc1Nc1nccc(-c2cnc3c(c2)C(C)(CO)CN3)n1] | B5 |
| Compound 242 | 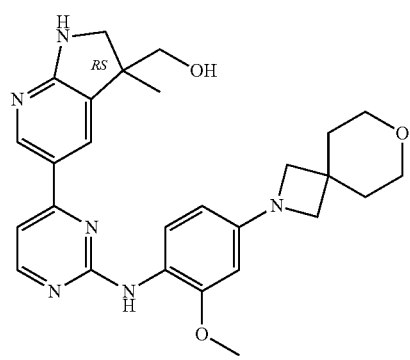 [SMILES: COc1cc(N2CC3(CCOCC3)C2)ccc1Nc1nccc(-c2cnc3c(c2)C(C)(CO)CN3)n1] | B4 |
| Compound 243 | 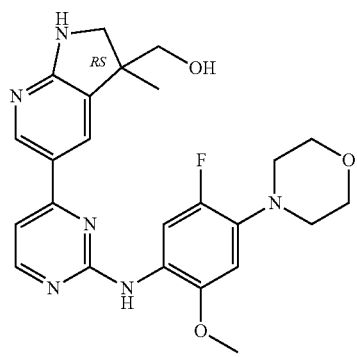 [SMILES: COc1cc(N2CCOCC2)c(F)cc1Nc1nccc(-c2cnc3c(c2)C(C)(CO)CN3)n1] | B5 |
| Compound 244 | 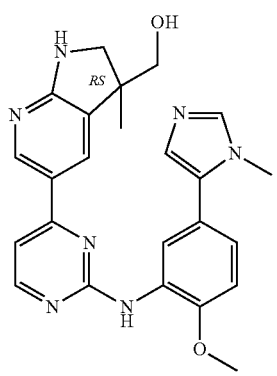 [SMILES: COc1ccc(-c2cncn2C)cc1Nc1nccc(-c2cnc3c(c2)C(C)(CO)CN3)n1] | B5 |

-continued

| Compound number | Structure | Method |
|---|---|---|
| Compound 245 | 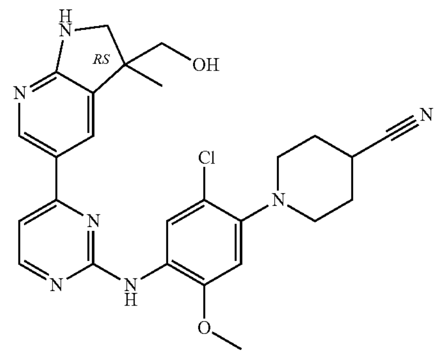 [SMILES: COc1cc(N2CCC(C#N)CC2)c(Cl)cc1Nc1nccc(-c2cnc3c(c2)C(C)(CO)CN3)n1] | B5 |
| Compound 246 | 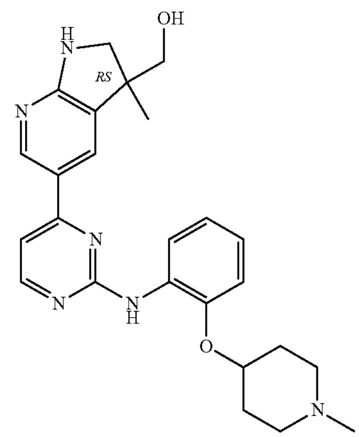 [SMILES: CN1CCC(Oc2ccccc2Nc2nccc(-c3cnc4c(c3)C(C)(CO)CN4)n2)CC1] | B5 |
| Compound 247 | 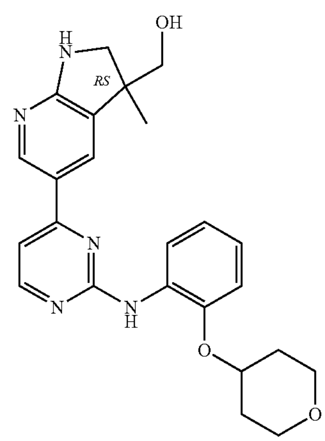 [SMILES: CC1(CO)CNc2ncc(-c3ccnc(Nc4ccccc4OC4CCOCC4)n3)cc21] | B5 |
| Compound 250 | 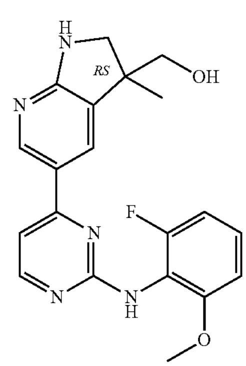 [SMILES: COc1cccc(F)c1Nc1nccc(-c2cnc3c(c2)C(C)(CO)CN3)n1] | B5 |

-continued
| Compound number | Structure | Method |
|---|---|---|
| Compound 251 | 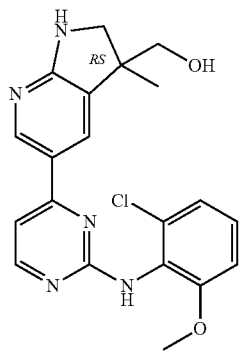 [SMILES: COc1cccc(Cl)c1Nc1nccc(-c2cnc3c(c2)C(C)(CO)CN3)n1] | B5 |
| Compound 252 | 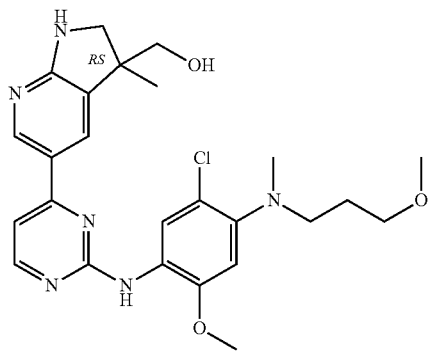 [SMILES: COCCCN(C)c1cc(OC)c(Nc2nccc(-c3cnc4c(c3)C(C)(CO)CN4)n2)cc1Cl] | B5 |
| Compound 267 | 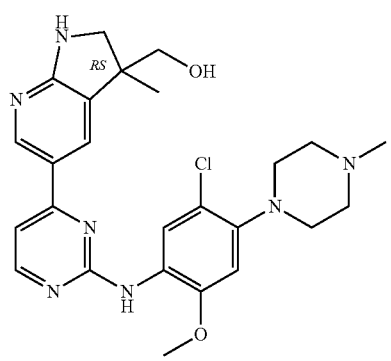 [SMILES: COc1cc(N2CCN(C)CC2)c(Cl)cc1Nc1nccc(-c2cnc3c(c2)C(C)(CO)CN3)n1] | B5 |
| Compound 268 | 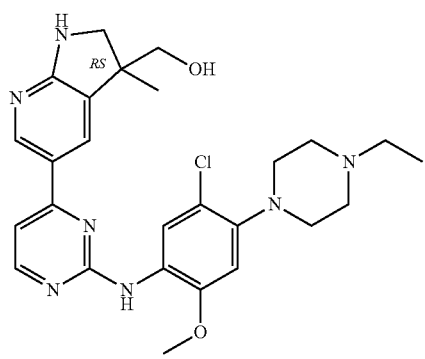 [SMILES: CCN1CCN(c2cc(OC)c(Nc3nccc(-c4cnc5c(c4)C(C)(CO)CN5)n3)cc2Cl)CC1] | B5 |

-continued
| Compound number | Structure | Method |
|---|---|---|
| Compound 269 | 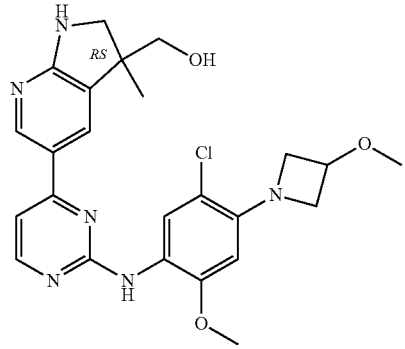 [SMILES: COc1cc(N2CC(OC)C2)c(Cl)cc1Nc1nccc(-c2cnc3c(c2)C(C)(CO)CN3)n1] | B5 |
| Compound 270 | 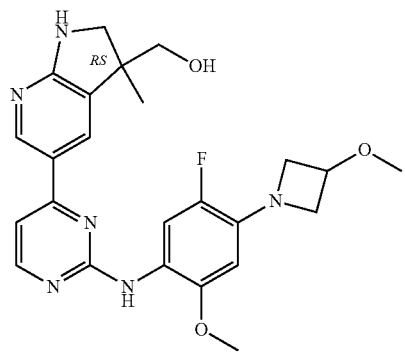 [SMILES: COc1cc(N2CC(OC)C2)c(F)cc1Nc1nccc(-c2cnc3c(c2)C(C)(CO)CN3)n1] | B5 |
| Compound 271 | 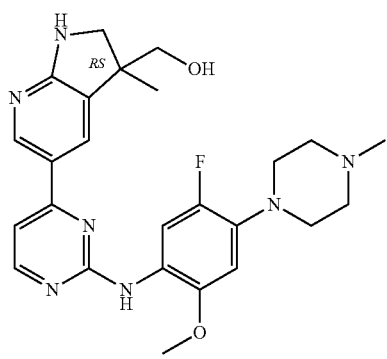 [SMILES: COc1cc(N2CCN(C)CC2)c(F)cc1Nc1nccc(-c2cnc3c(c2)C(C)(CO)CN3)n1] | B5 |
| Compound 275 | 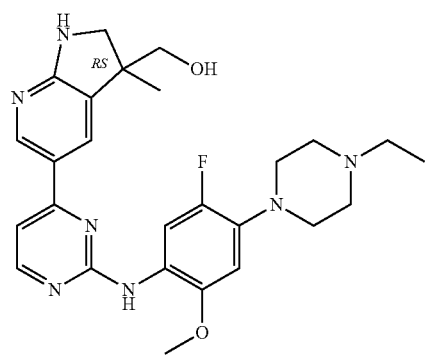 | B5 |

-continued
| Compound number | Structure | Method |
|---|---|---|
| Compound 277 | 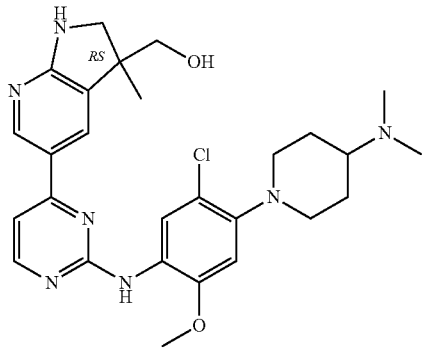 [SMILES: COc1cc(N2CCC(N(C)C)CC2)c(Cl)cc1Nc1nccc(-c2cnc3c(c2)C(C)(CO)CN3)n1] | B5 |
| Compound 278 | 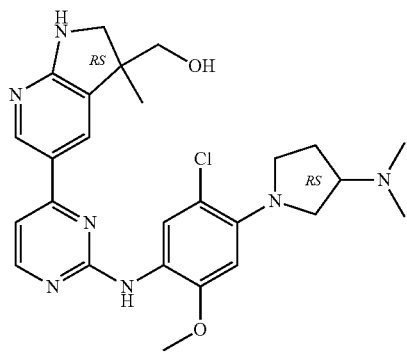 [SMILES: COc1cc(N2CCC(N(C)C)C2)c(Cl)cc1Nc1nccc(-c2cnc3c(c2)C(C)(CO)CN3)n1] | B5 |
| Compound 279 | 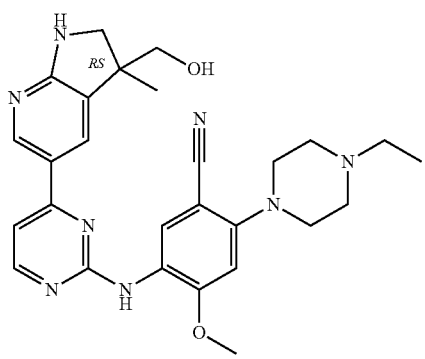 [SMILES: CCN1CCN(c2cc(OC)c(Nc3nccc(-c4cnc5c(c4)C(C)(CO)CN5)n3)cc2C#N)CC1] | B6 |
| Compound 280 | 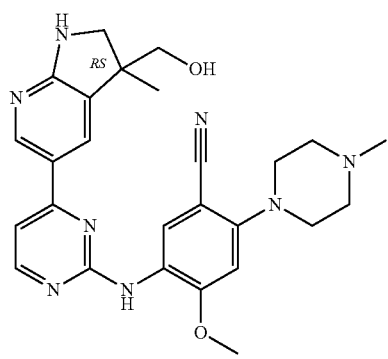 [SMILES: COc1cc(N2CCN(C)CC2)c(C#N)cc1Nc1nccc(-c2cnc3c(c2)C(C)(CO)CN3)n1] | B6 |

-continued
| Compound number | Structure | Method |
|---|---|---|
| Compound 281 | 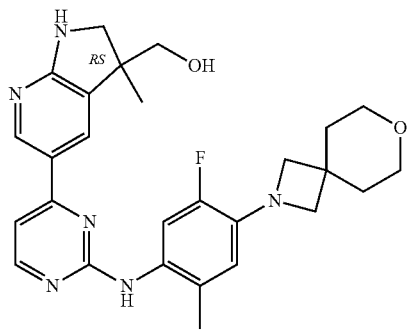 [SMILES: Cc1cc(N2CC3(CCOCC3)C2)c(F)cc1Nc1nccc(-c2cnc3c(c2)C(C)(CO)CN3)n1] | B5 |
| Compound 282 | 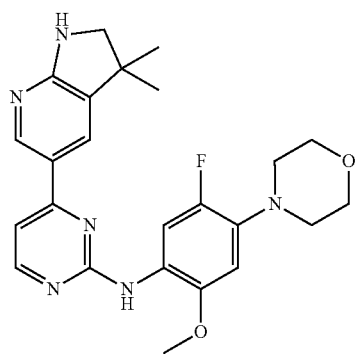 [SMILES: COc1cc(N2CCOCC2)c(F)cc1Nc1nccc(-c2cnc3c(c2)C(C)(C)CN3)n1] | B4 |
| Compound 283 | 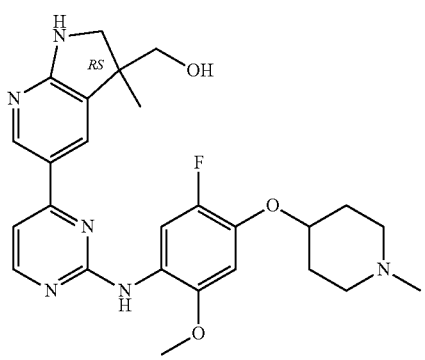 [SMILES: COc1cc(OC2CCN(C)CC2)c(F)cc1Nc1nccc(-c2cnc3c(c2)C(C)(CO)CN3)n1] | B5 |
| Compound 284 | 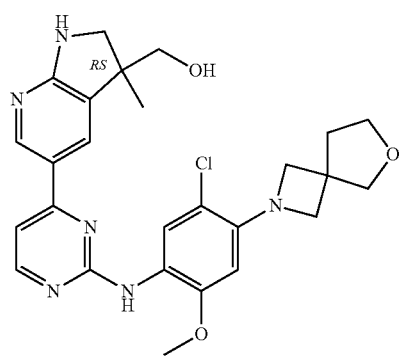 [SMILES: COc1cc(N2CC3(CCOC3)C2)c(Cl)cc1Nc1nccc(-c2cnc3c(c2)C(C)(CO)CN3)n1] | B5 |

US 11,236,084 B2
267                                    268
-continued
| Compound number | Structure | Method |
|---|---|---|
| Compound 285 | 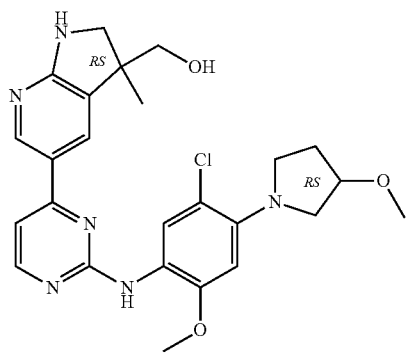 [SMILES: COc1cc(N2CCC(OC)C2)c(Cl)cc1Nc1nccc(-c2cnc3c(c2)C(C)(CO)CN3)n1] | B5 |
| Compound 290 | 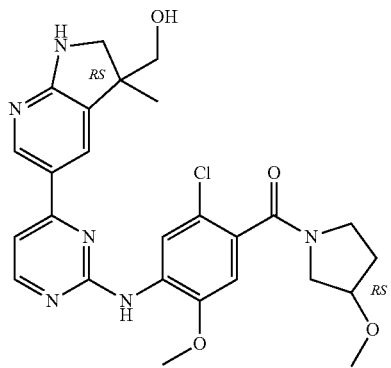 [SMILES: COc1cc(C(=O)N2CCC(OC)C2)c(Cl)cc1Nc1nccc(-c2cnc3c(c2)C(C)(CO)CN3)n1] | B5 |
| Compound 292 | 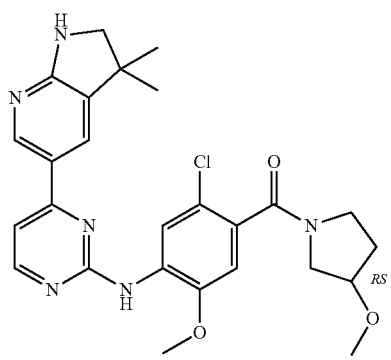 [SMILES: COc1cc(C(=O)N2CCC(OC)C2)c(Cl)cc1Nc1nccc(-c2cnc3c(c2)C(C)(C)CN3)n1] | B4 |
| Compound 294 | 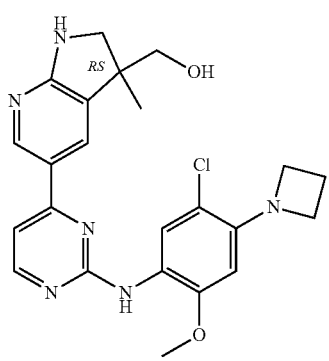 [SMILES: COc1cc(N2CCC2)c(Cl)cc1Nc1nccc(-c2cnc3c(c2)C(C)(CO)CN3)n1] | B5 |

-continued
| Compound number | Structure | Method |
|---|---|---|
| Compound 296 | 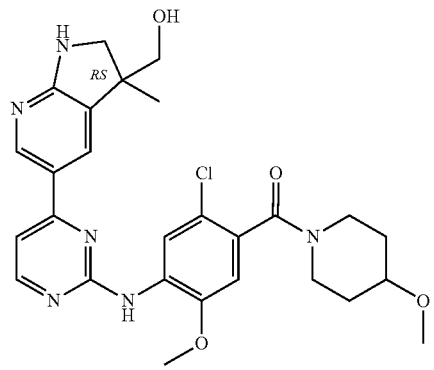 [SMILES: COc1cc(C(=O)N2CCC(OC)CC2)c(Cl)cc1Nc1nccc(-c2cnc3c(c2)C(C)(CO)CN3)n1] | B5 |
| Compound 299 | 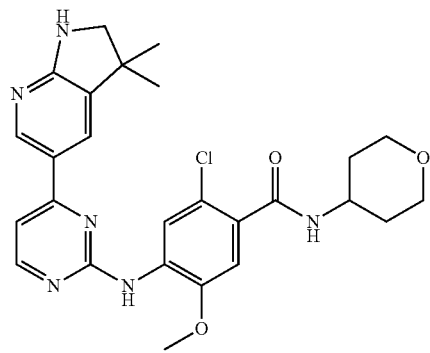 [SMILES: COc1cc(C(=O)NC2CCOCC2)c(Cl)cc1Nc1nccc(-c2cnc3c(c2)C(C)(C)CN3)n1] | B4 |
| Compound 301 | 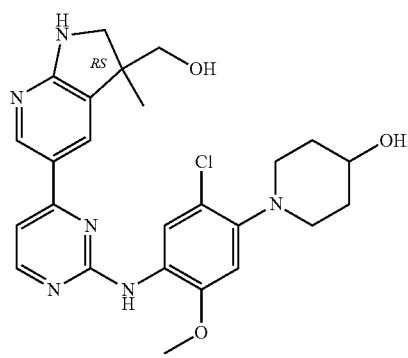 [SMILES: COc1cc(N2CCC(O)CC2)c(Cl)cc1Nc1nccc(-c2cnc3c(c2)C(C)(CO)CN3)n1] | B5 |
| Compound 302 | 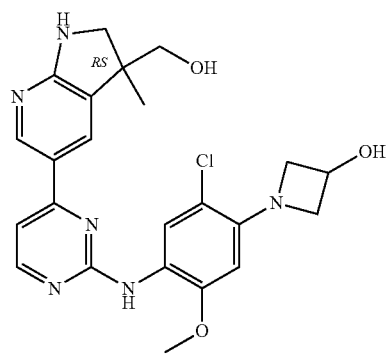 [SMILES: COc1cc(N2CC(O)C2)c(Cl)cc1Nc1nccc(-c2cnc3c(c2)C(C)(CO)CN3)n1] | B5 |

-continued
| Compound number | Structure | Method |
|---|---|---|
| Compound 304 | 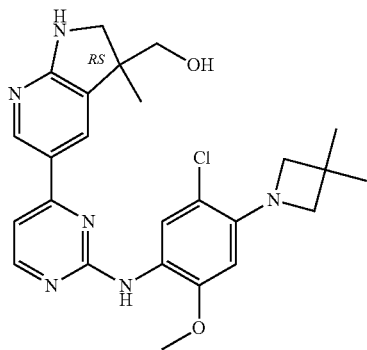 [SMILES: COc1cc(N2CC(C)(C)C2)c(Cl)cc1Nc1nccc(-c2cnc3c(c2)C(C)(CO)CN3)n1] | B5 |
| Compound 307 | 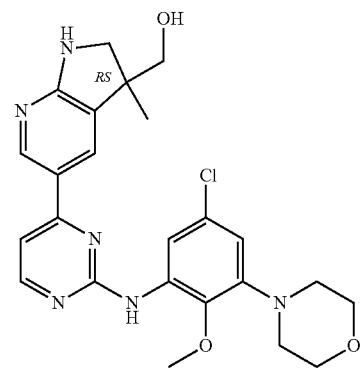 [SMILES: COc1c(Nc2nccc(-c3cnc4c(c3)C(C)(CO)CN4)n2)cc(Cl)cc1N1CCOCC1] | B4 |
| Compound 309 | 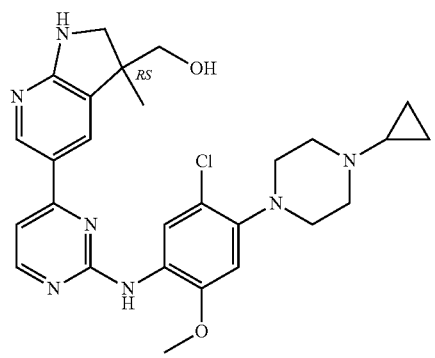 [SMILES: COc1cc(N2CCN(C3CC3)CC2)c(Cl)cc1Nc1nccc(-c2cnc3c(c2)C(C)(CO)CN3)n1] | B5 |
| Compound 311 | 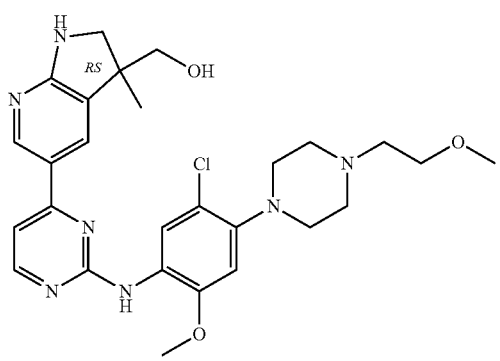 [SMILES: COCCN1CCN(c2cc(OC)c(Nc3nccc(-c4cnc5c(c4)C(C)(CO)CN5)n3)cc2Cl)CC1] | B5 |

-continued
| Compound number | Structure | Method |
|---|---|---|
| Compound 313 | 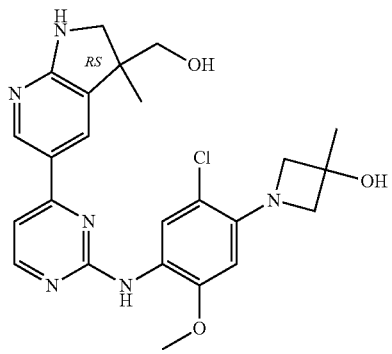 [SMILES: COc1cc(N2CC(C)(O)C2)c(Cl)cc1Nc1nccc(-c2cnc3c(c2)C(C)(CO)CN3)n1] | B5 |
| Compound 314 | 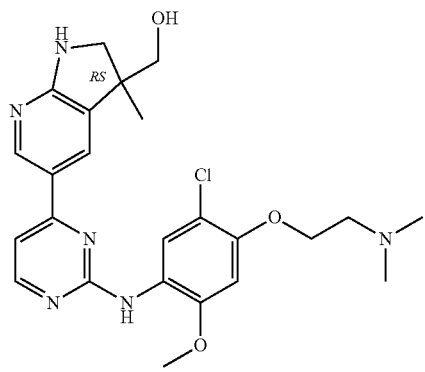 [SMILES: COc1cc(OCCN(C)C)c(Cl)cc1Nc1nccc(-c2cnc3c(c2)C(C)(CO)CN3)n1] | B4 |
| Compound 317 | 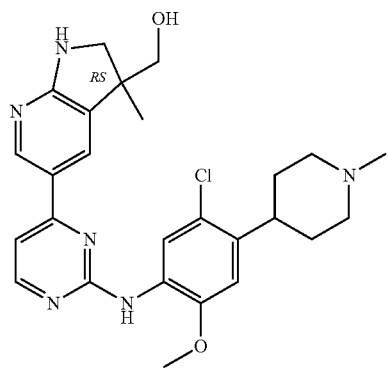 [SMILES: COc1cc(C2CCN(C)CC2)c(Cl)cc1Nc1nccc(-c2cnc3c(c2)C(C)(CO)CN3)n1] | B4 |
| Compound 318 | 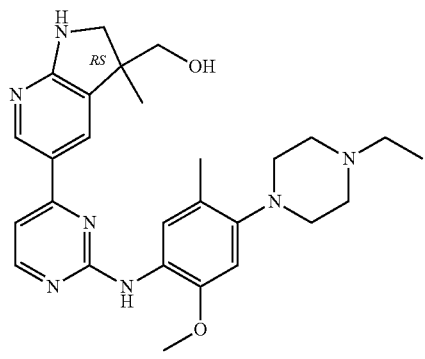 [SMILES: CCN1CCN(c2cc(OC)c(Nc3nccc(-c4cnc5c(c4)C(C)(CO)CN5)n3)cc2C)CC1] | B5 |

-continued
| Compound number | Structure | Method |
|---|---|---|
| Compound 319 | 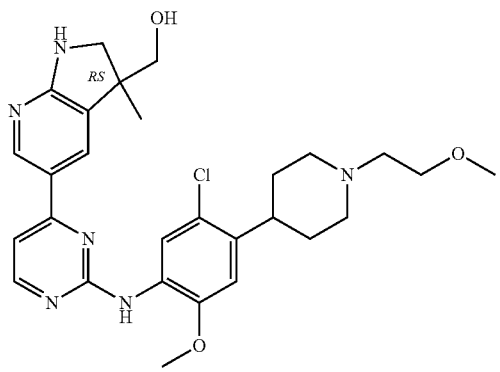 [SMILES: COCCN1CCC(c2cc(OC)c(Nc3nccc(-c4cnc5c(c4)C(C)(CO)CN5)n3)cc2Cl)CC1] | B4 |
| Compound 320 | 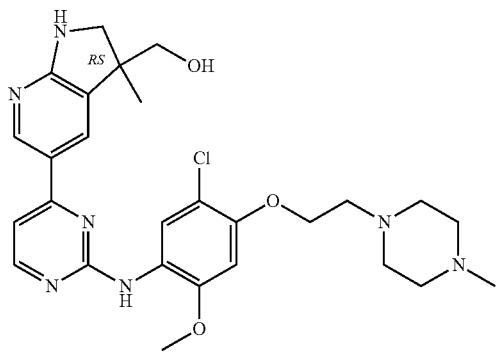 [SMILES: COc1cc(OCCN2CCN(C)CC2)c(Cl)cc1Nc1nccc(-c2cnc3c(c2)C(C)(CO)CN3)n1] | B4 |
| Compound 321 (from intermediate 156) | 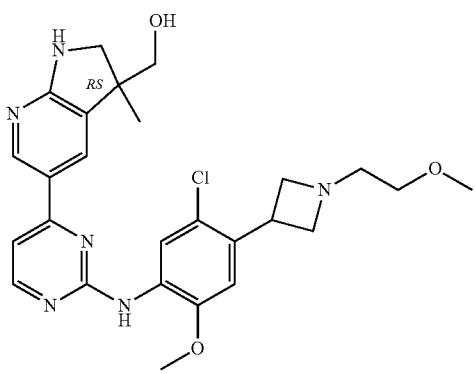 [SMILES: COCCN1CC(c2cc(OC)c(Nc3nccc(-c4cnc5c(c4)C(C)(CO)CN5)n3)cc2Cl)C1] | B4 |
| Compound 322 | 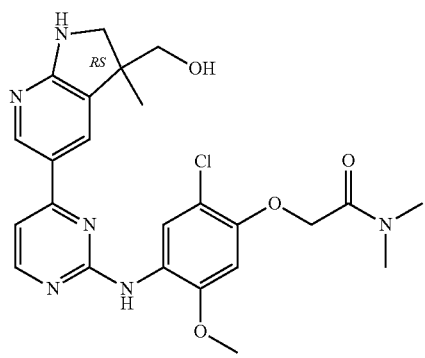 [SMILES: COc1cc(OCC(=O)N(C)C)c(Cl)cc1Nc1nccc(-c2cnc3c(c2)C(C)(CO)CN3)n1] | B5 |

-continued
| Compound number | Structure | Method |
|---|---|---|
| Compound 323 | 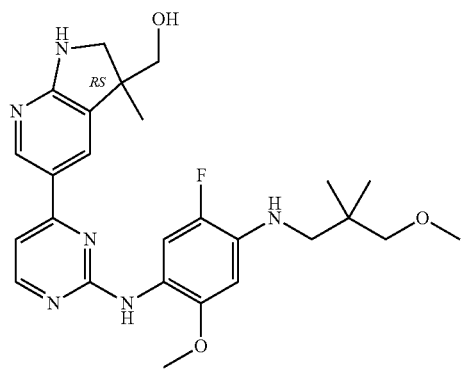 [SMILES: COCC(C)(C)CNc1cc(OC)c(Nc2nccc(-c3cnc4c(c3)C(C)(CO)CN4)n2)cc1F] | B4 |
| Compound 324 | 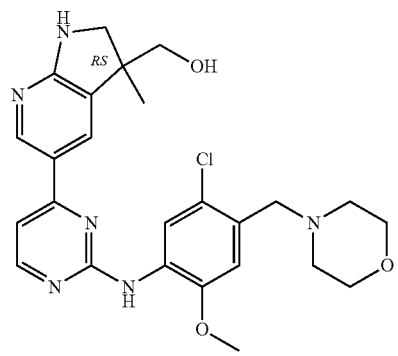 [SMILES: COc1cc(CN2CCOCC2)c(Cl)cc1Nc1nccc(-c2cnc3c(c2)C(C)(CO)CN3)n1] | B5 |
| Compound 325 | 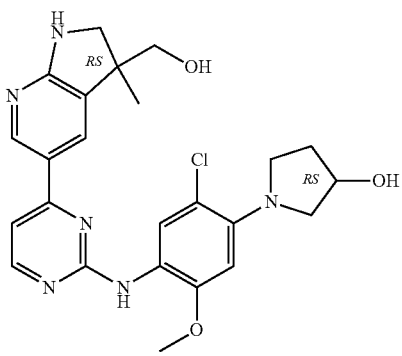 [SMILES: COc1cc(N2CCC(O)C2)c(Cl)cc1Nc1nccc(-c2cnc3c(c2)C(C)(CO)CN3)n1] | B5 |
| Compound 327 | 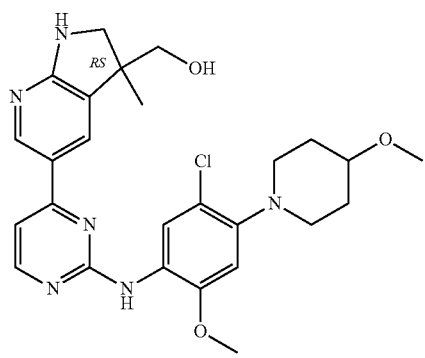 [SMILES: COc1cc(N2CCC(OC)CC2)c(Cl)cc1Nc1nccc(-c2cnc3c(c2)C(C)(CO)CN3)n1] | B4 |

| Compound number | Structure | Method |
|---|---|---|
| Compound 328 (from intermediate 159) | 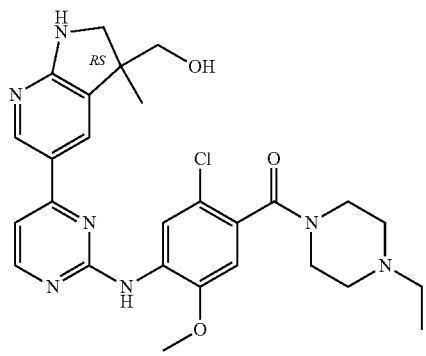 [SMILES: CCN1CCN(C(=O)c2cc(OC)c(Nc3nccc(-c4cnc5c(c4)C(C)(CO)CN5)n3)cc2Cl)CC1] | B5 |
| Compound 329 | 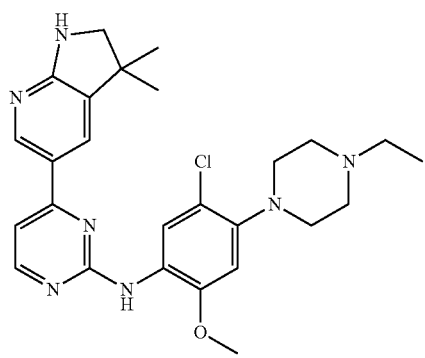 [SMILES: CCN1CCN(c2cc(OC)c(Nc3nccc(-c4cnc5c(c4)C(C)(C)CN5)n3)cc2Cl)CC1] | B4 |
| Compound 330 | 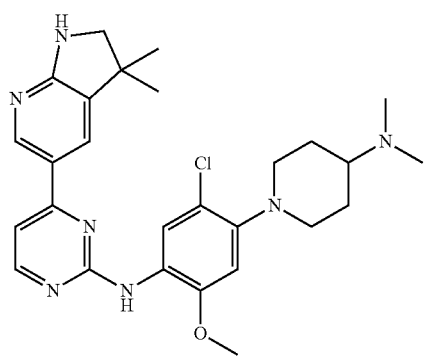 [SMILES: COc1cc(N2CCC(N(C)C)CC2)c(Cl)cc1Nc1nccc(-c2cnc3c(c2)C(C)(C)CN3)n1] | B4 |
| Compound 330 | 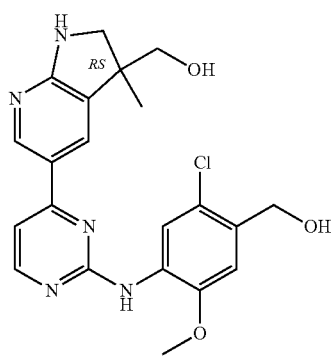 [SMILES: COc1cc(CO)c(Cl)cc1Nc1nccc(-c2cnc3c(c2)C(C)(CO)CN3)n1] | B5 |

-continued
| Compound number | Structure | Method |
|---|---|---|
| Compound 332 (from intermediate 166) | 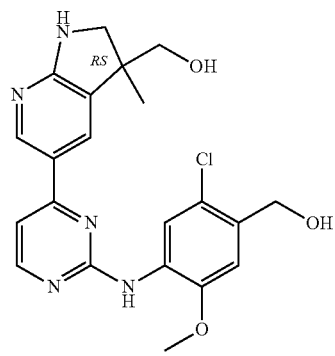 [SMILES: COc1cc(CO)c(Cl)cc1Nc1nccc(-c2cnc3c(c2)C(C)(CO)CN3)n1] | B5 |
| Compound 333 | 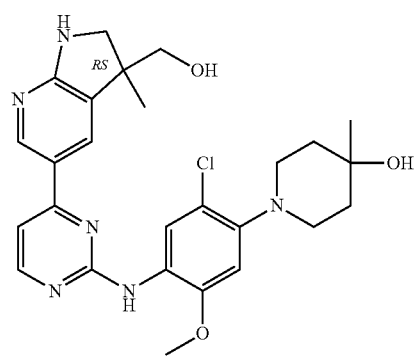 [SMILES: COc1cc(N2CCC(C)(O)CC2)c(Cl)cc1Nc1nccc(-c2cnc3c(c2)C(C)(CO)CN3)n1] | B5 |
| Compound 334 | 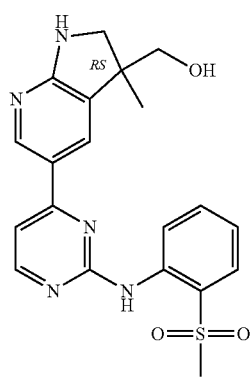 [SMILES: CC1(CO)CNc2ncc(-c3ccnc(Nc4ccccc4S(C)(=O)=O)n3)cc21] | B5 |
| Compound 335 | 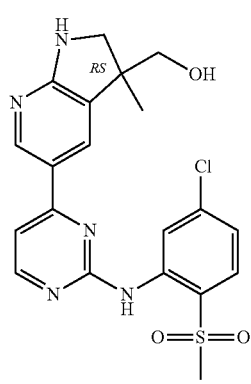 [SMILES: CC1(CO)CNc2ncc(-c3ccnc(Nc4cc(Cl)ccc4S(C)(=O)=O)n3)cc21] | B5 |

-continued
| Compound number | Structure | Method |
|---|---|---|
| Compound 336 | 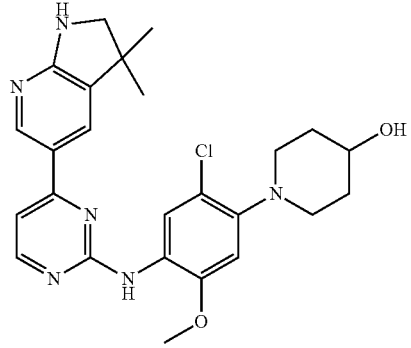 [SMILES: COc1cc(N2CCC(O)CC2)c(Cl)cc1Nc1nccc(-c2cnc3c(c2)C(C)(C)CN3)n1] | B4 |
| Compound 337 | 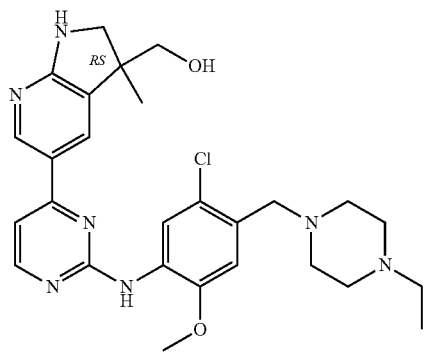 [SMILES: CCN1CCN(Cc2cc(OC)c(Nc3nccc(-c4cnc5c(c4)C(C)(CO)CN5)n3)cc2Cl)CC1] | B4 |
| Compound 338 | 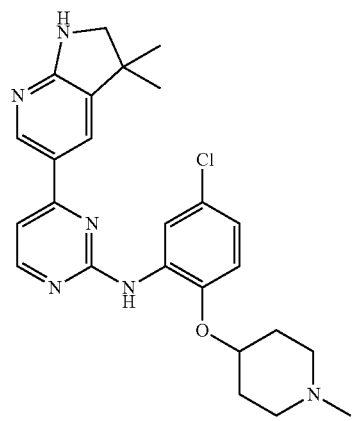 [SMILES: CN1CCC(Oc2ccc(Cl)cc2Nc2nccc(-c3cnc4c(c3)C(C)(C)CN4)n2)CC1] | B4 |
| Compound 339 | 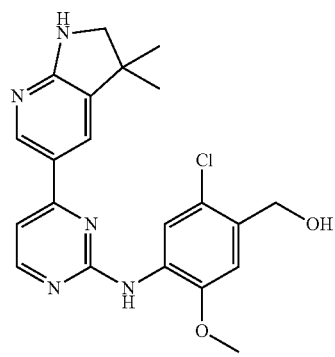 [SMILES: COc1cc(CO)c(Cl)cc1Nc1nccc(-c2cnc3c(c2)C(C)(C)CN3)n1] | B4 |

-continued
| Compound number | Structure | Method |
|---|---|---|
| Compound 340 | 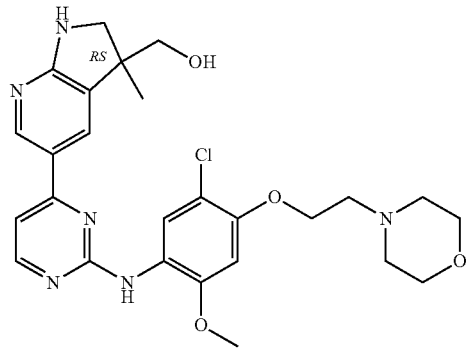 [SMILES: COc1cc(OCCN2CCOCC2)c(Cl)cc1Nc1nccc(-c2cnc3c(c2)C(C)(CO)CN3)n1] | B4 |
| Compound 342 | 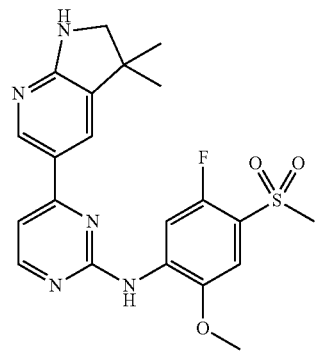 [SMILES: COc1cc(S(C)(=O)=O)c(F)cc1Nc1nccc(-c2cnc3c(c2)C(C)(C)CN3)n1] | B4 |
| Compound 343 starting from intermediate 14R | 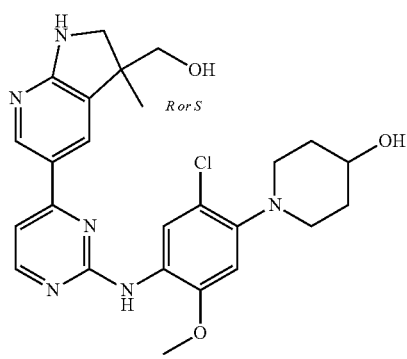 [SMILES: COc1cc(N2CCC(O)CC2)c(Cl)cc1Nc1nccc(-c2cnc3c(c2)C(C)(CO)CN3)n1] | B5 |
| Compound 345 starting from intermediate 12S | 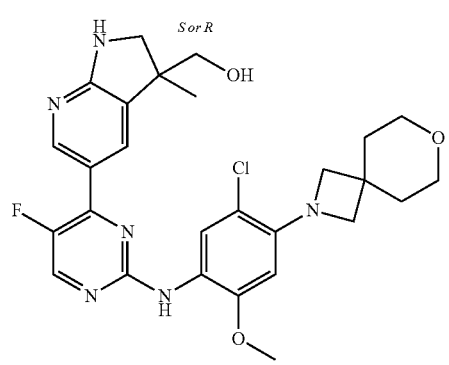 [SMILES: COc1cc(N2CC3(CCOCC3)C2)c(Cl)cc1Nc1ncc(F)c(-c2cnc3c(c2)C(C)(CO)CN3)n1] | B5 |

| Compound number | Structure | Method |
|---|---|---|
| Compound 346 starting from intermediate 12R | 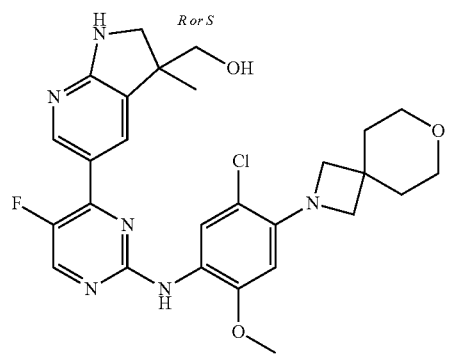 [SMILES: COc1cc(N2CC3(CCOCC3)C2)c(Cl)cc1Nc1ncc(F)c(-c2cnc3c(c2)C(C)(CO)CN3)n1] | B5 |
| Compound 347 starting from intermediate 12S | 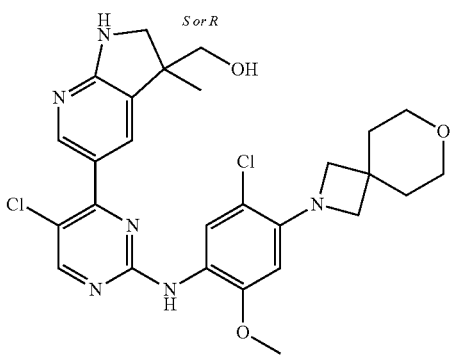 [SMILES: COc1cc(N2CC3(CCOCC3)C2)c(Cl)cc1Nc1ncc(Cl)c(-c2cnc3c(c2)C(C)(CO)CN3)n1] | B5 |
| Compound 348 starting from intermediate 12R | 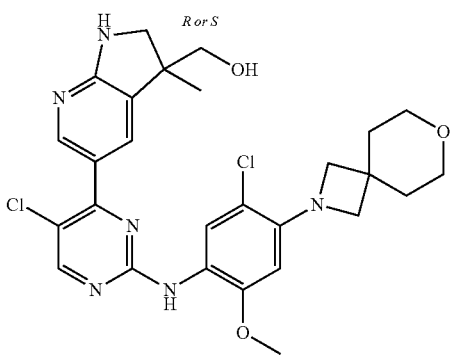 [SMILES: COc1cc(N2CC3(CCOCC3)C2)c(Cl)cc1Nc1ncc(Cl)c(-c2cnc3c(c2)C(C)(CO)CN3)n1] | B5 |
| Compound 349 starting from intermediate 12R | 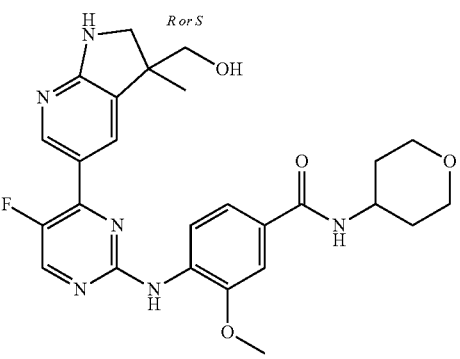 [SMILES: COc1cc(C(=O)NC2CCOCC2)ccc1Nc1ncc(F)c(-c2cnc3c(c2)C(C)(CO)CN3)n1] | B4 |

-continued
| Compound number | Structure | Method |
|---|---|---|
| Compound 350 starting from intermediate 12S | 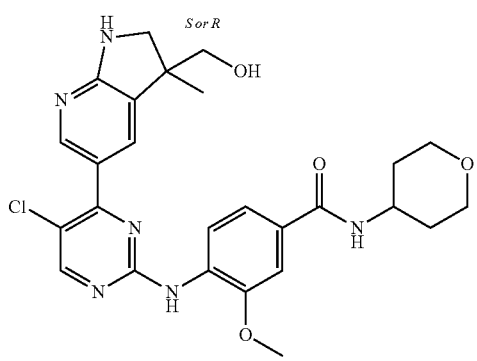 [SMILES: COc1cc(C(=O)NC2CCOCC2)ccc1Nc1ncc(Cl)c(-c2cnc3c(c2)C(C)(CO)CN3)n1] | B4 |
| Compound 351 starting from intermediate 12R | 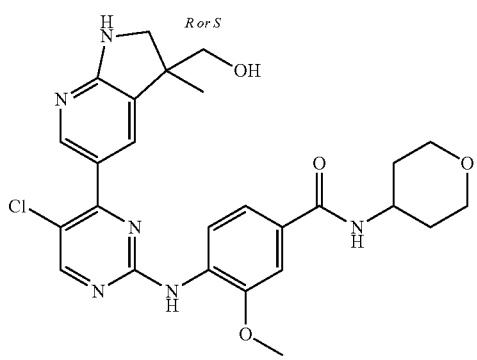 [SMILES: COc1cc(C(=O)NC2CCOCC2)ccc1Nc1ncc(Cl)c(-c2cnc3c(c2)C(C)(CO)CN3)n1] | B5 |
| Compound 352 starting from intermediate 12S | 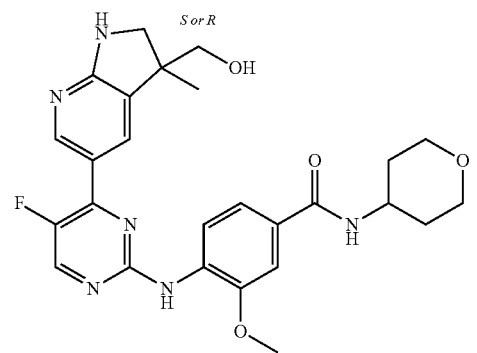 [SMILES: COc1cc(C(=O)NC2CCOCC2)ccc1Nc1ncc(F)c(-c2cnc3c(c2)C(C)(CO)CN3)n1] | B4 |
| Compound 353 | 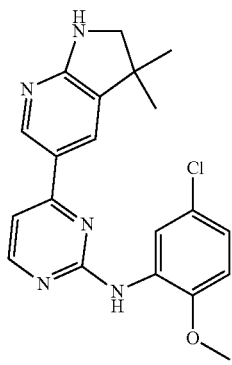 [SMILES: COc1ccc(Cl)cc1Nc1nccc(-c2cnc3c(c2)C(C)(C)CN3)n1] | B4 |

-continued
| Compound number | Structure | Method |
|---|---|---|
| Compound 356 (from intermediate 172) starting from intermediate 14S | 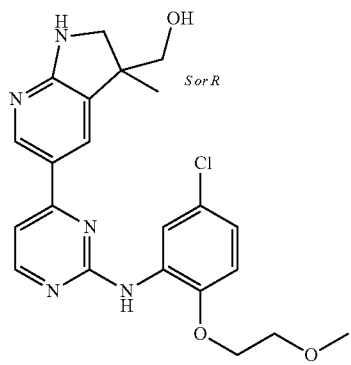 [SMILES: COCCOc1ccc(Cl)cc1Nc1nccc(-c2cnc3c(c2)C(C)(CO)CN3)n1] | B7 |
| Compound 357 | 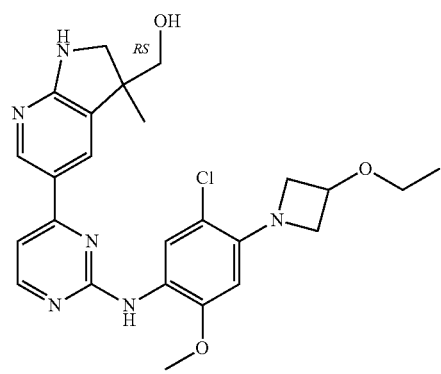 [SMILES: CCOC1CN(c2cc(OC)c(Nc3nccc(-c4cnc5c(c4)C(C)(CO)CN5)n3)cc2Cl)C1] | B4 |
| Compound 359 | 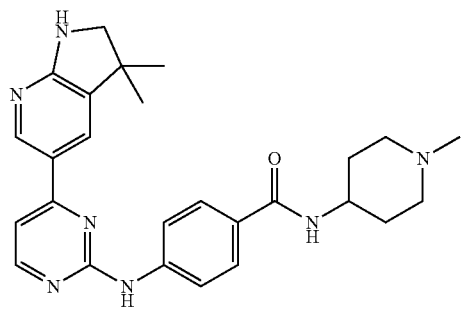 [SMILES: CN1CCC(NC(=O)c2ccc(Nc3nccc(-c4cnc5c(c4)C(C)(C)CN5)n3)cc2)CC1] | B4 |

Example B3

Method B9:
Preparation of Compound 130:

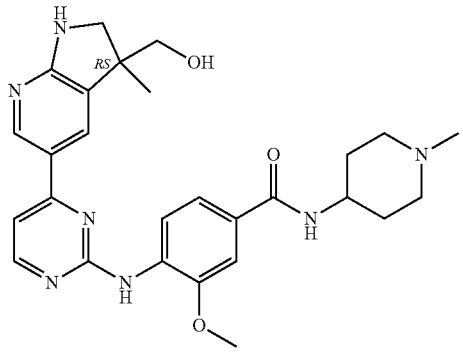 [SMILES: COc1cc(C(=O)NC2CCN(C)CC2)ccc1Nc1nccc(-c2cnc3c(c2)C(C)(CO)CN3)n1]

A mixture of intermediate 114 (100 mg, 0.16 mmol), 4-methoxy piperidine (24.19 mg, 0.21 mmol), HATU (69.75 mg, 0.18 mmol) and TEA (69 μL, 0.49 mmol) was stirred in DMF (3 mL) at room temperature for 2 h. The mixture was diluted with water and extracted with DCM (twice). The combined organic layers were isolated by passing through a phase separator SPE and evaporated to dryness. The residue was dissolved in TFA (2 mL) and DCM (2 mL) and stirred at room temperature. After 4 h, the mixture was evaporated to dryness and the residue was purified by MDAP under basic conditions to give 59 mg of compound 130 (73% yield).

Method B10:
Preparation of Compound 160:

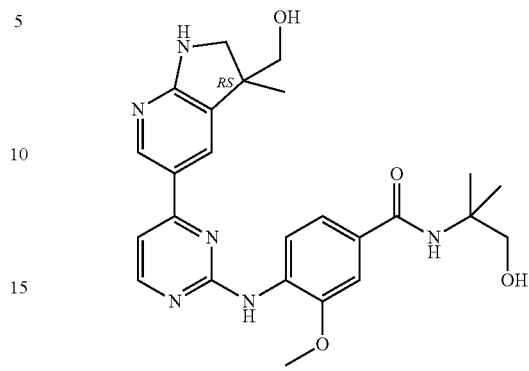

To a solution of intermediate 121 (210 mg, 0.52 mmol), HATU (215.00 mg, 0.57 mmol) and DIPEA (134.00 μL, 0.77 mmol) in DMF (5 mL) was added 2-amino-2-methyl-propanol (57.00 mg, 0.64 mmol) in one portion. The reaction was stirred at room temperature overnight. The reaction was diluted with water and ethyl acetate, washed with brine, dried over sodium sulfate, filtered and concentrated in vacuo. The reaction was purified by preparative chromatography using basic eluent to give 29 mg of compound 160 (11% yield, amorphous white powder).

The compounds in the Table below were prepared by using an analogous method as described in methods B9 or B1, starting from the respective starting materials.

| Compound number | Structure | Method |
|---|---|---|
| Compound 131 | 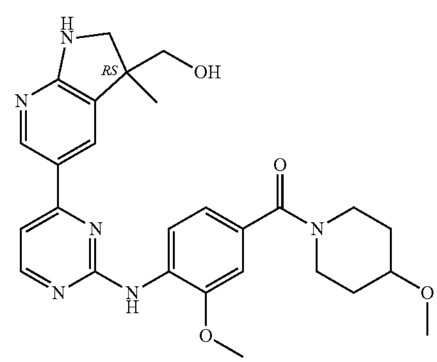 [SMILES: COc1cc(C(=O)N2CCC(OC)CC2)ccc1Nc1nccc(-c2cnc3c(c2)C(C)(CO)CN3)n1] | B9 |
| Compound 132 | 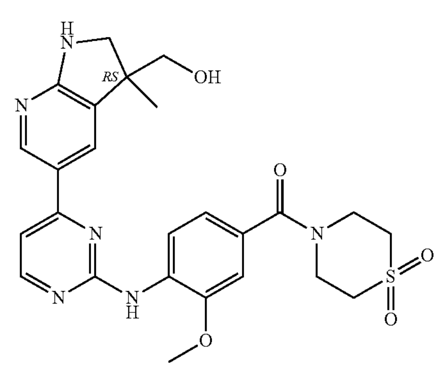 [SMILES: COc1cc(C(=O)N2CCS(=O)(=O)CC2)ccc1Nc1nccc(-c2cnc3c(c2)C(C)(CO)CN3)n1] | B9 |

-continued
| Compound number | Structure | Method |
|---|---|---|
| Compound 133 | 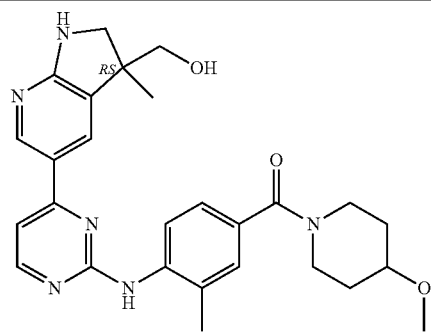 | B9 |
| Compound 134 | 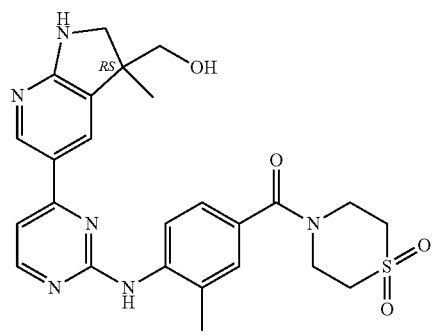 [SMILES: Cc1cc(C(=O)N2CCS(=O)(=O)CC2)ccc1Nc1nccc(-c2cnc3c(c2)C(C)(CO)CN3)n1] | B9 |
| Compound 136 | 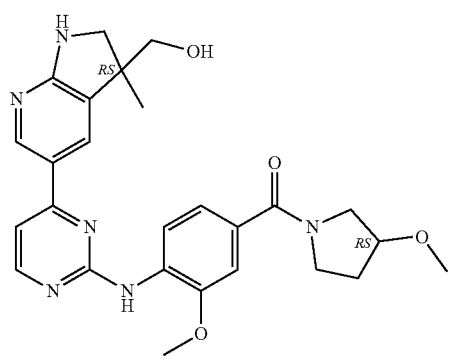 [SMILES: COc1cc(C(=O)N2CCC(OC)C2)ccc1Nc1nccc(-c2cnc3c(c2)C(C)(CO)CN3)n1] | B9 |
| Compound 137 | 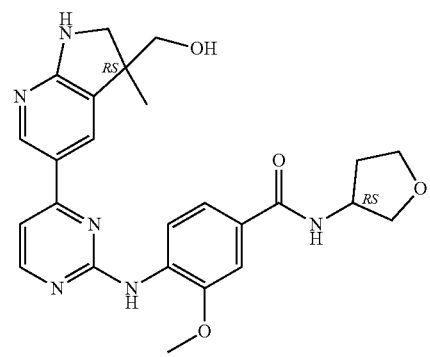 [SMILES: COc1cc(C(=O)NC2CCOC2)ccc1Nc1nccc(-c2cnc3c(c2)C(C)(CO)CN3)n1] | B9 |

-continued
| Compound number | Structure | Method |
|---|---|---|
| Compound 138 | 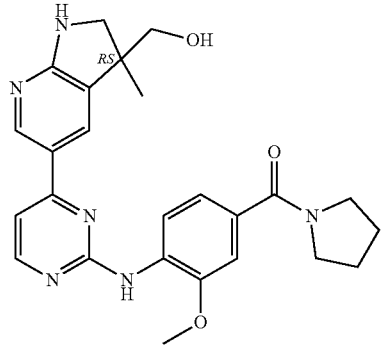 [SMILES: COc1cc(C(=O)N2CCCC2)ccc1Nc1nccc(-c2cnc3c(c2)C(C)(CO)CN3)n1] | B9 |
| Compound 139 | 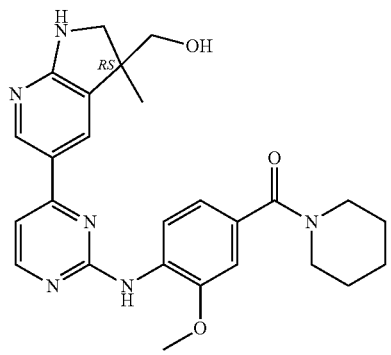 [SMILES: COc1cc(C(=O)N2CCCCC2)ccc1Nc1nccc(-c2cnc3c(c2)C(C)(CO)CN3)n1] | B9 |
| Compound 141 | 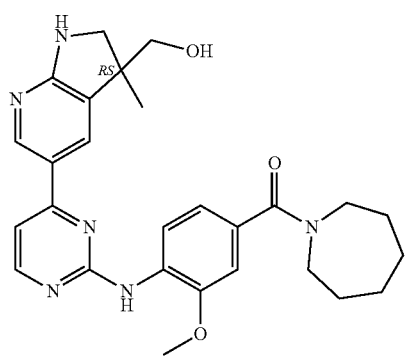 [SMILES: COc1cc(C(=O)N2CCCCCC2)ccc1Nc1nccc(-c2cnc3c(c2)C(C)(CO)CN3)n1] | B9 |
| Compound 142 | 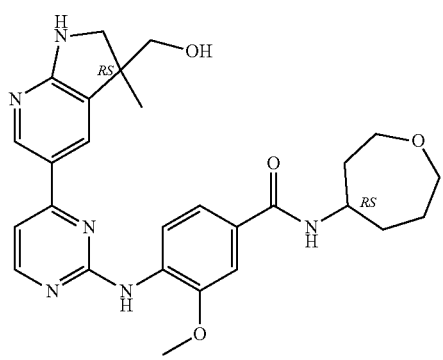 [SMILES: COc1cc(C(=O)NC2CCCOCC2)ccc1Nc1nccc(-c2cnc3c(c2)C(C)(CO)CN3)n1] | B9 |

-continued

| Compound number | Structure | Method |
|---|---|---|
| Compound 143 | 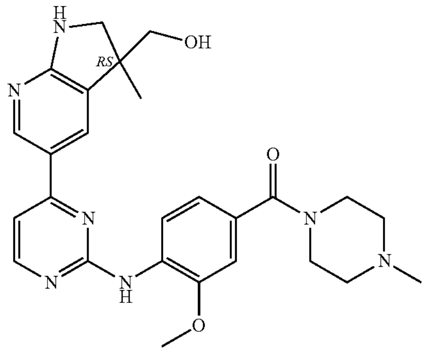 [SMILES: COc1cc(C(=O)N2CCN(C)CC2)ccc1Nc1nccc(-c2cnc3c(c2)C(C)(CO)CN3)n1] | B9 |
| Compound 150 | 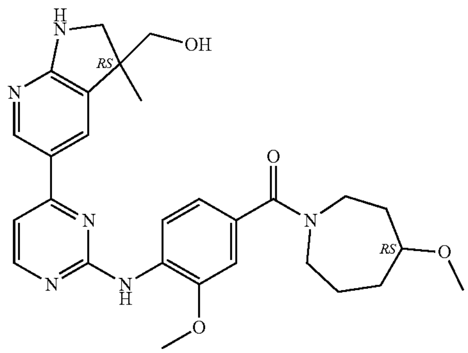 [SMILES: COc1cc(C(=O)N2CCCC(OC)CC2)ccc1Nc1nccc(-c2cnc3c(c2)C(C)(CO)CN3)n1] | B9 |
| Compound 152 | 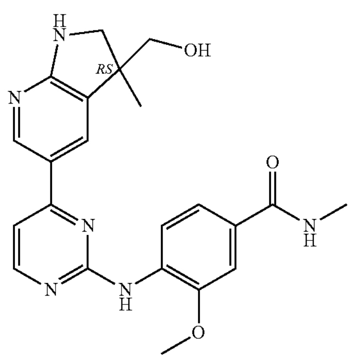 [SMILES: CNC(=O)c1ccc(Nc2nccc(-c3cnc4c(c3)C(C)(CO)CN4)n2)c(OC)c1] | B9 |
| Compound 153 | 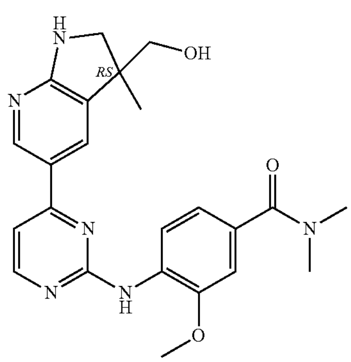 [SMILES: COc1cc(C(=O)N(C)C)ccc1Nc1nccc(-c2cnc3c(c2)C(C)(CO)CN3)n1] | B9 |

Example B5

Preparation of Compound 176:

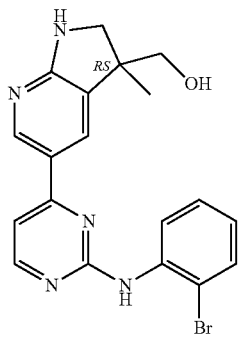 [SMILES: CC1(CO)CNc2ncc(-c3ccnc(Nc4ccccc4Br)n3)cc21]

A suspension of intermediate 14 (150 mg, 0.31 mmol), 2-bromoaniline (106.65 mg, 0.62 mmol) and conc. HCl (0.5 mL) in 1,4-dioxane (2 mL) was heated to 120° C. in the microwave for 30 min. The reaction mixture was diluted with MeOH and loaded onto a 5 g SCX-2 cartridge, washed with MeOH and eluted with 2 M ammonia in MeOH. The basic fractions were concentrated in vacuo. The residue was taken up in EtOAc and washed with sat. NaHCO₃ solution. The organic layer was dried over Na₂SO₄, filtered and concentrated in vacuo. The crude residue was purified by MDAP (basic column) to give 16 mg of compound 176 (13% yield, off-white solid).

The compounds in the Table below were prepared by using an analogous method, starting from the respective starting materials.

| Compound number | Structure |
|---|---|
| Compound 181 | |
| Compound 182 | |
| Compound 183 | 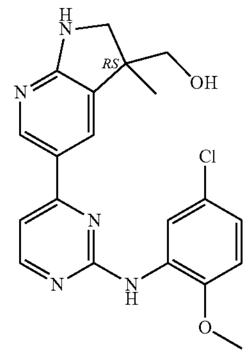 [SMILES: COc1ccc(Cl)cc1Nc1nccc(-c2cnc3c(c2)C(C)(CO)CN3)n1] |
| Compound 184 | 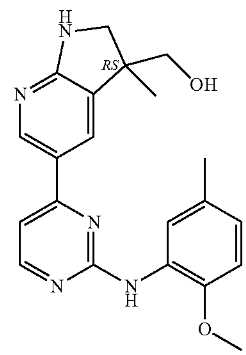 [SMILES: COc1ccc(C)cc1Nc1nccc(-c2cnc3c(c2)C(C)(CO)CN3)n1] |
| Compound 185 | 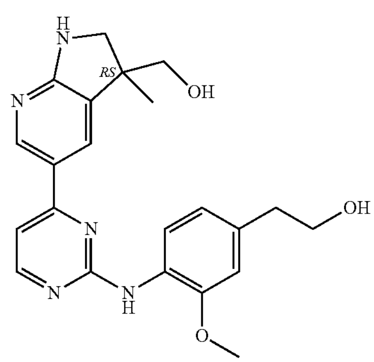 [SMILES: COc1cc(CCO)ccc1Nc1nccc(-c2cnc3c(c2)C(C)(CO)CN3)n1] |
| Compound 187 | 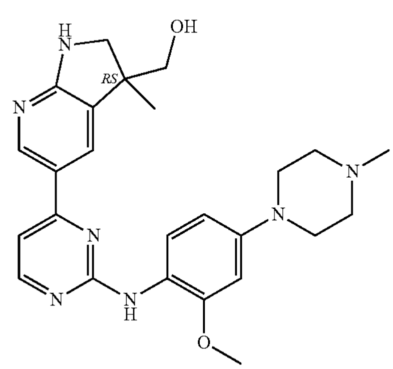 [SMILES: COc1cc(N2CCN(C)CC2)ccc1Nc1nccc(-c2cnc3c(c2)C(C)(CO)CN3)n1] |

| Compound number | Structure |
|---|---|
| Compound 188 | 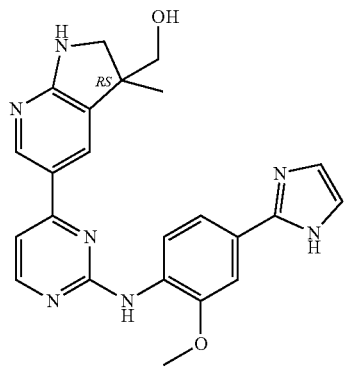 |
| Compound 196 | 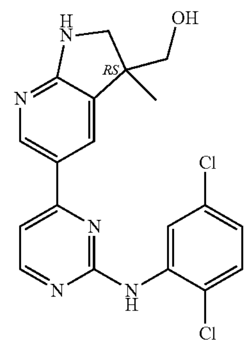 [SMILES: CC1(CO)CNc2ncc(-c3ccnc(Nc4cc(Cl)ccc4Cl)n3)cc21] |

Example B6

Preparation of Compound 163:

Intermediate 124 (150 mg, 0.25 mmol), 2-bromoimidazole (46 mg, 0.31 mmol) and sodium carbonate (79 mg, 0.75 mmol) were suspended in 1,4-dioxane (3 mL) and water (0.25 mL). The reaction mixture was degassed with argon (5 minutes), Pd(PPh$_3$)$_4$ (29 mg, 0.025 mmol) was added and the reaction mixture was heated at 110° C. for 12 h in a microwave reactor. The cooled reaction mixture was filtered through celite, washed with EtOAc, then DCM and the filtrate was evaporated in vacuo. The crude material was dissolved in THF (4 mL) and TBAF (1M in THF) (1 mL) and heated to 40° C. for 2 hours. The reaction mixture was concentrated in vacuo and purified by preparative chromatography using acidic eluent. The material was retrieved and purified by preparative chromatography using basic eluent to give 6.2 mg of compound 163 (6% yield, pale yellow amorphous solid).

Example B7

Preparation of Compound 331

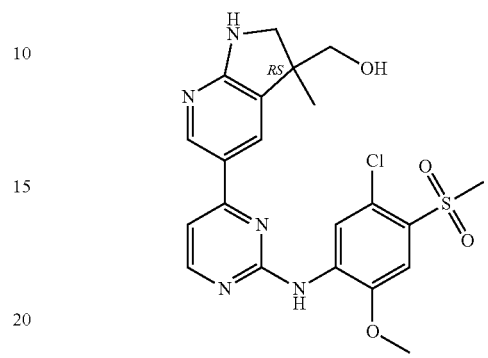

A mixture of intermediate 163 (295 mg, 0.43 mmol) and TBAF (1M in THF) (0.47 mL, 0.47 mmol) in anhydrous THF (5.0 mL) was stirred at rt for 2 hours. The mixture was concentrated in vacuo. The residue was purified by SCX-2 eluting with MeOH and 2M ammonia solution. The residue was then purified by reverse phase preparative HPLC, eluting with a mixture of MeCN and water containing 0.1% ammonium hydroxide (1:9 to 49:1 by volume over 20 minutes) to give after freeze drying 15.6 mg of compound 331 (8% yield, pale yellow solid).

The compounds in the Table below were prepared by using an analogous method, starting from the respective starting materials.

| Compound number | Structure |
|---|---|
| Compound 354 starting from intermediate 14S | 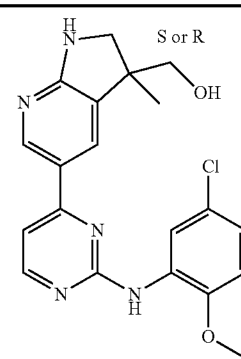 |
| Compound 355 starting from intermediate 14S | 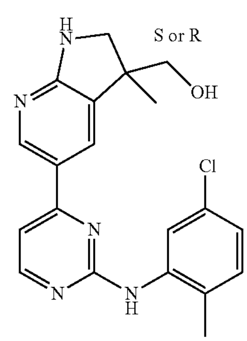 [SMILES: Cc1ccc(Cl)cc1Nc1nccc(-c2cnc3c(c2)C(C)(CO)CN3)n1] |

Example B9

Preparation of Compound 3R and 3S:

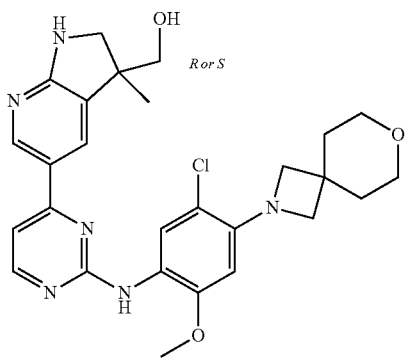
compound 3R

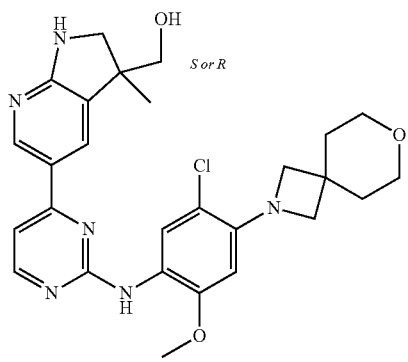
compound 3S

Compound 3 (40 mg) was separated by SFC (YMC Amylose-C, 55/45 iPrOH (0.1% DEA)/CO$_2$, 70 mL/min, 120 bar, 40° C.). The pure fractions were collected and evaporated to dryness to give 18 mg of compound 3S (45% yield, ee=100%) and 13 mg of compound 3R (33% yield, ee=98.8%).

Preparation of Compound 4R and 4S:

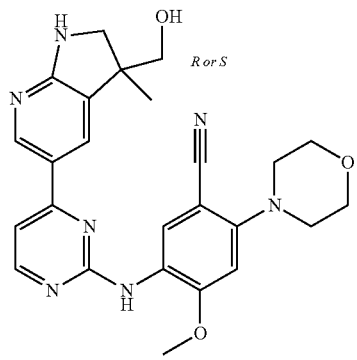
compound 4R

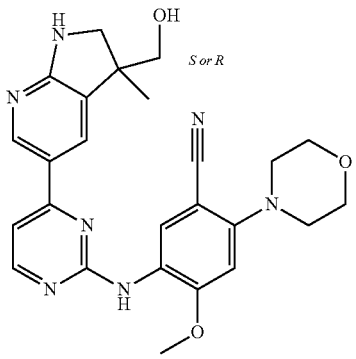
compound 4S

Compound 4 (28 mg) was separated by SFC (YMC Amylose-C, 55/45 iPrOH (0.1% DEA)/CO$_2$, 70 mL/min, 120 bar, 40° C.). The pure fractions were collected and evaporated to dryness to give 8 mg of compound 4S (29% yield, ee=100%) and 13 mg of compound 4R (46% yield, ee=98.5%).

Preparation of Compound 5R and 5S:

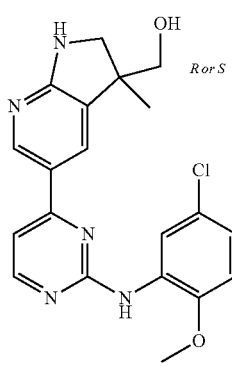
compound 5R

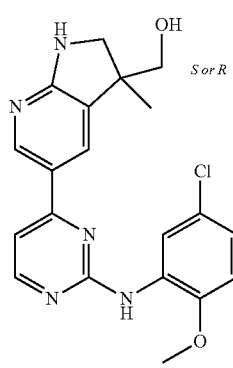
compound 5S

Compound 5 (17 mg) was separated by SFC (YMC Amylose-C, 55/45 iPrOH (0.1% DEA)/CO$_2$, 70 mL/min, 120 bar, 40° C.). The pure fractions were collected and evaporated to dryness to give 7 mg of compound 5S (41% yield, ee=100%) and 7 mg of compound 5R (41% yield, ee=97.9%).

Preparation of Compound 6R and 6S:

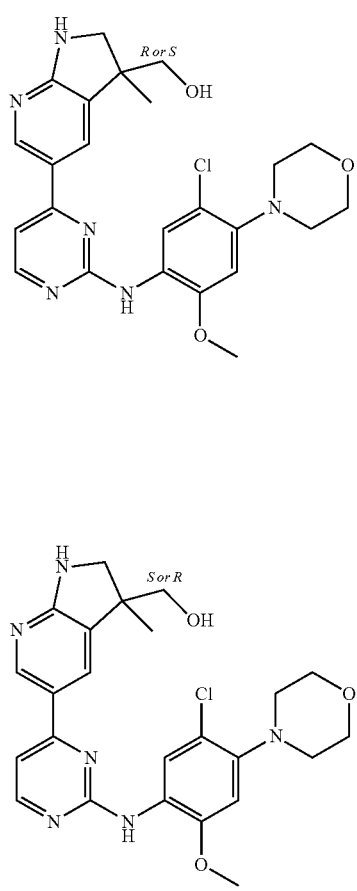

compound 6R compound 6S

Compound 6 (44 mg) was separated by SFC (YMC Amylose-C, 55/45 iPrOH (0.1% DEA)/CO$_2$, 100 mL/min, 120 bar, 40° C.). The pure fractions were collected and evaporated to dryness to give 21 mg of compound 6S (48% yield, ee=98.4%) and 20 mg of compound 6R (45% yield, ee=95.2%).

Preparation of Compound 7R and 7S

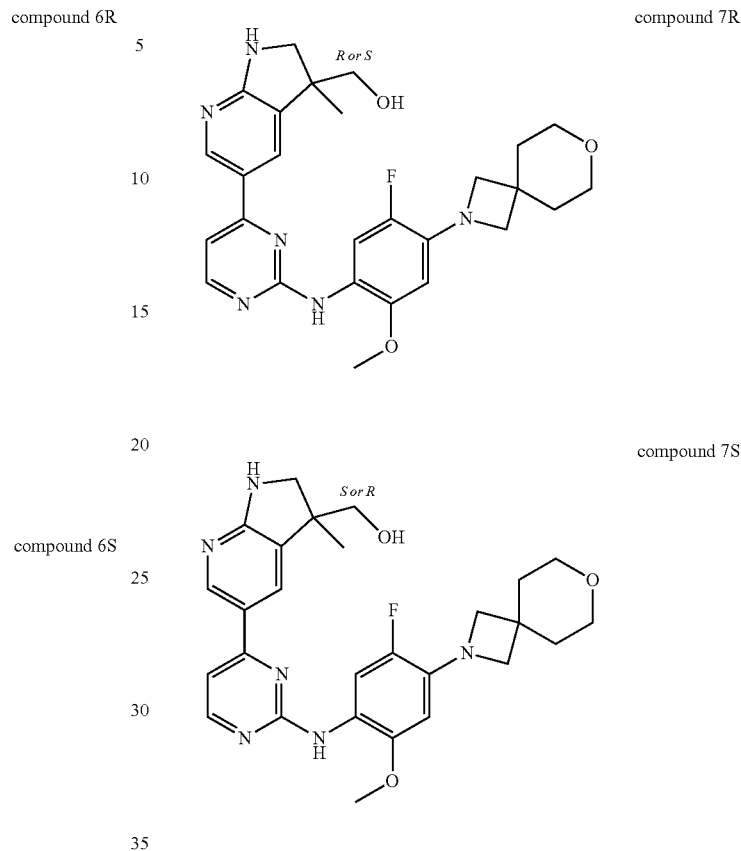

compound 7R compound 7S

Compound 7 (448 mg) was separated by SFC (YMC Amylose-C, 55/45 iPrOH (0.1% DEA)/CO$_2$, 70 mL/min, 120 bar, 40° C.). The pure fractions were collected and freeze-dried to give 169 mg of compound 7S (38% yield, ee=98.5%) and 174 mg of compound 7R (39% yield, ee=98.1%).

The compounds in the Table below were prepared by using an analogous method, starting from the respective starting materials.

| Compound number | Structure |
| --- | --- |
| Compound 156<br>Using the following purification method<br>CHIRALPAK IA 55/45 MeOH/CO$_2$, 70 ml/min, 120 bar,<br>40° C., GLS 40 PSI, SYSTEM 3400 DROP 115 Bar,<br>2767 A/S, 300 nm<br>Then<br>CHIRALPAK IA 55/45 MeOH/CO$_2$, 5.0 ml/min, 120 bar,<br>40° C. | (structure shown) |

-continued

| Compound number | Structure |
|---|---|
| Compound 157<br>using a chiral SCF separation with the following conditions:<br>CHIRALPAK IA 55/45 MeOH/CO$_2$, 70 ml/min, 120 bar, 40° C., GLS 40 PSI, SYSTEM 3400 DROP 115 Bar, 2767 A/S, 300 nm<br>Then<br>CHIRALPAK IA 55/45 MeOH/CO$_2$, 5.0 ml/min, 120 bar, 40° C. | R or S |
| Compound 248<br>using a chiral SCF separation with the following conditions:<br>YMC AMYLOSE-C, 55/45 IPA (0.1% DEA)/CO2, 90 mL/min, 120 bar, 40° C. | S or R |
| Compound 249<br>using a chiral SCF separation with the following conditions:<br>YMC AMYLOSE-C, 55/45 IPA (0.1% DEA)/CO2, 90 mL/min, 120 bar, 40° C. | R or S |
| Compound 254<br>using a chiral SCF separation with the following conditions:<br>YMC AMYLOSE-C, 55/45 IPA (0.1% DEA)/CO2, 70 mL/min, 120 bar, 40° C.) | S or R |

-continued

| Compound number | Structure |
|---|---|
| Compound 253 using a chiral SCF separation with the following conditions: YMC AMYLOSE-C, 55/45 IPA (0.1% DEA)/CO2, 70 mL/min, 120 bar, 40° C.) | |
| Compound 255 using a chiral SCF separation with the following conditions: Chiralpak IA, 55/45 IPA (0.1% DEA)/CO2, 100 mL/min, 120 bar, 40° C. | |
| Compound 256 using a chiral SCF separation with the following conditions: Chiralpak IA, 55/45 IPA (0.1% DEA)/CO2, 100 mL/min, 120 bar, 40° C. | |
| Compound 257 using a chiral SCF separation with the following conditions: Chiralpak IA, 55/45 IPA (0.1% DEA)/CO$_2$, 100 mL/min, 120 bar, 40° C. | |

-continued

| Compound number | Structure |
| --- | --- |
| Compound 258 using a chiral SCF separation with the following conditions: Chiralpak IA, 55/45 IPA (0.1% DEA)/CO$_2$, 100 mL/min, 120 bar, 40° C. | 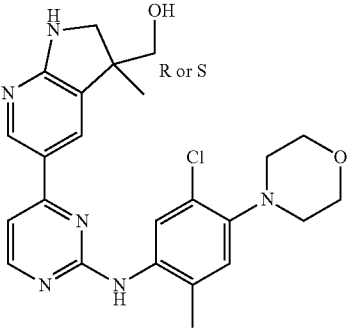 [SMILES: Cc1cc(N2CCOCC2)c(Cl)cc1Nc1nccc(-c2cnc3c(c2)C(C)(CO)CN3)n1] |
| Compound 259 using a chiral SCF separation with the following conditions: Chiralpak IA, 55/45 IPA (0.1% DEA)/CO$_2$, 100 mL/min, 120 bar, 40° C. | 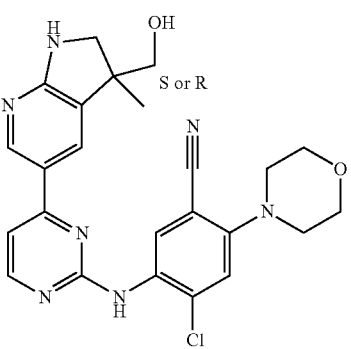 [SMILES: CC1(CO)CNc2ncc(-c3ccnc(Nc4cc(C#N)c(N5CCOCC5)cc4Cl)n3)cc21] |
| Compound 260 using a chiral SCF separation with the following conditions: Chiralpak IA, 55/45 IPA (0.1% DEA)/CO$_2$, 100 mL/min, 120 bar, 40° C. | 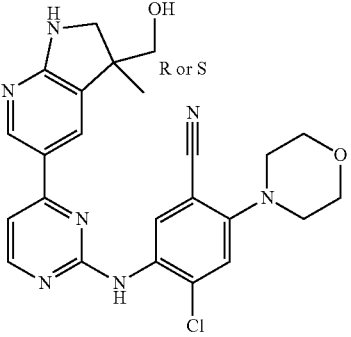 [SMILES: CC1(CO)CNc2ncc(-c3ccnc(Nc4cc(C#N)c(N5CCOCC5)cc4Cl)n3)cc21] |
| Compound 261 using a chiral SCF separation with the following conditions: Chiralpak IA, 55/45 IPA (0.1% DEA)/CO$_2$, 100 mL/min, 120 bar, 40° C. | 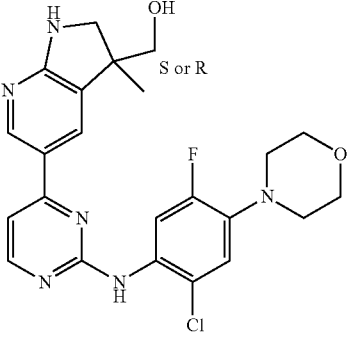 [SMILES: CC1(CO)CNc2ncc(-c3ccnc(Nc4cc(F)c(N5CCOCC5)cc4Cl)n3)cc21] |

-continued

| Compound number | Structure |
|---|---|
| Compound 263<br>using a chiral SCF separation with the following conditions:<br>Chiralpak IA, 55/45 IPA (0.1% DEA)/CO$_2$, 100 mL/min, 120 bar. 40° C. | 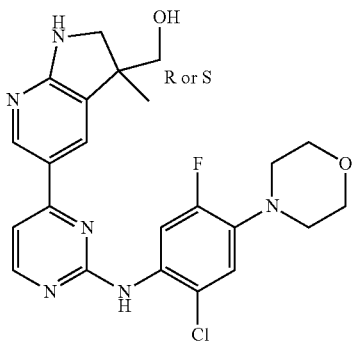 [SMILES: CC1(CO)CNc2ncc(-c3ccnc(Nc4cc(F)c(N5CCOCC5)cc4Cl)n3)cc21] |
| Compound 264<br>using a chiral SCF separation with the following:<br>Chiralpak<br>IA, 55/45 IPA (0.1% DEA)/CO$_2$, 100 mL/min, 120 bar, 40° C. | 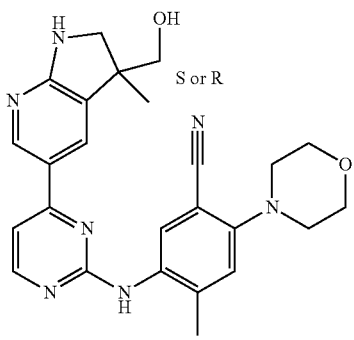 [SMILES: Cc1cc(N2CCOCC2)c(C#N)cc1Nc1nccc(-c2cnc3c(c2)C(C)(CO)CN3)n1] |
| Compound 262<br>using a chiral SCF separation with the following:<br>Chiralpak<br>IA, 55/45 IPA (0.1% DEA)/CO$_2$, 100 mL/min, 120 bar, 40° C. | 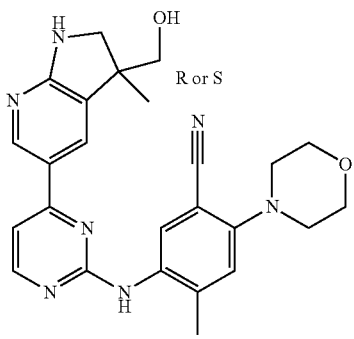 [SMILES: Cc1cc(N2CCOCC2)c(C#N)cc1Nc1nccc(-c2cnc3c(c2)C(C)(CO)CN3)n1] |
| Compound 266<br>using a chiral SCF separation with the following:<br>Chiralpak IA, 55/45 IPA (0.1% DEA)/CO2, 100 mL/min, 120 bar, 40° C. | 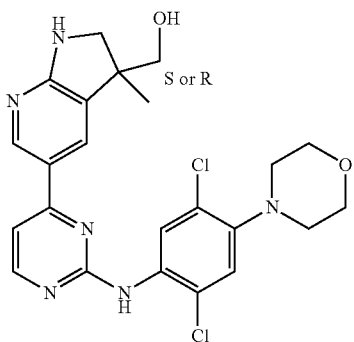 [SMILES: CC1(CO)CNc2ncc(-c3ccnc(Nc4cc(Cl)c(N5CCOCC5)cc4Cl)n3)cc21] |

| Compound number | Structure |
|---|---|
| Compound 265<br>using a chiral SCF separation with the following:<br>Chiralpak IA, 55/45 IPA (0.1% DEA)/CO2, 100 mL/min,<br>120 bar, 40° C. | 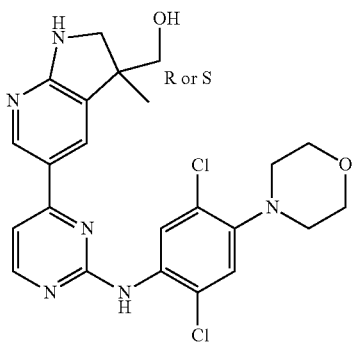 [SMILES: CC1(CO)CNc2ncc(-c3ccnc(Nc4cc(Cl)c(N5CCOCC5)cc4Cl)n3)cc21] |
| Compound 272 | 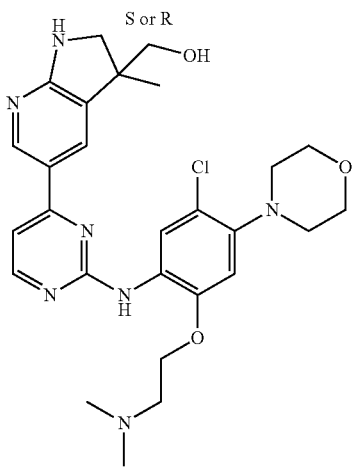 [SMILES: CN(C)CCOc1cc(N2CCOCC2)c(Cl)cc1Nc1nccc(-c2cnc3c(c2)C(C)(CO)CN3)n1] |
| Compound 274 | 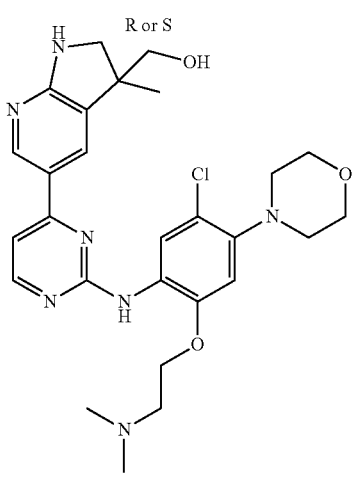 [SMILES: CN(C)CCOc1cc(N2CCOCC2)c(Cl)cc1Nc1nccc(-c2cnc3c(c2)C(C)(CO)CN3)n1] |

-continued
| Compound number | Structure |
|---|---|
| Compound 297 | 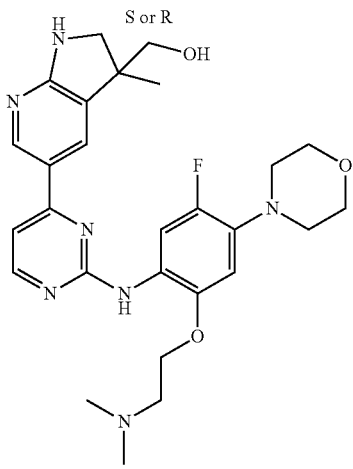 [SMILES: CN(C)CCOc1cc(N2CCOCC2)c(F)cc1Nc1nccc(-c2cnc3c(c2)C(C)(CO)CN3)n1] |
| Compound 286 | 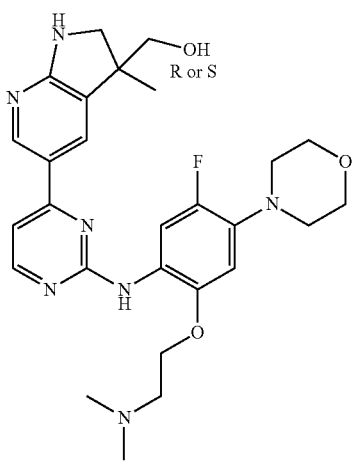 [SMILES: CN(C)CCOc1cc(N2CCOCC2)c(F)cc1Nc1nccc(-c2cnc3c(c2)C(C)(CO)CN3)n1] |
| Compound 287 using a chiral SCF separation with the following: YMC amylose-C 55/45 IPA (0.1% DEA)/CO$_2$, 70 ml/min, 120 bar, 40° C. | 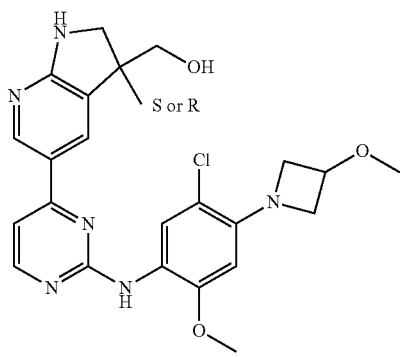 [SMILES: COc1cc(N2CC(OC)C2)c(Cl)cc1Nc1nccc(-c2cnc3c(c2)C(C)(CO)CN3)n1] |

-continued

| Compound number | Structure |
|---|---|
| Compound 300<br>using a chiral SCF separation with the following:<br>YMC amylose-C 55/45 IPA (0.1% DEA)/CO$_2$, 70 ml/min, 120 bar, 40° C. | 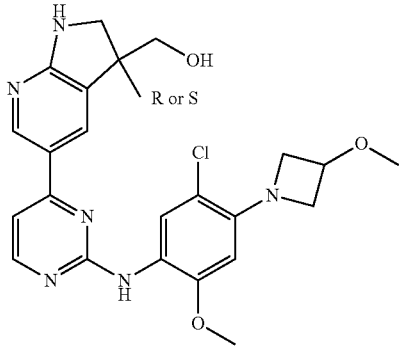 [SMILES: COc1cc(N2CC(OC)C2)c(Cl)cc1Nc1nccc(-c2cnc3c(c2)C(C)(CO)CN3)n1] |
| Compound 298<br>using a chiral SCF separation with the following:<br>Chiralpak IC, 55/45 IPA (0.1% DEA)/CO$_2$, 70 mL/min, 120 bar, 40° C. | 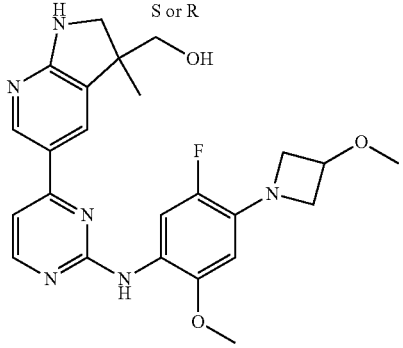 [SMILES: COc1cc(N2CC(OC)C2)c(F)cc1Nc1nccc(-c2cnc3c(c2)C(C)(CO)CN3)n1] |
| Compound 288<br>using a chiral SCF separation with the following:<br>Chiralpak IC, 55/45 IPA (0.1% DEA)/CO$_2$, 70 mL/min, 120 bar, 40° C. | 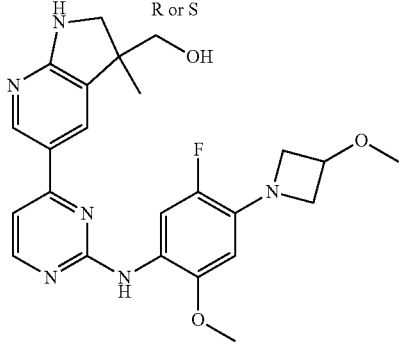 [SMILES: COc1cc(N2CC(OC)C2)c(F)cc1Nc1nccc(-c2cnc3c(c2)C(C)(CO)CN3)n1] |
| Compound 291<br>using a chiral SCF separation with the following:<br>YMC amylose-C 40/60 IPA (0.1% DEA)/CO$_2$, 70 ml/min, 120 bar, 40° C. | 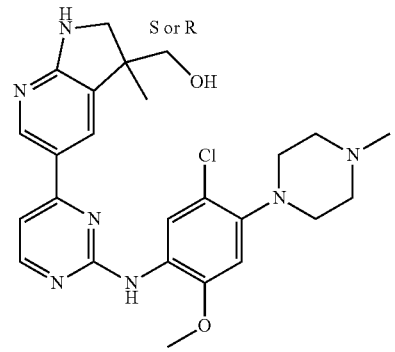 [SMILES: COc1cc(N2CCN(C)CC2)c(Cl)cc1Nc1nccc(-c2cnc3c(c2)C(C)(CO)CN3)n1] |

| Compound number | Structure |
|---|---|
| Compound 303 using a chiral SCF separation with the following: YMC amylose-C 40/60 IPA (0.1% DEA)/CO$_2$, 70 ml/min, 120 bar, 40° C. | (structure with R or S configuration, 7-azaindoline bearing methyl and CH$_2$OH, linked to pyrimidine, NH-phenyl with Cl, OMe, and 4-methylpiperazine) |
| Compound 295 using a chiral SCF separation with the following: YMC amylose-C 55/45 IPA (0.1% DEA)/CO$_2$, 70 ml/min, 120 bar, 40° C. | (structure with S or R configuration, 7-azaindoline bearing methyl and CH$_2$OH, linked to pyrimidine, NH-phenyl with Cl, OMe, and 4-ethylpiperazine) |
| Compound 293 using a chiral SCF separation with the following: YMC amylose-C 55/45 IPA (0.1% DEA)/CO$_2$, 70 ml/min, 120 bar, 40° C. | (structure with R or S configuration, 7-azaindoline bearing methyl and CH$_2$OH, linked to pyrimidine, NH-phenyl with Cl, OMe, and 4-ethylpiperazine) |

The compounds in the table below were prepared by analogous chemical protocols as described throughout the experimental part.
Compound 361
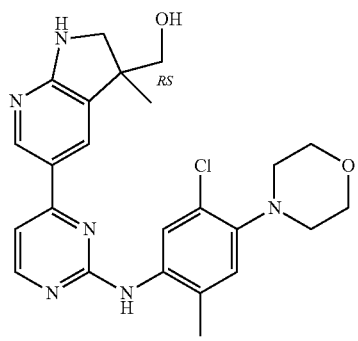
Compound 362
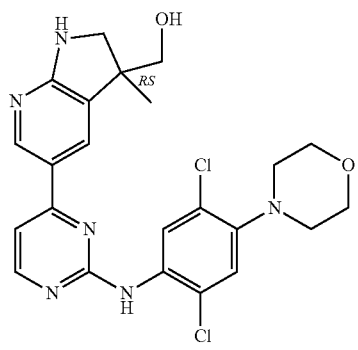
Compound 363
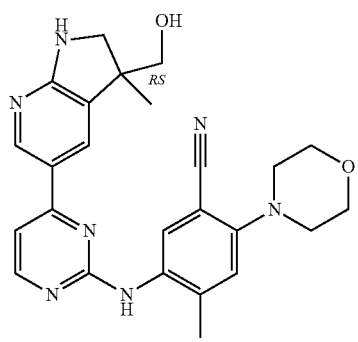
Compound 364
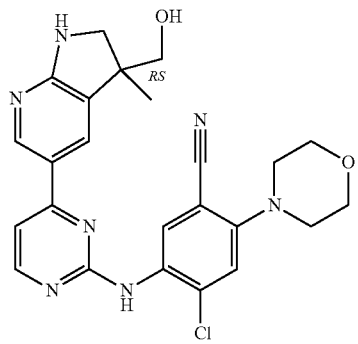
-continued
Compound 365
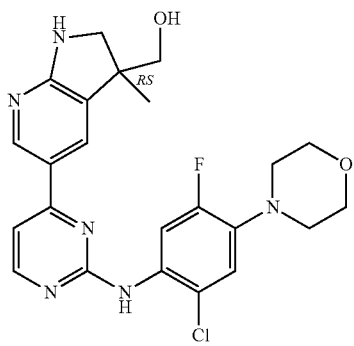
Compound 366
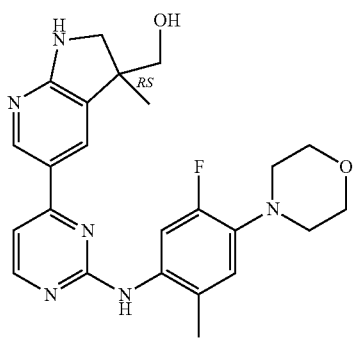
Compound 367
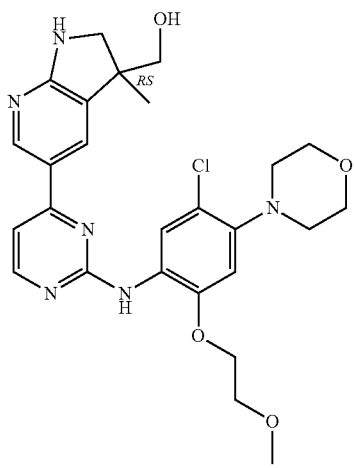
Compound 368
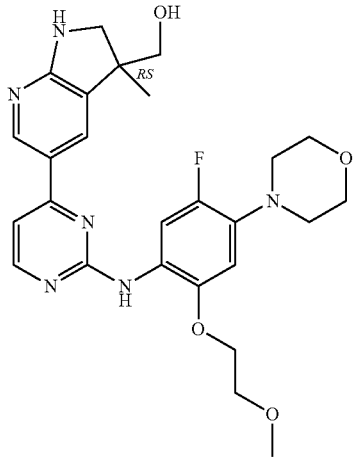

Compound 369
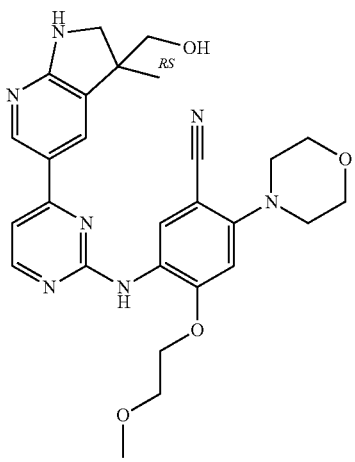

Compound 372
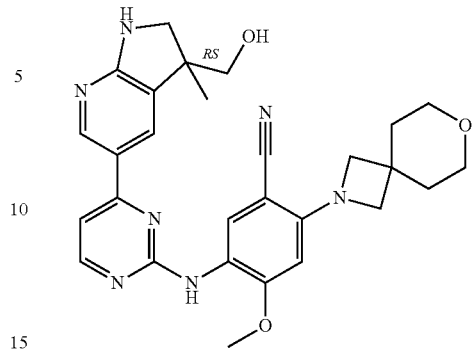

Compound 373
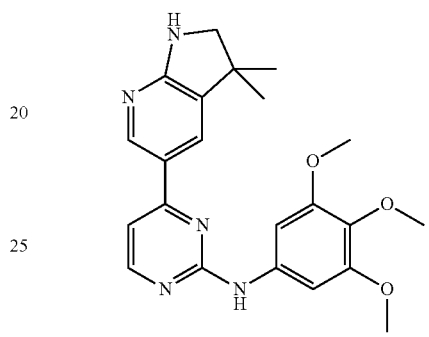

Compound 370
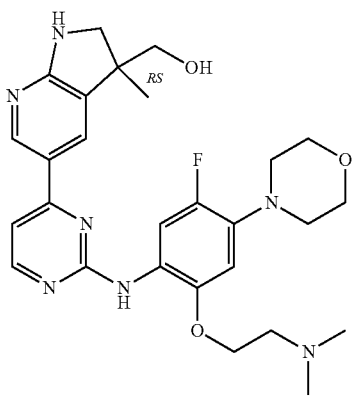

Compound 125
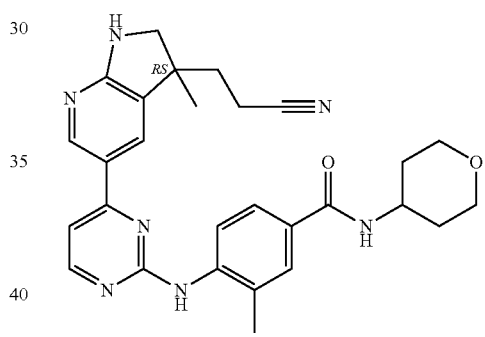

Compound 371
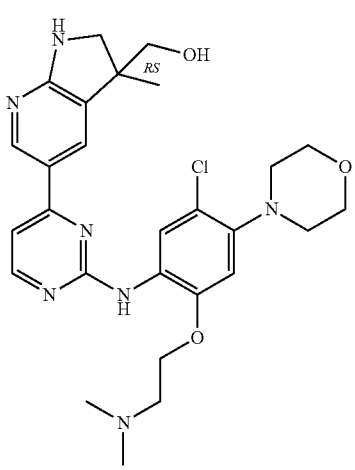

Analytical Part

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+HCOO]$^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector, "PDA" Photo Diode Array Detector.

TABLE

LCMS Method codes (Flow expressed in mL/min; column temperature (T) in °C.; Run time in minutes).

| Method code | Instrument | Column | Mobile phase | gradient | Flow (mL/min) T (°C.) | Run time |
|---|---|---|---|---|---|---|
| Method 1 | Waters: Acquity UPLC ® - PDA and SQD | Waters: BEH C18 (1.7 μm, 2.1 × 100 mm) | A: H$_2$O + 0.1% HCOOH/B: CH$_3$CN + 0.1% HCOOH | From 95% A for 0.40 min, to 5% A in 5.2 min, held for 0.80 min. | 0.40 40 | 6.4 |
| Method 2 | Waters: Acquity UPLC ® - DAD and Quattro Micro ™ | Waters: BEH C18 (1.7 μm, 2.1 × 100 mm) | A: CH$_3$COONH$_4$ 7 mM/B: CH$_3$CN | From 84.2% A for 0.49 min, to 10.5% A in 2.18 min, held for 1.94 min, back to 84.2% A in 0.73 min, held for 0.73 min. | 0.343 40 | 6.2 |
| Method 3 | Waters: Acquity UPLC ® H-Class - DAD and SQD 2 | Waters: BEH C18 (1.7 μm, 2.1 × 100 mm) | A: CH$_3$COONH$_4$ 7 mM/B: CH$_3$CN | From 84.2% A to 10.5% A in 2.18 min, held for 1.94 min, back to 84.2% A in 0.73 min, held for 0.73 min. | 0.343 40 | 6.1 |

Melting Point (DSC or K1)

For a number of compounds, melting points (MP) were determined with an DSC1 (Mettler-Toledo) (indicated in the table by DSC). Melting points were measured with a temperature gradient of 10° C./minute. Maximum temperature was 350° C. Values are peak values.

For a number of compounds, melting points were obtained with a Kofler (K) hot bench, consisting of a heated plate with linear temperature gradient, a sliding pointer and a temperature scale in degrees Celsius. (indicated in the table by K)

TABLE

No. means compound number; MP means melting point (° C.); R$_t$ means retention time (min)

| No | MP (° C.) | MP method | Rt | [M + H]$^+$ | LC/MS Method |
|---|---|---|---|---|---|
| 1 | — | — | 2.62 | 491 | Method 1 |
| 2 | — | — | 2.76 | 509.28 | Method 1 |
| 3 | — | — | 3.27 | 523 | Method 1 |
| 3R | — | — | 3.27 | 523 | Method 1 |
| 3S | — | — | 3.26 | 523 | Method 1 |
| 4 | — | — | 2.90 | 474 | Method 1 |
| 4R | — | — | 2.90 | 474 | Method 1 |
| 4S | — | — | 2.89 | 474 | Method 1 |
| 5 | — | — | 2.97 | 485 | Method 1 |
| 5R | — | — | 2.98 | 485 | Method 1 |
| 5S | — | — |  |  | Method 1 |
| 6 | — | — | 3.14 | 483 | Method 1 |
| 6R | — | — | 3.15 | 483 | Method 1 |
| 6S | — | — | 3.17 | 483 | Method 1 |
| 7 | — | — | 3.09 | 507 | Method 1 |
| 7R | — | — | 3.08 | 507 | Method 1 |
| 7S | — | — | 3.08 | 507 | Method 1 |
| 8 | — | — | 2.61 | 525 | Method 1 |
| 9 | — | — | 3.27 | 524 | Method 1 |
| 11 | — | — | 2.53 | 413 | Method 1 |
| 12 | — | — | 2.71 | 460 | Method 1 |
| 14 | — | — | 2.28 | 524 | Method 1 |
| 15 | — | — | 2.36 | 481 | Method 1 |
| 16 | >260 | K | 2.66 | 497 | Method 1 |
| 17 | — | — | 2.59 | 389 | Method 1 |
| 21 | — | — | 2.67 | 419 | Method 1 |

TABLE-continued

No. means compound number; MP means melting point (° C.); R$_t$ means retention time (min)

| No | MP (° C.) | MP method | Rt | [M + H]$^+$ | LC/MS Method |
|---|---|---|---|---|---|
| 22 | — | — | 2.69 | 463 | Method 1 |
| 24 | — | — | 2.11 | 458 | Method 1 |
| 28 | — | — | 2.02 | 347 | Method 1 |
| 31 | — | — | 2.69 | 445 | Method 1 |
| 32 | — | — | 2.65 | 419 | Method 1 |
| 33 | — | — | 2.40 | 405 | Method 1 |
| 34 | — | — | 2.07 | 416 | Method 1 |
| 35 | — | — | 2.15 | 472 | Method 1 |
| 36 | — | — | 2.76 | 459 | Method 1 |
| 42 | — | — | 2.52 | 403 | Method 1 |
| 43 | — | — | 2.67 | 403 | Method 1 |
| 44 | — | — | 2.55 | 403 | Method 1 |
| 46 | — | — | 2.61 | 424 | Method 1 |
| 49 | — | — | 2.62 | 433 | Method 1 |
| 50 | — | — | 2.95 | 475 | Method 1 |
| 51 | — | — | 2.11 | 474 | Method 1 |
| 53 | — | — | 2.73 | 487 | Method 1 |
| 54 | — | — | 2.52 | 459 | Method 1 |
| 55 | — | — | 2.16 | 444 | Method 1 |
| 60 | — | — | 2.33 | 488 | Method 1 |
| 62 | — | — | 2.70 | 419 | Method 1 |
| 63 | — | — | 2.86 | 467 | Method 1 |
| 64 | — | — | 2.71 | 417 | Method 1 |
| 65 | — | — | 2.89 | 431 | Method 1 |
| 66 | — | — | 2.68 | 433 | Method 1 |
| 67 | — | — | 2.93 | 457 | Method 1 |
| 72 | — | — | 2.80 | 423 | Method 1 |
| 74 | — | — | 2.75 | 417 | Method 1 |
| 75 | — | — | 2.93 | 431 | Method 1 |
| 76 | — | — | 2.70 | 433 | Method 1 |
| 77 | — | — | 3.01 | 473 | Method 1 |
| 78 | — | — | 2.72 | 445 | Method 1 |
| 79 | — | — | 2.95 | 473 | Method 1 |
| 80 | — | — | 2.60 | 445 | Method 1 |
| 81 | — | — | 2.05 | 458 | Method 1 |
| 82 | — | — | 3.13 | 511 | Method 1 |
| 83 | — | — | 2.63 | 407 | Method 1 |
| 84 | — | — | 2.9 | 449 | Method 1 |
| 85 | — | — | 2.85 | 455 | Method 1 |

TABLE-continued

No. means compound number; MP means melting point (° C.); R*t* means retention time (min)

| No | MP (° C.) | MP method | Rt | [M + H]⁺ | LC/MS Method |
|---|---|---|---|---|---|
| 86 | — | — | 2.23 | 419 | Method 1 |
| 87 | — | — | 2.46 | 475 | Method 1 |
| 89 | — | — | 1.89 | 460 | Method 1 |
| 90 | — | — | 1.87 | 490 | Method 1 |
| 91 | — | — | 2.45 | 526 | Method 1 |
| 94 | — | — | 3.17 | 513 | Method 1 |
| 96 | — | — | 2.73 | 403 | Method 1 |
| 97 | — | — | 2.79 | 376 | Method 1 |
| 98 | — | — | 2.89 | 501 | Method 1 |
| 99 | — | — | 2.88 | 468 | Method 1 |
| 100 | — | — | 2.64 | 493 | Method 1 |
| 103 | — | — | 2.35 | 492 | Method 1 |
| 104 | — | — | 3.06 | 479 | Method 1 |
| 105 | — | — | 2.67 | 489 | Method 1 |
| 106 | — | — | 2.65 | 463 | Method 1 |
| 107 | — | — | 2.53 | 489 | Method 1 |
| 108 | — | — | 2.73 | 475 | Method 1 |
| 109 | — | — | 2.21 | 475 | Method 1 |
| 110 | — | — | 2.94 | 495 | Method 1 |
| 112 | — | — | 2.77 | 461 | Method 1 |
| 113 | — | — | 2.79 | 475 | Method 1 |
| 114 | — | — | 2.56 | 475 | Method 1 |
| 115 | — | — | 3.26 | 357 | Method 1 |
| 116 | — | — | 3.43 | 373 | Method 1 |
| 117 | — | — | 2.83 | 417 | Method 1 |
| 119 | — | — | 2.96 | 426 | Method 1 |
| 120 | — | — | 2.34 | 461 | Method 1 |
| 121 | — | — | 2.58 | 489 | Method 1 |
| 124 | — | — | 2.44 | 489 | Method 1 |
| 125 | — | — | 2.64 | 498 | Method 1 |
| 126 | — | — | 2.63 | 484 | Method 1 |
| 128 | — | — | 3.13 | 520 | Method 1 |
| 129 | — | — | 3.20 | 525 | Method 1 |
| 130 | — | — | 2.02 | 504 | Method 1 |
| 131 | — | — | 2.74 | 505 | Method 1 |
| 132 | — | — | 2.42 | 525 | Method 1 |
| 133 | — | — | 2.61 | 489 | Method 1 |
| 134 | — | — | 2.30 | 509 | Method 1 |
| 135 | — | — | 2.84 | 433 | Method 1 |
| 136 | — | — | 2.60 | 491 | Method 1 |
| 137 | — | — | 2.48 | 477 | Method 1 |
| 138 | — | — | 2.73 | 461 | Method 1 |
| 139 | — | — | 2.98 | 475 | Method 1 |
| 140 | — | — | 2.70 | 527 | Method 1 |
| 141 | — | — | 3.12 | 489 | Method 1 |
| 142 | — | — | 2.68 | 505 | Method 1 |
| 143 | — | — | 1.86 | 490 | Method 1 |
| 145 | — | — | 2.29 | 435 | Method 1 |
| 147 | — | — | 2.84 | 500 | Method 1 |
| 148 | — | — | 3.02 | 514 | Method 1 |
| 150 | — | — | 2.82 | 519 | Method 1 |
| 151 | — | — | 2.89 | 364 | Method 1 |
| 152 | — | — | 2.44 | 421 | Method 1 |
| 153 | — | — | 2.52 | 435 | Method 1 |
| 154 | — | — | 3.02 | 514 | Method 1 |
| 155 | — | — | 3.20 | 528 | Method 1 |
| 156 | — | — | 3.05 | 475 | Method 1 |
| 157 | — | — | 3.05 | 475 | Method 1 |
| 158 | — | — | 2.72 | 519 | Method 1 |
| 159 | — | — | 2.88 | 533 | Method 1 |
| 160 | — | — | 2.60 | 479 | Method 1 |
| 163 | — | — | 2.04 | 430 | Method 1 |
| 164 | — | — | 2.32 | 394 | Method 1 |
| 165 | — | — | 1.93 | 463 | Method 1 |
| 166 | — | — | 2.82 | 408 | Method 1 |
| 167 | — | — | 2.94 | 362 | Method 1 |
| 168 | — | — | 2.78 | 364 | Method 1 |
| 169 | — | — | 2.73 | 444 | Method 1 |
| 170 | — | — | 2.02 | 444 | Method 1 |
| 171 | — | — | 2.51 | 449 | Method 1 |
| 172 | — | — | 3.31 | 398 | Method 1 |
| 173 | — | — | 3.45 | 4.32 | Method 1 |
| 174 | — | — | 3.15 | 378 | Method 1 |
| 175 | — | — | 3.27 | 392 | Method 1 |
| 176 | — | — | 2.98 | 412 | Method 1 |
| 177 | — | — | 2.68 | 352 | Method 1 |
| 178 | — | — | 2.93 | 368 | Method 1 |
| 179 | — | — | 2.63 | 348 | Method 1 |
| 180 | — | — | 3.01 | 402 | Method 1 |
| 181 | — | — | 3.28 | 442 | Method 1 |
| 182 | — | — | 3.02 | 382 | Method 1 |
| 183 | — | — | 3.19 | 398 | Method 1 |
| 184 | — | — | 3.03 | 378 | Method 1 |
| 185 | — | — | 2.36 | 408 | Method 1 |
| 186 | — | — | 1.89 | 421 | Method 1 |
| 187 | — | — | 1.84 | 462 | Method 1 |
| 188 | — | — | 2.62 | 444 | Method 1 |
| 189 | — | — | 2.76 | 444 | Method 1 |
| 190 | — | — | 2.80 | 389 | Method 1 |
| 191 | — | — | 2.90 | 430 | Method 1 |
| 192 | — | — | 2.83 | 444 | Method 1 |
| 193 | — | — | 3.31 | 432 | Method 1 |
| 194 | — | — | 2.00 | 477 | Method 1 |
| 195 | — | — | 3.32 | 404 | Method 1 |
| 196 | — | — | 3.41 | 402 | Method 1 |
| 197 | — | — | 3.22 | 386 | Method 1 |
| 198 | — | — | 2.94 | 366 | Method 1 |
| 199 | — | — | 3.14 | 382 | Method 1 |
| 200 | — | — | 1.99 | 463 | Method 1 |
| 202 | — | — | 2.12 | 444 | Method 1 |
| 203 | — | — | 2.85 | 444 | Method 1 |
| 204 | — | — | 2.42 | 394 | Method 1 |
| 205 | — | — | 3.03 | 393 | Method 1 |
| 206 | — | — | 3.29 | 392 | Method 1 |
| 207 | — | — | 2.57 | 431 | Method 1 |
| 208 | — | — | 2.80 | 373 | Method 1 |
| 209 | — | — | 3.49 | 406 | Method 1 |
| 210 | — | — | 3.45 | 432 | Method 1 |
| 211 | — | — | 2.36 | 405 | Method 1 |
| 212 | — | — | 2.87 | 362 | Method 1 |
| 213 | — | — | 2.28 | 477 | Method 1 |
| 214 | — | — | 2.72 | 378 | Method 1 |
| 215 | — | — | 2.63 | 472 | Method 1 |
| 216 | — | — | 2.40 | 433 | Method 1 |
| 217 | — | — | 3.24 | 483 | Method 1 |
| 218 | — | — | 1.89 | 493 | Method 1 |
| 219 | — | — | 2.30 | 405 | Method 1 |
| 220 | — | — | 2.78 | 378 | Method 1 |
| 221 | — | — | 2.45 | 421 | Method 1 |
| 222 | — | — | 3.20 | 398 | Method 1 |
| 223 | — | — | 2.64 | 373 | Method 1 |
| 224 | — | — | 3.05 | 382 | Method 1 |
| 225 | — | — | 3.00 | 398 | Method 1 |
| 226 | — | — | 2.88 | 403 | Method 1 |
| 227 | — | — | 3.34 | 402 | Method 1 |
| 228 | — | — | 1.99 | 477 | Method 1 |
| 229 | — | — | 1.93 | 463 | Method 1 |
| 230 | — | — | 3.23 | 412 | Method 1 |
| 233 | — | — | 1.98 | 477 | Method 1 |
| 234 | — | — | 2.67 | 351 | Method 1 |
| 238 | — | — | 2.03 | 462 | Method 1 |
| 239 | — | — | 2.84 | 444 | Method 1 |
| 241 | — | — | 1.97 | 449 | Method 1 |
| 242 | — | — | 2.79 | 489 | Method 1 |
| 243 | — | — | 2.93 | 467 | Method 1 |
| 244 | — | — | 1.67 | 444 | Method 1 |
| 245 | — | — | 3.49 | 506 | Method 1 |
| 246 | — | — | 2.14 | 447 | Method 1 |
| 247 | — | — | 3.02 | 434 | Method 1 |
| 248 | — | — | 3.01 | 389 | Method 1 |
| 249 | — | — | 2.99 | 389 | Method 1 |
| 250 | — | — | 2.61 | 382 | Method 1 |
| 251 | — | — | 2.74 | 398 | Method 1 |
| 252 | — | — | 3.00 | 499 | Method 1 |
| 253 | — | — | 2.94 | 467 | Method 1 |
| 254 | — | — | 2.95 | 467 | Method 1 |
| 255 | — | — | 2.74 | 451 | Method 1 |
| 256 | — | — | 2.73 | 451 | Method 1 |
| 257 | — | — | 2.97 | 467 | Method 1 |
| 258 | — | — | 2.93 | 467 | Method 1 |

TABLE-continued

No. means compound number; MP means melting point (° C.); R$_t$ means retention time (min)

| No | MP (° C.) | MP method | Rt | [M + H]⁺ | LC/MS Method |
|---|---|---|---|---|---|
| 259 | — | — | 3.01 | 478 | Method 1 |
| 260 | — | — | 3.00 | 478 | Method 1 |
| 261 | — | — | 3.07 | 471 | Method 1 |
| 262 | — | — | 2.74 | 458 | Method 1 |
| 263 | — | — | 3.07 | 471 | Method 1 |
| 264 | — | — | 2.72 | 458 | Method 1 |
| 265 | — | — | 3.26 | 487 | Method 1 |
| 266 | — | — | 3.27 | 487 | Method 1 |
| 267 | — | — | 2.13 | 496 | Method 1 |
| 268 | — | — | 2.20 | 510 | Method 1 |
| 269 | — | — | 3.09 | 483 | Method 1 |
| 270 | — | — | 2.97 | 467 | Method 1 |
| 271 | — | — | 2.03 | 480 | Method 1 |
| 272 | — | — | 2.33 | 540 | Method 1 |
| 274 | — | — | 2.34 | 540 | Method 1 |
| 275 | — | — | 2.08 | 494 | Method 1 |
| 277 | — | — | 2.22 | 524 | Method 1 |
| 278 | — | — | 2.18 | 510 | Method 1 |
| 279 | — | — | 2.15 | 501 | Method 1 |
| 280 | — | — | 2.09 | 487 | Method 1 |
| 281 | — | — | 2.96 | 491 | Method 1 |
| 282 | — | — | 3.36 | 451 | Method 1 |
| 283 | — | — | 2.16 | 495 | Method 1 |
| 284 | — | — | 3.06 | 509 | Method 1 |
| 285 | — | — | 3.21 | 497 | Method 1 |
| 286 | — | — | 2.16 | 524 | Method 1 |
| 287 | — | — | 3.08 | 483 | Method 1 |
| 288 | — | — | 2.95 | 467 | Method 1 |
| 289 | — | — | 2.09 | 496 | Method 1 |
| 290 | — | — | 2.74 | 525 | Method 1 |
| 291 | — | — | 2.11 | 496 | Method 1 |
| 292 | — | — | 3.09 | 509 | Method 1 |
| 293 | — | — | 2.19 | 510 | Method 1 |
| 294 | — | — | 3.17 | 453 | Method 1 |
| 295 | — | — | 2.19 | 510 | Method 1 |
| 296 | — | — | 2.87 | 539 | Method 1 |
| 297 | — | — | 2.16 | 524 | Method 1 |
| 298 | — | — | 2.94 | 467 | Method 1 |
| 299 | — | — | 2.97 | 509 | Method 1 |
| 300 | — | — | 3.08 | 438 | Method 1 |
| 301 | — | — | 2.65 | 497 | Method 1 |
| 302 | — | — | 2.55 | 469 | Method 1 |
| 303 | — | — | 2.12 | 496 | Method 1 |
| 304 | — | — | 3.75 | 481 | Method 1 |
| 307 | — | — | 3.38 | 483 | Method 1 |
| 309 | — | — | 2.25 | 522 | Method 1 |
| 311 | — | — | 2.24 | 540 | Method 1 |
| 313 | — | — | 2.75 | 483 | Method 1 |
| 314 | — | — | 2.10 | 485 | Method 1 |
| 317 | — | — | 2.22 | 495 | Method 1 |
| 318 | — | — | 2.12 | 490 | Method 1 |
| 319 | — | — | 2.34 | 539 | Method 1 |
| 320 | — | — | 2.12 | 540 | Method 1 |
| 321 | — | — | 2.21 | 511 | Method 1 |
| 322 | — | — | 2.71 | 499 | Method 1 |
| 323 | — | — | 3.58 | 497 | Method 1 |
| 324 | — | — | 2.11 | 497 | Method 1 |
| 325 | — | — | 2.64 | 483 | Method 1 |
| 327 | — | — | 3.33 | 511 | Method 1 |
| 328 | — | — | 2.02 | 538 | Method 1 |
| 329 | — | — | 2.54 | 494 | Method 1 |
| 330 | — | — | 2.56 | 508 | Method 1 |
| 331 | — | — | 2.80 | 476 | Method 1 |
| 332 | — | — | 2.64 | 428 | Method 1 |
| 333 | — | — | 2.83 | 511 | Method 1 |
| 334 | — | — | 2.63 | 412 | Method 1 |
| 335 | — | — | 3.03 | 446 | Method 1 |
| 336 | — | — | 3.07 | 481 | Method 1 |
| 337 | — | — | 2.20 | 524 | Method 1 |
| 338 | — | — | 2.68 | 465 | Method 1 |
| 339 | — | — | 3.09 | 412 | Method 1 |
| 340 | — | — | 2.13 | 527 | Method 1 |
| 342 | — | — | 3.18 | 444 | Method 1 |
| 343 | — | — | 2.66 | 497 | Method 1 |
| 345 | >250 | K | 2.86 | 541 | Method 2 |
| 346 | >250 | K | 2.86 | 541 | Method 2 |
| 347 | >250 | K | 2.75 | 556 | Method 3 |
| 348 | >250 | K | 2.75 | 556 | Method 3 |
| 349 | >250 | K | 2.03 | 509 | Method 3 |
| 350 | >250 | K | 2.18 | 525 | Method 3 |
| 351 | >250 | K | 2.07 | 525 | Method 3 |
| 352 | >250 | K | 1.97 | 509 | Method 3 |
| 353 | 210 | K | 3.35 | 382 | Method 2 |
| 354 | 236 | DSC | 2.73 | 398 | Method 2 |
| 355 | 221 | DSC | 2.64 | 382 | Method 2 |
| 356 | 208 | K | 2.69 | 442 | Method 2 |
| 357 | — | — | 3.35 | 497 | Method 1 |
| 359 | — | — | 2.11 | 458 | Method 1 |
| 360 | — | — | 2.14 | 419 | Method 1 |
| 361 | — | — | 2.98 | 467 | Method 1 |
| 362 | — | — | 3.26 | 487 | Method 1 |
| 363 | — | — | 2.76 | 458 | Method 1 |
| 364 | — | — | 3.01 | 478 | Method 1 |
| 365 | — | — | 3.08 | 471 | Method 1 |
| 366 | — | — | 2.74 | 451 | Method 1 |
| 367 | — | — | 3.13 | 527 | Method 1 |
| 368 | — | — | 2.94 | 511 | Method 1 |
| 369 | — | — | 2.87 | 518 | Method 1 |
| 370 | — | — | 2.13 | 524 | Method 1 |
| 371 | — | — | 2.32 | 540 | Method 1 |
| 372 | — | — | 3.04 | 514 | Method 1 |

NMR

The NMR experiments were carried out using a Bruker Avance 500 III using internal deuterium lock and equipped with reverse triple-resonance ($^1$H, $^{13}$C, $^{15}$N TXI) probe head or using a Bruker Avance DRX 400 spectrometer at ambient temperature, using internal deuterium lock and equipped with reverse double-resonance ($^1$H, $^{13}$C, SEI) probe head with z gradients and operating at 400 MHz for the proton and 100 MHz for carbon. Chemical shifts (δ) are reported in parts per million (ppm). J values are expressed in Hz.

Compound 2: $^1$H NMR (500 MHz, DMSO-d$_6$): δ ppm 8.55 (s, 1H) 8.53 (d, J=4.1 Hz, 1H) 8.35 (d, J=8.2 Hz, 1H) 8.23 (s, 1H) 8.19 (d, J=7.9 Hz, 1H) 7.90 (s, 1H) 7.51-7.54 (m, 2H) 7.31 (s, 1H) 5.01-5.06 (m, 1H) 3.97-4.06 (m, 1H) 3.95 (s, 3H) 3.87-3.92 (n, 2H) 3.56 (d, J=9.8 Hz, 1H) 3.36-3.49 (m, 4H) 3.22 (d, J=9.8 Hz, 1H) 1.73-1.81 (m, 2H) 1.50-1.67 (m, 2H) 1.29 (s, 3H).

Compound 3S: $^1$H NMR (500 MHz, DMSO-d$_6$): δ ppm 8.54-8.61 (m, 1H) 8.32 (d, J=5.4 Hz, 1H) 8.12 (s, 1H) 7.90-7.94 (m, 1H) 7.84 (s, 1H) 7.24 (d, J=5.4 Hz, 1H) 7.11 (s, 1H) 6.27 (s, 1H) 4.98 (t, J=5.4 Hz, 1H) 3.86 (s, 3H) 3.79 (s, 4H) 3.54-3.62 (m, 5H) 3.41-3.47 (m, 1H) 3.35-3.40 (m, 1H) 3.18 (d, J=9.1 Hz, 1H) 1.75 (t, J=5.0 Hz, 4H) 1.28 (s, 3H).

Compound 6S: $^1$H NMR (500 MHz, DMSO-d$_6$): δ ppm 8.60 (d, J=1.9 Hz, 1H) 8.45 (s, 1H) 8.36-8.40 (m, 1H) 7.91-7.98 (m, 2H) 7.31 (d, J=5.4 Hz, 1H) 7.15 (s, 1H) 6.86 (s, 1H) 4.99 (t, J=5.4 Hz, 1H) 3.91 (s, 3H) 3.72-3.79 (m, 4H) 3.58 (d, J=9.8 Hz, 1H) 3.41-3.49 (m, 1H) 3.35-3.41 (m, 1H) 3.19 (d, J=9.8 Hz, 1H) 2.96-3.02 (m, 4H) 1.29 (s, 3H).

Compound 7S: $^1$H NMR (500 MHz, DMSO-d$_6$): δ ppm 8.57 (d, J=1.9 Hz, 1H) 8.32 (d, J=5.4 Hz, 1H) 7.90-7.97 (m, 2H) 7.83 (s, 1H) 7.22 (d, J=5.4 Hz, 1H) 7.10 (s, 1H) 6.23 (d, J=8.5 Hz, 1H) 4.99 (br t, J=5.0 Hz, 1H) 3.83 (s, 3H) 3.68-3.72 (m, 4H) 3.53-3.58 (m, 5H) 3.40-3.46 (m, 1H) 3.34-3.40 (m, 1H, partially obscured by solvent peak) 3.18 (d, J=9.5 Hz, 1H) 1.76 (br t, J=5.2 Hz, 4H) 1.28 (s, 3H).

Compound 8: $^1$H NMR (500 MHz, DMSO-d$_6$): δ ppm 8.62-8.67 (m, 2H) 8.46 (d, J=5.4 Hz, 1H) 8.33 (d, J=7.6 Hz, 1H) 8.10 (s, 1H) 7.95-7.98 (m, 1H) 7.41 (d, J=5.4 Hz, 1H) 7.20 (s, 1H) 7.08 (s, 1H) 5.00 (t, J=5.4 Hz, 1H) 3.91-4.03 (m, 4H) 3.84-3.89 (m, 2H) 3.59 (d, J=9.5 Hz, 1H) 3.43-3.48 (m, 1H) 3.36-3.43 (m, 3H) 3.20 (d, J=9.8 Hz, 1H) 1.76-1.83 (m, 2H) 1.48-1.58 (m, 2H) 1.30 (s, 3H).

Compound 9: $^1$H NMR (500 MHz, DMSO-d$_6$): δ ppm 8.62-8.66 (m, 2H) 8.46 (d, J=5.4 Hz, 1H) 8.12 (s, 1H) 7.98-8.04 (m, 1H) 7.42 (d, J=5.4 Hz, 1H) 7.21 (s, 1H) 7.05 (d, J=9.1 Hz, 1H) 3.93-4.02 (m, 1H) 3.91 (d, J=3.5 Hz, 3H) 3.41-3.48 (m, 1H) 3.33-3.35 (m, 4H, partially obscured by solvent peak) 3.26 (s, 3H) 3.02-3.15 (m, 1H) 1.85-1.97 (m, 1H) 1.76-1.85 (m, 1H) 1.41-1.57 (m, 2H) 1.32 (s, 6H).

Compound 12: $^1$H NMR (500 MHz, DMSO-d$_6$): δ ppm 8.68-8.72 (m, 1H) 8.64-8.67 (m, 1H) 8.53 (d, J=5.4 Hz, 1H) 8.41 (s, 1H) 7.96-8.00 (m, 1H) 7.50 (d, J=5.4 Hz, 1H) 7.30 (d, J=6.3 Hz, 1H) 7.23 (s, 1H) 5.02 (t, J=5.5 Hz, 1H) 3.99 (s, 3H) 3.58 (d, J=9.8 Hz, 1H) 3.43-3.49 (m, 1H) 3.36-3.42 (m, 1H) 3.30 (s, 3H) 3.21 (d, J=9.5 Hz, 1H) 1.30 (s, 3H).

Compound 14: $^1$H NMR (500 MHz, DMSO-d$_6$): δ ppm 8.58-8.63 (m, 1H) 8.41 (s, 1H) 8.37 (d, J=5.4 Hz, 1H) 7.94-7.96 (m, 1H) 7.92 (s, 1H) 7.31 (d, J=5.4 Hz, 1H) 7.14 (s, 1H) 6.85 (s, 1H) 4.99 (t, J=5.4 Hz, 1H) 3.90 (s, 3H) 3.58 (d, J=9.5 Hz, 1H) 3.42-3.47 (m, 1H) 3.36-3.41 (m, 1H) 3.19 (d, J=9.5 Hz, 1H) 2.95-3.01 (m, 4H) 2.67-2.74 (m, 1H) 2.58-2.63 (m, 4H) 1.29 (s, 3H) 1.02 (s, 3H) 1.01 (s, 3H).

Compound 15: $^1$H NMR (500 MHz, DMSO-d$_6$) δ ppm 8.61-8.64 (m, 2H) 8.45 (d, J=5.4 Hz, 1H) 7.95-7.98 (m, 1H) 7.94 (s, 1H) 7.40 (d, J=5.4 Hz, 1H) 7.19 (s, 1H) 7.14 (d, J=8.8 Hz, 1H) 6.99 (dd, J=8.7, 2.7 Hz, 1H) 4.98-5.02 (m, 1H) 4.46-4.58 (m, 1H) 3.59 (d, J=9.5 Hz, 1H) 3.42-3.48 (m, 1H) 3.36-3.41 (m, 1H) 3.20 (d, J=9.5 Hz, 1H) 2.52-2.53 (m, 2H, partially obscured by solvent peak) 2.20-2.29 (m, 2H) 2.17 (s, 3H) 1.90-1.99 (m, 2H) 1.69-1.80 (m, 2H) 1.30 (s, 3H).

Compound 16: $^1$H NMR (500 MHz, DMSO-d$_6$): δ ppm 8.51-8.65 (m, 1H) 8.41 (s, 1H) 8.37 (d, J=5.4 Hz, 1H) 7.93-7.98 (m, 1H) 7.91 (s, 1H) 7.30 (d, J=5.7 Hz, 1H) 7.12-7.16 (m, 1H) 6.83 (s, 1H) 4.99 (t, J=5.4 Hz, 1H) 4.69 (d, J=4.4 Hz, 1H) 3.89 (s, 3H) 3.54-3.70 (m, 2H) 3.35-3.48 (m, 2H) 3.08-3.24 (m, 3H) 2.70-2.82 (m, 2H) 1.80-1.91 (m, 2H) 1.49-1.63 (m, 2H) 1.29 (s, 3H).

OR

Optical Rotation is measured with a polarimeter such as e.g. 341 Perkin Elmer, an Autopol IV automatic polarimeter (Rodolph research analytical) or a P-2000 (Jasco).

Specific rotation (OR): $[α]^θ_λ = (100*α)/(c*l)$

α (measured rotation) is the angle through which plane polarized light is rotated by a solution of mass concentration c and path length l. Concentration is in grams per 100 mL; path length l is in decimeters and is 1.000 decimeter.

θ is the temperature (° C.) and λ the wavelength of the light used.

Unless otherwise indicated, temperature is 20° C., and the sodium D line is used (589 nanometer).

OR data: Solvent: DMF (unless otherwise indicated); temperature: 20° C. (unless otherwise indicated); wavelength: 589 nm (unless otherwise indicated); 'Conc.' means concentration of the sample in grams per 100 mL; 'OR' means optical rotation (specific rotation); 'No' means compound number

| No | OR (°) | Concentration (g/100 mL) |
|---|---|---|
| 16 | +31.85 | 0.270 |
| 345 | −35.96 | 0.236 |
| 346 | +33.93 | 0.195 |
| 354 | +39.67 | 0.300 |
| 355 | +30.00 | 0.290 |
| 356 | +23.58 | 0.255 |

Pharmacological Part
Biological Assay A
Inhibition of Recombinant Human NF-kappaB-Inducing Kinase (NIK/MAP3K14) Activity Assay buffer was 50 mM Tris pH 7.5 containing 1 mM EGTA (ethylene glycol tetraacetic acid), 1 mM DTT (dithiothreitol), 0.1 mM Na$_3$VO$_4$, 5 mM MgCl$_2$, 0.01% Tween® 20. Assays were carried out in 384 well Mesoscale high binding plates which had been coated with myelin basic protein (MBP) and blocked with bovine serum albumin to prevent non-specific protein binding. All compounds tested were dissolved in dimethyl sulfoxide (DMSO) and further dilutions were made in assay buffer. Final DMSO concentration was 1% (v/v) in assays. Incubations consisted of compound (1% DMSO in control and blank wells), 25 μM Adenosine-Υ-triphosphate (ATP), and 10 nM NIK/MAP3K14 substituting enzyme with buffer in the blank wells. Incubations were carried out for 1 h at 25° C. and were followed by washing and sequential incubation with rabbit anti-phospho-MBP and anti-rabbit Ig Sulfotag antibody before reading bound Sulfotag on a Mesoscale Discovery. Signal obtained in the wells containing blank samples was subtracted from all other wells and IC$_5$'s were determined by fitting a sigmoidal curve to % inhibition of control versus Log$_{10}$ compound concentration.

Biological Assay B
Inhibition of Auto-Phosphorylation of Recombinant Human NF-kappaB-Inducing Kinase (NIK/MAP3K14) Activity (AlphaScreen®)

NIK/MAP3K14 auto-phosphorylation activity was measured using the AlphaScreen® (αscreen) format (Perkin Elmer). All compounds tested were dissolved in dimethyl sulfoxide (DMSO) and further dilutions were made in assay buffer. Final DMSO concentration was 1% (v/v) in assays. Assay buffer was 50 mM Tris pH 7.5 containing 1 mM EGTA (ethylene glycol tetraacetic acid), 1 mM DTT (dithiothreitol), 0.1 mM Na$_3$VO$_4$, 5 mM MgCl$_2$, 0.01% Tween® 20. Assays were carried out in 384 well Alphaplates (Perkin Elmer). Incubations consisted of compound, 25 microM Adenosine-5'-triphosphate (ATP), and 0.2 nM NIK/MAP3K14. Incubations were initiated by addition of GST-tagged NIK/MAP3K14 enzyme, carried out for 1 h at 25° C. and terminated by addition of stop buffer containing anti-phospho-IKK Ser176/180 antibody. Protein A Acceptor and Glutathione-Donor beads were added before reading using an EnVision® Multilabel Plate Reader (Perkin Elmer). Signal obtained in the wells containing blank samples was subtracted from all other wells and IC$_{50}$'s were determined by fitting a sigmoidal curve to % inhibition of control versus Log$_{10}$ compound concentration.

Assay B was performed at 2 different locations. The results for each location are reported in a separate column of the table below.

Biological Assay C
Effect of Compounds on P-IKKα Levels in L363 (NIK Translocated Multiple Myeloma) Cells All compounds tested were dissolved in DMSO and further dilutions were made in culture medium. Final DMSO concentration was 1% (v/v) in cell assays. The human L363 cells (ATCC) were cultured in RPMI 1640 medium supplemented with GlutaMax and 10% fetal calf serum (PAA). Cells were routinely maintained at densities of $0.2 \times 10^6$ cells per ml-$1 \times 10^6$ cells per ml at 37° C. in a humidified 5% $CO_2$ atmosphere. Cells were passaged twice a week splitting back to obtain the low density. Cells were seeded in 96 well plates (Nunc 167008) at $2 \times 10^6$ per ml media in a volume of 75 µl per well plus 25 µl µg/ml recombinant human B-cell activating factor (BAFF/BLyS/TNFSF13B). Seeded cells were incubated at 37° C. in a humidified 5% $CO_2$ atmosphere for 24 hr. Drugs and/or solvents were added (20 µl) to a final volume of 120 µl. Following 2 hr treatment plates were removed from the incubator and cell lysis was achieved by the addition of 30 µl 5× lysis buffer followed by shaking on a plate shaker at 4° C. for 10 min. At the end of this incubation lysed cells were centrifuged at 800×g for 20 min at 4° C. and the lysate was assessed for P-IKKα levels by sandwich immuno-assay carried out in anti-rabbit antibody coated Mesoscale plates. Within an experiment, the results for each treatment were the mean of 2 replicate wells. For initial screening purposes, compounds were tested using an 8 point dilution curve (serial 1:3 dilutions). For each experiment, controls (containing MG132 and BAFF but no test drug) and a blank incubation (containing MG132 and BAFF and 1 µM ADS125117, a test concentration known to give full inhibition) were run in parallel. The blank incubation value was subtracted from all control and sample values. To determine the $IC_{50}$ a sigmoidal curve was fitted to the plot of % inhibition of control P-IKKα levels versus $Log_{10}$ compound concentration.

Assay C was performed at 2 different locations. The results for each location are reported in a separate column of the table below.

Data for the compounds of the invention in the above assays are provided in Table A (the values in Table are averaged values over all measurements on all batches of a compound; values as IC50 (nM)). ('n.c.' means not calculated: 'Co.' means compound)

TABLE A

| Co. | Assay A Biochemical (MSD MBP) IC50 (nM) | Assay B location 1 IC50 (nM) | Assay B location 2 IC50 (nM) | Assay C location 1 IC50 (nM) | Assay C location 2 IC50 (nM) |
|---|---|---|---|---|---|
| 17 | n.d. | n.d. | n.d. | n.d. | n.d. |
| 21 | n.d. | n.d. | n.d. | n.d. | n.d. |
| 22 | n.d. | n.d. | n.d. | n.d. | n.d. |
| 24 | n.d. | n.d. | n.d. | n.d. | n.d. |
| 359 | n.d. | n.d. | n.d. | n.d. | n.d. |
| 28 | n.d. | n.d. | n.d. | n.d. | n.d. |
| 31 | n.d. | n.d. | n.d. | n.d. | n.d. |
| 32 | n.d. | n.d. | n.d. | n.d. | n.d. |
| 33 | n.d. | n.d. | n.d. | n.d. | n.d. |
| 34 | n.d. | n.d. | 1.6 | n.d. | n.d. |
| 35 | n.d. | n.d. | n.d. | n.d. | 851.1 |
| 36 | n.d. | n.d. | n.d. | n.d. | 616.6 |
| 42 | n.d. | n.d. | n.d. | n.d. | 166.0 |
| 43 | n.d. | n.d. | n.d. | n.d. | 281.8 |
| 44 | 20.0 | n.d. | 2.5 | n.d. | 243.2 |
| 46 | 3.3 | n.d. | 2.8 | n.d. | ~129 |
| 49 | 6.2 | n.d. | 1.8 | 549.5 | 43.7 |
| 50 | 7.4 | n.d. | 1.2 | n.d. | 81.3 |
| 51 | 6.9 | n.d. | n.d. | n.d. | 112.2 |
| 53 | 4.1 | n.d. | n.d. | n.d. | 173.8 |
| 54 | 8.9 | n.d. | 3.4 | 263.0 | 372.8 |
| 55 | 32.4 | n.d. | 3.3 | n.d. | 288.4 |
| 60 | 5.5 | n.d. | 1.2 | n.d. | 407.4 |
| 62 | 5.5 | n.d. | 1.4 | n.d. | 43.7 |
| 63 | 8.3 | n.d. | n.d. | n.d. | 75.9 |
| 64 | 13.5 | n.d. | n.d. | n.d. | 407.4 |
| 65 | 24.0 | n.d. | n.d. | n.d. | 616.6 |
| 66 | 10.7 | n.d. | n.d. | n.d. | 363.1 |
| 67 | 45.7 | n.d. | n.d. | n.d. | 1659.6 |
| 72 | 6.5 | n.d. | n.d. | n.d. | 53.7 |
| 74 | 6.8 | n.d. | n.d. | n.d. | 67.6 |
| 75 | 12.3 | n.d. | n.d. | n.d. | 134.9 |
| 76 | 13.5 | n.d. | n.d. | n.d. | 182.0 |
| 77 | 56.2 | n.d. | n.d. | n.d. | 125.9 |
| 78 | 16.6 | n.d. | n.d. | n.d. | >10000 |
| 79 | 11.8 | n.d. | 1.3 | 660.7 | 74.1 |
| 80 | 39.8 | n.d. | n.d. | n.d. | 645.7 |
| 81 | 14.8 | n.d. | 2.6 | n.d. | 588.8 |
| 82 | 24.6 | n.d. | 2.7 | n.d. | 281.8 |
| 83 | 35.5 | n.d. | n.d. | n.d. | 2691.5 |
| 84 | 5.4 | n.d. | 4.8 | n.d. | 49.0 |
| 85 | 14.1 | n.d. | 3.0 | n.d. | 67.6 |
| 86 | 15.1 | n.d. | 11.2 | n.d. | 549.5 |
| 87 | 21.4 | 17.8 | 13.5 | n.d. | 1148.2 |
| 360 | 77.6 | n.d. | 33.9 | n.d. | 912.0 |
| 89 | 63.1 | n.d. | 20.4 | n.d. | 5011.9 |
| 1 | 12.0 | n.d. | 2.6 | n.d. | 128.8 |
| 90 | 14.8 | n.d. | 5.1 | n.d. | 758.6 |
| 91 | 338.8 | n.d. | n.d. | n.d. | >10000 |
| 94 | 346.7 | n.d. | n.d. | n.d. | ~10000 |
| 96 | 13.5 | n.d. | n.d. | n.d. | ~6309 |
| 97 | ~501 | >10000 | n.d. | n.d. | n.d. |
| 98 | 13.5 | n.d. | n.d. | n.d. | 93.3 |
| 99 | 7.4 | n.d. | n.d. | n.d. | 144.5 |
| 100 | 6.6 | n.d. | n.d. | n.d. | 173.8 |
| 103 | 154.9 | n.d. | n.d. | n.d. | 3090.3 |
| 104 | 61.7 | n.d. | n.d. | n.d. | 398.1 |
| 105 | 30.2 | n.d. | n.d. | n.d. | 436.5 |
| 106 | 15.9 | n.d. | n.d. | n.d. | 95.5 |
| 107 | 13.5 | n.d. | n.d. | n.d. | 72.4 |
| 108 | 15.1 | n.d. | n.d. | n.d. | 102.3 |
| 109 | 10.2 | n.d. | 5.5 | n.d. | 309.0 |
| 110 | 128.8 | n.d. | n.d. | n.d. | 2344.2 |
| 112 | 416.9 | n.d. | n.d. | n.d. | n.d. |
| 113 | 288.4 | n.d. | n.d. | n.d. | n.d. |
| 114 | 251.2 | n.d. | n.d. | n.d. | >10000 |
| 115 | 457.1 | n.d. | n.d. | n.d. | n.d. |
| 116 | 309.0 | n.d. | n.d. | n.d. | 3162.3 |
| 117 | 162.2 | n.d. | n.d. | n.d. | >10000 |
| 119 | 295.1 | n.d. | n.d. | n.d. | 5495.4 |
| 120 | 9.3 | n.d. | 7.8 | n.d. | 426.6 |
| 121 | 11.2 | n.d. | 7.2 | n.d. | 380.2 |
| 124 | 7.8 | n.d. | n.d. | n.d. | 2754.2 |
| 125 | 12.3 | 31.6 | n.d. | n.d. | 1230.3 |
| 126 | 8.7 | 14.8 | n.d. | n.d. | 537.0 |
| 128 | 7.9 | n.d. | n.d. | n.d. | 190.6 |
| 129 | 15.9 | n.d. | n.d. | n.d. | 229.1 |
| 130 | 10.2 | n.d. | 10.7 | n.d. | 660.7 |
| 131 | 4.5 | n.d. | 0.9 | n.d. | 70.8 |
| 132 | 3.3 | 10.0 | 3.1 | n.d. | 512.9 |
| 133 | 5.8 | n.d. | n.d. | n.d. | 128.8 |
| 134 | 3.9 | n.d. | 4.4 | n.d. | 776.3 |
| 135 | >10000 | n.d. | n.d. | n.d. | n.d. |
| 136 | n.d. | n.d. | 3.3 | 354.8 | 229.1 |
| 137 | n.d. | n.d. | 5.0 | 338.8 | 346.7 |
| 138 | n.d. | n.d. | 6.3 | n.d. | 234.4 |
| 139 | n.d. | n.d. | 6.9 | 166.0 | 102.3 |
| 140 | n.d. | n.d. | 4.5 | n.d. | 1071.5 |
| 141 | n.d. | n.d. | 10.2 | n.d. | 147.9 |
| 142 | n.d. | n.d. | 13.5 | 309.0 | 204.2 |
| 143 | n.d. | 17.0 | 14.5 | n.d. | 223.9 |
| 145 | n.d. | n.d. | 7.2 | n.d. | 323.6 |
| 147 | n.d. | n.d. | 4.1 | n.d. | 52.5 |
| 148 | n.d. | n.d. | 4.8 | n.d. | 158.5 |
| 2 | n.d. | 5.5 | | n.d. | 69.2 |
| 150 | n.d. | n.d. | 5.4 | n.d. | 104.7 |
| 151 | n.d. | n.d. | 17.8 | ~912 | 676.1 |
| 152 | n.d. | n.d. | 11.2 | n.d. | n.d. |
| 153 | n.d. | 18.6 | n.d. | n.d. | 426.6 |
| 154 | n.d. | n.d. | 19.1 | n.d. | n.d. |

TABLE A-continued

| Co. | Assay A Biochemical (MSD MBP) IC50 (nM) | Assay B location 1 IC50 (nM) | Assay B location 2 IC50 (nM) | Assay C location 1 IC50 (nM) | Assay C location 2 IC50 (nM) |
| --- | --- | --- | --- | --- | --- |
| 155 | n.d. | n.d. | 38.0 | n.d. | n.d. |
| 156 | n.d. | n.d. | 3.2 | n.d. | n.d. |
| 157 | n.d. | n.d. | 63.1 | n.d. | n.d. |
| 158 | n.d. | n.d. | 15.1 | n.d. | n.d. |
| 159 | n.d. | n.d. | 12.6 | n.d. | n.d. |
| 160 | n.d. | n.d. | 18.6 | n.d. | n.d. |
| 163 | n.d. | n.d. | 12.0 | n.d. | n.d. |
| 164 | n.d. | n.d. | 5.6 | n.d. | n.d. |
| 165 | n.d. | n.d. | 23.4 | n.d. | n.d. |
| 166 | n.d. | n.d. | 18.2 | n.d. | n.d. |
| 167 | n.d. | n.d. | 19.1 | n.d. | n.d. |
| 168 | n.d. | n.d. | 3.6 | n.d. | n.d. |
| 169 | n.d. | n.d. | 8.9 | n.d. | n.d. |
| 170 | n.d. | 45.7 | 27.6 | n.d. | n.d. |
| 171 | n.d. | n.d. | 12.3 | n.d. | n.d. |
| 172 | n.d. | 75.9 | 71.6 | n.d. | n.d. |
| 173 | n.d. | n.d. | 10.0 | n.d. | n.d. |
| 174 | n.d. | n.d. | 32.4 | n.d. | n.d. |
| 175 | n.d. | n.d. | 33.9 | n.d. | n.d. |
| 176 | n.d. | n.d. | 12.6 | n.d. | n.d. |
| 177 | n.d. | n.d. | 32.4 | n.d. | n.d. |
| 178 | n.d. | n.d. | 14.1 | n.d. | n.d. |
| 179 | n.d. | n.d. | 22.4 | n.d. | n.d. |
| 180 | n.d. | n.d. | 204.2 | n.d. | n.d. |
| 181 | n.d. | n.d. | 2.2 | n.d. | n.d. |
| 182 | n.d. | n.d. | 3.0 | n.d. | n.d. |
| 183 | n.d. | n.d. | 1.4 | n.d. | n.d. |
| 184 | n.d. | n.d. | 3.4 | n.d. | n.d. |
| 185 | n.d. | n.d. | 3.8 | n.d. | n.d. |
| 186 | n.d. | n.d. | 40.7 | n.d. | n.d. |
| 187 | n.d. | n.d. | 18.2 | n.d. | n.d. |
| 188 | n.d. | n.d. | 5.5 | n.d. | n.d. |
| 189 | n.d. | n.d. | 6.9 | n.d. | n.d. |
| 190 | n.d. | n.d. | 2.2 | n.d. | n.d. |
| 191 | n.d. | n.d. | ~27 | n.d. | n.d. |
| 192 | n.d. | n.d. | 26.9 | n.d. | n.d. |
| 193 | n.d. | n.d. | 22.9 | n.d. | n.d. |
| 194 | n.d. | n.d. | 21.9 | n.d. | n.d. |
| 195 | n.d. | n.d. | 49.0 | n.d. | n.d. |
| 196 | n.d. | n.d. | 4.0 | n.d. | n.d. |
| 197 | n.d. | n.d. | 11.2 | n.d. | n.d. |
| 198 | n.d. | n.d. | 8.5 | n.d. | n.d. |
| 199 | n.d. | n.d. | 4.5 | n.d. | n.d. |
| 200 | n.d. | n.d. | 131.8 | n.d. | n.d. |
| 202 | n.d. | n.d. | 26.9 | n.d. | n.d. |
| 203 | n.d. | n.d. | 30.9 | n.d. | n.d. |
| 204 | n.d. | n.d. | 10.7 | n.d. | n.d. |
| 205 | n.d. | n.d. | 5.1 | n.d. | n.d. |
| 206 | n.d. | n.d. | 38.0 | n.d. | n.d. |
| 207 | n.d. | n.d. | 16.6 | n.d. | n.d. |
| 208 | n.d. | n.d. | 5.0 | n.d. | n.d. |
| 209 | n.d. | n.d. | 109.7 | n.d. | n.d. |
| 210 | n.d. | n.d. | 30.9 | n.d. | n.d. |
| 211 | n.d. | n.d. | 49.0 | n.d. | n.d. |
| 212 | n.d. | n.d. | 22.4 | n.d. | n.d. |
| 213 | n.d. | n.d. | 13.8 | n.d. | n.d. |
| 214 | n.d. | n.d. | 12.0 | n.d. | n.d. |
| 215 | n.d. | n.d. | 12.9 | n.d. | n.d. |
| 216 | n.d. | n.d. | 47.9 | n.d. | n.d. |
| 217 | n.d. | n.d. | 27.5 | n.d. | n.d. |
| 218 | n.d. | n.d. | 15.1 | n.d. | n.d. |
| 219 | n.d. | n.d. | 61.7 | n.d. | n.d. |
| 220 | n.d. | n.d. | 2.5 | n.d. | n.d. |
| 221 | n.d. | n.d. | 10.5 | n.d. | n.d. |
| 222 | n.d. | n.d. | 2.6 | n.d. | n.d. |
| 223 | n.d. | n.d. | 63.1 | n.d. | n.d. |
| 224 | n.d. | n.d. | 38.0 | n.d. | n.d. |
| 225 | n.d. | 13.2 | 10.2 | n.d. | n.d. |
| 226 | n.d. | 7.4 | 4.1 | n.d. | n.d. |
| 227 | n.d. | 72.4 | 41.7 | n.d. | n.d. |
| 228 | n.d. | n.d. | 26.3 | n.d. | n.d. |
| 229 | n.d. | 45.7 | 37.2 | n.d. | n.d. |
| 230 | n.d. | 7.4 | 6.6 | n.d. | n.d. |
| 233 | n.d. | 32.4 | 33.1 | n.d. | n.d. |
| 234 | n.d. | 61.7 | 38.9 | n.d. | n.d. |
| 238 | n.d. | ~6607 | >10000 | n.d. | n.d. |
| 239 | n.d. | 389.1 | 354.8 | n.d. | n.d. |
| 241 | n.d. | 1862.1 | ~3090 | n.d. | n.d. |
| 242 | n.d. | 35.5 | 13.8 | n.d. | n.d. |
| 243 | n.d. | n.d. | 10.0 | n.d. | n.d. |
| 6 | n.d. | 4.7 | 4.0 | n.d. | n.d. |
| 244 | n.d. | n.d. | n.d. | n.d. | n.d. |
| 5 | n.d. | 6.3 | 4.1 | n.d. | n.d. |
| 4 | n.d. | 10.5 | 2.9 | 138.0 | n.d. |
| 3 | n.d. | 10.0 | 2.2 | n.d. | n.d. |
| 245 | n.d. | n.d. | 3.6 | n.d. | n.d. |
| 246 | n.d. | 30.9 | 17.8 | ~1995 | n.d. |
| 247 | n.d. | 38.0 | 22.4 | n.d. | n.d. |
| 248 | n.d. | n.d. | 1.3 | n.d. | n.d. |
| 249 | n.d. | n.d. | 17.8 | n.d. | n.d. |
| 250 | n.d. | 912.0 | 1230.3 | n.d. | n.d. |
| 251 | n.d. | >10000 | 6760.8 | n.d. | n.d. |
| 252 | n.d. | n.d. | 7.4 | n.d. | n.d. |
| 3S | n.d. | 6.7 | 1.3 | 17.3 | n.d. |
| 3R | n.d. | 18.3 | 5.7 | n.d. | n.d. |
| 5R | n.d. | n.d. | 31.6 | n.d. | n.d. |
| 4S | n.d. | n.d. | 2.3 | ~151 | n.d. |
| 4R | n.d. | 55.0 | 36.3 | n.d. | n.d. |
| 5S | n.d. | n.d. | 1.6 | n.d. | n.d. |
| 253 | n.d. | 102.3 | 42.7 | n.d. | n.d. |
| 254 | n.d. | 6.5 | 3.6 | n.d. | n.d. |
| 365 | n.d. | 13.8 | 11.0 | n.d. | n.d. |
| 362 | n.d. | 6.9 | 3.6 | n.d. | n.d. |
| 363 | n.d. | 17.8 | 10.7 | n.d. | n.d. |
| 366 | n.d. | 22.9 | 12.9 | n.d. | n.d. |
| 361 | n.d. | 7.8 | 3.7 | n.d. | n.d. |
| 364 | n.d. | 10.2 | 6.9 | n.d. | n.d. |
| 6S | n.d. | 4.0 | 2.4 | n.d. | n.d. |
| 6R | n.d. | 19.1 | 27.7 | n.d. | n.d. |
| 255 | n.d. | 10.2 | 7.2 | n.d. | n.d. |
| 256 | n.d. | 154.9 | 154.9 | n.d. | n.d. |
| 257 | n.d. | 3.0 | 3.4 | n.d. | n.d. |
| 258 | n.d. | 91.2 | 25.7 | n.d. | n.d. |
| 259 | n.d. | 3.6 | 3.8 | n.d. | n.d. |
| 260 | n.d. | 117.5 | 70.8 | n.d. | n.d. |
| 261 | n.d. | 8.3 | 7.2 | n.d. | n.d. |
| 262 | n.d. | 128.8 | 128.8 | n.d. | n.d. |
| 263 | n.d. | 128.8 | 53.7 | n.d. | n.d. |
| 264 | n.d. | 6.6 | 6.0 | n.d. | n.d. |
| 265 | n.d. | 47.9 | 35.5 | n.d. | n.d. |
| 266 | n.d. | 5.0 | 1.9 | n.d. | n.d. |
| 368 | n.d. | 190.6 | 112.2 | n.d. | n.d. |
| 367 | n.d. | 87.1 | 21.9 | n.d. | n.d. |
| 369 | n.d. | 123.0 | 64.6 | n.d. | n.d. |
| 370 | n.d. | 1621.8 | 977.2 | n.d. | n.d. |
| 371 | n.d. | 436.5 | 208.9 | n.d. | n.d. |
| 7 | n.d. | 15.5 | 2.6 | n.d. | n.d. |
| 267 | n.d. | 4.7 | 0.5 | 28.8 | n.d. |
| 268 | n.d. | 4.5 | 0.7 | n.d. | n.d. |
| 269 | n.d. | n.d. | 1.8 | 41.7 | n.d. |
| 270 | n.d. | 21.4 | 5.8 | n.d. | n.d. |
| 271 | n.d. | 10.2 | 2.6 | n.d. | n.d. |
| 7S | n.d. | 7.8 | 1.6 | n.d. | n.d. |
| 272 | n.d. | 151.4 | 123.0 | 9120.1 | n.d. |
| 274 | n.d. | 2691.5 | 1445.4 | n.d. | n.d. |
| 7R | n.d. | 70.8 | 19.1 | n.d. | n.d. |
| 275 | n.d. | 4.0 | 2.6 | n.d. | n.d. |
| 277 | n.d. | ~3 | 0.4 | 23.4 | n.d. |
| 278 | n.d. | 4.7 | 1.0 | n.d. | n.d. |
| 279 | n.d. | n.d. | 2.7 | n.d. | n.d. |
| 280 | n.d. | 6.9 | 2.5 | n.d. | n.d. |
| 281 | n.d. | 15.9 | 3.0 | n.d. | n.d. |
| 282 | n.d. | 77.6 | 13.8 | n.d. | n.d. |
| 283 | n.d. | 5.3 | 2.8 | n.d. | n.d. |
| 372 | n.d. | 13.4 | 1.6 | n.d. | n.d. |
| 284 | n.d. | 7.4 | 1.1 | n.d. | n.d. |
| 285 | n.d. | 7.8 | 1.8 | n.d. | n.d. |
| 286 | n.d. | 7244.4 | 3388.4 | n.d. | n.d. |
| 8 | n.d. | 4.6 | 1.6 | 8.3 | n.d. |
| 287 | n.d. | 3.9 | 1.3 | n.d. | n.d. |

TABLE A-continued

| Co. | Assay A Biochemical (MSD MBP) IC50 (nM) | Assay B location 1 IC50 (nM) | Assay B location 2 IC50 (nM) | Assay C location 1 IC50 (nM) | Assay C location 2 IC50 (nM) |
|---|---|---|---|---|---|
| 288 | n.d. | 112.2 | 57.5 | n.d. | n.d. |
| 289 | n.d. | 3.6 | 1.2 | n.d. | n.d. |
| 290 | n.d. | 3.1 | 1.4 | n.d. | n.d. |
| 291 | n.d. | 1.4 | 0.5 | n.d. | n.d. |
| 292 | n.d. | 4.3 | 1.6 | n.d. | n.d. |
| 293 | n.d. | 1.5 | 0.5 | n.d. | n.d. |
| 294 | n.d. | 12.0 | 2.3 | n.d. | n.d. |
| 295 | n.d. | 12.3 | 5.1 | n.d. | n.d. |
| 296 | n.d. | 5.3 | 1.2 | n.d. | n.d. |
| 297 | n.d. | 708.0 | 309.0 | n.d. | n.d. |
| 298 | n.d. | 8.1 | 2.3 | n.d. | n.d. |
| 299 | n.d. | 3.2 | 0.9 | 29.5 | n.d. |
| 300 | n.d. | 37.2 | 13.2 | n.d. | n.d. |
| 301 | n.d. | 5.4 | 1.1 | 23.4 | n.d. |
| 302 | n.d. | n.d. | 1.7 | n.d. | n.d. |
| 303 | n.d. | 13.8 | 4.8 | n.d. | n.d. |
| 304 | n.d. | 18.2 | 5.9 | n.d. | n.d. |
| 9 | n.d. | 5.3 | 1.8 | n.d. | n.d. |
| 307 | n.d. | 12.3 | 3.1 | n.d. | n.d. |
| 309 | n.d. | 6.8 | 2.2 | n.d. | n.d. |
| 311 | n.d. | 3.9 | 0.9 | n.d. | n.d. |
| 357 | n.d. | 12.0 | 10.0 | n.d. | n.d. |
| 313 | n.d. | 6.9 | 4.9 | n.d. | n.d. |
| 314 | n.d. | 4.1 | 3.1 | n.d. | n.d. |
| 11 | n.d. | 6.2 | 0.7 | n.d. | n.d. |
| 317 | n.d. | 1.6 | 1.7 | n.d. | n.d. |
| 318 | n.d. | 4.9 | 1.5 | n.d. | n.d. |
| 319 | n.d. | 4.2 | 1.2 | n.d. | n.d. |
| 320 | n.d. | 2.7 | 1.0 | n.d. | n.d. |
| 321 | n.d. | 3.6 | 1.6 | n.d. | n.d. |
| 322 | n.d. | n.d. | 1.7 | n.d. | n.d. |
| 12 | n.d. | 5.4 | 1.6 | 26.9 | n.d. |
| 323 | n.d. | 22.9 | 7.2 | n.d. | n.d. |
| 324 | n.d. | 7.9 | 3.8 | n.d. | n.d. |
| 325 | n.d. | n.d. | 3.6 | n.d. | n.d. |
| 14 | n.d. | ~3 | 0.9 | 19.5 | n.d. |
| 327 | n.d. | 6.3 | 2.3 | n.d. | n.d. |
| 328 | n.d. | n.d. | 1.5 | n.d. | n.d. |
| 329 | n.d. | 3.8 | 1.7 | n.d. | n.d. |
| 330 | n.d. | 3.6 | 0.7 | n.d. | n.d. |
| 331 | n.d. | 6.5 | n.d. | 79.4 | n.d. |
| 332 | n.d. | n.d. | 1.1 | n.d. | n.d. |
| 333 | n.d. | n.d. | 2.2 | n.d. | n.d. |
| 334 | n.d. | 3981.1 | n.d. | >10000 | n.d. |
| 335 | n.d. | 269.2 | n.d. | >10000 | n.d. |
| 15 | n.d. | 8.5 | n.d. | 478.6 | n.d. |
| 16 | n.d. | 3.2 | n.d. | 19.1 | n.d. |
| 336 | n.d. | n.d. | 3.6 | n.d. | n.d. |
| 337 | n.d. | n.d. | 1.6 | n.d. | n.d. |
| 338 | n.d. | 19.1 | n.d. | 3890.5 | n.d. |
| 339 | n.d. | n.d. | 5.6 | n.d. | n.d. |
| 340 | n.d. | n.d. | 2.6 | n.d. | n.d. |
| 342 | n.d. | 7.9 | 4.6 | 154.9 | n.d. |
| 343 | n.d. | 19.1 | n.d. | ~7413.1 | n.d. |
| 345 | n.d. | 19.1 | n.d. | n.d. | n.d. |
| 346 | n.d. | 7.4 | n.d. | n.d. | n.d. |
| 347 | n.d. | 144.5 | n.d. | n.d. | n.d. |
| 348 | n.d. | 14.8 | n.d. | nd. | n.d. |
| 349 | n.d. | 3.6 | n.d. | n.d. | n.d. |
| 350 | n.d. | 295.1 | n.d. | n.d. | n.d. |
| 351 | n.d. | 24.0 | n.d. | n.d. | n.d. |
| 352 | n.d. | 33.9 | n.d. | n.d. | n.d. |
| 353 | n.d. | 72.4 | n.d. | n.d. | n.d. |
| 354 | n.d. | 3.0 | n.d. | n.d. | n.d. |
| 355 | n.d. | 2.5 | n.d. | n.d. | n.d. |
| 356 | n.d. | 24.6 | n.d. | n.d. | n.d. |

Prophetic Composition Examples

"Active ingredient" (a.i.) as used throughout these examples relates to a compound of Formula (I), including any tautomer or stereoisomeric form thereof, or a pharmaceutically acceptable addition salt, or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:
1. A compound of Formula (I):

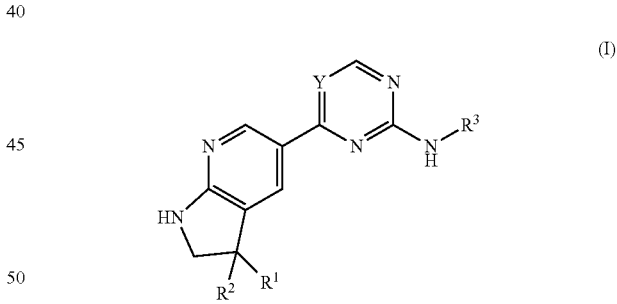

a tautomer or a stereoisomeric form thereof, wherein
$R^1$ represents $C_{1-4}$alkyl;
$R^2$ represents $C_{1-6}$alkyl, or $C_{1-6}$alkyl substituted with one $R^5$;
Y represents $CR^4$ or N;
$R^4$ represents hydrogen or halo;
$R^5$ represents halo, cyano, $Het^{3a}$, $-NR^{6a}R^{6b}$, or $-OR^7$;
$R^{6a}$ represents hydrogen or $C_{1-4}$alkyl;
$R^{6b}$ represents hydrogen; $C_{1-4}$alkyl; $C_{3-6}$cycloalkyl; $-C(=O)-C_{1-4}$alkyl; $-C(=O)-Het^4$; $-S(=O)_2-C_{1-4}$alkyl; $-C(=O)-C_{1-4}$alkyl substituted with one substituent selected from the group consisting of $-OH$ and $-NR^{16a}R^{16b}$; or $C_{1-4}$alkyl substituted with one substituent selected from the group consisting of $-OH$ and $-S(=O)_2-C_{1-4}$alkyl;

R$^7$ represents hydrogen, C$_{1-4}$alkyl, —C$_{1-4}$alkyl-NR$^{8a}$R$^{8b}$, —C(=O)—R$^9$, —S(=O)$_2$—OH, —P(=O)$_2$—OH, —(C=O)—CH(NH$_2$)—C$_{1-4}$alkyl-Ar$^1$, or —C$_{1-4}$alkyl-Het$^{3b}$;

R$^{8a}$ represents hydrogen or C$_{1-4}$alkyl;

R$^{8b}$ represents hydrogen, C$_{1-4}$alkyl, or C$_{3-6}$cycloalkyl;

R$^9$ represents C$_{1-4}$alkyl, or C$_{1-6}$alkyl substituted with one substituent selected from the group consisting of —NH$_2$, —COOH, and Het$^6$;

R$^{16a}$ and R$^{16b}$ each independently represents hydrogen, C$_{1-4}$alkyl or C$_{3-6}$cycloalkyl;

R$^3$ represents phenyl optionally substituted with one, two or three substituents each independently selected from the group consisting of halo; cyano; C$_{1-6}$alkyl; —O—C$_{1-4}$alkyl; —C(=O)—R$^{10}$; —S(=O)$_2$—C$_{1-4}$alkyl; —S(=O)(=N—R$^{20a}$)—C$_{1-4}$alkyl; —O—C$_{1-4}$alkyl substituted with one, two or three halo atoms; —O—C$_{1-4}$alkyl-R$^{12}$; C$_{3-6}$cycloalkyl; —O—C$_{3-6}$cycloalkyl; Het$^{1a}$; —O-Het$^{1b}$; R$^{18}$; R$^{21}$; —P(=O)—(C$_{1-4}$alkyl)$_2$; —NH—C(=O)—C$_{1-4}$alkyl; —NH—C(=O)—Het$^{1g}$; —NR$^{17a}$R$^{17b}$; C$_{1-6}$alkyl substituted with one, two or three halo atoms; C$_{1-4}$alkyl substituted with one, two or three —OH substituents; C$_{1-4}$alkyl substituted with one R$^{13}$; C$_{1-4}$alkyl substituted with one R$^{18}$; C$_{2-6}$alkenyl; C$_{2-6}$alkenyl substituted with one R$^{13}$; C$_{2-6}$alkynyl; and C$_{2-6}$alkynyl substituted with one R$^{13}$;

R$^{10}$ represents —OH, —O—C$_{1-4}$alkyl, —NR$^{11a}$R$^{11b}$ or Het$^2$;

R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;

R$^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with C$_{1-4}$alkyl or C$_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl in Het$^{1a}$, Het$^{1c}$ and Het$^{1d}$ may optionally be substituted, where possible, on one, two or three ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl or said 6- to 11-membered bicyclic saturated heterocyclyl in Het$^{1a}$, Het$^{1c}$ and Het$^{1d}$ may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, NH$_2$, —NH(C$_{1-4}$alkyl), and —N(C$_{1-4}$alkyl)$_2$;

Het$^{1b}$, Het$^{1e}$, Het$^{1g}$, Het$^4$, Het$^7$ and Het$^8$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$, Het$^4$, Het$^7$ and Het$^8$ containing one or two heteroatoms each independently selected from O, S, S(=O)$_p$ and N;

wherein said 4- to 7-membered monocyclic saturated heterocyclyl in Het$^{1b}$, Het$^{1e}$, Het$^{1g}$, Het$^4$, Het$^7$, and Het$^8$ may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl in Het$^{1b}$, Het$^{1e}$, Het$^{1g}$, Het$^4$, Het$^7$, and Het$^8$ may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^2$ represents a heterocyclyl of formula (b-1):

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with a substituent each independently selected from the group consisting of C$_{1-4}$alkyl, C$_{3-6}$cycloalkyl and Het$^7$; and wherein (b-1) may optionally be substituted on one, two or three ring C-atoms with one or two substituents each independently selected from the group consisting of halo, —OH, cyano, C$_{1-4}$alkyl, —O—C$_{1-4}$alkyl, —NH$_2$, —NH(C$_{1-4}$alkyl), —N(C$_{1-4}$alkyl)$_2$, and C$_{1-4}$alkyl-OH;

R$^{11b}$ represents hydrogen; Het$^{1e}$; C$_{1-4}$alkyl; —C$_{1-4}$alkyl-Het$^5$; —C$_{1-4}$alkyl-Het$^8$; C$_{1-4}$alkyl substituted with one, two or three substituents each independently selected from the group consisting of halo, —OH and —O—C$_{1-4}$ alkyl; C$_{3-6}$cycloalkyl; or C$_{3-6}$cycloalkyl substituted with one, two or three substituents each independently selected from the group consisting of halo, —OH and —O—C$_{1-4}$alkyl;

R$^{13}$ represents —O—C$_{1-4}$alkyl, —C(=O)NR$^{15a}$R$^{15b}$, —NR$^{19a}$R$^{19b}$, C$_{3-6}$cycloalkyl, Het$^{1d}$, or —C(=O)—Het$^{1f}$;

R$^{12}$ represents —OH, —O—C$_{1-4}$alkyl, —NR$^{14a}$R$^{14b}$, —C(=O)NR$^{14c}$R$^{14d}$, —S(=O)$_2$—C$_{1-4}$alkyl, —S(=O)(=N—R$^{20b}$)—C$_{1-4}$alkyl, C$_{3-6}$cycloalkyl, Ar$^2$, or Het$^{1c}$;

Ar$^1$ represents phenyl optionally substituted with one hydroxy;

Ar$^2$ represents phenyl optionally substituted with one C$_{1-4}$alkyl;

Het$^{3a}$, Het$^{3b}$, Het$^5$, Het$^6$ and Het$^{1f}$ each independently represents a heterocyclyl of formula (c-1):

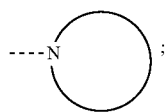

(c-1)

(c-1) represents a N-linked 4- to 7-membered monocyclic saturated heterocyclyl optionally containing one additional heteroatom selected from O, S, S(=O)$_p$ and N;
wherein in case (c-1) contains one additional N-atom, said additional N-atom may optionally be substituted with C$_{1-4}$alkyl or C$_{3-6}$cycloalkyl; and
wherein (c-1) may optionally be substituted on one or two ring C-atoms atoms with one or two substituents each independently selected from the group consisting of halo, C$_{1-4}$alkyl, and C$_{3-6}$cycloalkyl;
R$^{11a}$, R$^{14a}$, R$^{14c}$, R$^{15a}$, R$^{17a}$ and R$^{19a}$ each independently represents hydrogen or C$_{1-4}$alkyl;
R$^{14b}$, R$^{14d}$, R$^{15b}$, R$^{17b}$ and R$^{19b}$ each independently represents hydrogen; C$_{1-6}$alkyl; C$_{3-6}$cycloalkyl; —C(=O)—C$_{1-4}$alkyl; C$_{1-4}$alkyl substituted with one substituent selected from the group consisting of halo, —OH and —O—C$_{1-4}$alkyl; —C(=O)—C$_{1-4}$alkyl substituted with one substituent selected from the group consisting of halo, —OH and —O—C$_{1-4}$alkyl; or —S(=O)$_2$—C$_{1-4}$alkyl;
R$^{20a}$ and R$^{20b}$ each independently represents hydrogen; C$_{1-4}$alkyl; C$_{3-6}$cycloalkyl; or C$_{1-4}$alkyl substituted with one substituent selected from the group consisting of —OH and —O—C$_{1-4}$alkyl; and
p represents 1 or 2;
or a pharmaceutically acceptable addition salt, or a solvate thereof.

2. The compound according to claim 1, wherein
Y represents CR$^4$;
R$^5$ represents cyano or —OR$^7$;
R$^7$ represents hydrogen;
R$^3$ represents phenyl optionally substituted with one, two or three substituents each independently selected from the group consisting of halo; cyano; C$_{1-6}$alkyl; —O—C$_{1-4}$alkyl; —C(=O)—R$^{10}$; —S(=O)$_2$—C$_{1-4}$alkyl; —O—C$_{1-4}$alkyl substituted with one, two or three halo atoms; —O—C$_{1-4}$alkyl-R$^{12}$; C$_{3-6}$cycloalkyl; Het$^{1a}$; —O-Het$^{1b}$; R$^{18}$; —NH—C(=O)—C$_{1-4}$alkyl; —NR$^{17a}$R$^{17b}$; C$_{1-4}$alkyl substituted with one, two or three halo atoms; C$_{1-4}$alkyl substituted with one, two or three —OH substituents; C$_{1-4}$alkyl substituted with one R$^{13}$; and C$_{1-4}$alkyl substituted with one R$^{18}$;
R$^{10}$ represents —OH, —NR$^{11a}$R$^{11b}$ or Het$^2$;
R$^{18}$ represents a 5-membered aromatic ring containing one, two or three N-atoms; wherein said 5-membered aromatic ring may optionally be substituted with one C$_{1-4}$alkyl;
Het$^{1a}$, Het$^{1c}$ and Het$^{1d}$ each independently represents a 4- to 7-membered monocyclic saturated heterocyclyl containing one or two heteroatoms each independently selected from O and N; or a 6- to 11-membered bicyclic saturated heterocyclyl, including fused, spiro and bridged cycles, containing one, two or three heteroatoms each independently selected from O and N;
wherein said 4- to 7-membered monocyclic saturated heterocyclyl or said 6- to 11-membered bicyclic saturated heterocyclyl in Het$^{1a}$, Het$^{1c}$ and Het$^{1d}$ may optionally be substituted, where possible, on one, two or three ring N-atoms with a substituent each independently selected from the group consisting of C$_{1-4}$alkyl, C$_{3-6}$cycloalkyl, and C$_{1-4}$alkyl substituted with one —O—C$_{1-4}$alkyl; and
wherein said 4- to 7-membered monocyclic saturated heterocyclyl or said 6- to 11-membered bicyclic saturated heterocyclyl in Het$^{1a}$, Het$^{1c}$ and Het$^{1d}$ may optionally be substituted on one, two or three ring C-atoms with one or two substituents each independently selected from the group consisting of —OH, halo, C$_{1-4}$alkyl, cyano, —O—C$_{1-4}$alkyl, and —N(C$_{1-4}$alkyl)$_2$;
Het$^{1b}$ and Het$^{1e}$ each independently represents a 4- to 7-membered monocyclic saturated heterocyclyl, attached to the remainder of the molecule of Formula (I) through any available ring carbon atom, said Het$^{1b}$ and Het$^{1e}$ containing one or two heteroatoms each independently selected from O and N;
wherein said 4- to 7-membered monocyclic saturated heterocyclyl in Het$^{1b}$ and Het$^{1e}$ may optionally be substituted, where possible, on one or two ring N-atoms with C$_{1-4}$alkyl;
Het$^2$ represents a heterocyclyl of formula (b-1):

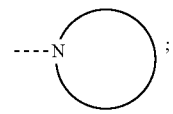

(b-1)

(b-1) represents a N-linked 4- to 7-membered monocyclic saturated heterocyclyl optionally containing one additional heteroatom selected from O, S(=O)$_p$ and N;
wherein in case (b-1) contains one or two additional N-atoms, said one or two N-atoms may optionally be substituted with C$_{1-4}$alkyl; and
wherein (b-1) may optionally be substituted on one, two or three ring C-atoms with one or two substituents each independently selected from the group consisting of —OH, cyano, C$_{1-4}$alkyl, —O—C$_{1-4}$alkyl, and C$_{1-4}$alkyl-OH;
R$^{11b}$ represents Het$^{1e}$; C$_{1-4}$alkyl; C$_{1-4}$alkyl substituted with one, two or three substituents each independently selected from the group consisting of —OH and —O—C$_{1-4}$alkyl;
R$^{13}$ represents —O—C$_{1-4}$alkyl, —NR$^{19a}$R$^{19b}$, or Het$^{1d}$;
R$^{12}$ represents —O—C$_{1-4}$alkyl, —NR$^{14a}$R$^{14b}$, —C(=O)NR$^{14c}$R$^{14d}$, or Het$^{1c}$;
R$^{11a}$, R$^{14a}$, R$^{14c}$, R$^{17a}$ and R$^{19a}$ each independently represents hydrogen or C$_{1-4}$alkyl;
R$^{14b}$, R$^{14d}$, R$^{17b}$ and R$^{19b}$ each independently represents hydrogen; C$_{1-6}$alkyl; —C(=O)—C$_{1-4}$alkyl; C$_{1-6}$alkyl substituted with one —O—C$_{1-4}$alkyl; or —C(=O)—C$_{1-4}$alkyl substituted with one —O—C$_{1-4}$alkyl; and
p represents 2.

3. The compound according to claim 2, wherein
R$^2$ represents C$_{1-6}$alkyl substituted with one R$^5$;
R$^4$ represents hydrogen;
R$^5$ represents —OR$^7$;
R$^3$ represents phenyl optionally substituted with one, two or three substituents each independently selected from the group consisting of halo; C$_{1-6}$alkyl; —O—

$C_{1-4}$alkyl; —C(=O)—$R^{10}$; $Het^{1a}$; —O-$Het^{1b}$; and $C_{1-4}$alkyl substituted with one $R^{13}$;

$R^{10}$ represents —$NR^{11a}R^{11b}$ or $Het^2$;

$Het^{1a}$ represents a 4- to 7-membered monocyclic saturated heterocyclyl containing one or two heteroatoms each independently selected from O and N; or a 6- to 11-membered bicyclic saturated heterocyclyl, including fused, spiro and bridged cycles, containing one, two or three heteroatoms each independently selected from O and N;

wherein said 4- to 7-membered monocyclic saturated heterocyclyl or said 6- to 11-membered bicyclic saturated heterocyclyl in $Het^{1a}$ may optionally be substituted, where possible, on one, two or three ring N-atoms with $C_{1-4}$alkyl;

$Het^{1b}$ and $Het^{1e}$ each independently represents a 4- to 7-membered monocyclic saturated heterocyclyl, attached to the remainder of the molecule of Formula (I) through any available ring carbon atom, said $Het^{1b}$ and $Het^{1e}$ containing one or two heteroatoms each independently selected from O and N;

wherein said 4- to 7-membered monocyclic saturated heterocyclyl in $Het^{1b}$ and $Het^{1e}$ may optionally be substituted, where possible, on one or two ring N-atoms with $C_{1-4}$alkyl;

$Het^2$ represents a heterocyclyl of formula (b-1):

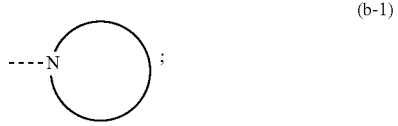

(b-1)

(b-1) represents a N-linked 4- to 7-membered monocyclic saturated heterocyclyl;

wherein (b-1) may optionally be substituted on one, two or three ring C-atoms with one —O—$C_{1-4}$alkyl;

$R^{11b}$ represents $Het^{1e}$;

$R^{13}$ represents —$NR^{19a}R^{19b}$;

$R^{11a}$ and $R^{19a}$ each independently represents hydrogen; and $R^{19b}$ represents —C(=O)—$C_{1-4}$alkyl.

4. The compound according to claim 1, wherein Y represents $CR^4$.

5. The compound according to claim 4, wherein $R^4$ represents hydrogen.

6. The compound according to claim 1, wherein
$R^2$ represents $C_{1-6}$alkyl substituted with one $R^5$;
$R^4$ represents hydrogen;
$R^5$ represents —$OR^7$;
$R^7$ represents hydrogen; and
$R^3$ represents phenyl substituted with one, two or three substituents each independently selected from the group consisting of halo; cyano; and $C_{1-6}$alkyl.

7. The compound according to claim 6, wherein
$R^1$ represents methyl;
$R^2$ represents methyl or —$CH_2$—OH.

8. A pharmaceutical composition comprising a compound as claimed in claim 1 and a pharmaceutically acceptable carrier or diluent.

9. A pharmaceutical composition comprising a compound as claimed in claim 2 and a pharmaceutically acceptable carrier or diluent.

10. A pharmaceutical composition comprising a compound as claimed in claim 3 and a pharmaceutically acceptable carrier or diluent.

11. A pharmaceutical composition comprising a compound as claimed in claim 4 and a pharmaceutically acceptable carrier or diluent.

12. A pharmaceutical composition comprising a compound as claimed in claim 5 and a pharmaceutically acceptable carrier or diluent.

13. A pharmaceutical composition comprising a compound as claimed in claim 6 and a pharmaceutically acceptable carrier or diluent.

14. A pharmaceutical composition comprising a compound as claimed in claim 7 and a pharmaceutically acceptable carrier or diluent.

15. A method of treating a cell proliferative disease in a warm-blooded animal which comprises administering to the said animal an effective amount of a pharmaceutical composition as claimed in claim 8.

* * * * *